US007709500B2

(12) United States Patent
Alcaraz et al.

(10) Patent No.: US 7,709,500 B2
(45) Date of Patent: May 4, 2010

(54) CHEMICAL COMPOUNDS

(75) Inventors: Lilian Alcaraz, Loughborough (GB); Mark Furber, Loughborough (GB); Mark Purdie, Loughborough (GB); Brian Springthorpe, Loughborough (GB)

(73) Assignee: AstraZeneca AB (SE)

(*) Notice: Subject to any disclaimer, the term of this patent is extended or adjusted under 35 U.S.C. 154(b) by 923 days.

(21) Appl. No.: 10/504,936

(22) PCT Filed: Feb. 17, 2003

(86) PCT No.: PCT/SE03/00258

§ 371 (c)(1), (2), (4) Date: Aug. 17, 2004

(87) PCT Pub. No.: WO03/068743

PCT Pub. Date: Aug. 21, 2003

(65) Prior Publication Data

US 2005/0107428 A1    May 19, 2005

(30) Foreign Application Priority Data

Feb. 18, 2002    (SE) .................................... 0200465
Sep. 9, 2002    (SE) .................................... 0202673

(51) Int. Cl.
A61K 31/445    (2006.01)
C07D 211/44    (2006.01)
C07D 41/02    (2006.01)

(52) U.S. Cl. .................. 514/318; 514/249; 514/269; 514/307; 514/323; 514/326; 544/315; 544/353; 546/141; 546/193; 546/210

(58) Field of Classification Search ................ 514/249, 514/269, 307, 318, 323, 326; 544/315, 353; 546/141, 193, 201, 210
See application file for complete search history.

(56) References Cited

U.S. PATENT DOCUMENTS

| | | | |
|---|---|---|---|
| 5,935,974 | A | 8/1999 | Rae et al. |
| 6,124,319 | A | 9/2000 | MacCoss et al. |
| 6,140,349 | A | 10/2000 | Caldwell et al. |
| 6,166,037 | A | 12/2000 | Budhu et al. |
| 6,331,541 | B1 | 12/2001 | Ko et al. |
| 6,358,979 | B1 | 3/2002 | Finke et al. |
| 6,444,686 | B1 | 9/2002 | Ko et al. |
| 6,489,354 | B1 | 12/2002 | Bao et al. |
| 6,566,376 | B1 | 5/2003 | Baxter et al. |
| 6,605,623 | B1 | 8/2003 | Ko et al. |
| 6,627,629 | B2 | 9/2003 | Ko et al. |
| 6,627,646 | B2 | 9/2003 | Bakale et al. |
| 7,265,227 | B2 * | 9/2007 | Evans et al. .......... 546/216 |
| 2005/0107428 | A1 | 5/2005 | Alcaraz et al. |
| 2007/0054924 | A1 | 3/2007 | Alcaraz et al. |

| | | |
|---|---|---|
| 2008/0108661 | A1 | 5/2008 Cage et al. |

FOREIGN PATENT DOCUMENTS

| | | |
|---|---|---|
| EP | 0903349 A2 | 3/1999 |
| WO | WO 97/10207 | 3/1997 |
| WO | WO 97/23458 | 7/1997 |
| WO | WO 98/18761 | 5/1998 |
| WO | WO 99/04794 A1 | 2/1999 |
| WO | WO 00/12478 | 3/2000 |
| WO | WO 00/29377 | 5/2000 |
| WO | WO 00/31022 | 6/2000 |
| WO | WO 00/31033 A1 | 6/2000 |
| WO | WO 00/35449 | 6/2000 |
| WO | WO 00/35451 | 6/2000 |
| WO | WO 00/35452 | 6/2000 |
| WO | WO 00/35453 | 6/2000 |
| WO | WO 00/35454 | 6/2000 |
| WO | WO 00/58305 | 10/2000 |
| WO | WO 01/02381 | 1/2001 |
| WO | WO 01/62728 | 8/2001 |
| WO | WO 01/62729 | 8/2001 |
| WO | WO 01/62757 | 8/2001 |
| WO | WO 01/77101 | 10/2001 |
| WO | WO 01/98269 | 12/2001 |
| WO | WO 01/98270 | 12/2001 |

(Continued)

OTHER PUBLICATIONS

King et al. "Medicinal Chemistry . . . " Cambridge, p. 206-209 (1994).*
Patani et al. "Bioisosterism . . . " Chem. Rev. 96, 3147-48, 3170 (1996).*
Cohen et al. "Cytokine function . . . " CA 125:31527 (1996).*
Rollins "Chemokines" Blood, v.90(3)p. 909-928 (1997).*

(Continued)

*Primary Examiner*—Celia Chang
(74) *Attorney, Agent, or Firm*—Fish & Richardson P.C.

(57) ABSTRACT

The invention provides compounds of formula (I):

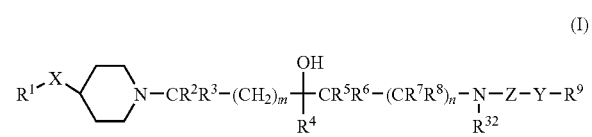

(I)

wherein: X is $CH_2$, O, $S(O)_2$ or $NR^{10}$; Y is a bond, $CH_2$, $NR^{35}$, $CH_2NH$, $CH_2NHC(O)$, $CH(OH)$, $CH(NHCOR^{33})$, $CH(NHSO_2R^{34})$, $CH_2O$ or $CH_2S$; Z is C(O), or when Y is a bond Z can also be $S(O)_2$; $R^1$ is optionally substituted aryl, optionally substituted heterocyclyl or $C_{4-6}$ cycloalkyl fused to a benzene ring; and $R^2$, $R^3$, $R^4$, $R^5$, $R^6$, $R^7$ and $R^8$, $R^9$, $R^{10}$, $R^{32}$, $R^{33}$, $R^{34}$ and $R^{35}$ are as defined herein; are modulators of chemokine (especially CCR3) activity (for use in, for example, treating asthma). The invention also provides a process for making 4-(3,4-dichlorophenoxy)piperidine, which is useful as an intermediate for making certain compounds of the invention.

14 Claims, No Drawings

FOREIGN PATENT DOCUMENTS

| WO | WO 02/20484 | 3/2002 |
| WO | WO 02/30899 A1 | 4/2002 |
| WO | WO 02/39125 | 5/2002 |
| WO | WO 02/50070 | 6/2002 |
| WO | WO 03/018556 A1 | 3/2003 |
| WO | WO 03/068743 | 8/2003 |
| WO | WO 03/082190 | 10/2003 |
| WO | WO 2005/073192 A1 | 8/2005 |
| WO | WO 2007/114770 | 10/2007 |

OTHER PUBLICATIONS

Barnes "Cytokine directed . . . " Cytokine & growth factor rev. 14, p. 511-522 (2003).*

Boskabady et al. "The effect of exposure . . . " Pathophysiology v.14, p. 97-104 (2007).*

Hodgson et al., "Chemokines and Drug Discovery", *Drug News Perspect* 17(5):335-338 (2004).

Baggiolini, M., "Chemokines in pathology and medicine", *Journal of Internal Medicine* 250:91-104 (2001).

Bernstein, "Polymorphism in Molecular Crystals", Clarendon Press, Oxford, pp. 117-188 and 272 (2002).

Davidovich et al., "Detection of Polymorphism by Powder X-Ray Diffraction: Interference by Preferred Orientation", *Am. Pharm. Rev.* 7, pp. 10, 12, 14, 16, 100 (2004).

Dean, "Analytical Chemistry Handbook", pp. 10.24-10.26 (1995).

Doelker, "Crystalline modifications and polymorphism changes during drug manufacturing", *Ann. Pharm. Fr.* 60(3):161-176 (2002), CAPLUS abstract.

Doelker, "Physiochemical behavior of active substances. Consequences for the feasibility and stability of pharmaceutical forms", *S.T.P. Pharma Pratiques* 9(5):399-409 (1999), CAPLUS abstract.

Gould, "Salt selection for basic drugs", *International Journal of Pharmaceutics* 33:201-217 (1986).

Jain et al., "Polymorphism in Pharmacy", *Indian Drugs* 23(6):315-329 (1986).

Muzaffar et al., "Polymorphism and Drug Availability", *J. Phar.* 1(1):59-66 (1979).

Otsuka et al., "Effect of Polymorphic Forms of Bulk Powders on Pharmaceutical Properties of Carbamazepine Granules", *Chem. Pharm. Bull.* 47(6):852-856 (1999).

Singhal et al., "Drug polymorphism and dosage form design: a practical perspective", *Advanced Drug Delivery Reviews* 56:335-347 (2004).

US Pharmacopia #23, National Formulary #18, pp. 1843-1844 (1995).

* cited by examiner

CHEMICAL COMPOUNDS

CROSS-REFERENCE TO RELATED APPLICATIONS

This application is the national phase application under 35 U.S.C. §371 of PCT International Application No. PCT/SE03/00258, filed Feb. 17, 2003, which claims priority to Swedish Application Serial No. 0200465-3, filed Feb. 18, 2002 and Swedish Application Serial No. 0202673-0, filed Sep. 9, 2002.

The present invention concerns piperidine derivatives having pharmaceutical activity, to processes for preparing such derivatives, to pharmaceutical compositions comprising such derivatives and to the use of such derivatives as active therapeutic agents. The invention also provides a process for making 4-(3,4-dichlorophenoxy)piperidine, which is useful as an intermediate for making certain compounds of the invention.

Pharmaceutically active piperidine derivatives are disclosed in WO 01/62728, WO 01/62729 and WO 01/62757.

Chemokines are chemotactic cytokines that are released by a wide variety of cells to attract-macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes, but not neutrophils, such as human monocyte chemotactic proteins 1-3 (MCP-1, MCP-2 and MCP-3), RANTES (Regulated on Activation, Normal T Expressed and Secreted), eotaxins and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, especially rhinitis and urticaria Antagonists of H1 are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

The present invention provides a compound of formula (I):

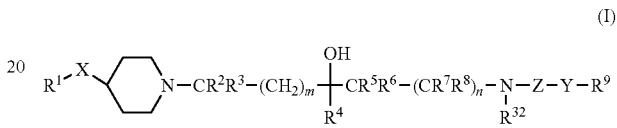

(I)

wherein:

X is $CH_2$, O, $S(O)_2$ or $NR^{10}$;

Y is a bond, $CH_2$, $NR^{35}$, $CH_2NH$, $CH_2NHC(O)$, $CH(OH)$, $CH(NHC(O)R^{33})$, $CH(NHS(O)_2R^{34})$, $CH_2O$ or $CH_2S$;

Z is $C(O)$, or when Y is a bond Z can also be $S(O)_2$;

$R^1$ is optionally substituted aryl, optionally substituted heterocyclyl or $C_{4-6}$ cycloalkyl fused to a benzene ring;

$R^4$ is hydrogen, $C_{1-6}$ alkyl (optionally substituted by $C_{3-6}$ cycloalkyl) or $C_{3-6}$ cycloalkyl;

$R^2$, $R^3$, $R^5$, $R^6$, $R^7$ and $R^8$ are, independently, hydrogen, $C_{1-6}$ alkyl or $C_{3-6}$ cycloalkyl;

m and n are, independently, 0 or 1;

$R^9$ is optionally substituted aryl or optionally substituted heterocyclyl;

$R^{10}$, $R^{32}$ and $R^{35}$ are, independently, hydrogen, $C_{1-6}$ alkyl or $C_{3-6}$ cycloalkyl;

$R^{33}$ and $R^{34}$ are $C_{1-6}$ alkyl or $C_{3-6}$ cycloalkyl;

wherein the foregoing aryl and heterocyclyl moieties are, where possible, optionally substituted by: halogen, cyano, nitro, hydroxy, oxo, $S(O)_rR^{12}$, $OC(O)NR^{13}R^{14}$, $NR^{15}R^{16}$, $NR^{17}C(O)R^{18}$, $NR^{19}C(O)NR^{20}R^{21}$, $S(O)_2NR^{22}R^{23}$, $NR^{24}S(O)_2R^{25}$, $C(O)NR^{26}R^{27}$, $C(O)R^{28}$, $CO_2R^{29}$, $NR^{30}CO_2R^{31}$, $C_{1-6}$ alkyl (itself optionally mono-substituted by NHC(O)phenyl), $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{2-6}$ alkenyl, $C_{2-6}$ alkynyl, $C_{3-10}$ cycloalkyl, methylenedioxy, difluoromethylenedioxy, phenyl, phenyl($C_{1-4}$)alkyl, phenoxy, phenylthio, phenyl($C_{1-4}$)alkoxy, morpholinyl, heteroaryl, heteroaryl($C_{1-4}$)alkyl, heteroaryloxy or heteroaryl($C_{1-4}$)alkoxy, wherein any of the immediately foregoing phenyl and heteroaryl moieties are optionally substituted with halogen, hydroxy, nitro, $S(O)_r(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

k and r are, independently, 0, 1 or 2;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{29}$ and $R^{30}$ are, independently, hydrogen, $C_{1-6}$ alkyl (optionally substituted by halogen, hydroxy or $C_{3-10}$ cycloalkyl), $CH_2(C_{2-6}$ alkenyl), $C_{3-6}$ cycloalkyl, phenyl (itself optionally substituted by halogen, hydroxy, nitro, $NH_2$, $NH(C_{1-4}$ alkyl), $NH(C_{1-4}$ alkyl$)_2$, $S(O)_2(C_{1-4}$ alkyl), $S(O)_2NH_2$, $S(O)_2NH(C_{1-4}$ alkyl), $S(O)_2N(C_{1-4}$ alkyl$)_2$, cyano, $C_{1-4}$ alkyl, $C(O)NH_2$, $C(O)NH(C_{1-4}$ alkyl), $C(O)N(C_{1-4}$ alkyl$)_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$, $S(O)_2(C_{1-4}$ alkyl), $S(O)_2NH_2$, $S(O)_2NH(C_{1-4}$ alkyl), $S(O)_2N(C_{1-4}$ alkyl$)_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^{13}R^{14}$, $NR^{15}R^{16}$, $NR^{20}R^{21}$, $NR^{22}R^{23}$, $NR^{26}R^{27}$, may, independently, form a 4-7 membered heterocyclic ring selected from the group: azetidine (itself optionally substituted by hydroxy or $C_{1-4}$ alkyl), pyrrolidine, piperidine, azepine, 1,4-morpholine or 1,4-piperazine, the latter optionally substituted by $C_{1-4}$ alkyl on the distal nitrogen; $R^{12}$, $R^{25}$, $R^{28}$ and $R^{31}$ are, independently, $C_{1-6}$ alkyl (optionally substituted by halogen, hydroxy or $C_{3-10}$ cycloalkyl), $CH_2(C_{2-4}$ alkenyl), phenyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

provided that when X is $CH_2$ and m and n are both 0 then Y is not $NR^{35}$;

or an N-oxide thereof, or a pharmaceutically acceptable salt, solvate or solvate of a salt thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, sulfate, acetate, diacetate, fumarate, maleate, tartrate, citrate, oxalate, methanesulfonate or p-toluenesulfonate.

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl or tert-butyl. Alkyl groups preferably comprise 1-6 carbon atoms.

Alkenyl is, for example, vinyl or allyl. Alkenyl groups preferably comprise 2-6 carbon atoms.

Alkynyl is, for example, propargyl. Alkynyl groups preferably comprise 2-6 carbon atoms.

Cycloalkyl is monocyclic and is, for example, cyclopropyl, cyclopentyl or cyclohexyl. Cycloalkyl groups preferably comprise 3-6 carbon atoms.

Cycloalkyl fused to a benzene ring is, for example, bicyclo[4.2.0]octa-1,3,5-trienyl.

Aryl is preferably phenyl or naphthyl.

Heterocyclyl is an aromatic or non-aromatic 5 or 6 membered ring, optionally fused to one or more other rings, comprising at least one heteroatom selected from the group comprising nitrogen, oxygen and sulfur; or an N-oxide thereof, or an S-oxide or S-dioxide thereof. Heterocyclyl is; for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl, 1,6-dihydropyridinyl (for example in a 6-oxo-1,6-dihydropyridinyl moiety), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in a 1,1-dioxo-2,3-dihydrobenz[b]thienyl moiety), indazolyl, benzimidazolyl, bentriazolyl, benzoxazolyl benzthiazolyl, 1,2-dihydrobenzthiazolyl (for example in a 1H-benzthiazol-2-one-yl moiety), 2,3-dihydrobenzthiazolyl (for example in a 2,3-dihydrobenzthiazol-2-one-yl moiety), 1,2,3-benzothiadiazolyl, an imidazopyridinyl (such as imidazo[1,2-a]pyridinyl), thieno[3,2-b]pyridin-6-yl, 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, 3,4-dihydro-1H-2,1-benzothiazinyl (for example in a 2-dioxo-3,4-dihydro-1H-2,1-benzothiazinyl moiety), a pyrazolopyridine (for example 1H-pyrazolo[3,4-b]pyridinyl), a purine, 3,7-dihydro-purinyl (for example in a 3,7-dihydro-purinyl (for example in a 3,7-dihydro-purin-2,6-dione-8-yl moiety), quinolinyl, isoquinolinyl, 1,2-dihydroisoquinolinyl (for example in a 2H-isoquinolin-1-one-yl (alternatively called 1-oxo-1,2-dihydroisoquinolinyl or 1,2-dihydroisoquinolinyl-1-one) moiety), a naphthyridinyl (for example [1,6]naphthyridinyl or [1,8]naphthyridinyl), 1,4-dihydro[1,8]naphthyridinyl (for example in a 1H-[1,8]naphthyridin-4-one-yl moiety), or a benzothiazinyl, 4H-benzo[1,4]thiazinyl (for example in a 4H-benzo[1,4]thiazin-3-one-yl moiety); or an N-oxide thereof (such as a pyridine N-oxide), or an S-oxide or S-dioxide thereof. 1,2-Dihydropyridinyl (an alternative numbering for a 1,6-dihydropyridinyl) can also be present in a 2-oxo-1,2-dihydropyridinyl moiety; and 2,3-dihydro-1H-indazolyl can also be present in a 3-oxo-2,3-dihydro-1H-indazolyl moiety.

Heterocyclyl also includes cinnolinyl, phthalazinyl, 3,4-dihydrophthalazinyl (for example in a 4-oxo-3,4-dihydrophthalazinyl moiety), benzoxazinyl, 2,3-dihydro-4H-1,4-benzoxazinyl (for example in a 3-oxo-2,3-dihydro-4H-1,4-benzoxazinyl moiety), 3,4-dihydro-2H-1,4-benzoxazinyl (for example in a 3-oxo-3,4-dihydro-2H-1,4-benzoxazinyl moiety), isoindolyl, 1,3-dihydro-2H-isoindolyl (for example in a 1,3-dioxo-1,3-dihydro-2H-isoindolyl moiety), pyrazolotriazinyl (for example pyrazolo[5,1-c][1,2,4]triazinyl), pyrazinyl, pyridazinyl, 9H-purinyl, pyrazolopyriminyl (for example pyrazolo[1,5-a]pyrimidinyl), imidazobenzothiazolyl (for example imidazo[2,1-b][1,3]benzothiazolyl), 1,2,5-oxadiazolyl, imidazopyrimidinyl (for example imidazo[1,2-a]pyrimidinyl), quinolinyl, 1,2-dihydroquinolinyl (for example in a 2-oxo-1,2-dihydroquinolinyl moiety) or 2,1,3-benzoxadiazolyl (for example as a 1-oxide); or it may additionally be an N-oxide thereof, or an S-oxide or S-dioxide thereof. Further examples of heterocyclyl are 1,3-benzothiazole, 2,3-dihydro-1,3-benzothiazole (for example in a 2-oxo-2,3-dihydro-1,3-benzothiazole moiety), 4,5,6,7-tetrahydroindazole, 2,3-dihydro-1H-benzimidazole (for example in a 2-oxo-2,3-dihydro-1H-benzimidazole moiety) and 1,4-dihydroquinoline (for example in a 4-oxo-1,4-dihydroquinoline moiety).

An N-oxide of a compound of formula (I) or (Ia) is, for example, a 1-oxy-piperidinyl compound.

Heteroaryl is an aromatic heterocyclyl. Thus it is, for example furyl, thienyl, pyrrolyl, thiazolyl, pyrazolyl, oxazolyl, isoxazolyl, imidazolyl, pyridinyl, pyrimidinyl, indolyl, benzo[b]furyl, benz[b]thienyl, indazolyl, benzimidazolyl, benztriazolyl, benzoxazolyl, benzthiazolyl, 1,2,3-benzothiadiazolyl, an imidazopyridinyl, thieno[3,2-b]pyridin-6-yl 1,2,3-benzoxadiazolyl, 2,1,3-benzothiadiazolyl, benzofurazan, quinoxalinyl, a pyrazolopyridine, a purine, quinolinyl, isoquinolinyl, a naphthyridinyl, a benzothiazinyl, cinnolinyl, phthalazinyl, benzoxazinyl, isoindolyl, pyrazolotriazinyl pyrazinyl, pyridazinyl, pyrazolopyrimidinyl, imidazobenzothiazolyl, imidazopyrimidinyl quinolinyl or 2,1,3-benzoxadiazolyl; or an N-oxide thereof (such as a pyridine N-oxide), or an S-oxide or S-dioxide thereof.

Haloalkyl is an alkyl group carrying one or more (such as 1 to 6) halogen atoms and is, for example, $CF_3$. Alkoxyalkyl is, for example, $CH_3OCH_2$, $CH_3CH_2OCH_2$ or $CH_3CH_2O(CH_2)_2$. Haloalkyloxy is an alkoxy group carrying one or more (such as 1 to 6) halogen atoms and is, for example, $OCF_3$. Alkoxyalkoxy is, for example, $CH_3OCH_2O$, $CH_3CH_2OCH_2O$ or $CH_3CH_2O(CH_2)_2O$. Phenylalkyl is, for example, benzyl, phenyleth-1-yl or phenyleth-2-yl. Phenylalkoxy is, for example benzyloxy. Heteroarylalkyl is, for example, pyridinylmethyl or pyrimidinylmethyl. Heteroaryloxy is, for example, pyridinyloxy or pyrimidinyloxy. Heteroarylalkoxy is, for example, pyridinylmethoxy or pyrimidinylmethoxy.

In one aspect the present invention provides a compound of formula (I) wherein: X is $CH_2$, O, $S(O)_2$ or $NR^{10}$; Y is a bond, $CH_2$, $NR^{35}$, $CH_2NH$, $CH_2NHC(O)$, CH(OH), $CH(NHC(O)R^{33})$, $CH(NHS(O)_2R^{34})$, $CH_2O$ or $CH_2S$; Z is C(O), or when Y is a bond Z can also be $S(O)_2$; $R^1$ is optionally substituted aryl, optionally substituted heterocyclyl or $C_{4-6}$-cycloalkyl fused to a benzene ring; $R^4$ is hydrogen, $C_{1-6}$ alkyl (optionally substituted by $C_{3-6}$ cycloalkyl) or $C_{3-6}$ cycloalkyl; $R^2$, $R^3$, $R^5$, $R^6$, $R^7$ and $R^8$ are, independently, hydrogen, $C_{1-6}$ alkyl or $C_{3-6}$ cycloalkyl; m and n are, independently, 0 or 1; $R^9$ is optionally substituted aryl or optionally substituted heterocyclyl; $R^{10}$, $R^{32}$, $R^{33}$ and $R^{35}$ are, independently, hydrogen or $C_{1-6}$ alkyl, $R^{34}$ is $C_{1-6}$ alkyl; wherein the foregoing aryl and heterocyclyl moieties are, where possible, optionally substituted by halogen, cyano, nitro, hydroxy, oxo, $S(O)_kR^{12}$, $OC(O)NR^{13}R^{14}$, $NR^{15}R^{16}$, $NR^{17}C(O)R^{18}$, $NR^{19}C(O)NR^{20}R^{21}$, $S(O)_2NR^{22}R^{23}$, $NR^{24}S(O)_2R^{25}$, $C(O)NR^{26}R^{27}$, $C(O)R^{28}$, $CO_2R^{29}$, $NR^{30}CO_2R^{31}$, $C_{1-6}$ alkyl, $C_{1-6}$ alkylthio, $C_{1-6}$ alkoxy$(C_{1-6})$alkyl, $C_{1-6}$ alkoxy, $C_{1-6}$ haloalkoxy, $C_{1-6}$ alkoxy$(C_{1-6})$alkoxy, $C_{1-6}$ alkyl $C_{2-6}$ alkenyl, $C_{2-6}$ alkynyl, $C_{3-10}$ cycloalkyl, methylenedioxy, difluoromethylenedioxy, phenyl, phenyl$(C_{1-4})$alkyl, phenoxy, phenylthio, phenyl$(C_{1-4})$alkoxy, heteroaryl, heteroaryl$(C_{1-4})$alkyl, heteroaryloxy or heteroaryl$(C_{1-4})$alkoxy, wherein any of the immediately foregoing phenyl and heteroaryl moieties are optionally substituted with halogen, hydroxy, nitro, $S(O)_r(C_{1-4}$ alkyl), $S(O)_2NH_2$, cyano, $C_{1-4}$ alkyl, $C_{1-6}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; k and r are, independently, 0, 1 or 2; $R^{13}$, $R^{14}$, $R^{15}R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{29}$, $R^{30}$, and $R^{31}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $NH(C_{1-4}$ alkyl$)_2$, $S(O)_2(C_{1-4}$ alkyl), $S(O)_2NH$, $S(O)_2NH(C$ alkyl), $S(O)_2N(C_{1-4}$ alkyl$)_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$alkyl), $N(C_{1-4}$ alkyl$)_2$, $S(O)_2(C_{1-4}$ alkyl), $S(O)_2NH_2$, $S(O)_2NH(C_{1-4}$ alkyl), $S(O)_2N(C_{1-4}$ alkyl$)_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$, $CO_2H$, $CO_2(C_{1-4}$ alkyl), $NHC(O)(C_{1-4}$ alkyl NHS $(O)_2(C_{1-4}$ alkyl), $C(O)(C_{1-4}$ alkyl), $CF_3$ or $OCF_3$); alternatively $NR^{13}R^{14}$, $NR^{15}R^{16}$, $NR^{20}R^{21}$, $NR^{22}R^{23}$, $NR^{26}R^{27}$, may, independently, form a 4-7 membered heterocyclic ring, azetidine, pyrrolidine, piperidine, azepine, 1,4-morpholine or 1,4-piperazine, the latter optionally substituted by $C_{1-4}$ alkyl on the distal nitrogen; $R^{12}$, $R^{25}$ and $R^{28}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), NHS $(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these allyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$-alkyl), $C(O)N(C_{1-4}$ alkyl$)_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); provided that when X is $CH_2$ and m and n are both 0 then Y is not $NR^{35}$; or an N-oxide thereof; or a pharmaceutically acceptable salt, solvate or solvate of a salt thereof.

In another aspect the present invention provides a compound of formula (Ia):

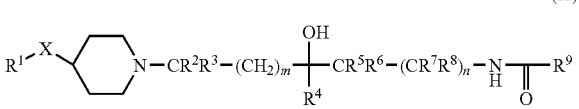

(Ia)

wherein: X is $CH_2$, O, $S(O)_2$ or $NR^{10}$; $R^1$ is optionally substituted aryl or optionally substituted heterocyclyl; $R^4$ is hydrogen, $C_{1-6}$ alkyl (optionally substituted by $C_{3-6}$ cycloalkyl) or $C_{3-6}$ cycloalkyl; $R^2$, $R^3$, $R^5$, $R^6$, $R^7$ and $R^8$ are, independently, hydrogen, $C_{1-6}$ alkyl or $C_{3-6}$ cycloalkyl; m and n are, independently, 0 or 1; $R^9$ is optionally substituted aryl or optionally substituted heterocyclyl; $R^{10}$ is hydrogen or $C_{1-6}$ alkyl; wherein the foregoing aryl and heterocyclyl moieties are, where possible, optionally substituted by: halogen, cyano, nitro, hydroxy, oxo, $S(O)_kR^{12}$, $OC(O)NR^{13}R^{14}$, $NR^{15}R^{16}$, $NR^{17}C(O)R^{18}$, $NR^{19}C(O)NR^{20}R^{21}$, $S(O)_2NR^{22}R^{23}$, $NR^{24}S(O)_2R^{25}$, $C(O)NR^{26}R^{27}$, $C(O)R^{28}$, $CO_2R^{29}$, $NR^{30}CO_2R^{31}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{2-6}$ alkenyl, $C_{2-6}$ alkynyl, $C_{3-10}$ cycloalkyl, methylenedioxy, difluoromethylenedioxy, phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl($C_{1-4}$)alkoxy; wherein any of the immediately foregoing phenyl and heteroaryl moieties are optionally substituted with halogen, hydroxy, nitro, $S(O)_r(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; k and r are, independently, 0, 1 or 2; $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{29}$, $R^{30}$, and $R^{31}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $NH(C_{1-4}$ alkyl)$_2$, $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ allyl), $S(O)_2NH_2$, $S(O)_2NH(C_{1-4}$ alkyl), S/O alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^{13}R^{14}$, $NR^{15}R^{16}$, $NR^{20}R^{21}$, $NR^{22}R^{23}$, $NR^{26}R^{27}$, may independently, form a 4-7 membered heterocyclic ring, azetidine, pyrrolidine, piperidine, azepine, 1,4-morpholine or 1,4-piperazine, the latter optionally substituted by $C_{1-4}$ alkyl on the distal nitrogen; $R^{12}$, $R^{25}$ and $R^{28}$ are, independently, $C_{1-6}$ allyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl) (and these alkyl groups may join to form a ring as described for $R^{13}$ and $R^{14}$ above), $S(O)_2(C_{1-4}$ allyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$alkyl), $C(O)N(C_{1-4}$ alkyl)$_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-14}$ alkyl)$_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); or an N-oxide thereof; or a pharmaceutically acceptable salt, solvate or solvate of a salt thereof.

In a further aspect the present invention provides a compound of formula (I) wherein: X is O; Y is a bond, $CH_2$, $NR^{35}$, $CH_2NH$, $CH(OH)$, $CH(NHC(O)R^{33})$, $CH(NHS(O)_2R^{34})$ or $CH_2O$; Z is $C(O)$, or when Y is a bond Z can also be $S(O)_2$; $R^1$ is optionally substituted phenyl; $R^4$ is hydrogen or $C_{1-6}$ alkyl; $R^2$, $R^3$, $R^5$, $R^6$, $R^7$ and $R^8$ are, when present, all hydrogen; m and n are, independently, 0 or 1; $R^9$ is optionally substituted aryl or optionally substituted heterocyclyl; $R^{32}$ and $R^{35}$ are, independently, hydrogen or $C_{1-6}$ alkyl; $R^{33}$ and $R^{34}$ are $C_{1-6}$ alkyl; wherein the foregoing phenyl, aryl and heterocyclyl moieties are, where possible, optionally substituted by: halogen, cyano, hydroxy, oxo, $S(O)_2R^{12}$, $NR^{15}R^{16}$, $NR^{17}C(O)R^{18}$, $S(O)_2NR^{22}R^{23}$, $NR^{24}S(O)_2R^{25}$, $C(O)NR^{26}R^{27}$, $CO_2R^{29}$, $C_{1-6}$ alkyl (itself optionally mono-substituted by NHC(O)phenyl), $CF_3$, $OCF_3$, phenyl or heteroaryl; wherein any of the immediately foregoing phenyl and heteroaryl moieties are optionally substituted with halogen, $C_{1-4}$ alkyl, $C_{1-4}$ alkoxy or $CF_3$; $R^{15}$, $R^{16}$, $R^{17}$, $R^{18}$, $R^{22}$, $R^{23}$, $R^{24}$, $R^{26}$, $R^{27}$ and $R^{29}$ are, independently, hydrogen, $C_{1-6}$ alkyl (optionally substituted by hydroxy) or $C_{3-6}$ cycloalkyl; alternatively $NR^{22}R^{23}$ may form an azetidine ring (itself optionally substituted by hydroxy or $C_{1-4}$ alkyl); $R^{12}$ and $R^{25}$ are, independently, $C_{1-6}$ alkyl or phenyl; or a pharmaceutically acceptable salt thereof.

In a still further aspect $R^1$ is phenyl optionally substituted (for example with one, two or three of) by halogen (especially fluoro or chloro), cyano, $C_{1-4}$ alkyl (especially methyl), $C_{1-4}$ alkoxy (especially methoxy), $S(O)_2(C_{1-4}$ alkyl), $S(O)_2NH_2$, $S(O)_2NH(C_{1-4}$ alkyl), $S(O)_2NH(C_{3-6}$ cycloalkyl), $C(O)_2(C_{1-4}$ alkyl), $C(O)NH(C_{1-4}$ alkyl) or $C(O)NH_2$.

In another aspect $R^1$ is phenyl optionally substituted (for example with one, two or three of) by halogen (especially fluoro or chloro), cyano, $C_{1-4}$ alkyl (especially methyl) or $C_{1-4}$ alkoxy (especially methoxy). In a further aspect $R^1$ is phenyl substituted by one, two or three of: fluoro, chloro, methyl or cyano. In another aspect $R^1$ is phenyl substituted by one, two or three of: fluoro, chloro or methyl. Thus, $R^1$ is, for example, 2-methyl-4-chlorophenyl, 3-methyl-2,4-dichlorophenyl, 3,4-difluorophenyl, 3-fluoro-4-chlorophenyl or 4-chlorophenyl. In a still further aspect $R^1$ is 3,4-dichlorophenyl.

In another aspect X is O.

In yet another aspect Y is a bond.

In another aspect Z is $C(O)$.

In a further aspect m is 0.

In a still further aspect n is 0.

In another aspect m and n are both 0.

In another aspect $R^4$ is hydrogen or $C_{1-6}$ alkyl (such as methyl). In yet another aspect $R^4$ is hydrogen.

In yet another aspect $R^2$, $R^3$, $R^5$, $R^6$, $R^7$ and $R^8$ are all hydrogen; and in a further aspect n is 0, and $R^2$, $R^3$, $R^5$ and $R^6$ are all hydrogen.

In a further aspect $R^2$, $R^3$, $R^4$, $R^5$, $R^6$, $R^7$ and $R^8$ are, when present, all hydrogen.

In a still further aspect $R^9$ is mono- or di-substituted phenyl, unsubstituted heterocyclyl or mono- or di-substituted heterocyclyl, the substituents being chosen from those described above.

In another aspect $R^9$ is optionally substituted heterocyclyl wherein the heterocyclyl group is: thienyl, pyrrolyl, thiazolyl, pyrazolyl, oxazolyl, isoxazolyl, imidazolyl, 1,2,5-oxadiazolyl, pyridinyl, 1,6-dihydropyridinyl (for example in a 6-oxo-1,6-dihydropyridinyl or a 2-oxo-1,2-dihydropyridinyl moiety), pyrimidinyl, indolyl, indazolyl, 2,3-dihydro-1H-indazolyl (for example in a 3-oxo-2,3-dihydro-1H-indazloyl moiety), an imidazopyridinyl (such as imidazo[1,2-a]pyridinyl), 2,1,3-benzothiadiazolyl, quinoxalinyl, quinolinyl, 1,2-dihydroquinolinyl (for example in a 2-oxo-1,2-dihydroquinolinyl moiety), 1,4-dihydroquinoline (for example in a 4-oxo-1,4-dihydroquinoline moiety), isoquinolinyl, 1,2-dihydroisoquinolinyl (for example in a 2H-isoquinolin-1-one-yl (alternatively called 1-oxo-1,2-dihydroisoquinolinyl or 1,2-dihydroisoquinolinyl-1-one) moiety), cinnolinyl 3,4-dihydrophthalazinyl (for example in a 4-oxo-3,4-dihydrophthalazinyl moiety), 2,3-dihydro-4H-1,4-benzoxazinyl (for example in a 3-oxo-2,3-dihydro-4H-1,4-benzoxazinyl moiety), 3,4-dihydro-2H-1,4-benzoxazinyl (for example in a 3-oxo-3,4-dihydro-2H-1,4-benzoxazinyl moiety), 1,3-dihydro-2H-isoindolyl (for example in a 1,3-dioxo-1,3-dihydro-2H-isoindolyl moiety), pyrazolotriazinyl (for example pyrazolo[5,1-c][1,2,4]triazinyl), pyrazolopyrimidinyl (for example pyrazolo[1,5-a]pyrimidinyl), imidazobenzothiazolyl (for example imidazo[2,1-b][1,3]benzothiazolyl), imidazopyrimidinyl (for example imidazo[1,2-a]pyrimidinyl), or 2,1,3-benzoxadiazolyl (for example as a 1-oxide), 1,3-benzothiazole, 2,3-dihydro-1,3-benzothiazole (for example in a 2-oxo-2,3-dihydro-1,3-benzothiazole moiety), 4,5,6,7-tetrahydroindazole or 2,3-dihydro-1H-benzimidazole (for example in a 2-oxo-2,3-dihydro-1H-benzimidazole moiety).

In yet another aspect the aryl (such as phenyl) or heterocyclyl group $R^9$ is unsubstituted or substituted by one or more of: oxo (where possible), halogen, $C_{1-4}$ alkyl, $CF_3$, $C_{1-4}$ alkoxy, $S(O)_2(C_{1-4}$ alkyl), $S(O)_2NH_2$, $S(O)_2NH(C_{1-4}$ alkyl), $S(O)_2N(C_{1-4}$ alkyl)$_2$ or $OCF_3$.

In a further aspect when $R^9$ is heterocyclyl it is an optionally substituted thienyl, quinolinyl, 1,2-dihydroquinolinyl, 1,3-benzthiazolyl, 2,3-dihydro-1,3-benzothiazolyl imidazo[1,2-a]pyridinyl, isoquinolinyl or 1,2-dihydroisoquinolinyl; or a 1,2-dihydropyridone, a 1,6-dihydropyridone, a pyrazolyl, a pyrrolyl or an indolyl.

In yet another aspect $R^9$ is phenyl or heterocyclyl (as defined anywhere above), either of which is optionally substituted by: halo, hydroxy, nitro, cyano, oxo, amino, $C_{1-4}$ alkyl (itself optionally substituted by $S(O)_2(C_{1-4}$ alkyl), or $S(O)_2$-phenyl), $C_{1-4}$ alkoxy, $S(O)R^{12}$ {wherein k is 0, 1 or 2 (preferably 2); and $R^{12}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl}, $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$ (and these alkyl groups may join to form a ring as described for $R^{13}$ and $R^{14}$ above).

In another aspect $R^{32}$ is hydrogen.

In a further aspect $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{29}$, $R^{30}$, and $R^{31}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen or $C_{1-4}$ alkyl) or heterocyclyl (itself optionally substituted by halogen or $C_{1-4}$ alkyl); and $R^{12}$, $R^{25}$ and $R^{28}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen or $C_{1-4}$ alkyl) or heterocyclyl (itself optionally substituted by halogen or $C_{1-4}$ alkyl).

In a still further aspect $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{29}$ and $R^{30}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen or $C_{1-4}$ alkyl) or heterocyclyl (itself optionally substituted by halogen or $C_{1-4}$ alkyl); and $R^{12}$, $R^{25}$, $R^{28}$ and $R^{31}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen or $C_{1-4}$ alkyl) or heterocyclyl (itself optionally substituted by halogen or $C_{1-4}$ alkyl).

In yet another aspect $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{29}$ and $R^{30}$ are, independently, hydrogen or $C_{1-6}$ alkyl; and $R^{12}$, $R^{25}$, $R^{28}$ and $R^{31}$ are, independently, $C_{1-6}$ alkyl (optionally substituted by hydroxy) or phenyl.

In a further aspect $R^{10}$ is hydrogen.

In another aspect $R^{35}$ is hydrogen or $C_{1-6}$ alkyl (such as methyl); (for example $R^{35}$ is hydrogen).

In yet another aspect $R^{33}$ is $C_{1-6}$ alkyl (such as methyl).

In a further aspect $R^{34}$ is $C_{1-6}$ alkyl (such as methyl).

In a still further aspect the present invention provides a compound of formula (I) or (Ia) wherein: $R^1$ is phenyl optionally substituted by 2 halogens (such as chlorine); X is O; m is 0; n is 0 or 1; $R^2$, $R^3$, $R^4$, $R^5$, $R^6$, $R^7$ and $R^8$ are all hydrogen; and $R^9$ is phenyl, thienyl, quinolinyl, 1,3-benzthiazolyl, 2,3-dihydro-1,3-benzothiazolyl, imidazo[1,2-a]pyridinyl or 1,2-dihydroisoquinolinyl optionally substituted by $S(O)_2(C_{1-4}$ alkyl) (for example $S(O)_2CH_3$), halogen (for example chlorine or fluorine), $NH_2$, $C_{1-4}$ alkoxy (such as $OCH_3$), cyano or, where possible, oxo.

In another aspect the present invention provides a compound of formula (I) or (Ia) wherein: $R^1$ is phenyl optionally substituted by 1 or 2 halogens (such as chlorine), or by 1 or 2 halogens (such as chlorine) and a $C_{1-4}$ alkyl (such as methyl); X is O; m is 0; n is 0 or 1; $R^2$, $R^3$, $R^4$, $R^5$ and $R^6$ and, when present, $R^7$ and $R^8$ are all hydrogen; and $R^9$ is phenyl, thienyl, quinolinyl, 1,3-benzthiazolyl, 2,3-dihydro-1,3-benzothiazolyl, imidazo[1,2-a]pyridinyl, 1,2-dihydroisoquinolinyl, 1,2-dihydropyridinyl, 1,6-dihydropyridinyl or pyrazolyl, all optionally substituted by $S(O)_2(C_{1-4}$ alkyl) (for example $S(O)_2CH_3$), $S(O)_2NH_2$, $S(O)_2NH(C_{1-4}$ alkyl), $S(O)_2N(C_{1-4}$ alkyl)$_2$ (and the two alkyl groups may join together to form an azetidine ring), halogen (for example chlorine or fluorine), $NH_2$, $C_{1-4}$ alkyl (such as $CH_3$), $C_{1-4}$ alkoxy (such as $OCH_3$), $CF_3$, cyano or, where possible, oxo.

In a further aspect the present invention provides a compound of formula (I) or (Ia) wherein: $R^1$ is phenyl optionally substituted by 1 or 2 halogens (such as chlorine), and optionally substituted by 0 or 1 $C_{1-6}$ alkyl (such as methyl); X is O; m is 0; n is 0 or 1; $R^2$, $R^3$, $R^4$, $R^5$ and $R^6$, and, when present, $R^7$ and $R^8$ are all hydrogen; and $R^9$ is phenyl, thienyl, quinolinyl, 1,3-benzthiazolyl, 2,3-dihydro-1,3-benzothiazolyl, imidazo[1,2-a]pyridinyl, 1,2-dihydroisoquinolinyl, 1,2-dihydropyridinyl, 1,6-dihydropyridinyl, pyrazolyl, pyrrolyl or indolyl, all of which are optionally substituted by $S(O)_2(C_{1-4}$ alkyl) (for example $S(O)_2CH_3$), $S(O)_2NH_2$, $S(O)_2NH(C_{1-4}$ alkyl), $S(O)_2N(C_{1-4}$ alkyl)$_2$, halogen (for example chlorine or fluorine), $NH_2$, $C_{1-4}$ alkoxy (such as $OCH_3$), $C_{1-4}$ alkyl (such as methyl), $CF_3$, $OCF_3$, cyano or, where possible, oxo.

In a still further aspect the present invention provides a compound of formula (I) or (Ia) wherein: $R^1$ is phenyl optionally substituted by 1 or 2 halogens (such as chlorine), and optionally substituted by 0 or 1 $C_{1-6}$ alkyl (such as methyl); X is O; m is 0; n is 0 or 1; $R^2$, $R^3$, $R^4$, $R^5$, $R^6$, $R^7$ and $R^8$ are all hydrogen; and $R^9$ is phenyl, thienyl, quinolinyl, 1,3-benzthiazolyl, 2,3-dihydro-1,3-benzothiazolyl, imidazo[1,2-a]pyridinyl or 1,2-dihydroisoquinolinyl, all of which are optionally substituted by $S(O)_2(C_{1-4}$ alkyl) (for example $S(O)_2CH_3$), halogen (for example chlorine or fluorine), $NH_2$, $C_{1-4}$ alkoxy (such as $OCH_3$), $C_{1-4}$ alkyl (such as methyl), $CF_3$, $OCF_3$, cyano or, where possible, oxo.

In another aspect the present invention provides a compound of formula (I) or (Ia) wherein $R^9$ is isoquinolinyl, 1-oxo-1,2-dihydroisoquinolinyl, quinolinyl, 2-oxo-1,2-dihydroquinolinyl, 2-oxo-1,2-dihydropyridinyl, 6-oxo-1,6-dihydropyridinyl or pyrazolyl; each optionally substituted by halogen (such as fluorine), $C_{1-4}$ alkyl (such as methyl or ethyl), $CF_3$, $C_{1-4}$ alkoxy (such as methoxy), $S(O)_2(C_{1-4}$ alkyl) (for example $S(O)_2CH_3$), $S(O)NH_2$, $S(O)_2NH(C_{1-4}$ allyl), $S(O)_2N(C_{1-4}$ alkyl)$_2$ or $OCF_3$.

In a further aspect the present invention provides a compound of formula (I) or (Ia) wherein $R^9$ is isoquinolinyl, 1-oxo-1,2-dihydroisoquinolinyl, quinolinyl or 2-oxo-1,2-dihydroquinolinyl; each optionally substituted by halogen (such as fluorine), $C_{1-4}$ alkyl (such as methyl or ethyl), $CF_3$, $C_{1-4}$ alkoxy (such as methoxy), $S(O)_2(C_{1-4}$ alkyl) (for example $S(O)_2CH_3$) or $OCF_3$.

In a still further aspect $R^9$ is 1-oxo-1,2-dihydroisoquinolinyl optionally substituted by halogen (such as fluorine), $C_{1-4}$ alkyl (such as methyl or ethyl), $CF_3$, $C_{1-4}$ alkoxy (such as methoxy), $S(O)_2(C_{1-4}$ alkyl) (for example $S(O)_2CH_3$) or $OCF_3$. Alternatively, $R^9$ is 2-oxo-1,2-dihydroquinolinyl optionally substituted by halogen (such as fluorine), $C_{1-4}$ allyl (such as methyl or ethyl), $CF_3$, $C_{1-4}$ alkoxy (such as methoxy), $S(O)_2(C_{1-4}$ alkyl) (for example $S(O)_2CH_3$) or $OCF_3$.

In another aspect $R^9$ is an oxo-substituted dihydropyridinyl (such as 6-oxo-1,6-dihydropyridin-3-yl, 2-oxo-1,2-dihydropyridin-5-yl or 2-oxo-1,2-dihydropyridin-4-yl), an oxo-substituted dihydroisoquinolinyl (such as 1-oxo-1,2-dihydroisoquinolinyl), an oxo-substituted dihydrophthalazinyl (such as 4-oxo-3,4-dihydrophthalazin-1-yl), pyrazinyl (such as pyrazinyl), pyrrolyl (such as pyrrol-3-yl) or indolyl (such as indol-3-yl), each of which is not further substituted or substituted by halogen (such as chloro or fluoro), $C_{1-4}$ alkyl (such as methyl), $CF_3$ or $C_{3-5}$ cycloalkyl (such as cyclopropyl).

In a further aspect $R^9$ is an oxo-substituted dihydropyridinyl (such as 6-oxo-1,6-dihydropyridin-3-yl, 2-oxo-1,2-dihydropyridin-5-yl or 2-oxo-1,2-dihydropyridin-4-yl), an oxo-substituted dihydroisoquinolinyl (such as 1-oxo-1,2-dihydroisoquinolinyl-4-yl) or pyrazinyl (such as pyrazinyl-4-yl), each of which is not further substituted or substituted by: halogen (such as chloro or fluoro), $C_{1-4}$ alkyl (such as methyl) or $CF_3$.

An example of a compound of formula (I) or (Ia) is:

N-{(2R)-3-[4(3,4-dichlorophenoxy)piperidin-1-yl]-2-hydroxypropyl}-2-(methylsulfonyl)benzamide;

N-{(2R)-3-[4(3,4-dichlorophenoxy)piperidin-1-yl]-2-hydroxypropyl}-4-(methylsulfonyl)benzamide;

2-chloro-N-{(2R)-3-[4-(3,4-dichlorophenoxy)piperidin-1-yl]-2-hydroxypropyl}-4-(methylsulfonyl)benzamide;

4-amino-N-{(2R)-3-[4-(3,4-dichlorophenoxy)piperidin-1-yl]-2-hydroxypropyl}-3-methoxybenzamide;

N-{(2R)-3-[4-(3,4-dichlorophenoxy)piperidin-1-yl]-2-hydroxypropyl}-3-(methylsulfonyl)benzamide;

N-{(2R)-3-[4-(3,4-dichlorophenoxy)piperidin-1-yl]-2-hydroxypropyl}-5-(methylsulfonyl)thiophene-2-carboxamide;

N-{(2R)-3-[4-(3,4-dichlorophenoxy)piperidin-1-yl]-2-hydroxypropyl}quinoline-carboxamide;

N-{(2R)-3-[4-(3,4-dichlorophenoxy)piperidin-1-yl]-2-hydroxypropyl}-2-oxo-2,3-dihydro-1,3-benzothiazole-6-carboxamide acetate salt N-{(2R)-3-[4-(3,4-dichlorophenoxy)piperidin-1-yl]-2-hydroxypropyl}-6-fluoroimidazo[1,2-a]pyridine-2-carboxamide;

N-{(2R)-3-[4-(3,4-dichlorophenoxy)piperidin-1-yl]-2-hydroxypropyl}-1-oxo-1,2-dihydroisoquinoline-4-carboxamide;

N-{(2R)-3-[4-(3,4-dichlorophenoxy)piperidin-1-yl]-2-hydroxypropyl}-1,3-benzothiazole-6-carboxamide;

3-cyano-N-{(2R)-3-[4-(3,4-dichlorophenoxy)piperidin-1-yl]-2-hydroxypropyl}benzamide;

N-{4-[4-(3,4-dichlorophenoxy)piperidin-1-yl]-3-hydroxybutyl}-2-(methylsulfonyl)benzamide;

N-{4-[4-(3,4-dichlorophenoxy)piperidin-1-yl]-3-hydroxybutyl}-2-oxo-2,3-dihydro-1,3-benzothiazole-6-carboxamide;

4-amino-N-{4-[4-(3,4-dichlorophenoxy)piperidin-1-yl]-3-hydroxybutyl}-3-methoxybenzamide;

N-{4-[4-(3,4-dichlorophenoxy)piperidin-1-yl]-2-hydroxybutyl}-2-(methylsulfonyl)benzamide;

N-{(2R)-3-[4-(2,4-dichloro-3-methylphenoxy)piperidin-1-yl]-2-hydroxypropyl}-2-(methylsulfonyl)benzamide;

N-{(2R)-3-[4-(2,4-dichloro-3-methylphenoxy)piperidin-1-yl]-2-hydroxypropyl}-1-oxo-1,2-dihydroisoquinoline-4-carboxamide;

N-{(2-S)-3-[4-(3,4-dichlorophenoxy)piperidin-1-yl]-2-hydroxypropyl}-2-(methylsulfonyl)benzamide;

N-{(2R)-3-[4-(3,4-dichlorophenoxy)piperidin-1-yl]-2-hydroxypropyl}-3-[(methylamino)sulfonyl]benzamide;

3,5-bis(acetylamino)-N-{(2R)-3-[4-(3,4-dichlorophenoxy)piperidin-1-yl]-2-hydroxypropyl}benzamide;

3-(Acetylamino)-N-{(2R)-3-[4-(3,4-dichlorophenoxy)piperidin-1-yl]-2-hydroxypropyl}benzamide;

N-{(2R)-3-[4-(3,4-dichlorophenoxy)piperidin-1-yl]-2-hydroxypropyl}-1H-pyrazole-4-carboxamide;

2-(Acetylamino)-5-bromo-N-{(2R)-3-[4-(3,4-dichlorophenoxy)piperidin-1-yl]-2-hydroxypropyl}benzamide;

N-{(2R)-3-[4-(3,4-dichlorophenoxy)piperidin-1-yl]-2-hydroxypropyl}-2-oxo-1,2-dihydropyridine-3-carboxamide;

N-{(2R)-3-[4-(3,4-Dichlorophenoxy)piperidin-1-yl]-2-hydroxypropyl}-1-oxo-1,2-dihydroisoquinoline-5-carboxamide;

N-{(2R)-3-[4(3,4-dichlorophenoxy)piperidin-1-yl]-2-hydroxypropyl}quinoline-4-carboxamide;

N-{(2R)-3-[4-(3,4-dichlorophenoxy)piperidin-1-yl]-2-hydroxypropyl}-1H-indole-4-carboxamide;

2-(Acetylamino)-N-{(2R)-3-[4-(3,4-dichlorophenoxy)piperidin-1-yl]-2-hydroxypropyl}benzamide;

2-Acetylamino-5-chloro-N-{(2R)-3-[4-(3,4-dichlorophenoxy)piperidin-1-yl]-2-hydroxypropyl}benzamide;

2-(Acetylamino)-4-chloro-N-{(2R)-3-[4(3,4-dichlorophenoxy)piperidin-1-yl]-2-hydroxypropyl}benzamide;

5-Chloro-N-{(2R)-3-[4-(3,4-dichlorophenoxy)piperidin-1-yl]-2-hydroxypropyl}-2-[(methylsulphonyl)amino]benzamide;

4-Chloro-N-{(2R)-3-[4-(3,4-dichlorophenoxy)piperidin-1-yl]-2-hydroxypropyl}-2-[(methylsulphonyl)amino]benzamide;

2-Amino-4-chloro-N-{(2R)-3-[4-(3,4-dichlorophenoxy)piperidin-1-yl]-2-hydroxypropyl}benzamide;

5-Chloro-N-{(2R)-3-[4-(3,4-dichlorophenoxy)piperidin-1-yl]-oxo-1,6-dihydropyridine-3-carboxamide;

2-(Aminosulphonyl)-4-chloro-N-{(2R)-3-[4-(3,4-dichlorophenoxy)piperidin-1-yl]-2-hydroxypropyl}benzamide;

N-{(2R)-3-[4-(3,4-dichlorophenoxy)piperidin-1-yl]-2-hydroxypropyl}-1H-indazole-3-carboxamide;

1-tert-Butyl-N-{(2R)-3-[4(3,4-dichlorophenoxy)piperidin-1-yl]-2-hydroxypropyl}-3-methyl-1H-pyrazole-5-carboxamide;

N-{(2R)-3-[4-(3,4-Dichlorophenoxy)piperidin-1-yl]-2-hydroxypropyl}4,5,6,7-tetrahydro-2H-indazole-3-carboxamide;

N-{(2R)-3-[4-(3,4-Dichlorophenoxy)piperidin-1-yl]-2-hydroxypropyl}-3-(tifuoromethyl)-1H-pyrazole-4-carboxamide;

N-{(2R)-3-[4-(3,4-Dichlorophenoxy)piperidin-1-yl]-2-hydroxypropyl}-2-methylimidazo[1,2-a]pyridine-3-carboxamide;

N-{(2R)-3-[4-(3,4-Dichlorophenoxy)piperidin-1-yl]-2-hydroxypropyl}-4(1H-pyrazol-3-yl)benzamide;

N-{(2R)-3-[4-(3,4-Dichlorophenoxy)piperidin-1-yl]-2-hydroxypropyl}cinnoline-4-carboxamide;

N-{(2R)-3-[4-(3,4-Dichlorophenoxy)piperidin-1-yl]-2-hydroxypropyl}-2-hydroxyquinoline-4-carboxamide;

N-{3-[4-(3,4-dichlorophenoxy)piperidin-1-yl]-2-hydroxypropyl}-2-oxo-2,3-dihydro-1H-benzimidazole-1-carboxamide;

N-{(2R)-3-[4-(3,4-Dichlorophenoxy)piperidin-1-yl]-2-hydroxypropyl}-4-oxo-3,4-dihydrophthalazine-1-carboxamide;
N-{(2R)-3-[4-(3,4-Dichlorophenoxy)piperidin-1-yl]-2-hydroxypropyl}-1H-indole-3-carboxamide;
N-{(2R)-3-[4-(4-Chlorophenoxy)piperidin-1-yl]-2-hydroxypropyl}-2-(methylsulfonyl)benzamide;
N-{(2R)-3-[(4-Chlorophenoxy)piperidin-1-yl]-2-hydroxypropyl}-1-oxo-1,2-dihydroisoquinoline-4-carboxamide;
N-{(2R)-3-[4 Chloro-3-fluorophenoxy)piperidin-1-yl]-2-hydroxypropyl}-1-oxo-1,2-dihydroisoquinoline-4-carboxamide;
N-{(2R)-3-[4-(3,4-Difluorophenoxy)piperidin-1-yl]-2-hydroxypropyl}-1-oxo-1,2-dihydroisoquinoline-4-carboxamide;
N-{(2S)-3-[4-(3,4-Dichlorophenoxy)piperidin-1-yl]-2-hydroxypropyl}-N-methyl-1-oxo-1,2-dihydroisoquinoline-4-carboxamide;
N-{(2S)-3-[4-(3,4-Dichlorophenoxy)piperidin-1-yl]-2-hydroxypropyl}-N-methyl-1H-indazole-3-carboxamide;
N-{(2S)-3-[4-(3,4-Dichlorophenoxy)piperidin-1-yl]-2-hydroxypropyl}-N-methyl-4-oxo-3,4-dihydrophthalazine-1-carboxamide;
Benzoic acid, 3-[[2-[[(2R)-3-[4-(3,4-dichlorophenoxy)-1-piperidinyl]-2-hydroxypropyl]amino]-2-oxoethyl]amino]-, methyl ester;
Propanamide, N-[2-[[2-[[(2R)-3-[4(3,4-dichlorophenoxy)-1-piperidinyl]-2-hydroxypropyl]amino]-2-oxoethyl]amino]phenyl]-;
Propanamide, N-[2-[[2-[[(2R)-3-[4-(3,4-dichlorophenoxy)-1-piperidinyl]-2-hydroxypropyl]amino]-2-oxoethyl]amino]phenyl]-;
(2-S)-N-{(2R)-3-[4-(3,4-dichlorophenoxy)piperidin-1-yl]-2-hydroxypropyl}-2-hyroxy-2-phenylethanamide;
2-[2-({(2R)-3-[4-(3,4-dichlorophenoxy)piperidin-1-yl]-2-hydroxypropyl}amino)-2-oxoethoxy]benzamide;
N-{(2R)-3-[4-(3,4-dichlorophenoxy)piperidin-1-yl]-2-hydroxypropyl}-2-(3-oxo-2,3-dihydro-4H-1,4-benzoxazin-4-yl)acetamide;
N-{(2R)-3-[4-(3,4-dichlorophenoxy)piperidin-1-yl]-2-hydroxypropyl}-2-methoxybenzamide;
N-{(2R)-3-[4-(3,4-dichlorophenoxy)piperidin-1-yl]-2-hydroxypropyl}-2-(methylamino)benzamide;
N-{(2R)-3-[4-(3,4-dichlorophenoxy)piperidin-1-yl]-2-hydroxypropyl}nicotinamide;
N-{(2R)-3-[4-(3,4-dichlorophenoxy)piperidin-1-yl]-2-hydroxypropyl}isonicotinamide;
N-{(2R)-3-[4-(3,4-dichlorophenoxy)piperidin-1-yl]-2-hydroxypropyl}-3-(dimethylamino)benzamide;
N-{(2R)-3-[4-(3,4-dichlorophenoxy)piperidin-1-yl]-2-hydroxypropyl}-2-(1,3-oxo-1,3-dihydro-2H-isoindol-2-yl)acetamide;
N-{(2R)-3-[4-(3,4-dichlorophenoxy)piperidin-1-yl]-2-hydroxypropyl}-6-hydroxynicotinamide;
N-{(2R)-3-[4-(3,4-dichlorophenoxy)piperidin-1-yl]-2-hydroxypropyl}-2-(1H-indol-3-yl)acetamide;
N-{(2R)-3-[4-(3,4-dichlorophenoxy)piperidin-1-yl]-2-hydroxypropyl}bicyclo[4.2.0]octa-1,3,5-triene-7-carboxamide;
N-{(2R)-3-[4-(3-dichlorophenoxy)piperidin-1-yl]-2-hydroxypropyl}4,7-dimethylpyrazolo[5,1-c][1,2,4]triazine-3-carboxamide;
N-{(2R)-3-[4-3-4-dichlorophenoxy)piperidin-1-yl]-2-hydroxypropyl}pyrazine-2-carboxamide;
N-{(2R)-3-[4-(3,4-dichlorophenoxy)piperidin-1-yl]-2-hydroxypropyl}-9H-purine-6-carboxamide;
N-{(2R)-3-[4-(3,4-dichlorophenoxy)piperidin-1-yl]-2-hydroxypropyl}quinoline-6-carboxamide;
N-{(2R)-3-[4-(3-dichlorophenoxy)piperidin-1-yl]-2-hydroxypropyl}-2,7-dimethylpyrazolo[1,5-a]pyrimidine-6-carboxamide;
N-{(2R)-3-[4-(3,4-dichlorophenoxy)piperidin-1-yl]-2-hydroxypropyl}-2-(pyrimidin-2-ylthio)acetamide;
N-{(2R)-3-[4-(3,4-dichlorophenoxy)piperidin-1-yl]-2-hydroxypropyl}-5-fluoro-1H-indole-2-carboxamide;
N-{(2R)-3-[4-(3,4-dichlorophenoxy)piperidin-1-yl]-2-hydroxypropyl}-1,3-benzothiazole-6-carboxamide;
N-{(2R)-3-[4-(3,4-dichlorophenoxy)piperidin-1-yl]-2-hydroxypropyl}-5-phenyl-1,3-oxazole-4-carboxamide;
N-{(2R)-3-[4-(3,4-dichlorophenoxy)piperidin-1-yl]-2-hydroxypropyl}-6-hydroxypyridine-2-carboxamide;
N-{(2R)-3-[4-(3,4-dichlorophenoxy)piperidin-1-yl]-2-hydroxypropyl}-3-oxo-3,4-dihydro-2H-1,4-benzoxazine-7-carboxamide;
N-{(2R)-3-[4-(3,4-dichlorophenoxy)piperidin-1-yl]-2-hydroxypropyl}-3-hydroxypyridine-2-carboxamide;
N-{(2R)-3-[4-(3,4-dichlorophenoxy)piperidin-1-yl]-2-hydroxypropyl})-1H-benzimidazole-5-carboxamide;
N-{(2R)-3-[4-(3,4-dichlorophenoxy)piperidin-1-yl]-2-hydroxypropyl}-1H-indole-5-carboxamide;
N-{(2R)-3-[4-(3,4-dichlorophenoxy)piperidin-1-yl]-2-hydroxypropyl}-1-methyl-1H-indole-2-carboxamide;
N-{(2R)-3-[4-(3,4-dichlorophenoxy)piperidin-1-yl]-2-hydroxypropyl}-1H-imidazole-4-carboxamide;
N-{(2R)-3-[4-(3,4-dichlorophenoxy)piperidin-1-yl]-2-hydroxypropyl}-1H-indole-6-carboxamide;
N-{(2R)-3-[4-(3,4-dichlorophenoxy)piperidin-1-yl]-2-hydroxypropyl}-1-methyl-1H-indole-3-carboxamide;
N-{(2R)-3-[4-(3,4-dichlorophenoxy)piperidin-1-yl]-2-hydroxypropyl}-1H-indole-7-carboxamide;
N-{(2R)-3-[4-(3,4-dichlorophenoxy)piperidin-1-yl]-2-hydroxypropyl}-3-[(methylamino)sulfonyl]benzamide;
N-{(2R)-3-[4-(3,4-dichlorophenoxy)piperidin-1-yl]-2-hydroxypropyl}-3,4-bis(methylsulfonyl)benzamide;
N-{(2R)-3-[4-(3,4-dichlorophenoxy)piperidin-1-yl]-2-hydroxypropyl}-2-pyridin-3-ylacetamide;
N-{(2R)-3-[4-(3,4-dichlorophenoxy)piperidin-1-yl]-2-hydroxypropyl}-5-hydroxy-1H-indole-2-carboxamide;
N-{(2R)-3-[4-(3,4-dichlorophenoxy)piperidin-1-yl]-2-hydroxypropyl}-1,5-dimethyl-1H-pyrazole-3-carboxamide;
N-{(2R)-3-[4-(3,4-dichlorophenoxy)piperidin-1-yl]-2-hydroxypropyl}-5-methylsulfonyl) 1H-indole-2-carboxamide;
N-{(2R)-3-[4-(3,4-dichlorophenoxy)piperidin-1-yl]-2-hydroxypropyl}quinoxaline-6-carboxamide;
N-{(2R)-3-[4-(3,4-dichlorophenoxy)piperidin-1-yl]-2-hydroxypropyl}-1,8-naphthyridine-2-carboxamide;
N-{(2R)-3-[4-(3,4-dichlorophenoxy)piperidin-1-yl]-2-hydroxypropyl}imidazo[2,1-b][1,3]benzothiazole-2-carboxamide;
N-{(2R)-3-[4-(3,4-dichlorophenoxy)piperidin-1-yl]-2-hydroxypropyl}-2,6-dimethylimidazo[1,2-a]pyridine-3-carboxamide;
N-{(2R-3-[4-(3,4-dichlorophenoxy)piperidin-1-yl]-2-hydroxypropyl}-3-oxo-2,3-dihydro 1H-indazole-4-carboxamide;
N-{(2R)-3-[4-(3,4-dichlorophenoxy)piperidin-1-yl]-2-hydroxypropyl}-3-hydroxy-1H-indazole-6-carboxamide;
N-{(2R)-3-[4-(3,4-dichlorophenoxy)piperidin-1-yl]-2-hydroxypropyl}-3-(trifluoromethyl)-1H-pyrazole-4-carboxamide;

2-(1H-benzimidazol-1-yl)-N-{(2R)-3-[4-(3,4-dichlorophenoxy)piperidin-1-yl]-2-hydroxypropyl}acetamide;

N-{(2R)-3-[4-(3,4-dichlorophenoxy)piperidin-1-yl]-2-hydroxypropyl}-1-ethyl-3-methyl-1H-pyrazole-5 carboxamide;

N-{(2R)-3-[4-(3,4-dichlorophenoxy)piperidin-1-yl]-2-hydroxypropyl}-5-methyl-1H-pyrazole-3-carboxamide;

N-{(2R)-3-[4-(3,4-dichlorophenoxy)piperidin-1-yl]-2-hydroxypropyl}-4-methyl-1,2,5-oxadiazole-3-carboxamide;

6-chloro-N-{(2R)-3-[4-(3,4-dichlorophenoxy)piperidin-1-yl]-2-hydroxypropyl}imidazo[1,2-a]pyridine-2-carboxamide;

N-{(2R)-3-[4-(3,4-dichlorophenoxy)piperidin-1-yl]-2-hydroxypropyl}-2-methylimidazo[1,2-a]pyridine-3-carboxamide;

N-{(2R)-3-[4-(3,4-dichlorophenoxy)piperidin-1-yl]-2-hydroxypropyl}imidazo[1,2-a]pyrimidine-2-carboxamide;

N-{(2R)-3-[4-(3,4-dichlorophenoxy)piperidin-1-yl]-2-hydroxypropyl}-2-[(4-methylpyrimidin-2-yl)thio]acetamide;

N-{(2R)-3-[4-(3,4-dichlorophenoxy)piperidin-1-yl]-2-hydroxypropyl}-4-hydroxyquinoline-2-carboxamide;

N-{(2R)-3-[4-(3,4-dichlorophenoxy)piperidin-1-yl]-2-hydroxypropyl}quinoline-8-carboxamide;

N-{(2R)-3-[4-(3,4-dichlorophenoxy)piperidin-1-yl]-2-hydroxypropyl}-5-methylimidazo[1,2-a]pyridine-2-carboxamide;

N-{(2R)-3-[4-(3,4-dichlorophenoxy)piperidin-1-yl]-2-hydroxypropyl}imidazo[1,2-a]pyridine-2-carboxamide;

N-{(2R)-3-[4-(3,4-dichlorophenoxy)piperidin-1-yl]-2-hydroxypropyl}-1,6-naphthyridine-2-carboxamide;

N-{(2R)-3-[4-(3,4-dichlorophenoxy)piperidin-1-yl]-2-hydroxypropyl}-2,1,3-benzoxadiazole-5-carboxamide 1-oxide;

N-{(2R))-3-[4-(3,4-Dichlorophenoxy)piperidin-1-yl]-2-hydroxypropyl}-6-oxo-1,6-dihydropyridine-3-carboxamide;

4-Chloro-N-{(2R)-3-[4-(3,4-dichlorophenoxy)piperidin-1-yl]-2-hydroxypropyl}-1H-pyrazole-3-carboxamide;

N-{(2R)-3-[4-(3,4-dichlorophenoxy)piperidin-1-yl]-2-hydroxypropyl}-5-phenyl-1,3-oxazole-4-carboxamide;

N-{(2R)-3-[4-(3,4-dichlorophenoxy)piperidin-1-yl]-2-hydroxypropyl}-3,5-dimethyl-1H-pyrazole-4-carboxamide;

(2-R)-2-Acetylamino)-N-{(2R)-3-[4-(3,4-dichlorophenoxy)piperidin-1-yl]-2-hydroxypropyl}-2-phenylethanamide;

N-{(2R)-3-[4-(3,4-Dichlorophenoxy)piperidin-1-yl]-2-hydroxypropyl}-2-(2-hydroxyphenyl)acetamide;

(2R)-N-{(2R)-3-[4-(3,4-Dichlorophenoxy)piperidin-1-yl]-2-hydroxypropyl}-2-[(methylsulfonyl)amino]-2-phenylethanamide;

(2S)-2-(Acetylamino)-N-{(2R)-3-[4-(3,4-dichlorophenoxy)piperidin-1-yl]-2-hydroxypropyl}-2-phenylethanamide;

(2S)-N-{(2R)-3-[4-(3,4-Dichlorophenoxy)piperidin-1-yl]-2-hydroxypropyl}-2-[(methylsulfonyl)amino]-2-phenylethanamide;

1-{(R)-3-[4-(3,4-Dichlorophenoxy)piperidin-1-yl]-2-hydroxypropyl}-3-o-tolyl-urea;

1-{(R)-3-[4-(3,4-Dichlorophenoxy)piperidin-1-yl]-2-hydroxypropyl}-3-p-tolyl-urea;

N-{(2S)-3-[4-(3,4-Dichlorophenoxy)piperidin-1-yl]-2-hydroxy-2-methylpropyl}-1-oxo-1,2-dihydroisoquinoline-4-carboxamide;

N-{(2S)-3-[4-(3,4-Dichlorophenoxy)piperidin-1-yl]-2-hydroxy-2-methylpropyl}-2-oxo-1,2-dihydroquinoline-4-carboxamide;

N-{(2S)-3-[4-(3,4-Dichlorophenoxy)piperidin-1-yl]-2-hydroxy-2-methylpropyl}oxo-3,4-dihydrophthalazine-1-carboxamide;

(2S)N-{(2S)-3-[4-(3,4-Dichlorophenoxy)piperidin-1-yl]-2-hydroxy-2-methylpropyl}-2-hydroxy-2-phenethanamide;

N-{(2R)-3-[4-(4-Chloro-2-methylphenoxy)piperidin-1-yl)-2-hydroxypropyl}-1-oxo-1,2-dihydroisoquinoline-4-carboxamide;

N-((2R)-3-{4-[2-Aminocarbonyl)-(3,4-dichlorophenoxy]piperidin-1-yl-2-hydroxypropyl}1-oxo-1,2-dihydroisoquinoline-4-carboxamide;

3-Cyano-N-{(2S)-3-[4-(3,4-dichlorophenoxy)piperidin-1-yl]-2-hydroxypropyl}benzenesulfonamide;

5-[({(2S)-3-[4-(3,4-Dichlorophenoxy)piperidin-1-yl]-2-hydroxypropyl}amino)-sulfonyl]-2-methoxybenzamide;

N-{(2S)-3-[4-(3,4-dichlorophenoxy)piperidin-1-yl]-2-hydroxypropyl}-1-oxo-1,2-dihydroisoquinoline-4-sulfonamide acetate salt;

N-{(2S)-3-[4-(3,4-Dichlorophenoxy)piperidin-1-yl]-2-hydroxypropyl}-(2,4-difluorobenzenesulfonamide;

N-{(2S)-3-[(4,3-dichlorophenoxy)piperidin-1-yl]-2-hydroxypropyl}methanesulfonamide;

N-{(2S)-3-[4-(3,4-dichlorophenoxy)piperidin-1-yl]-2-hydroxypropyl}benzenesulfonamide;

N-{(2S)-3-[4-(3,4-dichlorophenoxy)piperidin-1-yl]-2-hydroxypropyl}-1-phenylmethanesulfonamide;

N-{(2S)-3-[4-(3,4-dichlorophenoxy)piperidin-1-yl]-2-hydroxypropyl}-4-methoxybenzenesulfonamide;

N-({5-[({(2S)-3-[4-(3,4-dichlorophenoxy)piperidin-1-yl]-2-hydroxypropyl}amino)sulfonyl]-2-thienyl}methyl)benzamide;

4-cyano-N-{(2S)-3-[4-(3,4-dichlorophenoxy)piperidin-1-yl]-2-hydroxypropyl}benzenesulfonamide;

N-{5-[({(2S)-3-[4-(3,4-dichlorophenoxy)piperidin-1-yl]-2-hydroxypropyl}amino)sulfonyl]-4-methyl-1,3-thiazol-2-yl}acetamide;

N-{(2S)-3-[4-(3,4-dichlorophenoxy)piperidin-1-yl]-2-hydroxypropyl}thiophene-2-sulfonamide;

4-[({(2S)-3-[4-(3,4-dichlorophenoxy)piperidin-1-yl]-2-hydroxypropyl}amino)sulfonyl]benzoic acid;

N-{(2S)-3-[4-(3,4-dichlorophenoxy)piperidin-1-yl]-2-hydroxypropyl}-2,5-dimethoxybenzenesulfonamide;

N-{(2S)-3-[4-(3,4-dichlorophenoxy)piperidin-1-yl]-2-hydroxypropyl}4 (phenylsulfonyl)thiophene-2-sulfonamide;

N-{(2S)-3-[4-(3,4-dichlorophenoxy)piperidin-1-yl]-2-hydroxypropyl}-5-(1,3-oxazol-5-yl)thiophene-2-sulfonamide;

N-{(2S)-3-[4-(3,4-dichlorophenoxy)piperidin-1-yl]-2-hydroxypropyl}-5-(1-methyl-5-(trifluoromethyl)-1H-pyrazol-3-ylthiophene-2-sulfonamide;

N-{(2S)-3-[4-(3,4-dichlorophenoxy)piperidin-1-yl]-2-hydroxypropyl}-5-pyridin-2-ylthiophene-2-sulfonamide;

5-chloro-N-{(2S)-3-[4-(3,4-dichlorophenoxy)piperidin-1-yl]-2-hydroxypropyl}-1,3-dimethyl-1H-pyrazole-4-sulfonamide;

N-{(2S)-3-[4-(3,4-dichlorophenoxy)piperidin-1-yl]-2-hydroxypropyl}-3,5-dimethylisoxazole-4-sulfonamide;

N-{(2S)-3-[4-(3,4-dichlorophenoxy)piperidin-1-yl]-2-hydroxypropyl}-2,1,3-benzothiadiazole-4-sulfonamide;

N-{(2S)-3-[4-(3,4-dichlorophenoxy)piperidin-1-yl]-2-hydroxypropyl}-1-methyl-1H-imidazole-sulfonamide;

N-{(2S)-3-[4-(3,4-dichlorophenoxy)piperidin-1-yl]-2-hydroxypropyl}-2,1,3-benzoxadiazole-4-sulfonamide;

N-{(2S)-3-[4-(3,4-dichlorophenoxy)piperidin-1-yl]-2-hydroxypropyl}-5-isoxazol-3-ylthiophene-2-sulfonamide;

methyl 3-[({(2S)-3-[4-(3,4-dichlorophenoxy)piperidin-1-yl]-2-hydroxypropyl}amino)sulfonyl]thiophene-2-carboxylate;

2,6-dichloro-N-{(2S)-3-[4-(3,4-dichlorophenoxy)piperidin-1-yl]-2-hydroxypropyl}benzenesulfonamide;

N-{(2S)-3-[4-(3,4-dichlorophenoxy)piperidin-1-yl]-2-hydroxypropyl}-3-methylbenzenesulfonamide;

3-chloro-N-{(2S)-3-[4-(3,4-dichlorophenoxy)piperidin-1-yl]-2-hydroxypropyl}benzenesulfonamide;

N-{(2S)-3-[4-(3,4-dichlorophenoxy)piperidin-1-yl]-2-hydroxypropyl}propane-2-sulfonamide;

N-{(2S)-3-[4-(3,4-dichlorophenoxy)piperidin-1-yl]-2-hydroxypropyl}propane-1-sulfonamide;

N-{(2S)-3-[4-(3,4-dichlorophenoxy)piperidin-1-yl]-2-hydroxypropyl}-5-methyl-1-phenyl-1H-pyrazole-4-sulfonamide;

3-chloro-N-{(2S)-3-[4-(3,4-dichlorophenoxy)piperidin-1-yl]-2-hydroxypropyl}-2-methylbenzenesulfonamide;

methyl 5-[({(2S)-3-[4-(3,4-dichlorophenoxy)piperidin-1-yl]-2-hydroxypropyl}amino)sulfonyl]-2-methyl-3-furoate;

methyl 5-[({(2S)-3-[4-(3,4-dichlorophenoxy)piperidin-1-yl]-2-hydroxypropyl}amino)sulfonyl]-1-methyl-1H-pyrrole-2-carboxylate;

N-{(2S)-3-[4-(3,4-dichlorophenoxy)piperidin-1-yl]-2-hydroxypropyl}-3,4-dimethoxybenzenesulfonamide;

5-chloro-N-{(2S)-3-[4-(3,4-dichlorophenoxy)piperidin-1-yl]-2-hydroxypropyl}thiophene-2-sulfonamide;

N-{(2S)-3-[4-(3,4-dichlorophenoxy)piperidin-1-yl]-2-hydroxypropyl}-6-morpholin-4-ylpyridine-3-sulfonamide;

N-2-chloro-4-[({(2S)-3-[4-(3,4-dichlorophenoxy)piperidin-1-yl]-2-hydroxypropyl}amino)sulfonyl]phenyl}acetamide;

N-{(2S)-3-[4-(3,4-dichlorophenoxy)piperidin-1-yl]-2-hydroxypropyl}-2,3-dihydroxyquinoxaline-6-sulfonamide;

N-{(2S)-3-[4-(3,4-dichlorophenoxy)piperidin-1-yl]-2-hydroxypropyl}-2,4-dimethoxybenzenesulfonamide;

5-[({(2S)-3-[4-(3,4-dichlorophenoxy)piperidin-1-yl]-2-hydroxypropyl}amino)sulfonyl]-2-methoxybenzamide;

N-{(2S)-3-[4-(3,4-dichlorophenoxy)piperidin-1-yl]-2-hydroxypropyl}-2-methylbenzenesulfonamide;

N-{(2S)-3-[4-(3,4-dichlorophenoxy)piperidin-1-yl]-2-hydroxypropyl}-2,4-dimethyl-1,3-thiazole-5-sulfonamide;

N-{(2S)-3-[4-(3,4-dichlorophenoxy)piperidin-1-yl]-2-hydroxypropyl}-2-hydroxyquinoxaline-6-sulfonamide;

N-{(2S)-3-[4-(3,4-dichlorophenoxy)piperidin-1-yl]-2-hydroxypropyl}-4-methyl-3,4-dihydro-2H-1,4-benzoxazine-7-sulfonamide;

N-{(2S)-3-[4-(3,4-dichlorophenoxy)piperidin-1-yl]-2-hydroxypropyl}pyridine-3-sulfonamide;

4'-cyano-N-{(2S)-3-[4-(3,4-dichlorophenoxy)piperidin-1-yl]-2-hydroxypropyl}biphenyl-2-sulfonamide;

N-{(2S)-3-[4-(3,4-dichlorophenoxy)piperidin-1-yl]-2-hydroxypropyl}-1,2-dimethyl-1H-imidazole-4-sulfonamide;

4-acetyl-N-{(2S)-3-[4-(3,4-dichlorophenoxy)piperidin-1-yl]-2-hydroxypropyl}benzenesulfonamide;

N-{(2S)-3-[4-(3,4-dichlorophenoxy)piperidin-1-yl]-2-hydroxypropyl}-4-(methylsulfonyl)benzenesulfonamide;

2-chloro-4-cyano-N-{(2S)-3-[(3,4-dichlorophenoxy)-piperidin-1-yl]-2-hydroxypropyl}benzenesulfonamide;

N-{(2S)-3-[4-(3,4-dichlorophenoxy)piperidin-1-yl]-2-hydroxypropyl}-1,3,5-trimethyl-1H-pyrazole-4-sulfonamide;

N-[(2R)-3-[4-(3,4-Dichlorophenoxy)-1-piperidinyl]-2-hydroxypropyl]-1,4-dihydro-4-oxo-3-quinolinecarboxamide;

N-{(2S)-3-[4-(4-Chloro-2-methylphenoxy)piperidin-1-yl]-2-hydroxypropyl}-1-oxo-1,2-dihydroisoquinoline-4-carboxamide acetate;

N-{(2S)-3-{4-(3,4-Dichlorophenoxy)piperidin-1-yl]-2-hydroxypropyl}-1-oxo-1,2-dihydroisoquinoline-4-carboxamide;

N-{(2S)-3-{4-(3,4-dichlorophenoxy)piperidin-1-yl]-2-hydroxypropyl}-1-oxo-1,2-dihydroisoquinoline-4-carboxamide;

N-{(2R)-3-[4-(3,4-Dichlorophenoxy)piperidin-1-yl]-2-hydroxypropyl}-7-[(methylamino)sulfonyl]-1-oxo-1,2-dihydroisoquinoline-4-carboxamide;

N-{(2R)-3-[4-(3,4-dichlorophenoxy)piperidin-1-yl]-2-hydroxypropyl}-7-{[(2-hydroxyethyl)amino]sulfonyl}-1-oxo-1,2-dihydroisoquinoline-4-carboxamide acetate salt;

7-[(Cyclopropylamino)sulfonyl]-N-{(2R)-3-[4-(3,4-dichlorophenoxy)piperidin-1-yl]-2-hydroxypropyl}-1-oxo-1,2-dihydroisoquinoline-4-carboxamide;

7-(Azetidin-1-ylsulfonyl)-N-{(2R)-3-[4-(3,4-dichlorophenoxy)piperidin-1-yl]-2-hydroxypropyl}-1-oxo-1,2-dihydroisoquinoline-4-carboxamide acetate salt;

7-(Aminosulfonyl)-N-{(2R)-3-[4-(3,4-dichlorophenoxy)piperidin-1-yl]-2-hydroxypropyl}-1-oxo-1,2-dihydroisoquinoline-4-carboxamide;

N-{(2R)-3-[4-(3,4-Dichlorophenoxy)piperidin-1-yl]-2-hydroxypropyl}-7-[(dimethylamino)sulfonyl]-1-oxo-1,2-dihydroisoquinoline-4-carboxamide;

N-{(2R)-3-[4-(3,4-Dichlorophenoxy)piperidin-1-yl]-2-hydroxypropyl}-7-[(3-hydroxy-3-methylazetidin-1-yl)sulfonyl]-1-oxo-1,2-dihydroisoquinoline-4-carboxamide acetate;

N-[(2R)-3-(4-{3,4-Dichloro-2-[(cyclopropylamino)carbonyl]phenoxy}piperidin-1-yl)-2-hydroxypropyl]-1-oxo-1,2-dihydroisoquinoline-4-carboxamide acetate salt;

N-{(2R)-3-[4-(3-Chlorocyanophenoxy)piperidin-1-yl]-2-hydroxypropyl}-1-oxo-1,2-dihydroisoquinoline-4-carboxamide;

N-((2R)-2-Hydroxy-3-{4-[4-(methylsulfonyl)phenoxy]piperidin-1-yl}propyl)-1-oxo-1,2-dihydroisoquinoline-4-carboxamide;

N-((2R)-3-[4-(4-Cyanophenoxy)piperidin-1-yl]-2-hydroxypropyl}-1-oxo-1,2-dihydroisoquinoline-4-carboxamide;

N-((2R)-3-{4-[2-(Aminocarbonyl)-4-chlorophenoxy]piperidin-1-yl}-2-hydroxypropyl)-1-oxo-1,2-dihydroisoquinoline-4-carboxamide;

N-[(2R)-3-(4-{4-Chloro-2-[(methylamino)carbonyl]phenoxy}piperidin-1-yl)-2-hydroxypropyl]-1-oxo-1,2-dihydroisoquinoline-4-carboxamide;

Methyl 5-chloro-2-{[1-((2R)-2-hydroxy-3-{[(1-oxo-1,2-dihydroisoquinolin-4-yl)carbonyl]amino}propyl)piperidin-4-yl]oxy}benzoate acetate salt;

N-((2R)-3-{4-[2-(Aminosulfonyl)-3,4-dichlorophenoxy]piperidin-1-yl}-2-hydroxypropyl)-1-oxo-1,2-dihydroisoquinoline-4-carboxamide trifluoroacetate salt;

N-[(2R)-3-(4-{3,4-Dichloro-2-[(methylamino)sulfonyl]phenoxy}piperidin-1-yl)-2-hydroxypropyl]-1-oxo-1,2-dihydroisoquinoline-4-carboxamide acetate salt;

N-[(2R)-3-(4-{3,4-Dichloro-2-[(cyclopropylamino)sulfonyl]phenoxy}piperidin-1-yl)-2-hydroxypropyl]-1-oxo-1,2-dihydroisoquinoline-4-carboxamide acetate salt N-{(2R)-3-[4-(3-Chloro-4-cyanophenoxy)piperidin-1-yl]-2-hydroxypropyl}-7-(methylsulfonyl)-1-oxo-1,2-dihydroisoquinoline-4-carboxamide;

N-{(2R)-3-{4-(4-Chloro-2-methylphenoxy)piperidin-1-yl]-2-hydroxy-2-methylpropyl}-6-(methylsulphonyl)-1H-indole-3-carboxamide;

N-{(2R)-3-{4-(3,4-Dichlorophenoxy)piperidin-1-yl]-2-hydroxypropyl}-6-(methylsulphonyl)-1H-indole-3-carboxamide;

N-{(2R)-3-[4-(3,4-Dichlorophenoxy)piperidin-1-yl]-2-hydroxypropyl}-7-fluoro-1-oxo-1,2-dihydroisoquinoline-4-carboxamide;

N-{(2R)-3-[4-(4-Chloro-2-methylphenoxy)piperidin-1-yl]-2-hydroxypropyl}-7-fluoro-1-oxo-1,2-dihydroisoquinoline-4-carboxamide;

N-{(2R)-3-[4-(4-Chloro-2-methylphenoxy)piperidin-1-yl]-2-hydroxypropyl}-6-(methylsulfonyl)-1-oxo-1,2-dihydroisoquinoline-4-carboxamide;

N-{(2R)-3-[4-(2,4-Dichloro-3-methylphenoxy)piperidin-1-yl]-2-hydroxypropyl}-6-(methylsulfonyl)-1-oxo-1,2-dihydroisoquinoline-4-carboxamide;

N-{(2R)-3-[4-(3,4-Dichlorophenoxy)piperidin-1-yl]-2-hydroxypropyl}-7-(methylsulfonyl)-1-oxo-1,2-dihydroisoquinoline-4-carboxamide acetate salt;

N-{(2R)-3-[4-(3,4-Dichlorophenoxy)piperidin-1-yl]-2-hydroxypropyl}-7-(methylsulfonyl)-1-oxo-1,2-dihydroisoquinoline-4-carboxamide acetate salt;

N-{(2R)-3-[4-(2,4-Dichloro-3-methylphenoxy)piperidin-1-yl]-2-hydroxypropyl}-7-(methylsulfonyl)-1-oxo-1,2-dihydroisoquinoline-4-carboxamide acetate salt;

N-(2R)-3-[4-(3,4-Dichlorophenoxy)piperidin-1-yl]-2-hydroxypropyl}-6-(methylsulfonyl)-1-oxo-1,2-dihydroisoquinoline-4-carboxamide;

N-{(2R)-3-[4-(3,4-Dichlorophenoxy)piperidin-1-yl]2-hydroxypropyl}-6-fluoro-1-oxo-1,2-dihydroisoquinoline-4-carboxamide;

N-{(2R)-3-[4-(4-Chloro-2-methylphenoxy)piperidin-1-yl]-2-hydroxypropyl}-6-fluoro-1-oxo-1,2-dihydroisoquinoline-4-carboxamide;

N-((2R)-3-{4-[3,4-Dichloro-2-(methylsulfonyl)phenoxy]piperidin-1-yl}-2-hydroxypropyl)-1-oxo-1,2-dihydroisoquinoline-4-carboxamide acetate salt, N-{(2R)-3-[4-(3,4-Dichlorophenoxy)piperidin-1-yl]-2-hydroxypropyl}-6-oxo-4-(trifluoromethyl)-1,6-dihydropyridine-3-carboxamide acetate salt;

N-{(2R)-3-[4-(4-Chloro-2-methylphenoxy)piperidin-1-yl]-2-hydroxypropyl}-6-oxo-4-(trifluoromethyl)-1,6-dihydropyridine-3-carboxamide acetate salt;

N-{(2R)-3-[4-(2,4-Dichloro-3-methylphenoxy)piperidin-1-yl]-2-hydroxypropyl}-6-oxo-4-(trifluoromethyl)-1,6-dihydropyridine-3-carboxamide;

{(2-R)-3-[4-(3,4-dichlorophenoxy)piperidin-1-yl]-2-hydroxypropyl}-2-(2-oxoquinoxalin-1-(2H)-yl)acetamide;

N-{(2R)-3-[4-(3,4-dichlorophenoxy)piperidin-1-yl]-2-hydroxypropyl}-3-oxo-3,4-dihydroquinoxaline-1(2H)-carboxamide;

N-{(2R)-3-[4-(4-Chloro-2-methylphenoxy)piperidin-1-yl]-2-hydroxypropyl}-3-(trifluoromethyl)-1H-pyrazole-4-carboxamide;

N-{(2R)-3-[4-(2,4-dichloro-3-methylphenoxy)piperidin-1-yl]-2-hydroxypropyl}-3-(trifluoromethyl)-1H-pyrazole-4-carboxamide;

N-{(2R)-3-{4-(3,4-dichlorophenoxy)piperidin-1-yl]-2-hydroxypropyl}-1-oxo-1,2-dihydro-2-methylisoquinoline-4-carboxamide;

N-{(2R)-3-{4-(3,4-dichlorophenoxy)piperidin-1-yl]-2-hydroxypropyl}-2-oxo-1,2-dihydro-1-methylquinoline-4-carboxamide;

N-{(2R)-3-[4-(3,4-dichlorophenoxy)piperidin-1-yl]-2-hydroxypropyl}-8-fluoro-1-oxo-1,2-dihydroisoquinoline-4-carboxamide; or, N-{(2R)-3-[4-(4-chloro-2-methylphenoxy)piperidin-1-yl]-2-hydroxypropyl}-8-fluoro-1-oxo-1,2-dihydroisoquinoline-4-carboxamide.

A compound of formula (I) or (Ia) can be prepared by reacting a compound of formula (II):

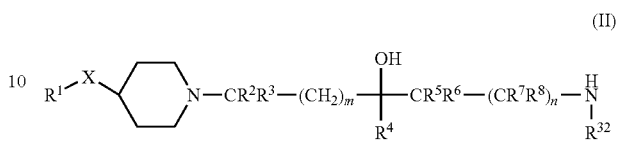

(II)

wherein X, $R^1$, $R^2$, $R^3$, $R^4$, $R^5$, $R^6$, $R^7$, $R^8$, $R^{32}$, m and n are as defined above, with:

(i) when Y is a bond, $CH_2$, $NR^{35}$, $CH_2NH$, $CH_2NHC(O)$, $CH(OH)$, $CH(NHCOR^{33})$, $CH(NHSO_2R^{34})$, $CH_2O$ or $CH_2S$, Z is C(O), $R^{35}$ is not hydrogen and, $R^{33}$ and $R^{34}$ are as defined above, a compound of formula (IIIa):

$L^1$-CO—Y—$R^9$ (IIIa)

wherein $R^9$ is as defined above and $L^1$ is a leaving group (for example a hydroxyl or chloride leaving group) in the presence of a base (for example diisopropylelthylamine), optionally in the presence of a coupling agent (for example bromo-tris-pyrrolidinophosphonium hexafluorophosphate, PyBrOP or O-(7-azabenzotriazol-1-yl)-N,N,N',N'-tetramethyluronium hexafluorophosphate); and, (ii) when Y is NH and Z is C(O), a compound of formula (IIIb):

O=N—$R^9$ (IIIb)

wherein $R^9$ is as defined above.

(iii) when Y is a bond and Z is $S(O)_2$, a compound of formula (IIIc):

$L^1$-$S(O)_2$—$R^9$ (IIIc)

wherein $R^9$ is as defined above and $L^1$ is a leaving group (for example a hydroxyl or chloride leaving group) in the presence of a base (for example pyridine).

A compound of formula (II) can be prepared as described in WO 00/58305 or WO 01/77101, or by reacting a compound of formula (IV):

(IV)

wherein X and $R^1$ are as defined above, with:

(i) when m and n are 0, $R^2$, $R^3$, $R^5$ and $R^6$ are hydrogen, and $R^4$ and $R^{32}$ are as defined for formula (I), a compound of formula (V):

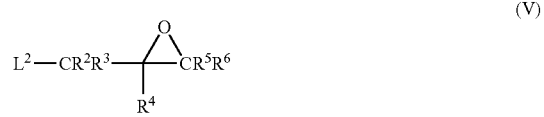

(V)

in which $L^2$ is a leaving group (for example chloro or nosyloxy{3-$NO_2$—$C_6H_4$—$S(O)_2O$—}) followed by reaction with ammonia, an amine $R^{32}$—$NH_2$ or with sodium azide and subsequent reduction with, for example, triphenylphosphine;

(ii) when m and n are 0, $R^2$ and $R^3$ are hydrogen and $R^{32}$ are as defined for formula (I), with a compound of formula (VI):

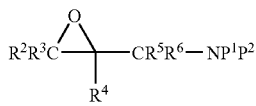

(VI)

in which $P^1$ and $P^2$ are, alone or together, suitable protective groups (for example together they form phthalamide), or either $P^1$ or $P^2$ is $R^{32}$, followed by deprotection using, for example when $P^1$ and $P^2$ form phthalamide, hydrazine;

(iii) when m is 0, n is 1, $R^2$ and $R^3$ are hydrogen and $R^4$, $R^5$, $R^6$, $R^7$, $R^8$ and $R^{32}$ are as defined for formula (I), with a compound of formula (VII):

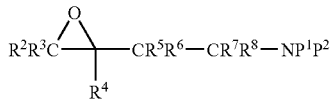

(VII)

in which $P^1$ and $P^2$ are, alone or together, suitable protective groups (for example together they form phthalamide), or either $P^1$ or $P^2$ is $R^{32}$, followed by deprotection using, for example when $P^1$ and $P^2$ form phtalamide, hydrazine;

(iv) when m and n are 1, $R^2$ and $R^3$ are hydrogen and $R^4$, $R^5$, $R^6$, $R^7$, $R^8$ and $R^{32}$ are as defined for formula (I), with a compound of formula (VIII):

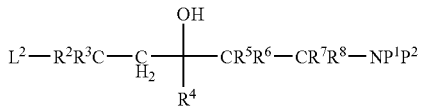

(VIII)

in which $L^2$ is as defined for formula (V) and $P^1$ and $P^2$ are, alone or together, suitable protective groups (for example together they form phthalamide), or either $P^1$ or $P^2$ is $R^{32}$, followed by deprotection using, for example when $P^1$ and $P^2$ form phthalamide, hydrazine;

(v) when m is 1 and n is 0, $R^2$ and $R^3$ are hydrogen, $R^5$ and $R^6$ are, independently, hydrogen, $C_{1-6}$ alkyl or $C_{3-6}$ cycloalkyl, and $R^4$ and $R^{32}$ are as defined for formula (I), with a compound of formula (IX):

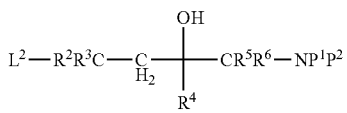

(IX)

in which $L^2$ is as defined for formula (V) and $P^1$ and $P^2$ are, alone or together, suitable protective groups (for example together they form phthalamide), or either $P^1$ or $P^2$ is $R^{32}$, followed by deprotection using, for example when $P^1$ and $P^2$ form phthalamide, hydrazine;

(vi) when m is 1 and n is 0, $R^2$, $R^3$, $R^5$ and $R^6$ are hydrogen and $R^4$ and $R^{32}$ are as defined for formula (I), with a compound of formula (X):

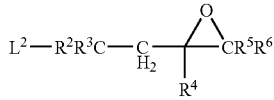

(X)

in which $L^2$ is a leaving group (for example bromine) followed by reaction with ammonia, an amine $R^{32}$—$NH_2$ or with sodium azide and subsequent reduction with, for example, triphenylphosphine;

(vii) when m is 1 and n is 0, $R^2$, $R^3$, $R^5$ and $R^6$ are, independently, hydrogen, $C_{1-6}$ alkyl or $C_{3-6}$ cycloalkyl, and $R^1$, $R^4$ and $R^{32}$ are as defined for formula (I), with a compound of formula (XI):

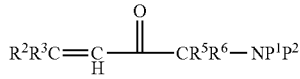

(XI)

in which $P^1$ and $P^2$ are, alone or together, suitable protective groups (for example together they form phthalamide), or either $P^1$ or $P^2$ is $R^{32}$, followed by hydride reduction (for example with sodium borohydride), or by adding an appropriate organometallic species (for example $R^4MgX$, where X is a halide); or, (viii) when m is 1 and n is 1, $R^2$, $R^3$, $R^5$, $R^6$, $R^7$ and $R^8$ are, independently, hydrogen, $C_{1-6}$ alkyl or $C_{3-6}$ cycloalkyl, and $R^1$, $R^4$ and $R^{32}$ are as defined for formula (I), with a compound of formula (XII):

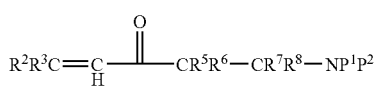

(XII)

in which $P^1$ and $P^2$ are, alone or together, suitable protective groups (for example together they form phthalamide), or either $P^1$ or $P^2$ is $R^{32}$, followed by hydride reduction (for example with sodium borohydride), or by adding an appropriate organometallic species (for example $R^4MgW$, where W is a halide).

When m is 0 and n is 0, $R^2$, $R^3$, $R^5$ and $R^6$ are, independently, hydrogen, $C_{1-6}$ alkyl or $C_{3-6}$ cycloalkyl, compounds or formula (II) can be prepared by reacting a compound of formula (XIII):

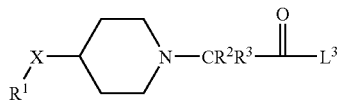

(XIII)

wherein X and $R^1$ are as defined for formula (I), and $L^3$ is hydrogen or a leaving group (for 4 example ethoxy, N,O- dimethylhydroxylamine), with a compound of formula (XIV):

in which M represents a metal (for example Li or Na) and $L^4$ is an amino group (for example ammonium) followed by rearrangement (for example with phenyliodonium diacetate, Tetrahedron Letters, 2001, 42, 1449.) and appropriate reduction (for example with sodium borohydride), or an appropriate organometalic addition (for example $R^4MgW$, where W is a halide).

When m is 0, n is 1 and $R^2$, $R^3$, $R^5$, $R^6$, $R^7$ and $R^8$ are, independently, hydrogen, $C_{1-6}$ alkyl or $C_{3-6}$ cycloalkyl, compounds of formula (II) can be prepared by reacting a compound of formula (XX):

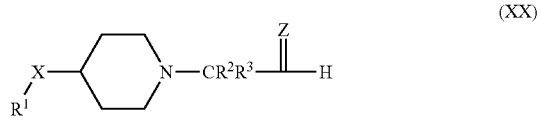

wherein X, $R^1$ and $R^4$ are as described in formula (I) above and Z is an aldehyde protective group (for example cyanohydrin or dithiane), with a compound of formula (XXI):

in which $R^5$, $R^6$, $R^7$ and $R^8$ are as described above, and $L^5$ is an alkoxy or amino group (for example ethoxy or ammonium) in presence of a base (for example LDA or n-butyllithium), followed by hydrolytic removal of the group $L^5$, rearrangement (for example with phenyliodonium diacetate) and appropriate reduction (for example with sodium borohydride), or an appropriate organometalic addition (for example $R^4MgW$, where W is a halide).

A compound of formula (V) can be prepared by reacting a compound of formula (XXII):

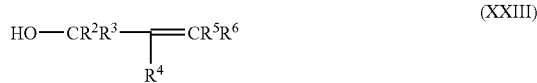

with a peracid (for example meta-chloroperbenzoic acid) or using Sharpless asymmetric epoxidation conditions (J. Am. Chem. Soc. 1980, 102, 5974-5976), followed by activation of the alcohol as a leaving group (for example as nosyloxy).

A compound of formula (VI) can be prepared:
(a) when both $R^5$ and $R^6$ are hydrogen, by reacting a compound of formula (XXIII):

with a peracid (for example meta-chloroperbenzoic acid) or using Sharpless asymmetric epoxidation conditions, followed, for example, by a Mitsunobu reaction using phthalimide, 1,1-(azodicarbonyl)dipiperidine and tibutylphosphine (Tetrahedron Lett. 1993, 34, 1639).

(b) when $R^5$ and $R^6$ are, independently, hydrogen, $C_{1-6}$ alkyl or $C_{3-6}$ cycloalkyl, by reacting a compound of formula (XXIV):

in which $P^1$ and $P^2$ are, alone or together, suitable protective groups (for example together they form phthalamide), or either $P^1$ or $P^2$ is $R^{32}$, with a sulphur ylide (for example trimethylsulfoniummethylide, J. Am. Chem. Soc. 1965, 87, 1353-1364); or a phosphonium ylide (for example tiphenylphosphoniummethylide); followed by epoxidation of the resulting alkene using a peracid (for example meta-chloroperbenzoic acid).

A compound of formula (VII) can be prepared by reacting a compound of formula (XXV):

in which $P^1$ and $P^2$ are, alone or together, suitable protective groups (for example together they form phthalamide), or either $P^1$ or $P^2$ is $R^{32}$, with a sulfur ylide (for example trimethylsulfoniummethylide), or a phosphonium ylide (for example tiphenylphosphoniummethylide) followed by epoxidation of the resulting alkene using a peracid (for example meta-chloroperbenzoic acid).

A compound of formula (VIM can be prepared by reacting a compound of formula (XXV) with the anion of ethyl acetate (which can be prepared by the action of lithium diisopropylamide on ethyl acetate) followed by reduction of the resulting ester, or with, for example, vinyl magnesium Grignard and subsequent hydroboration (for example cathechol borane)/oxidation (for example hydrogen peroxide) of the alkene.

A compound of formula (IX) can be prepared from a compound of formula (XXIV) in a similar way as for compound (VIII).

A compound of formula (X) can be prepared by reacting a compound of formula (XXVI):

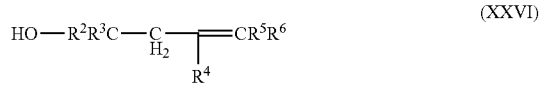

with a peracid (for example meta-chloroperbenzoic acid), followed by selective activation of the primary alcohol as a leaving group (for example nosyloxy).

Further, compounds of formula (I) and (Ia) can be prepared by or by routine adaptation of: the routes described above, methods described in the art, or the Examples recited below. The intermediates identified above are commercially available or can be prepared by using or adapting methods described in the art.

In a further aspect of the invention there is provided a process for preparing 4-(3,4-dichlorophenoxy)piperidine comprising the steps of:

a. reacting 4-hydroxypiperidine with a suitable base in a suitable solvent at room temperature; and, b. heating the mixture so produced together with 1,2-dichloro-4-fluorobenzene at a temperature in the range 50-90° C., or at reflux of the solvent used.

In a further aspect the present invention provides a process for preparing 4-(3,4-dichlorophenoxy)piperidine comprising reacting 4-hydroxypiperidine with a suitable base {such as an alkali metal (preferably sodium or potassium) $C_{1-10}$ alkoxide [such as a $C_{4-10}$ tertiary alkoxide (for example a $C_{4-6}$ tertiary alkoxide)], for example potassium tert-butoxide or potassium 3,7-dimethyl-3-octanoxide} in a suitable solvent {such as: an ether [for example tetrahydrofuran or methyl tert-butyl ester], an aromatic solvent [such as toluene] or a mixture of these solvents} at room temperature (10-30° C.); heating the mixture so produced together with 1,2-dichloro-4-fluorobenzene at a temperature in the range 50-90° C., or at reflux of the solvent used.

In a still further aspect the present invention provides a process for preparing 4 (3,4-dichlorophenoxy)piperidine comprising reacting 4-hydroxypiperidine with a suitable base {such as an alkali metal (preferably sodium or potassium) $C_{1-10}$ alkoxide (such as a $C_{4-10}$ tertiary alkoxide), for example a $C_{1-6}$ alkoxide (such as a $C_{4-6}$ tertiary alkoxide), for example potassium tert-butoxide} in a suitable solvent {such as: an ether [for example tetrahydrofuran or methyl tert-butyl ester], an aromatic solvent [such as toluene] or a mixture of these solvents} at room temperature (10-30° C.), and heating the mixture so produced to a temperature in the range 50-90° C., or at reflux of the solvent used, and adding 1,2-dichloro-4-fluorobenzene.

Examples of tertiary alkoxides are potassium tert-butoxide and potassium 3,7-dimethyl-3-octanoxide.

In another aspect the present invention provides processes for the preparation of compounds of formula (I) and (Ia).

The intermediates of formula (VI), (VII) and (VIII) defined herein are novel and these intermediates, and processes for their preparation, are provided as further features of the invention.

The compounds of the invention have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

In one aspect examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome, or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hasbimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

The compounds of the invention are also H1 antagonists and may be used in the treatment of allergic disorders.

The compounds of the invention may also be used to control a sign and/or symptom of what is commonly referred to as a cold (for example a sign and/or symptom of a common cold or influenza or other associated respiratory virus infection).

According to a further feature of the invention there is provided a compound of formula (I) or (Ia), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity), or antagonising H1, in a warm blooded animal, such as man, in need of such treatment, which comprises administering to said animal an effective amount of a compound of the formula (I) or (Ia), or a pharmaceutically acceptable salt thereof or a solvate thereof.

The invention also provides a compound of the formula (I) or (Ia), or a pharmaceutically acceptable salt thereof or a solvate thereof, for use as a medicament.

In another aspect the invention provides the use of a compound of formula (I) or (Ia), or a pharmaceutically acceptable salt thereof or a solvate thereof, in the manufacture of a medicament for use in therapy (for example modulating chemokine receptor activity (especially CCR3 receptor activity), or antagonising H1, in a warm blooded animal, such as man).

The invention further provides the use of a compound of formula (I) or (Ia), or a pharmaceutically acceptable salt thereof, in the manufacture of a medicament for use in the treatment of (1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle; in a warm blooded animal, such as man.

In a further aspect a compound of formula (I) or (Ia), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of formula (I) or (Ia), or a pharmaceutically acceptable salt thereof, is useful in the treatment of asthma.

The present invention also provides the use of a compound of formula (I) or Ia), or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) in a warm blooded animal, such as man, which comprises administering to a mammal in need of such treatment an effective amount of a compound of formula (I) or (Ia), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

Therefore in another aspect the present invention provides a pharmaceutical composition which comprises a compound of the formula (I) or (Ia), or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the Jung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The invention will now be illustrated by the following non-limiting Examples in which, unless stated otherwise:

(i) when given, $^1$H NMR data is quoted and is in the form of delta values for major diagnostic protons, given in parts per million (ppm) relative to tetramethylsilane CMS) as an internal standard, determined at 300 MHz or 400 MHz using perdeuterio DMSO-D6 (CD$_3$SOCD$_3$), methanol-D4 (CD$_3$OD) or CDCl$_3$ as the solvent unless otherwise stated;

(ii) mass spectra (MS) were run with an electron energy of 70 electron volts in the chemical ionisation (CI) mode using a direct exposure probe; where indicated ionisation was effected by electron impact (EI) or fast atom bombardment (FAB) or electrospray (ESI); where values for m/z are given, generally only ions which indicate the parent mass are reported, and unless otherwise stated the mass ion quoted is the positive mass ion—(M+H)$^+$;

(iii) the title and sub-title compounds of the examples and methods were named using the ACD/Index name program version 4.55 from Advanced Chemistry Development, Inc;

(iv) unless stated otherwise, reverse phase HPLC was conducted using a Symmetry, NovaPak or Xterra reverse phase silica column; and (v) the following abbreviations are used:

| APCI | Atmospheric pressure CI |
| --- | --- |
| DMF | N,N-dimethylformamide |
| HPLC | High pressure liquid chromatography |
| MTBE | Methyl tert-butyl ether |
| DMSO | dimethylsulfoxide |
| THF | tetrahydrofuran |
| DCM | dichloromethane |

Preparation 1

(2R)-1-Amino-3-[4-(3,4-dichlorophenoxy)piperidin-1-yl]propan-2-ol

Step 1: 2-{(2S)-3-[4-(3,4-dichlorophenoxy)piperidin-1-yl]-2-hydroxypropyl}-1H-isoindole-1,3-(2H)-dione

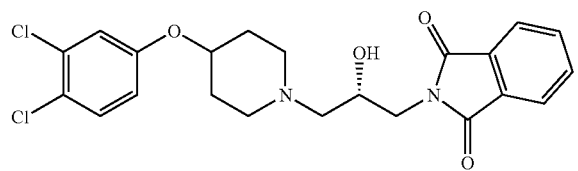

(R)-2-Oxiranylmethyl)-1H-isoindole-1,3-(2H)-dione (*Tetrahedron Asymmetry,* 1996, 7, 1641, 5 g) in a mixture of 50 ml of ethanol and 15 ml of DMF was treated with 4 (3,4-dichlorophenoxy)-piperidine (6 g). The mixture was stirred overnight at room temperature. The solution was concentrated under vacuum and the residue was azeotroped twice with toluene. The crude material was purified by chromatography (ethyl acetate) to give the subtitle compound as a yellow oil.

MS (APCI) 449/451 (M+H)$^+$ $^1$H NMR δ (CDCl$_3$) 7.92-7.81 (2H, m), 7.77-7.70 (2H, m), 7.30 (1H, d); 6.98 (1H, t), 6.74 (1H, dt), 4.34-4.20 (1H, m), 4.09-3.97 (1H, m), 3.83 (1H, dd), 3.73 (1H, dd), 2.93-2.79 (1H, m), 2.73-2.60 (1H, m), 2.59-2.37 (3H, m), 2.31 (1H, t), 2.02-1.86 (2H, m), 1.86-1.67 (2H, m).

Step 2: (2R)-1-amino-3-[4-(3,4-dichlorophenoxy)piperidin-1-yl]propan-2-ol

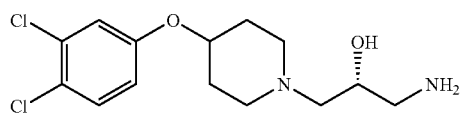

(S)-2-[3-[4-(3,4-Dichlorophenoxy)-1-piperidinyl]-2-hydroxypropyl]-1H-isoindole-1,3(2H)-dione (4 g) in ethanol (100 ml) was treated with 20 ml of hydrazine monohydrate and the resulting mixture was refluxed for 3 h. The reaction was cooled and filtered. The filtrate was evaporated and the product was chromatographed (ethyl acetate) to give the title compound as a yellow oil which solidified on standing (2.5 g).

MS (APCI) 319/321 (M+H)$^+$ $^1$H NMR δ (CDCl$_3$) 7.31 (1H, d), 7.00 (1H, d), 6.75 (1H, dd), 4.00 (1H, app. sept), 3.74-3.62 (1H, m), 2.94-2.84 (1H, m), 2.82 (1H, d), 2.72-2.61 (1H, m), 2.65 (1H, d); 2.60-2.49 (1H, m), 2.46-2.21 (3H, m), 2.06-1.91 (2H, m), 1.90-1.72 (2H, m).

Preparation 2

4-Amino-1-[4-(3,4-dichlorophenoxy)piperidin-1-yl]butan-2-ol

Step 1: 2-{4-[4-(3,4-dichlorophenoxy)piperidin-1-yl]-3-hydroxybutyl}-1H-isoindole-1,3(2H)-dione

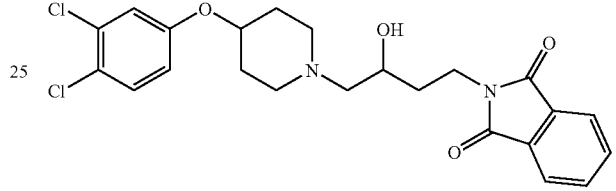

A mixture of 4-(3,4-dichlorophenoxy)piperidine (WO 0058305, WO 0177101) (4.40 g) and 2-(2-oxiran-2-ylethyl)-1H-isoindole-1,3(2H)-dione (*J. Med. Chem.* 1979, 22(6), 631-9. 5.00 g) in ethanol (50 ml) was stirred at 60° C. for 12 h. The mixture was cooled down and left overnight. The formed crystals were collected by filtration, washed with cold ethanol and dried under vacuum to afford the sub-title compound as a white solid (3.0 g).

MS (APCI) 463/465 (M+H)$^+$ $^1$H NMR δ (DMSO) 7.90-7.80 (4H, m), 7.49 (1H, d), 7.25 (1H, d), 6.97 (1H, dd), 4.53-4.33 (2H, m), 3.80-3.69 (1H, m), 3.69-3.58 (2H, m), 2.77-2.60 (2H, m), 2.38-2.17 (4H, m), 1.94-1.84 (2H, m), 1.85-1.75 (1H, m), 1.65-1.50 (3H, m).

Step 2: 4-amino-1-[4-(3,4-dichlorophenoxy)piperidin-1-yl]butan-2-ol

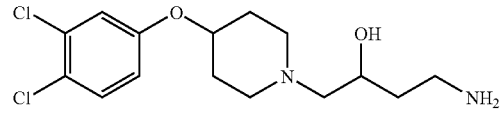

A solution of mixture of 2-{4-[4-(3,4-dichlorophenoxy)piperidin-1-yl]-3-hydroxybutyl}-1H-isoindole-1,3(2H)-dione (3.00 g) in a mixture of ethanol (75 ml) and 35% aqueous hydrazine (15 ml) was heated at reflux 4 h. The mixture was cooled down and the solvents removed under vacuum. The residue was triturated with warm dichloromethane. The white solid was removed by filtration and the filtrate dried over sodium sulfate. The mixture was filtered and the solvent was evaporated to afford the title compound as a yellow oil (2.10 g) which was used without further purification in the next step.

MS (APCI) 333/335 (M+H)⁺

¹H NMR δ (CDCl₃) 7.29 (1H, d), 6.96 (1H, d), 6.76 (1H, dd), 4.40-4.25 (1H, m), 3.95-3.85 (1H, m), 3.20-3.00 (2H, m), 2.96-2.79 (1H, m), 2.78-2.63 (1H, m), 2.60-2.45 (1H, m), 2.41-2.23 (3H, m), 2.10-1.88 (2H, m), 1.88-1.70 (3H, m), 1.70-1.58 (1H, m).

Preparation 3

1-Amino-4-[4-(3,4-dichlorophenoxy)piperidin-1-yl]butan-2-ol

Step 1: 4-(3,4-dichlorophenoxy)-1-(2-oxiran-2-yl-ethyl)piperidine

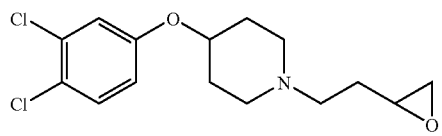

A mixture of 4-(3,4-dichlorophenoxy)piperidine (WO 0058305, WO 0177101) (2.00 g), 2-(2-bromoethyl)oxirane (*J. Am. Chem. Soc.* 1981, 103, 7520-8) (1.36 g) and potassium carbonate (2.2 g) in acetone (20 ml) was stirred at 50° C. for 12 h. The solvent was removed under vacuum. The residue was partitioned between water and ethyl acetate. The organic layer was washed with water, brine and dried over magnesium sulfate. The mixture was filtered and the solvent was evaporated to afford the subtitle compound as a yellow oil (2.50 g) which was used without further purification in the next step.

MS (APCI) 316/318 (M+H)⁺

¹H NMR δ (CDCl₃) 7.31 (1H, d), 7.00 (1H, d), 6.75 (1H, dd), 4.27 (1H, dquintet), 3.02-2.95 (1H, m), 2.78 (1H, t), 2.77-2.68 (2H, m), 2.57-2.49 (3H, m), 2.39-2.24 (2H, m), 2.03-1.94 (2H, m), 1.87-1.75 (2H, m), 1.77-1.72 (1H, m), 1.73-1.61 (1H, m).

Step 2: 1-amino-4-[4-(3,4-dichlorophenoxy)piperidin-1-yl]butan-2-ol

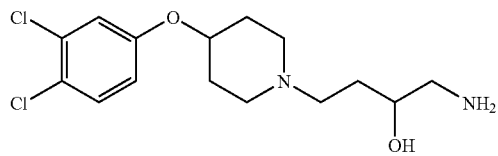

In a sealed metal tube, a solution of 4-(3,4-dichlorophenoxy)-1-(2-oxiran-2-ylethyl)piperidine (1.00 g) in 7N ammonia in methanol (25 ml) was heated at 70° C. for 12 h. The solvent was removed under vacuum and the residue purified on silicagel (0 to 10% 7N ammonia in methanol/dichloromethane) to afford the title compound as a yellow oil (0.55 g).

MS (APCI) 333/335 (M+H)⁺

¹H NMR δ (CDCl₃) 7.31 (1H, d), 6.99 (1H, d), 6.75 (1H, dd), 4.36-4.27 (1H, m), 3.79-3.70 (1H, in), 2.93-2.78 (1H, m), 2.76-2.59 (5H, m), 2.61-2.50 (1H, m), 2.37-2.27 (1H, m), 2.03-1.90 (2H, m), 1.89-1.76 (2H, m), 1.74-1.61 (1H, m), 1.54-1.46 (1H, m).

Preparation 4

(2R)-1-Amino-3-[4-(4-chlorophenoxy)piperidin-1-yl]propan-2-ol

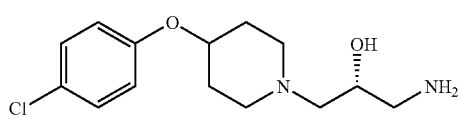

Prepared as described in Preparation 1.
¹H NMR δ (CD₃OD) 7.13 (2H, d), 6.80 (2H, d), 4.26 (1H, septet), 3.68-3.59 (1H, m), 2.77-2.65 (2H, m), 2.62 (1H, dd), 2.46 (1H, dd), 2.38-2.24 (4H, m), 1.95-1.85 (2H, m), 1.73-1.61 (2H, m).

Preparation 5

(2R)-1-Amino-3-[4-(4-chloro-3-fluorophenoxy)piperidin-1-yl]propan-2-ol

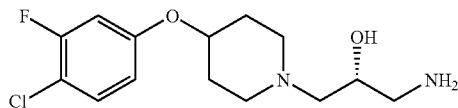

Prepared as described in Preparation 1.
MS (ESI) 303/305 (+H)⁺
¹H NMR δ (CD₃OD) 7.32 (1H, t), 6.86 (1H, dd), 6.77 (1H, ddd), 4.40 (1H, quintet), 3.74 (1H, ddd), 2.87-2.75 (2H, m), 2.72 (1H, dd), 2.56 (1H, dd), 2.50-2.37 (4H, m), 2.08-1.95 (2H, m), 1.85-1.72 (2H, m).

Preparation 6

(2R)-1-Amino-3-[4-(3,4-difluorophenoxy)piperidin-1-yl]propan-2-ol

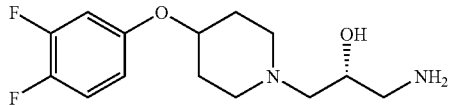

Prepared as described in Preparation 1.
MS (ESI) 287 (M+H)⁺
¹H NMR δ (CD₃OD) 7.14 (1H, dt), 6.87 (1H, ddd), 6.75-6.69 (1H, m), 4.35 (1H, septet), 3.80-3.71 (1H, m), 2.88-2.75 (2H, m), 2.75 (1H, dd), 2.58 (1H, dd), 2.51-2.34 (4H, m), 2.07-1.94 (2H, m), 1.85-1.71 (2H, m).

Preparation 7

2R)-1-Amino-3-[4-(3,4-dichlorophenoxy)piperidin-1-yl]propan-2-ol

Step 1: 4-(3,4-dichlorophenoxy)piperidine

4-Hydroxypiperidine (50 g, 494 mmol) was added portion-wise to a stirred suspension of potassium tert-butoxide (110.9 g, 990 mmol) in THF (900 ml) at room temperature and under nitrogen. The mixture was heated at reflux and 1,2-dichloro-4-fluorobenzene (98 g, 594 mmol) added dropwise over 30 minutes. The mixture was sired at reflux for another 1 hour then cooled down to room temperature, diluted with ethyl acetate (500 ml) and washed with water (500 ml). The organic phase was diluted further with ethyl acetate (500 ml) and extracted with 1M hydrochloric acid (200 ml), The aqueous extract was adjusted to pH>10 by addition of a solution of sodium hydroxide and extracted twice with tert-butylmethyl ether (750 ml). The organic extracts were dried over magnesium sulfate, filtered and concentrated under vacuum to yield the sub-title compound as a dark oil which was used as such in the next step.

MS (ESI) 246/248 (M+H)$^+$ $^1$H NMR δ (CDCl$_3$) 7.31 (1H, d), 7.00 (1H, d), 6.78 (1H, dd), 4.29-4.37 (1H, m), 3.15 (2H, dt), 2.75 (2H, td), 1.97-2.03 (2H, m), 1.60-1.70 (2H, m).

Alternative Step 1: 4-(3,4-dichlorophenoxy)piperidine

A thin slurry of 4-hydroxypiperidine (50 g, 494 mmol) in THF (200 ml) was added to a stirred suspension of potassium tert-butoxide (110.9 g, 990 mmol) in THF (650 ml) at room temperature and washed in with THF (50 ml). The resultant mixture was stirred under nitrogen for 20 minutes. 1,2-Dichloro-4-fluorobenzene (98 g, 594 mmol) was added and the resultant mixture heated at reflux for 90 minutes. The reaction mixture was cooled to room temperature and water (500 ml) added. The layers were separated and the solvent removed from the organic fraction. The material was then partitioned between MTBE and 10% aqueous citric acid solution. The layers separated and the aqueous layer washed with further MTBE (2×250 ml). The aqueous phase was basified to pH>10 by addition of 10N NaOH solution and the product extracted with iso-propyl acetate (2×30 ml). The organics were washed with brine (300 ml), dried over magnesium sulfate, filtered and concentrated under vacuum to yield the sub-title compound as a dark oil which was used as such in the next step (109.1 g, 90%).

Step 2: (2S)-1-azido-3-[4-(3,4-dichlorophenoxy)piperidin-1-yl]propan-2-ol

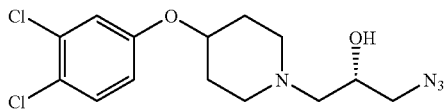

(2R)-Oxiran-2-ylmethyl 3-nitrobenzenesulfonate (21.1 g, 81.3 mmol) in DMF (300 ml) was treated with triethylamine (22.6 ml, 163.0 mmol) followed by 4-(3,4-dichlorophenoxy)-piperidine (20 g, 81.3 mmol). The mixture was stirred overnight at 60° C. Sodium azide (16 g, 243.9 mmol) was added to the mixture and the reaction was stirred for a further 72 h. The solution was carefully concentrated under vacuum and the residue was diluted with water (600 ml), extracted with ethyl acetate (1500 ml). The organic layer was washed twice with water (500 ml), then brine (200 ml) and concentrated under vacuum to afford an oil.

Step 3: (2R)-1-Amino-3-[4-(3,4-dichlorophenoxy)piperidin-1-yl]propan-2-ol

The resulting oil from Step 2 was dissolved in wet tetrahydrofuran (225 ml) and was treated with triphenylphosphine (53.3 g, 203 mmol). The reaction was heated at 60° C. and stirred for 4 h. The solvent was removed under vacuum, the residue re-dissolved into 2N hydrochloric acid (1000 ml) and the aqueous layer was extracted with ethyl acetate (3 times 700 ml). The aqueous phase was basified with a 2N sodium hydroxide solution and extracted with dichloromethane (3 times 1000 ml). The combined organic layers were washed with brine, dried over sodium sulfate, filtered and concentrated under vacuum. The crude material was purified by chromatography (8% 7N ammonia in methanol/DCM) to give the title compound as a yellow oil (17 g).

MS (APCI) 319/321 (M+H)$^+$ $^1$H NMR δ (CDCl$_3$) 7.31 (1H, d), 7.00 (1H, d), 6.75 (1H, dd), 4.0 (1H, app. sept), 3.74-3.62 (1H, m), 2.94-2.84 (1H, m), 2.82 (1H, d), 2.72-2.61 (1H, m), 2.65 (1H, d), 2.60-2.49 (1H, m), 2.46-2.21 (3H, m), 2.06-1.91 (2H, m), 1.90-1.72 (2H, m).

Preparation 8

(2R)-1-Amino-3-[4-(3,4-dichlorophenoxy)piperidin-1-yl]propan-2-ol

Step 1: (2S)-1-Chloro-3-[4-(3,4-chlorophenoxy)piperidin-1-yl]propan-2-ol

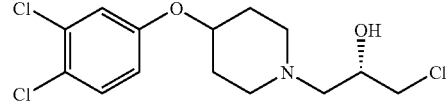

(S)-(+)-Epichlorohydrin (3.50 ml, 44.7 mmol) was added to a stirred solution of 4-(3,4-dichlorophenoxy)piperidine (10.0 g, 40.6 mmol) in ethanol (50 ml). After 20 h, water (50 ml) was added. The mixture stirred for a further 2 h then the precipitated solid was collected by filtration, washed with water and dried under vacuum at 50° C. for 2 h to give the sub-title compound.

MS (ESI) 338/340/342/344 (M+H)$^+$ $^1$H NMR δ (CDCl$_3$) 7.31 (1H, d), 7.00 (1H, d), 6.75 (1H, dd), 4.28-4.33 (1H, m), 3.89-3.96 (1H, m), 3.54-3.62 (3H, m), 2.84-2.92 (1H, m), 2.65-2.72 (1H, m), 2.45-2.59 (3H, m), 2.32-2.36 (1H, m), 1.90-2.01 (2H, m), 1.77-1.87 (2H, m).

Step 2: (2R)-1-Amino-3-[4-(3,4-dichlorophenoxy)piperidin-1-yl]propan-2-ol

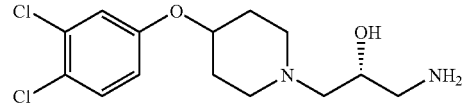

A solution of sodium hydroxide (1.62 g, 40.6 mmol) in methanol (200 ml) was added to the product of the previous step and the mixture stirred for 1 h whereupon all solid had dissolved. Aqueous ammonia solution (28%, 80 ml) was added and stirring continued at ambient temperature for 3 days. The solution was concentrated in vacuo to a volume of 100 ml then dissolved in hydrochloric acid (0.5M, 800 ml) and extracted with diethyl ether (2×200 ml). The aqueous extract was filtered to remove insoluble impurities then made alkaline by addition of sodium hydroxide and extracted with dichloromethane (4×200 ml) with filtration of the two-phase mixture to remove further insoluble impurities. Organic extracts were dried over anhydrous magnesium sulfate, filtered and evaporated under reduced pressure to provide the tide compound as an oil (10.6 g).

MS (APCI) 319/321 (M+H)+

¹H NMR δ (CDCl₃) 7.31 (1H, d), 7.00 (1H, d), 6.75 (1H, dd), 4.0 (1H, app. sept.), 3.74-3.62 (1H, m), 2.94-2.84 (1H, m), 2.82 (1H, d), 2.72-2.61 (1H, m), 2.65 (1H, d), 2.60-2.49 (1H, m), 2.46-2.21 (3H, m), 2.06-1.91 (2H, m), 1.90-1.72 (2H, m).

Preparation 9

(2S)-1-Amino-3-[4-(3,4-dichlorophenoxy)piperidin-1-yl]-2-methylpropan-2-ol

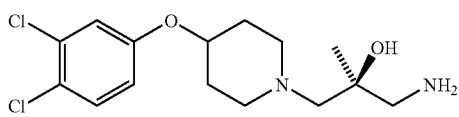

Prepared as described in Preparation 7 (Steps 2 and 3) using [(2R)-2-methyloxiran-2-yl]methyl-3-nitrobenzenesulfonate.

MS (APCI) 333/335 (M+H)+

¹H NMR δ (CDCl₃) 7.30 (1H, d), 6.99 (1H, d), 6.75 (1H, dd), 4.38-4.30 (1H, m) 3.48 (2H, s), 2.96-2.78 (2H, m), 2.62-2.30 (4H, m), 2.00-1.90 (2H, m), 1.85-1.72 (2H, m), 1.25 (3H, s).

Preparation 10

(2R)-1-Amino-3-[4-(4-chloro-2-methylphenoxy)-piperidin-1-yl]propan-2-ol

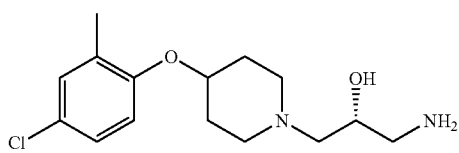

Prepared as described in Preparation 7 (Steps 2 and 3) from 4-(4-chloro-2-methylphenoxy)-piperidine.

MS (ESI) 299/301 (M+H)+

¹H NMR δ (CD₃OD) 7.12-7.05 (2H, m), 6.87 (1H, d), 4.39 (1H, septet), 3.77-3.70 (1H, m), 2.84-2.72 (2H, m), 2.71 (1H, dd), 2.55 (1H, dd), 2.50-2.39 (2H, m), 2.40 (1H, d), 2.39 (1H, d), 2.18 (3H, s), 2.04-1.95 (2H, m), 1.86-1.75 (2H, m).

Preparation 11

6-{1-[(2R)-3-Amino-2-hydroxypropyl]piperidin-4-yl}oxy)-2,3-dichlorobenzamide

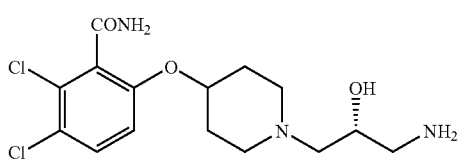

Step 1: Tert-Butyl 4-[2-(aminocarbonyl)-3,4-dichlorophenoxy]piperidine-1-carboxylate

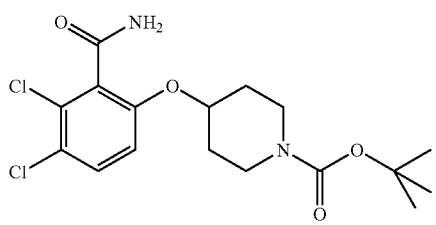

To a stirred solution of tert-butyl 4-[3,4-dichlorophenoxy]piperidine-1-carboxylate (7.0 g, 20.3 mmol) in dry THF (250 ml) at −70° C. under a nitrogen atmosphere was added dropwise sec-butyl lithium (18 ml, 1.3M in cyclohexane). The solution was stirred a further 30 min. at this temperature then treated with solid carbon dioxide pellets (excess). The cooling bath was removed and the mixture stirred vigorously whilst warming to room temperature over 1 h. After a further 1 h the solution was concentrated to ca 50 ml volume then partitioned between aqueous sodium hydrogen carbonate solution and diethyl ether. The aqueous phase was further washed with diethyl ether (3×), then acidified to pH 4 and extracted with dichloromethane (3×). The combined extracts were dried (magnesium sulphate) and concentrated. Treatment of the crude carboxylic acid (2.5 g, 6.4 mmol) with carbonyl-1,1-diimidazolide (1.25 g, 7.7 mmol) in dichloromethane (5 ml) at room temperature for 72 h gave the crude imidazolide which was concentrated in vacuo, redissolved in ethanol (20 ml) and treated with 35% aqueous ammonia (20 ml) in an autoclave at 100° C., for 2 h. The mixture was allowed to cool to room temperature slowly to allow crystallization of the title compound. The crystalline product was filtered and washed with water. Recrystallization from ethanol/water gave the sub-title compound (1.90 g).

MS (APCI) 289/291 (M+H−BOC)+

¹H NMR δ (CDCl₃) 7.40 (1H, d), 6.83 (1H, d), 5.91 (1H, s), 5.73 (1H, s), 4.52 (1H, m), 3.59 (2H, m), 3.41 (2H, m), 1.86 (4H, m), 1.43 (9H, s).

Step 2: 2,3-dichloro-6-(piperidin-4-yloxy)benzamide

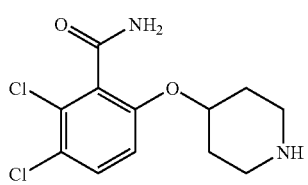

To a stirred solution of tert-butyl 4-[-[2-(aminocarbonyl)-3,4-dichlorophenoxy]piperidine-1-carboxylate (1.8 g, 4.6 mmol) in dichloromethane (10 ml) was added trifluoroacetic acid (10 ml). After 30 min at room temperature the solution was concentrated in vacuo and partitioned between saturated aqueous sodium hydrogen carbonate solution and dichloromethane. The aqueous was re-extracted a further three times with dichloromethane and three times with ethy acetate. The combined organic extracts were dried (anhydrous potassium carbonate) and concentrated to afford the sub-title compound as a white solid (1.15 g).

MS (APCI) 289/291 (M+H)⁺

¹H NMR δ (CD₃OD) 7.49 (1H, d), 7.09 (1H, d), 4.65 (1H, M), 3.15 (2H, 2.84 (2H, m), 2.02 (2H, m), 1.82 (2H, m).

Step 3: 6-({1-[(2R)-3-amino-2-hydroxypropyl]piperidin-4-yl}oxy)-2,3-dichlorobenzamide Step a: To a stirred solution of 2,3-dichloro-6-(piperidinyloxy)benzamide (1.1 g, 3.8 mmol) in dimethylformamide (10 ml) was added triethylamine (1.06 ml. 7.6 mmol) and (2R)-glycidyl-3-nitrobenzenesulfonate (1.0 g, 3.8 mmol) and the mixture heated at 60° C. for 3 h. Sodium azide (1.0 g, 15.2 mmol) was added and the temperature maintained for a further 48 h The mixture was concentrated in vacuo (blast shield) to almost dryness, and the product partitioned between dichloromethane and aqueous sodium hydrogen carbonate solution. The aqueous layer was reextracted with dichloromethane then with ethyl acetate. The combined organic extracts were dried (anhydrous potassium carbonate) and concentrated in vacuo.

Step b: The product was redissolved in tetrahydrofuran (50 ml) and treated with water (5 ml) and triphenylphosphine (2.4 g). The mixture was heated at 60° C. for 4 h, then concentrated in vacuo. The product was partitioned between ethyl acetate and 1N aqueous hydrochloric acid. The aqueous extracts were washed further with ethyl acetate then basified with 48% sodium hydroxide solution to pH 11. The aqueous layer was extracted with dichloromethane (3×), and the combined organic extracts dried (anhydrous potassium carbonate) and concentrated in vacuo to afford crude amine product which was used without any purification in the next step (See Example 132).

Preparation 12

(R)-1-[4-(3,4-Dichloro-phenoxy)-piperidin-1-yl]-3-methylamino-propan-2-ol

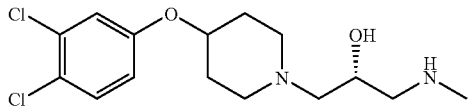

A solution of 4-(3,4-dichlorophenoxy)-1-[(2R)-oxiran-2-ylmethyl]piperidine (1 g, 3.31 mmol) and methylamine (2.56 ml 40% in H₂O, 33.1 mmol) in ethanol (15 ml) was heated at 60° C. in a sealed vessel for 16 h. The solvent was evaporated at reduced pressure and the residue purified by flash column chromatography eluting with 8% 7M ammonia methanol in dichloromethane to give the title compound (875 mg).

MS (APCI) 333/335 (M+H)⁺

¹H NMR δ (CDCl₃) 7.31 (1H, d), 6.99 (1H, d), 6.75 (1H, dd), 4.32-4.26 (1H, m), 3.86-3.80 (1H, m), 2.91-2.86 (1H, m), 2.71-2.65 (2H, m), 2.65 (1H, dd), 2.56-2.51 (2H, m), 2.54 (1H, dd), 2.48-2.42 (2H, m), 2.46 (3H, s), 2.38-2.27 (3H, m).

Preparation 13

(2R)-1-Amino-3-[4-(2,4-dichloro-3-methylphenoxy)piperidin-1-yl]propan-2-ol

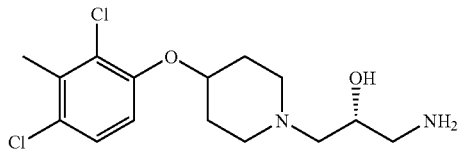

Prepared as described in Preparation 10 using 4-(2,4-dichloro-3-methylphenoxy)-piperidine.

MS (APCI) 333/335 (M+H)⁺

¹H NMR δ (CD₃OD) 7.25 (2H, d), 6.94 (2H, d), 4.54-4.37 (1H, m), 3.88-3.71 (1H, m), 3.35-3.24 (2H, m), 2.93-2.72 (4H, m), 2.72-2.57 (1H, m), 2.08-1.90 (2H, m), 1.92-1.75 (2H, m).

Preparation 14

(2S)-1-Amino-3-[4-(3,4-dichlorophenoxy)piperidin-1-yl]propan-2-ol

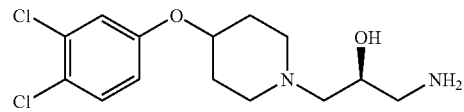

Prepared as described in Preparation 7 using (2S)-oxiran-2-ylmethyl-3-nitrobenzenesulfonate.

MS (ESI) 319/321 (M+H)⁺

¹H NMR δ (CDCl₃) 7.30 (1H, d), 6.99 (1H, d), 6.75 (1H, dd), 4.36-4.24 (1H, m), 3.75-3.65 (1H, m), 2.94-2.78 (2H, m), 2.70-2.60 (2H, m), 2.59-2.51 (1H, m), 2.41-2.25 (3H, m), 2.03-1.93 (2H, m), 1.87-1.77 (2H, m).

Preparation 15

(2R)-1-Amino-2-methyl-3-[4-(3,4-dichlorophenoxy)piperidin-1-yl]propan-2-ol

Step 1: 2-[[(2R)-2-methyloxiranyl]methyl]-1H-isoindole-1,3(2H)-dione

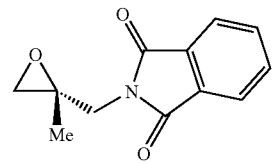

To a solution of (2S)-(2-methyloxiran-2-yl)methyl 3-nitrobenzenesulphonate (1.913 g, 7 mmoles) in dry dimethylformamide (15 ml), was added potassium phthalimide (1.304 g, 7 mmoles). The mixture was stirred at 50° C. for 5 h and then cooled to room temperature. The resulting mixture was partitioned between ethyl acetate and water. The aqueous phase was washed with ethyl acetate (2×100 ml) and the combined organic extracts were washed with water (3×100 ml), saturated brine solution, dried over sodium sulfate and concentrated in vacuo to leave a crude orange wax. Purification by chromatography (silica, 20% ethyl acetate in isohexane) afforded the subtitle compound as a white solid (0.864 g).

MS (ESI) 189 (M−CO)⁺

¹H NMR δ (CDCl₃) 7.90-7.85 (2H, m), 7.78-7.71 (2H, m), 4.02 (1H, d), 3.71 (1H, d), 2.82 (1H, d), 2.62 (1H, d), 1.39 (3H, s).

Step 2

2-[(2R)-3-[4-(3,4-dichlorophenoxy)piperidin 1-yl]-2-hydroxy-2-methylpropyl]-1H-isoindole-1,3(2H)-dione

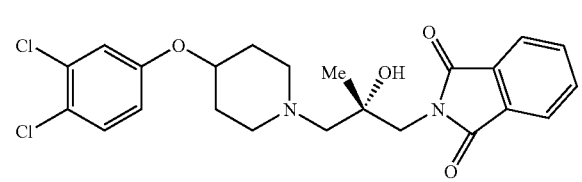

A solution of 4-(3,4-dichlorophenoxy)piperidine (0.985 g, 4 mmoles), 2-[[(2R)-2-methyloxiranyl]methyl]-1H-isoindole-1,3(2H)-dione (0.869 g, 4 mmoles) and triethylamine (0.809 g, 1.12 ml, 8 mmoles) in ethanol (20 ml) was stirred at 50° C. for 5 h. The resulting solution was cooled to room temperature and concentrated in vacuo to leave a crude yellow gum. Flash chromatography (silica, 2% of 7N methanolic ammonia in dichloromethane as eluant) afforded the subtitle compound as a yellow oil (1.24 g).

MS (APCI) 463/465/467 (M+H)$^+$ $^1$H NMR δ (CDCl$_3$) 7.89-7.85 (2H, m), 7.76-7.72 (2H, m), 7.30 (1H, d), 6.98 (1H, d), 6.78 (1H, dd), 4.27-4.21 (1H, m), 3.88 (1H, d), 3.70 (1H, d), 3.43 (1H, bd s), 2.96-2.81 (2H, m), 2.60-2.42 (4H, m), 1.95-1.89 (2H, m), 1.80-1.70 (2H, m), 1.15 (3H, s).

Step 3

(2R)-1-Amino-2-methyl-3-[4-(3,4-dichlorophenoxy)piperidin-1-yl]propan-2-ol

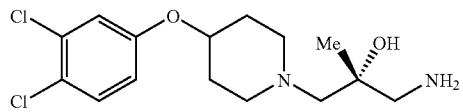

To a solution of 2-[(2S)-3-[4-(3,4-dichlorophenoxy)piperidin-1-yl]-2-hydroxy-2-methylpropyl]-1H-isoindole-1,3(2H)-dione (278 mg, 0.6 mmoles) in ethanol (5 ml) was added aqueous methylamine (40% wt. solution in water, 6 ml). The mixture was stirred at room temperature for 24 h and then concentrated in vacuo to leave a crude yellow glass. This glass was dissolved in methanol (2 ml), added to an Isolute Flash SCX cartridge (2 g), washed with methanol (25 ml) and 7N ammonia in methanol (25 ml). The methanolic ammonia was concentrated in vacuo to give the title compound as a yellow glass (165 mg).

MS (ESI) 333/335/337 (M+H)$^+$ $^1$H NMR δ (CDCl$_3$) 7.31 (1H, d), 6.99 (1H, d), 6.75 (1H, dd), 4.29-4.21 (1H, m), 2.96-2.80 (2H, m), 2.60-2.30 (4H, m), 2.00-1.90 (3H, m), 1.85-1.75 (3H, m), 1.13 (3H, s).

Preparation 16

7-(Chlorosulfonyl)-1-oxo-1,2-dihydroisoquinoline-4-carboxylic acid

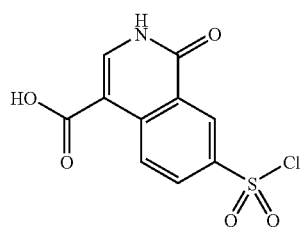

1-Oxo-7-sulfo 1,2-dihydroisoquinoline-4-carboxylic acid (5 g) was added to chlorosulphonic acid (25 ml). The mixture was heated at 100° C. for 84 h and then slowly dripped onto ice with sting. The mixture was filtered and the residue was washed with water and ether and dried to yield 7-(chlorosulfonyl)-1-oxo-1,2-dihydroisoquinoline-4-carboxylic acid as a buff solid (7.5 g).

MS (APCI) 286 (M−H)$^-$ $^1$H NMR δ (DMSO) 11.81 (1H, d), 8.79 (1H, d), 8.48 (1H, d), 8.03 (1H, d), 7.96 (1H, dd).

Preparation 17

7-[(Methylamino)sulfonyl]-1-oxo-1,2-dihydroisoquinoline-4-carboxylic acid

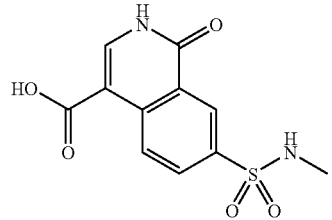

7-(Chlorosulfonyl)-1-oxo-1,2-dihydroisoquinoline-4-carboxylic acid (1 g) was added to aqueous methylamine (60 ml) and the mixture was stirred for 18 h. Concentrated hydrochloric acid was added to acidify the mixture, which was filtered to yield 7-[(methylamino)sulfonyl]-1-oxo-1,2-dihydroisoquinoline-1 carboxylic acid as a buff solid (0.84 g).

MS (APCI) 283 (M+H)$^+$ $^1$H NMR δ (DMSO) 12.93 (1H, s), 12.13 (1H, d), 9.03 (1H, d), 8.61 (1H, d), 8.16 (1H, d), 8.12 (1H, dd), 7.65 (1H, q), 2.43 (3H, d).

Preparation 18

1,2-Dihydro-7-[[(2-hydroxyethyl)amino]sulfonyl]-1-oxo-4-isoquinolinecarboxylic acid

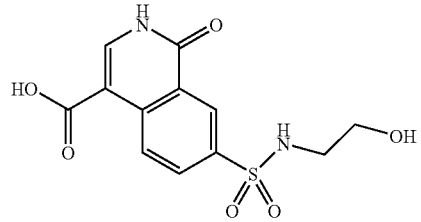

7-(Chlorosulfonyl)-1-oxo-1,2-dihydroisoquinoline-4-carboxylic acid (1 g) was added to ethanolamine (3 ml) in tetrahydrofuran (3 ml) and the mixture was stirred for 18 h. Hydrochloric acid was added to acidify the mixture, which was filtered to yield 1,2-dihydro-7-[[(2-hydroxyethyl)amino]sulfonyl]-1-oxo-4 isoquinolinecarboxylic acid as a white solid.

MS (APCI) 313 (M+H)$^+$ $^1$H NMR δ (DMSO) 12.92 (5H, s), 12.12 (5H, s), 9.01 (6H, d), 8.62 (6H, s), 8.16 (13H, d), 8.13 (13H, dd), 7.81 (6H, t), 4.67 (5H, s), 3.39-3.25 (84H, m), 2.81 (13H, q).

Preparation 19

7-[(Cyclopropylamino)sulfonyl]-1,2-dihydro-1-oxo-4-isoquinolinecarboxylic acid

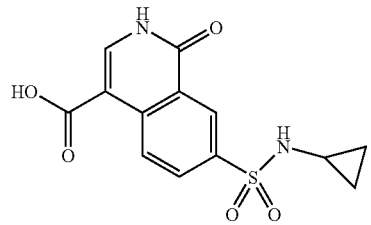

7-(Chlorosulfonyl)-1-oxo-1,2-dihydroisoquinoline-4-carboxylic acid (1 g) was added to cyclopropylamine (3 ml) in tetrahydrofuran (20 ml) and the mixture was stirred for 18 h. Hydrochloric acid was added to acidify the mixture which was filtered to yield 7-[(cyclopropylamino)sulfonyl]-1,2-dihydro-1-oxo-isoquinolinecarboxylic acid as a white solid.

MS (APCI) 307 (M−H)−

¹H NMR δ (DMSO) 12.93 (1H, s), 12.13 (1H, d), 9.03 (1H, d), 8.65 (1H, d), 8.16 (1H, d), 8.14 (1H, dd), 8.08 (1H, d), 2.13 (1H, dsextet), 0.48 (2H, td), 0.39-0.34 (2H, m).

Preparation 20

7-(Azetidin-1-ylsulfonyl)-1-oxo-1,2-dihydroisoquinoline-4-carboxylic acid

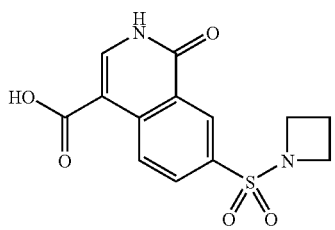

7-(Chlorosulfonyl)-1-oxo-1,2-dihydroisoquinoline-4-carboxylic acid (1 g) was added to azetidine (0.7 ml) and diisopropylethylamine (0.4 ml) in tetrahydrofuran (5 ml) and acetonitrile (5 ml) and the mixture was stirred for 72 h then evaporated. The solid was crystallised from methanol then hydrochloric acid was added to acidify the mixture, which was filtered to yield 7-(azetidin-1-ylsulfonyl)-1-oxo-1,2-dihydroisoquinoline-4-carboxylic acid as a white solid.

MS (APCI) 309 (M+H)+

¹H NMR δ (DMSO) 12.99 (1H, s), 12.21 (1H, d), 9.12 (1H, d), 8.54 (1H, d), 8.20 (1H, d), 8.16 (1H, dd), 3.70 (4H, t), 1.99 (2H, quintet).

Preparation 21

7-(Aminosulfonyl)-1-oxo-1,2-dihydroisoquinoline-4-carboxylic acid

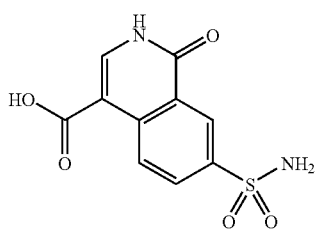

7-(Chlorosulfonyl)-1-oxo-1,2-dihydroisoquinoline-4-carboxylic acid (1 g) was added to 0.880 ammonia (60 ml) and the mixture was stirred for 18 h. Concentrated hydrochloric acid was added to acidify the mixture, which was filtered to yield 7-(aminosulfonyl)-1-oxo-1,2-dihydroisoquinoline-4-carboxylic acid as a white solid.

MS (APCI) 269 (M+H)+

¹H NMR δ (DMSO) 12.91 (1H, s), 12.08 (1H, d), 8.99 (1H, d), 8.68 (1H, d), 8.16 (1H, dd), 8.14 (1H, d), 7.53 (2H, s).

Preparation 22

7-[(Dimethylamino)sulfonyl]-1-oxo-1,2-dihydroisoquinoline-4-carboxylic acid

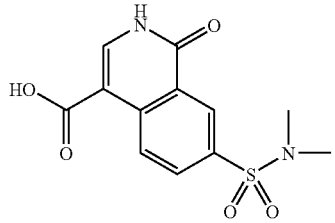

7-(Chlorosulfonyl)-1-oxo-1,2-dihydroisoquinoline-4-carboxylic acid (0.8 g) was added to dimethylamine (15 ml) and the mixture was stirred for 18 h. The mixture was acidified with concentrated hydrochloric acid and then filtered to yield 7-[(dimethylamino)sulfonyl]-1-oxo-1,2-dihydroisoquinoline-4-carboxylic acid as a white solid.

MS (APCI) 295 (M−H)−

¹H NMR δ (DMSO) 12.96 (1H, s), 12.19 (1H, d), 9.07 (1H, d), 8.50 (1H, d), 8.18 (1H, d), 8.11 (1H, dd), 2.65 (6H, s).

Preparation 23

7-[(3-Hydroxy-3-methylazetidin-1-yl)sulfonyl]-1-oxo-1,2-dihydroisoquinoline-4-carboxylic acid

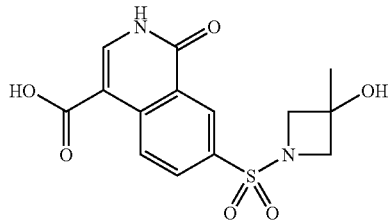

7-(Chlorosulfonyl)-1-oxo-1,2-dihydroisoquinoline-4-carboxylic acid (1 g), diisopropylethylamine (3 ml) and 3-methylazetidin-3-ol hydrochloride (0.8 g) in tetrahydrofuran (8 ml) were heated at 55° C. for 3 days. The mixture was acidified with hydrochloric acid and then filtered to yield 7-[(3-hydroxy-3-methylazetidin-1-yl)sulfonyl]-1-oxo-1,2-dihydroisoquinoline-4-carboxylic acid as a pale pink solid.

MS (ESI) 337 (M−H)−

¹NMR δ (DMSO) 12.99 (1H, s), 12.22 (1H, d), 9.11 (1H, d), 8.53 (1H, s), 8.21 (1H, d), 8.16 (1H, dd), 3.61 (2H, d), 3.46 (2H, d), 1.25 (3H, t).

Preparation 24

4-({1-[(2R)-3-Amino-2-hydroxypropyl]piperidin-4-yl}oxy)-2-chlorobenzonitrile

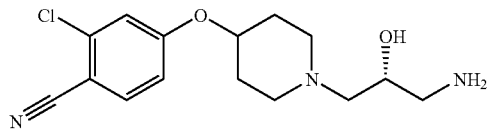

Step 1: Tert-Butyl 4-(3-chloro-4-cyanophenoxy)piperidine-1-carboxylate

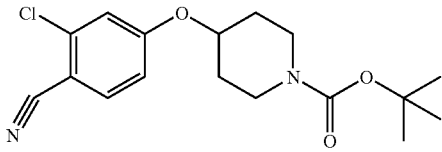

Potassium tert-butoxide (5.57 g, 49.68 mmol) was added to a solution of tert-butyl 4-hydroxypiperidine-1-carboxylate (5.00 g, 24.84 mmol) in glyme (100 ml) and the mixture stirred for 30 min. before addition of 2 chloro-4-fluoro-benzonitrile (7.73 g, 49.68 mmol). The reaction was stirred at room temperature overnight and then partitioned between ethyl acetate (250 ml) and water (200 ml). The organic layer was separated, dried over magnesium sulfate and the solvent evaporated. The residue was purified by flash chromatography eluting with ethyl acetate:isohexane (4:1) to give the subtitle compound as a colourless solid (3.45 g).

MS (ESI) 337 (M+H)$^+$ $^1$H NMR δ (CDCl$_3$) 1.47 (9H, s), 1.72-1.80 (2H, m), 1.90-1.97 (2H, m), 3.37 (2H, ddd), 3.68 (2H, ddd), 4.54 (1H, dquintet), 6.86 (1H, dd), 7.01 (1H, d), 7.57 (1H, d).

Step 2: 4-({1-[(2R)-3-Amino-2-hydroxypropyl]piperidin-4-yl}oxy)-2-chlorobenzonitrile To a solution of the tert-butyl 4-(3-chloro-4-cyanophenoxy)piperidine-1-carboxylate (2.75 g, 9.09 mmol) in dichloromethane (20 ml) was added trifluoroacetic acid (20 ml) and the mixture stirred for 90 min. The solvents were evaporated and the residue azeotroped with toluene (2×20 ml) before dissolving in water (30 ml) and addition of sodium hydroxide to bring the solution to pH 11. The free base was extracted with DCM (5×100 ml). The organics were combined, dried over sodium sulfate and the solvent removed under reduced pressure to give a thick oil which was dissolved in DMF (30 ml) before addition of (2R)-oxiran-2-ylmethyl-3-nitrobenzenesulfonate (2.35 g, 9.09 mmol) and triethylamine (2.54 ml, 18.18 mmol). The mixture was heated at 60° C. for 4 h before addition of sodium azide (1.36 g, 27.27 mmol). Heating was continued at 60° C. for a further 72 h. The reaction mixture was cooled and partitioned between water (50 ml) and ethyl acetate (100 ml). The organic layer was separated and the solvent removed under reduced pressure. The residue was dissolved in THF (20 ml) and water (2 ml) and triphenylphosphine (5.90 g, 22.72 mmol) added The mixture was heated at 60° C. for 16 h before dilution with ethyl acetate (100 ml). The solution was washed with 1N HCl (50 ml) and the aqueous layer was separated and adjusted to pH 11 with sodium hydroxide. The product was extracted with DCM (4×100 ml). The organics were combined and dried sodium over sulfate and the solvent removed under reduced pressure. The residue was purified by flash chromatography to give the title compound as a pale yellow solid (1.10 g).

MS (ESI) 310 (M+H)$^+$ $^1$H NMR δ (CDCl$_3$) 7.56 (1H, d), 7.00 (1H, d), 6.85 (1H, dd), 4.42 (1H, septet), 3.73-3.67 (1H, m), 2.93-2.86 (1H, m), 2.86-2.78 (1H, m), 2.71-2.62 (2H, m), 2.61-2.55 (1H, m), 2.45-2.30 (3H, m), 2.06-1.96 (2H, m), 1.91-1.79 (2H, m).

Preparation 25

(2R)-1-Amino-3-{4-[4-(methylsulfonyl)phenoxy]piperidin-1-yl}propan-2-ol

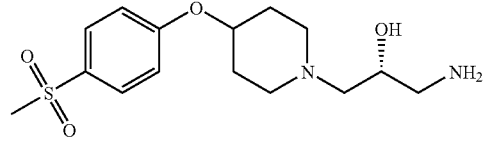

Prepared as described in Preparation 24 starting from 1-fluoro-4-(methylsulfonyl) benzene.

Step 1: tert-Butyl 4-[4-(methylsulfonyl)phenoxy]piperidine-1-carboxylate

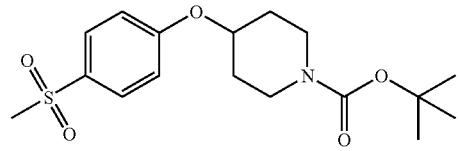

$^1$H NMR δ (CDCl$_3$) 1.48 (9H, s), 1.74-1.82 (2H, m), 1.91-1.99 (2H, m), 3.04 (3H, s), 3.38 (2H, ddd), 3.69 (2H, ddd), 4.57-4.62 (1H, m), 7.02 (2H, d), 7.86 (2H, d).

Step 2: (2R)-1-Amino-3-{4-[4-(methylsulfonyl)phenoxy]piperidin-1-yl}propan-2-ol

MS (ESI) 329 (M+H)$^+$ $^1$H NMR δ (CDCl$_3$) 7.85 (2H, d), 7.01 (2H, d), 4.47 (1H, septet), 3.73-3.67 (1H, m), 3.03 (3H, s), 2.95-2.88 (1H, m), 2.86-2.78 (1H, m), 2.72-2.62 (2H, m), 2.61-2.55 (1H, m), 2.45-2.30 (3H, m), 2.08-1.98 (2H, m), 1.92-1.81 (2H, m).

Preparation 26

4-({1-[(2R)-3-Amino-2-hydroxypropyl]piperidin-4-yl}oxy)benzonitrile

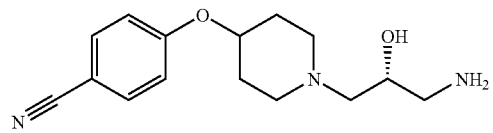

Prepared as described in Preparation 24 starting from 4-fluorobenzonitrile.

Step 1: tert-Butyl 4-(4-cyanophenoxy)piperidine-1-carboxylate

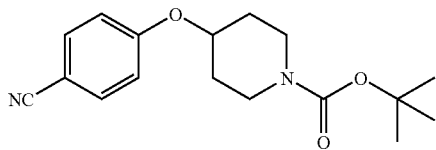

MS (ESI) 303 (M+H)⁺

$^1$H NMR δ (CDCl$_3$) 7.58 (2H, d), 6.95 (2H, d), 4.55 (1H, m), 3.69 (2H, ddd), 3.37 (2H, ddd), 1.97-1.90 (2H, m), 1.80-1.72 (2H, m), 1.47 (9H, s).

Step, 2: 4-({1-[(2R)-3-Amino-2-hydroxypropyl]piperidin-4-yl}oxy)benzonitrile

MS (ESI) 276 (M+H)⁺

$^1$H NMR δ (CDCl$_3$) 7.57 (2H, d), 6.94 (2H, d), 4.46-4.41 (1H, m), 3.74-3.68 (1H, m), 2.94-2.88 (1H, m), 2.83 (1H, dd), 2.73-2.66 (1H, m), 2.64 (1H, dd), 2.61-2.55 (1H, m), 2.46-2.30 (3H, m), 2.07-1.97 (2H, m), 1.91-1.80 (2H, m).

Preparation 27 tert-Butyl 4-[4-chloro-2-(methoxycarbonyl)phenoxy]piperidine-1-carboxylate

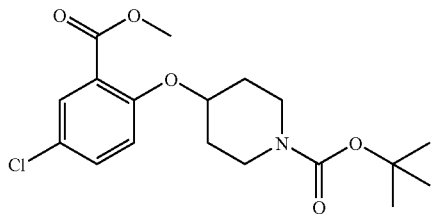

Diisopropylazodicarboxylate (5.2 ml, 26.8 mmol) was added dropwise to a solution of 5-chloro-2-hydroxy methylbenzoate (5.0 g, 26.8 mmol), tert-butyl 4-hydroxypiperidine-1-carboxylate (5.4 g, 26.8 mmol) and triphenylphosphine (7.02 g, 26.8 mmol) in THF (200 ml) at 0° C. The reaction mixture was allowed to warm to ambient temperature overnight The solvent was removed under reduced pressure and the residue triturated with diethyl ether (200 ml). The triphenylphosphineoxide was filtered off and the diethyl ether removed under reduced pressure. The residue was purified by flash column chromatography eluting with ethyl acetate:isohexane (1:9) to give the title compound as a brown oil (8.1 g).

MS (ESI) 370 (M+H)⁺

$^1$H NMR δ (DMSO) 1.47 (9H, s), 1.79-1.92 (4H, m), 3.45-3.54 (2H, m), 3.56-3.62 (2H, m), 3.89 (3H, s), 4.54-4.59 (1H, m), 6.92 (1H, d), 7.38 (1H, dd), 7.77 (1H, d).

Preparation 28

2-{[1-(tert-Butoxycarbonyl)piperidin-4-yl]oxy}-5-chlorobenzoic acid

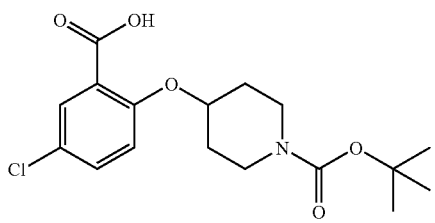

An aqueous solution of 2N sodium hydroxide (20 ml) was added to a solution of tert-butyl 4-[4-chloro-2-(methoxycarbonyl) phenoxy]piperidine-1-carboxylate (8.1 g, 22.0 mmol) in tetrahydrofuran (70 ml) at 45° C. The mixture was stirred vigorously for 3 h then adjusted to pH 2 with 2N hydrochloric acid. The product was extracted with ethyl acetate and the organic layer washed repeatedly with water until the washings were pH 6. The organic layer was dried over magnesium sulfate and evaporated. The residue was azeotroped with toluene to give the title compound as a colourless solid (7.5 g).

MS (ESI) 356 (M+H)⁺

$^1$H NMR δ (DMSO) 1.47 (9H, s), 1.79-1.88 (2H, m), 2.03-2.11 (2H, m), 3.30 (2H, ddd), 3.77-3.85 (2H, m), 4.72 (1H, m), 7.02 (1H, d), 7.49 (1H, dd), 8.12 (1H, d), 10.91 (1H, s).

Preparation 29

4-(4-Chloro-2-methylcarbamoyl-phenoxy)-piperidine-1-carboxylic acid tert-butyl ester

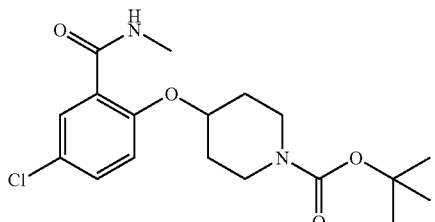

Bromo-tris-pyrrolidinophosphonium hexafluorophosphate (1.57 g, 3.37 mmol) was added to a vigorously stirred mixture of 2-{[1-(tert-butoxycarbonyl)piperidin-4-yl]oxy}-5-chlorobenzoic acid (1.00 g, 2.8 mmol) and 40% aq methylamine (2 ml) in DCM (10 ml). Stirring was continued for 30 min. before partitioning between 1N hydrochloric acid (10 ml) and dichloromethane (10 ml). The organic layer was separated and washed with saturated sodium bicarbonate solution (20 ml) and water (20 ml), then dried over sodium sulfate and the solvent removed under reduced pressure. The residue was purified by flash column chromatography eluting with ethyl acetate:isohexane (1:1) to give the title compound as a colourless solid (0.84 g).

MS (ESI) 369 (M+H)⁺

$^1$H NMR δ (CDCl$_3$) 8.17 (1H, d), 7.75 (1H, s), 7.35 (1H, dd), 6.91 (1H, d), 4.58 (1H, tt), 3.81-3.71 (2H, m), 3.29 (2H, ddd), 3.00 (3H, d), 2.08-1.98 (2H m), 1.48 (9H, s).

Preparation 30 tert-Butyl 4-[2-(aminocarbonyl)-4-chlorophenoxy]piperidine-1-carboxylate

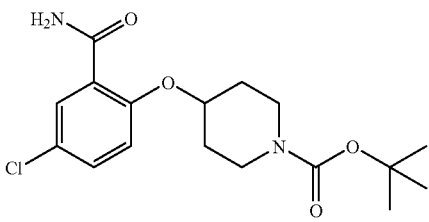

Prepared as described in Preparation 29 using aqueous ammonia.
MS (ESI) 355 (M+H)$^+$
$^1$H NMR δ (CDCl$_3$) 8.18 (1H, d), 7.67-7.61 (1H, m), 7.40 (1H, dd), 6.94 (1H, d) 5.83-5.76 (1H, m), 4.61 (1H, m), 3.84-3.76 (2H, m), 3.26 (2H, ddd), 2.09-2.01 (2H, m), 1.82-1.73 (2H, m), 1.47 (9H, s).

Preparation 31

Methyl 2-({1-[(2R)-3-amino-2-hydroxypropyl]piperidin-4-yl}oxy)-5-chlorobenzoate

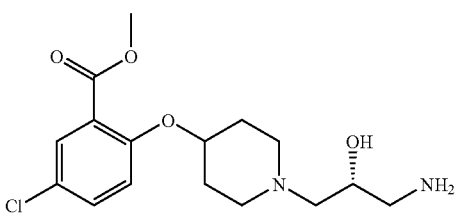

Prepared as described in Preparation 24, Step 2 from tert-butyl 4-[4-chloro-2-(methoxycarbonyl)phenoxy]piperidine-1-carboxylate.
MS (ESI) 343 (M+H)$^+$
$^1$H NMR δ (CDCl$_3$) 7.75 (1H, d), 7.37 (1H, dd), 6.92 (1H, d), 4.46-4.39 (1H, m), 3.89 (3H, s), 3.72-3.66 (1H, m), 2.93-2.87 (1H, m), 2.81 (1H, dd), 2.69-2.55 (2H, m), 2.63 (1H, dd), 2.43-2.31 (3H, m), 2.00-1.84 (−2H, m), 1.67-1.46 (2H, m).

Preparation 32

2-({1-[(2R)-3-Amino-2-hydroxypropyl]piperidin-4-yl}oxy)-5-chloro-N-methylbenzamide

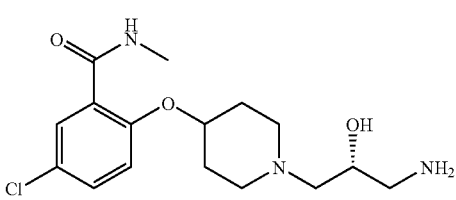

Prepared as described in Preparation 24, Step 2 from 4-(4-chloro-2-methylcarbamoyl-phenoxy)-piperidine-1-carboxylic acid tert-butyl ester.

MS (ESI) 342 (M+H)$^+$
$^1$H NMR δ (CDCl$_3$) 8.18 (1H, d), 7.88 (1H, s), 7.34 (1H, dd), 6.91 (1H, d), 4.54-4.48 (1H, m), 3.73-3.67 (1H, m), 3.01 (3H, d), 2.89-2.83 (1H, m), 2.83 (1H, dd) 2.68-2.56 (2H, m), 2.63 (1H, dd), 2.44 (1H, dd), 2.39-2.33 (1H, m), 2.34 (1H, dd), 2.13-2.03 (2H, m), 1.94-1.83 (2H, m).

Preparation 33

2-({1-[(2R)-3-Amino-2-hydroxypropyl]piperidin-4-yl}oxy)-5-chlorobenzamide

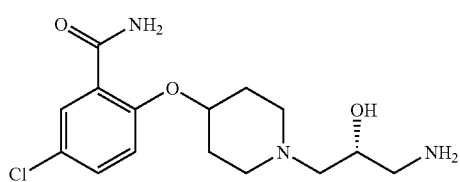

Prepared as described in Preparation 24, Step 2 from tert-butyl 4-[2-(aminocarbonyl)-4-chlorophenoxy]piperidine-1-carboxylate.
MS (ESI) 328 (M+H)$^+$
$^1$H NMR δ (CDCl$_3$) 8.19 (1H, d), 7.75 (1H, s), 7.39 (1H, dd), 6.93 (1H, d), 5.85 (1H, s), 4.56-4.48 (1H, m), 3.73-3.67 (1H, m), 2.93-2.86 (1H, m), 2.83 (1H, dd), 2.73-2.66 (1H, m), 2.63 (1H, dd), 2.61-2.54 (1H, m), 2.44 (1H, dd), 2.37-2.30 (1H, m), 2.35 (1H, dd), 2.15-2.05 (2H, m), 1.90 (2H, dtd).

Preparation 34

Tert-Butyl 4-{3,4-dichloro-2-[(cyclopropylamino)carbonyl]phenoxy}piperidine-1-carboxylate

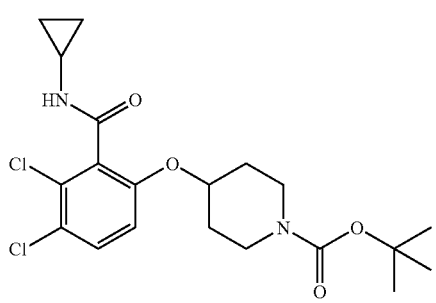

A solution of tert-butyl 4-[3,4-dichloro-2-(1H-imidazol-1-ylcarbonyl)phenoxy]piperidine-1-carboxylate (described in Preparation 11 step 1) (2.0 g, 4.5 mmol) in cyclopropylamine (12 ml) was heated at 50° C. for 14 h. The solution was concentrated in vacuo then partitioned between ethyl acetate and 1N aqueous hydrochloric acid. The organics were dried over magnesium sulfate and concentrated in vacuo. Crystallization from dichloromethane:isohexane gave the title compound as a white solid (0.64 g).
MS (ESI) 429/431 (M+H)$^+$
$^1$H NMR δ (DMSO) 8.46 (1H, d), 7.56 (1H, d), 7.17 (1H, d), 4.68 (1H, m), 3.42-3.27 (4H, m), 2.74 (1H, m), 1.78 (2H, m), 1.55 (2H, m), 0.68 (2H, m), 0.44 (2H, m).

Preparation 35

6-{[1-(3-Amino-2-hydroxypropyl)piperidin-4-yl]oxy}-2,3-dichloro-N-cyclopropylbenzamide

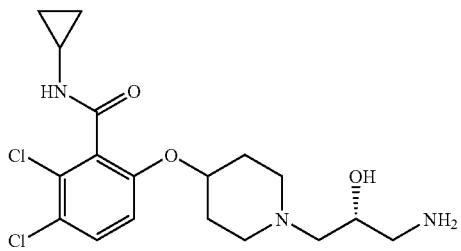

Prepared as described in Preparation 24, Step 2 following Preparation 34.

MS (ESI) 402 (M+H)$^+$ $^1$H NMR δ (CDCl$_3$) 7.35 (1H, d), 6.78 (1H, d), 5.82 (1H, s), 4.40-4.33 (1H, m), 3.68 (1H, tt), 2.92-2.85 (2H, m), 2.85-2.77 (2H, m), 2.81 (1H, dd), 2.62 (1H, dd), 2.42-2.29 (3H, m), 2.00-1.89 (2H, m), 1.88-1.79 (2H, m), 0.89 (2H, td), 0.66-0.62 (2H, m).

Preparation 36

Tert-Butyl 4-(3,4-dichloro-2-(chlorosulfonyl)phenoxy]piperidine-1-carboxylate

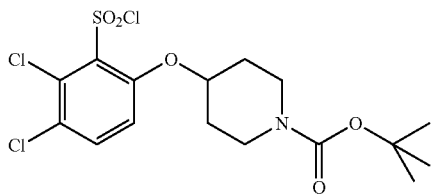

To a stirred solution of tert-butyl 4-[3,4-dichlorophenoxy]piperidine-1-carboxylate (10.0 g, 28.9 mmol) in dry THF (400 ml) at −70° C. under a nitrogen atmosphere was added dropwise sec-butyl lithium (26.7 ml, 1.3M in cyclohexane). The solution was stirred a further 15 min. at this temperature and then sulfur dioxide was bubbled through the mixture for 10 min. The cooling bath was removed and the mixture warmed to room temperature over 1 h. N-Chlorosuccinimide (4.63 g, 35 mmol) was added and the mixture stirred at room temperature for 72 h. The solution was concentrated in vacuo and partitioned between ethyl acetate and 1N aqueous hydrochloric acid. The organic extracts were dried (magnesium sulphate) and concentrated. Chromatography on silica (ethyl acetate: isohexane/1:3) gave the title compound (2.40 g).

MS (ESI) 445 (M+H)$^+$ $^1$H NMR δ (DMSO) 7.45 (1H, d), 7.03 (1H, d), 4.65 (1H, m), 3.59 (2H, m), 3.33 (3H, s), 1.66 (4H, m), 1.40 (9H, s).

Preparation 37

2,3-Dichloro-6-(piperidin-4-yloxy)benzenesulfonamide

tert-Butyl-4-[3,4-dichloro-2-(chlorosulfonyl)phenoxy]piperidine-1-carboxylate (0.80 g, 1.8 mmol) was dissolved in 7N ammonia in methanol and stirred at room temperature for 20 min. The solution was concentrated in vacuo and then azeotroped once with toluene. The residue was redissolved in dichloromethane:trifluoroacetic acid/1:1 (20 ml) and stirred at room temperature for 15 minutes. The solution was concentrated in vacuo, then partitioned between ethyl acetate and saturated aqueous sodium hydrogen carbonate solution. The aqueous was reextacted with ethyl acetate (4 times), and the combined organics dried over anhydrous potassium carbonate. Concentration in vacuo afforded the title compound as a white powder (0.54 g).

MS (ESI) 325/327 (M+H)$^+$ $^1$H NMR δ (DMSO) 7.74 (1H, d), 7.34 (1H, d), 4.66 (1H, m), 2.96 (2H, m), 2.55 (2H, m), 1.91 (2H, m), 1.63 (2H, m).

Preparation 38

2,3-Dichloro-N-methyl-6-(piperidin-4-yloxy)benzenesulfonamide

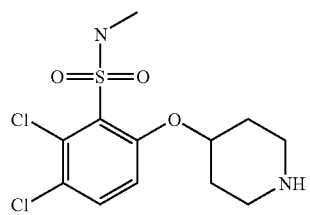

tert-Butyl 4-[3,4-dichloro-2-chlorosulfonyl)phenoxy]piperidine-1-carboxylate (0.70 g, 1.8 mmol) was dissolved in 40% aqueous methylamine in water (10 ml) and methanol (10 ml) and stirred at room temperature for 30 min. The solution was concentrated in vacuo and then azeotroped with toluene (4 times). The residue was redissolved in dichloromethane/trifluoroacetic acid (1:1) (20 ml) and stirred at room temperature for 15 minutes. The solution was concentrated in vacuo, then partitioned between ethyl acetate and saturated aqueous sodium hydrogen carbonate solution. The aqueous was reextracted with ethyl acetate (4 times), and the combined organics dried over anhydrous potassium carbonate. Concentration in vacuo afforded the title compound as a white powder (0.69 g).

MS (ESP) 339/341 (M+H)$^+$ $^1$H NMR δ (DMSO) 7.76 (1H, d), 7.35 (1H, d), 4.64 (1H, m), 2.96 (2H, m), 2.54 (3H, s), 2.54 (2H, m), 1.90 (2H, m), 1.61 (2H, m).

Preparation 39

2,3-Dichloro-N-cyclopropyl-6-(piperidin-4-yloxy)benzenesulfonamide

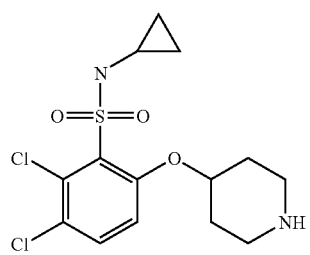

tert-Butyl 4-[3,4-dichloro-2-(chlorosulfonyl)phenoxy]piperidine-1-carboxylate (0.70 g, 1.8 mmol) was dissolved in cyclopropylamine (8 ml) and stirred at room temperature for 30 min. The solution was concentrated in in vacuo and then azeotroped with toluene (4 times). The residue was redissolved in dichloromethane: trifluoroacetic acid/1:1 (20 ml) and stirred at room temperature for 15 min. The solution was concentrated in vacuo, then partitioned between ethyl acetate and saturated aqueous sodium hydrogen carbonate solution. The aqueous was reextracted with ethyl acetate (4 times), and the combined organics dried over anhydrous potassium carbonate. Concentration in vacuo afforded the title compound as a white powder (0.70 g).

MS (ESI) 365/367 (M+H)+

¹H NMR δ (DMSO) 7.78 (1H, d), 7.36 (1H, d), 4.65 (1H, m), 2.97 (2H, m), 2.55 (2H, m), 2.27 (1H, m), 1.89 (2H, m), 1.63 (2H, m), 0.49 (4H, m);

Preparation 40

6-({1-[(2R)-3-Amino-2-hydroxypropyl]piperidin-4-yl}oxy)-2,3-dichlorobenzenesulfonamide

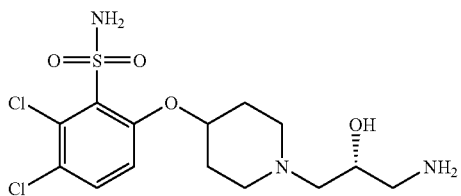

Prepared as described in Preparation 7 (Steps 2 and 3) following Preparation 37.

MS (ESI) 398/400 (M+H)+

Preparation 41

6-({1-(2R)-3-Amino-2-hydroxypropyl]piperidin-4-yl}oxy)-2,3-dichloro-N-methylbenzenesulfonamide

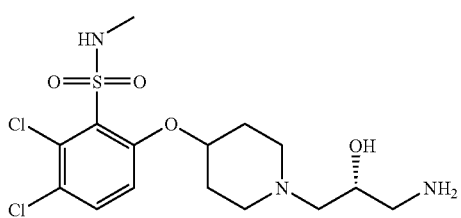

Prepared as described in Preparation 7 (Steps 2 and 3) following Preparation 38.

MS (ESI) 412/414 (M+H)+

Preparation 42

6-({1-[(2R)-3-Amino-2-hydroxypropyl]piperidin-4-yl}oxy)-2,3-dichloro-N-cyclopropylbenzenesulfonamide

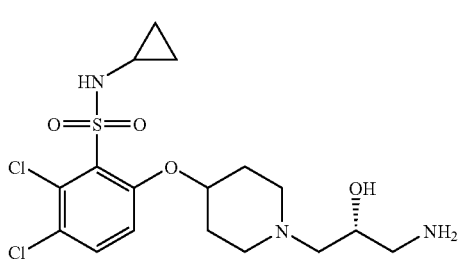

Prepared as described in Preparation 7 (Steps 2 and 3) following Preparation 39.

MS (ESI) 438/440 (M+H)+

Preparation 43

7-(Methylsulfonyl)-1-oxo-1,2-dihydroisoquinoline-4-carboxylic acid

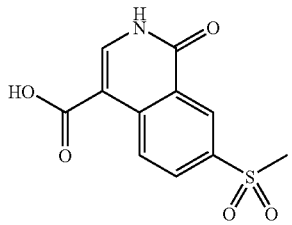

To a solution of sodium bicarbonate (500 mg) and sodium sulfite (353 mg) in 4 ml of water at 0° C. was added portionwise the 7-chlorosulfonyl-1-oxo-1,2-dihydroisoquinoline-4-carboxylic acid (see Preparation 16) (400 mg). The reaction was warmed to room temperature and then heated at 80° C. for 2 h. The reaction was cooled to 0° C. and acidified to pH-1 with concentrated hydrochloric acid. The suspension was diluted with 4 ml of water and stirred for 15 minutes at 0° C. then filtered under nitrogen. The solid was washed twice with water and was added to a degassed aqueous solution (3 ml) of potassium hydrogen carbonate (280 mg) at 45° C. Ethanol was then slowly added until the solution became slightly cloudy. Iodomethane (262 μl) was then added and the reaction refluxed (45-50° C.) for 5 h. The reaction was concentrated under vacuum, extracted with ethyl acetate and the aqueous phase acidified with concentrated hydrochloric acid. The reaction was stirred at 0° C. for 30 min. and the solid collected by filtration then recrystalised from acetone to yield the title compound as a white solid (325 mg).

MS (ESI) 266 (M−H)−

¹H NMR δ (DMSO) 12.97 (1H, bs), 12.19 (1H, d), 9.07 (1H, d), 8.70 (1H, d), 8.27 (1H, dd), 8.19 (1H, d), 3.30 (3H, s).

Preparation 44

6-(Methylsulphonyl)-1H-indole-3-carboxylic acid

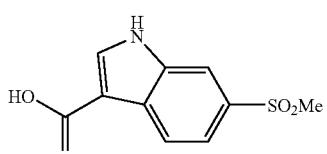

Prepared as described in Preparation 43 following Preparation 16 using indole-3-carboxylic acid.

MS (ES) 238 (M−H)−

¹H NMR δ (DMSO) 12.34 (1H, bd s), 12.29 (1H, v bd s), 8.31 (1H, s), 8.21 (1H, d), 8.03 (1H, d), 7.69 (1H, dd), 3.20 (1H, d).

Preparation 45

6-Fluoro-1-oxo-1,2-dihydroisoquinoline-4-carboxylic acid

Prepared following literature procedures: *Liebigs Annalen der Chemie*, 1981, 5, 819-27 and *Chemical & Pharmaceutical Bulletin*, 1983, 31, 1277-82.

Step 1: Dimethyl [5-fluoro-2-methoxycarbonyl)phenyl]malonate

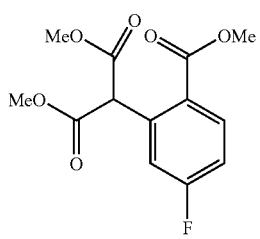

(Prepared according to U.S. Pat. No. 5,189,168)

To a rapidly stirred suspension of 2-bromo-4-fluorobenzoic acid (4.5 g) and copper(I) bromide (175 mg) in 25 ml of dimethylmalonate at 0° C. was added portionwise sodium hydride (60% in mineral oil, 1.3 g). After 10 min., the reaction warmed to room temperature and stirred for 30 minutes at room temperature then heated at 70° C. for 2 h. The solidified reaction was then diluted with water (80 ml) and was extracted with diethyl ether (3×50 ml). The aqueous layer was acidified with concentrated hydrochloric acid and extracted with ethyl acetate (3×100). The combined organic layers were dried over magnesium sulfate, filtered, concentrated under vacuum and the crude material recrystallised from diethyl ether/iso-hexane to yield the sub-title compound as a white solid (1.9 g).

$^1$H NMR δ (DMSO) 13.36 (1-H, bs), 8.05 (1H, dd), 7.35 (1H, ddd), 7.14 (1-H, dd), 5.08 (1H, s), 3.70 (6H, s).

Step 2: 2-(Carboxymethyl)-4-fluorobenzoic acid

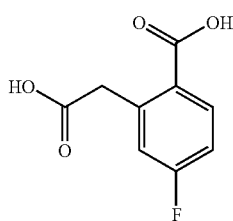

A suspension of dimethyl [5-fluoro-2-(methoxycarbonyl)phenyl]malonate (1.80 g) in concentrated hydrochloric acid (25 ml) was heated at 110° C. for 48 h. The reaction was cooled and the subtitle compound collected as a white solid by filtration (1.0 g).

MS (ESI) 197 (M-H)$^-$ $^1$H NMR δ (DMSO) 7.97 (1H, dd), 7.24 (1H, dd), 7.20 (1H, dd), 3.96 (2H, s).

Step 3: (4Z)-6-Fluoro (methoxymethylene)-1H-isochromene-1,3(4)-dione

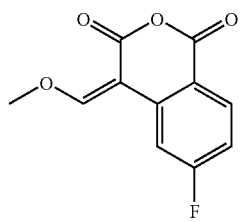

2-(Carboxymethyl)-4-fluorobenzoic acid (1.40 g) in a mixture of acetic acid (3 ml) and trimethylorthoformate (1 ml) was heated at 110° C. for 3 h. During this time the methyl acetate generated was distilled off. When finished, the reaction was cooled to 0° C. The white solid was collected by filtration and was washed with cold water and methanol (1.32 g).

MS (ESI) 207 (M-Me)$^-$

Step 4: Methyl 6-fluoro-1-oxo-1H-isochromene-4-carboxylate

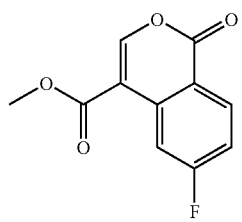

To a suspension of (4Z)-6-fluoro-4-(methoxymethylene)-1H-isochromene-1,3(4H)-dione (1.30 g) in methanol (20 ml) was slowly added sulfuric acid (1.5 ml). The mixture was heated at 40-50° C. for 3 h. As the reaction proceeded the sub-title compound crystallized out. The reaction was cooled to room temperature and a white solid was collected by filtration and washed with cold methanol.

MS (ESI) 222 (M+H)$^+$ $^1$H NMR δ (DMSO) 8.49 (1H, s), 8.30 (1H, dd), 8.25 (1H, dd), 7.56 (1H, td), 3.87 (3H, s).

Step 5: Methyl 6-fluoro-1-oxo-1,2-dihydroisoquinoline-4-carboxylate

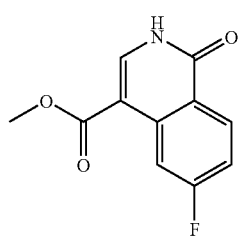

A mixture of methyl 6-fluoro-1-oxo-1H-isochromene-4-carboxylate (1.53 g) and ammonium acetate (2.5 g) in 4 ml of glacial acetic acid was heated at 80° C. for 16 h. The reaction was cooled to 40° C., diluted with 8 ml of water and the solid collected by filtration (1.38 g).

MS (ESI) 220 (M–H)⁻
¹H NMR δ (DMSO) 12.00 (1H, s), 8.46 (1H, dd), 8.32 (1H, dd), 8.10 (1H, s), 7.44 (1H, td), 3.83 (3H, s).

Step 6: 6-Fluoro-1-oxo-1,2-dihydroisoquinoline-4-carboxylic acid

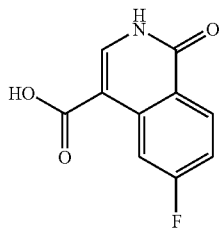

To a solution of methyl 6-fluoro-1-oxo-1,2-dihydroisoquinoline-4-carboxylate (1.3 g) in methanol (3 ml) was added a aqueous solution (3 ml) of sodium hydroxide (1 g) and the reaction mixture was heated at 80° C. for 3 h. The reaction was cooled to 20° C. and carefully acidified with concentrated hydrochloric acid. The white precipitate was isolated by filtration, washed with water and methanol to yield the title compound (1.16 g)

MS (ESI) 206 (M–H)⁻
¹H NMR δ (DMSO) 12.85 (1H, s), 11.91 (1H, d), 8.58 (1H, dd), 8.31 (1H, dd), 8.09 (1H, d), 7.41 (1H, td).

Preparation 46

7-Fluoro-1-oxo-1,2-dihydroisoquinoline-4-carboxylic acid

Prepared following literature procedures: *Liebigs Annalen der Chemie,* 1981, 5, 819-27 and *Chemical & Pharmaceutical Bulletin,* 1983, 31, 1277-82.

Step 1: Dimethyl [4-fluoro-2-(methoxycarbonyl)phenyl]malonate

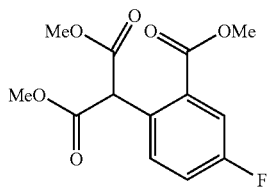

Prepared as described in Preparation 45, Step 1 using 2-bromo-5-fluorobenzoic acid.
MS (ESI) 269/237 (M–H)⁻
¹H NMR δ (DMSO) 7.70 (1H, dd), 7.49 (1H, td), 7.39 (1H, dd), 5.71 (1H, s), 3.68 (6H, s).

Step 2: 2-(Carboxymethyl)-5-fluorobenzoic acid

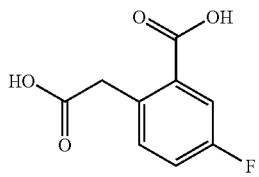

Prepared as described in Preparation 45, Step 2 using dimethyl (4-fluoro-2-(methoxycarbonyl)phenyl]malonate.

MS (ESI) 197 (M–H)⁻
¹H NMR δ (DMSO) 7.81-7.74 (1H, m), 7.62 (1H, dd), 7.41-7.35 (1H, m), 3.92 (2H, s).

Step 3: Methyl 7-fluoro-1-oxo-1-H-isochromene-4-carboxylate

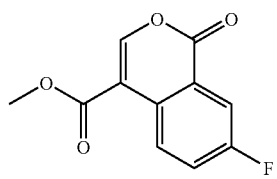

Prepared as described in Preparation 45, Steps 3 and 4 using 2-carboxymethyl)-5-fluorobenzoic acid.
MS (ESI) 223 (M+H)⁺
¹H NMR δ (DMSO) 8.60 (1H, dd), 8.42 (1H, s), 7.95 (1H, dd), 7.86 (1H, ddd), 3.87 (3H, s).

Step 4: Methyl 7-fluoro-1-oxo-1,2-dihydroisoquinoline-4-carboxylate

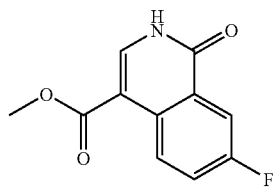

Prepared as described in Preparation 45, Step 5 using methyl 7-fluoro-1-oxo-1H-isochromene-4-carboxylate.
MS (ESI) 221 (M–H)⁻
¹H NMR δ (DMSO) 12.04 (1H, s), 8.82 (1H, dd), 8.03 (1H, s), 7.91 (1H, dd), 7.73 (1H, td), 3.83 (3H, s).

Step 5: 7-Fluoro-1-oxo-1,2-dihydroisoquinoline-4-carboxylic acid

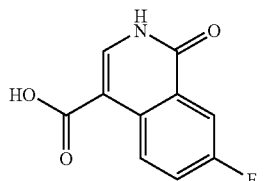

Prepared as described in Preparation 45, Step 6 using, methyl 7-fluoro-1-oxo-1,2-dihydroisoquinoline-4-carboxylate.
MS (ESI) 206 (M–H)⁻
¹H NMR δ (DMSO) 12.81 (1H, s), 12.00 (1H, d), 8.93 (1H, dd), 8.02 (1H, d), 7.90 (1H, dd), 7.71 (1H, td).

Preparation 47

6-(Methylsulfonyl)-1-oxo-1,2-dihydroisoquinoline-4-carboxylic acid

Prepared following literature procedures: *Liebigs Annalen der Chemie*, 1981, 5, 819-27 and *Chemical & Pharmaceutical Bulletin*, 1983, 31, 1277-82.

Step 1: 2-[2-Ethoxy-1-(ethoxycarbonyl)-2-oxoethyl] 44-methylsulfonyl)benzoic acid

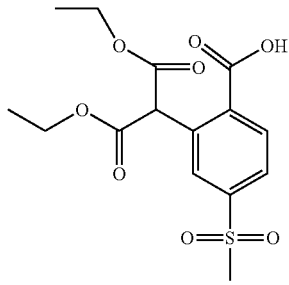

Prepared following literature procedure: *Journal of Organic Chemistry*, 1998, 63, 4116-4119.

To a very rapidly stirred suspension of 2-chloro-4-(methylsulfonyl)benzoic acid (10.0 g) and copper(I) bromide (0.1 g) in 50 ml of diethylmalonate at 20° C. was added portionwise sodium ethoxide (10.0 g). The reaction was stirred for 30 min. at room temperature then heated at 90° C. for 36 h. The slurry was diluted with water (200 ml), aqueous ammonia was added (3 ml) and the mixture extracted with diethyl ether (3×100 ml). The aqueous layer was acidified with concentrated hydrochloric acid and extracted with ethyl acetate (3×100 ml). The combined organic layers were dried over magnesium sulfate, filtered and concentrated under vacuum.

MS (ESI) 357/311 (M–H)⁻

¹H NMR δ (CD₃OD) 8.28 (1H, d), 8.06 (1H, dd), 7.99 (1H, d), 5.78 (1H, s), 4.20 (4H, q), 3.19 (3H, s), 1.28 (6H, t).

Step 2: 2-(Carboxymethyl)-4-(methylsulfonyl)benzoic acid

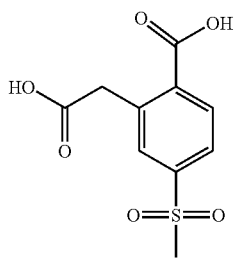

Prepared following literature procedure: *Journal of Organic Chemistry*, 1998, 63, 4116-4119.

The crude material of Step 1 was dissolved in methanol (200 ml) and a solution (200 ml) of sodium hydroxide (13 g) slowly added. The reaction was stirred at room temperature for 3 h. The methanol was removed under vacuum. The aqueous layer was extracted with diethyl ether (3×100 ml), acidified with concentrated hydrochloric acid, saturated with sodium chloride and extracted with ethyl acetate (3×100 ml). The combined organic layers were dried over magnesium sulfate, filtered, concentrated to one third volume and heated at 65° C. for 3 h to complete decarboxylation. A solid formed which was collected by filtration (7.1 g).

MS (ESI) 257/213 (M–H)⁻

¹H NMR δ (DMSO) 8.10 (1H, d), 7.95 (1H, d), 7.93 (1H, dd), 4.07 (2H, s), 3.28 (3H, s).

Step 3: (4Z)-4-(methoxymethylene)-6-(methylsulfonyl)-1H-isochromene-1,3(4H)-dione

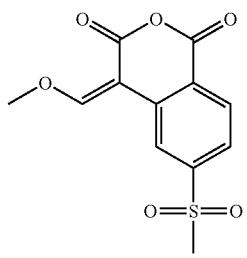

Prepared as described in Preparation 45, Step 3 using 2-(carboxymethyl)-4-(methylsulfonyl)benzoic acid.

MS (ESI) 267 (M–Me)⁻

¹H NMR δ (DMSO) 8.68 (1H, d), 8.32 (1H, d), 8.31 (1H, s), 7.98 (1H, dd), 4.36 (3H, s), 3.46 (3H, s).

Step 4: Methyl 6-methylsulfonyl)-1-oxo-1H-isochromene-4-carboxylate

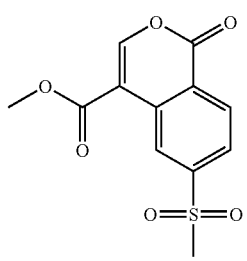

Prepared as described in Preparation 45, Step 4 using (4Z)-4-(methoxymethylene)-6-(methylsulfonyl)-1H-isochromene-1,3(4H)-dione.

¹H NMR δ (DMSO) 9.08 (1H, d), 8.56 (1H, s), 8.44 (1H, d), 8.18 (1H, dd), 3.89 (3H, s), 3.34 (3H, s).

Step 5: Methyl 6-(methylsulfonyl) 1-oxo-1,2-dihydroisoquinoline-4-carboxylate

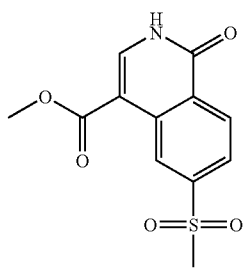

Prepared as described in Preparation 45, Step 5 using methyl 6-(methylsulfonyl)-1-oxo-1H-isochromene-4-carboxylate.

MS (ESI) 280 (M−H)⁻
¹H NMR δ (DMSO) 12.23 (1H, s), 9.35 (1H, d), 8.47 (1H, d), 8.17 (1H, s), 8.06 (1H, dd), 3.86 (3H, s), 3.78 (3H, s).

Step 6: 6-(Methylsulfonyl)-1-oxo-1,2-dihydroisoquinoline-4-carboxylic acid

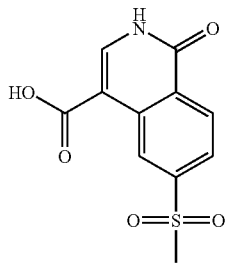

Prepared as described in Preparation 45, Step 6 using methyl 6-methylsulfonyl)-1-oxo-1,2-dihydroisoquinoline-4-carboxylate.
MS (ESI) 266 (M−H)⁻
¹H NMR δ (DMSO) 12.99 (1H, s), 12.14 (1H, d), 9.45 (1H, d), 8.46 (1H, d), 8.15 (1H, d), 8.04 (1H, dd), 3.30 (3H, s).

Preparation 48

(2R)-1-Amino-3-{4-[3,4-dichloro-2-methylsulfonyl)phenoxy]piperidin-1-yl}propan-2-ol

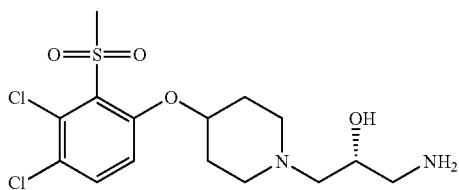

Step 1: Tert-butyl 4-[3,4-dichloro-2-(methylsulfonyl)phenoxy]piperidine-1-carboxylate

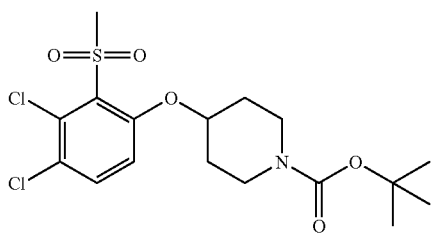

To a stirred solution of tert-butyl 4-[3,4-dichlorophenoxy]piperidine-1-carboxylate (10.0 g, 28.9 mmol) in dry THF (400 ml) at −70° C. under a nitrogen atmosphere was added dropwise sec-butyl lithium (26.7 ml, 1.3M in cyclohexane). The solution was stirred a further 15 min. at this temperature and then was treated with dimethyldisulfide (3.9 ml, 43 mmol). The solution was stirred at this temperature for 30 min. and then the cooling bath removed and the mixture stirred vigorously whilst warming to −30° C. over 30 mm. Saturated aqueous ammonium chloride solution (5 ml) was added and the mixture concentrated to ca 30 ml volume and partitioned between water and ethyl acetate. The organic extracts were dried over magnesium sulphate and concentrated. Treatment of the crude residue with meta-chloroperbenzoic acid (13.3 g, 57-86%) in dichloromethane (200 ml) at room temperature for 14 h gave the crude sulfone. The solution was shaken with sodium metabisulfite solution, then the organics dried over magnesium sulfate and concentrated in vacuo. Chromatography on silica (ethyl acetate: isohexane) gave the subtitle compound (0.65 g).
MS (ESI) 424/426 (M+H)⁺
¹H NMR δ (DMSO) 7.88 (1H, d), 7.42 (1H, d), 4.92 (1H, m), 3.52 (2H, m), 3.32 (3H, s), 3.36-3.27 (2H, m), 1.90 (2H, m), 1.69 (2H, m), 1.40 (9H, s).

Step 2: (2R)-1-Amino-3-{4-[3,4-dichloro-2-(methylsulfonyl)phenoxy]piperidin-1-yl}propan-2-ol Prepared as described in Preparation 24, Step 2 from tert-butyl 4-[3,4-dichloro-2-(methylsulfonyl)phenoxy]piperidine-1-carboxylate.
MS (ESI) 397/399 (M+H)⁺
¹H NMR δ (CDCl₃) 7.66 (1H, d), 6.94 (1H, d), 4.60-4.53 (1H, m), 3.73-3.67 (1H, m), 3.33 (3H, s), 3.02-2.96 (1H, m), 2.81 (1H, dd), 2.79-2.73 (1H, m), 2.64-2.56 (1H, m), 2.63 (1H, dd), 2.43-2.32 (3H, m), 2.11-1.91 (4H, m).

Preparation 49

8-Fluoro-1-oxo-1,2-dihydroisoquinoline-4-carboxylic acid

Step 1: 2-(Carboxymethyl)-6-fluorobenzoic acid

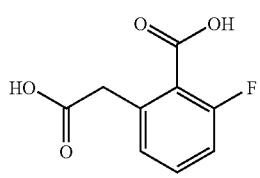

Prepared as described in Preparation 45, Step 1 and 2 using 2-bromo-6-fluorobenzoic acid.
MS (ESI) 197 (M−H)⁻
¹H NMR δ (DMSO) 7.46 (1H, td), 7.20 (1H, dd), 7.18 (1H, d), 3.77 (2H, s).

Step 2: (4Z)-8-Fluoro-4-(methoxymethylene)-1H-isochromene-1,3(4H)-dione

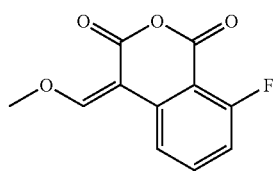

Prepared as described in Preparation 45, Step 3 using 2-(carboxymethyl)-6-fluorobenzoic acid.
MS (ESI) 207 (M−Me)⁻

Step 3: Methyl 8-fluoro-1-oxo-1H-isochromene-4-carboxylate

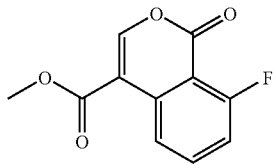

Prepared as described in Preparation 45, Step 4 using (4Z)-8-fluoro-4-(methoxymethylene)-1H-isochromene-1,3(4)-dione.

MS (ESI) 222 (M+H)$^+$ $^1$H NMR δ (DMSO) 8.42 (1H, s), 8.34 (1H, d), 7.96 (1H, td), 7.50 (1H, dd), 3.86 (2H, s).

Step 4: Methyl 8-fluoro-1-oxo-1,2-dihydroisoquoline-4-carboxylate

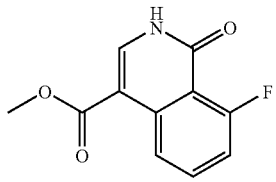

Prepared as described in Preparation 45, Step 5 using methyl 8-fluoro-1-oxo-1H-isochromene-4-carboxylate.

MS (ESI) 220 (M−H)$^−$ $^1$H NMR δ (DMSO) 11.86 (1H, s), 8.57 (1H, d), 8.03 (1H, s), 7.80 (1H, td), 7.30 (1H, dd), 3.82 (3H, s).

Step 5: 8-Fluoro-1-oxo-1,2-dihydroisoquinoline-4-carboxylic acid

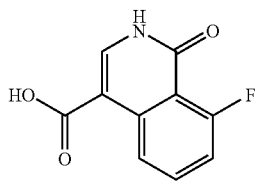

Prepared as described in Preparation 45, Step 6 using methyl 8-fluoro-1-oxo-1,2-dihydroisoquinoline-4-carboxylate.

MS (ESI) 206 (M−H)$^−$ $^1$H NMR δ (DMSO) 12.75 (19H, s), 11.76 (19H, d), 8.69 (2H, d), 8.02 (23H, d 7.78 (24H, td), 7.29 (22H, dd).

EXAMPLE 1

N-{(2-R)-3-[4-(3,4-Dichlorophenoxy)piperidin-1-yl]-2-hydroxypropyl}-2-(methylsulfonyl)benzamide

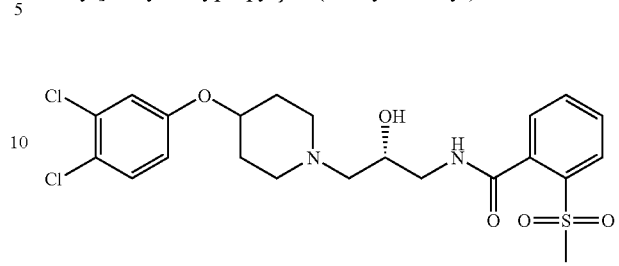

A mixture of 2-(methylsulphonyl)benzoic acid (0.063 g), (2R)-1-amino-3-[4-(3,4-dichlorophenoxy)piperidin-1-yl]propan-2-ol (0.1 g) and N,N-diisopropylethylamine (0.1 ml) in dry dimethylformamide (3 ml) was cooled to 0° C. with stirring. 2-(1H-9-Azabenzotriazole-1-yl)-1,1,3,3-tetramethyluronium hexafluorophosphate (0.13 g) was added and the mixture was stirred at 0° C. for 1-2 h. Saturated sodium bicarbonate solution (10 ml) was added. The mixture was extracted with ethyl acetate. The organic layer was separated and washed with brine and dried over sodium sulphate. The mixture was filtered and the solvent was evaporated. The resulting oil was purified by normal phase chromatography using methanol/dichloromethane as eluent, and by reverse phase HPLC using acetonitrile and 0.1% aqueous ammonium acetate as eluent, to give the title compound as a white solid (0.055 g).

MS (APCI) 501/503 (M+H)$^+$ $^1$H NMR δ (DMSO) 8.57 (1H, t), 7.96 (1H, dd), 7.78 (1H, td), 7.69 (1H, td), 7.57 (1H, dd), 7.49 (1H, d), 7.25 (1H, d), 6.98 (1H, dd), 4.48-4.37 (1H, m), 3.85-3.74 (1H, m), 3.40-3.25 (1H, m), 3.37 (3H, s), 3.26-3.13 (1H, m), 2.83-2.69 (2H, m), 2.37-2.26 (3H, m), 1.95-1.84 (2H, m), 1.65-1.50 (2H, m).

EXAMPLE 2

N-{(2R)-3-[4-(3,4-Dichlorophenoxy)piperidin-1-yl]-2-hydroxypropyl}-4-(methylsulfonyl)benzamide

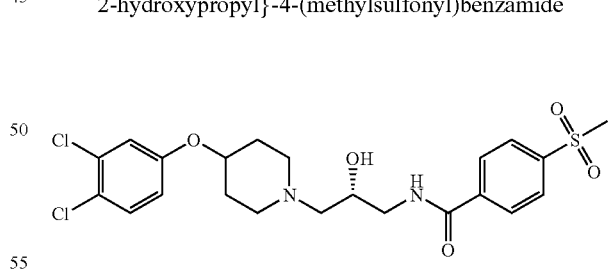

Prepared as described in Example 1 from (2R)-1-amino-3-[4-(3,4-dichlorophenoxy)piperidin-1-yl]propan-2-ol (0.1 g) and 4-(methylsulphonyl)benzoic acid (0.063 g). Title compound obtained as white solid (0.038 g).

MS (APCI) 501/503 (M+H)$^+$ $^1$H NMR δ (DMSO) 8.69 (1H, t), 8.05 (4H, dd), 7.9 (1H, d), 7.25 (1H d), 6.98 (1H, dd), 4.76 (1H, brs), 4.43 (1H, mult), 3.86-3.78 (1H, m), 3.43 (1H, dt), 3.26 (3H, s), 3.20 (1H, dd), 2.79-2.67 (2H, m), 2.41-2.24 (4H, m), 1.95-1.85 (2H, m), 1.66-1.54 (2H, m).

EXAMPLE 3

2-Chloro-N-{(2R)-3-[4-(3,4-dichlorophenoxy)piperidin-1-yl]-2-hydroxypropyl}-4-(methylsulfonyl)benzamide

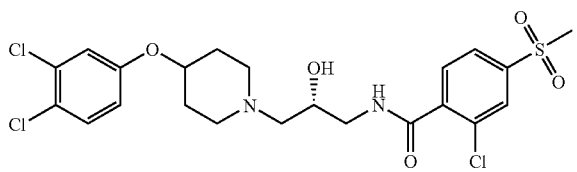

Prepared as described in Example 1 using (2R)-1-amino-3-[4-(3,4-dichlorophenoxy)piperidin-1-yl]propan-2-ol (0.1 g) and 3-(methylsulfonyl)benzoic acid (0.074 g). Title compound obtained as white solid (0.033 g).

MS (APCI) 535/537 (M+H)$^+$ $^1$H NMR δ (DMSO) 8.60 (1H, t), 8.03 (1H, d), 7.93 (1H, dd), 7.70 (1H, d), 7.49 (1H, d), 7.25 (1H, d), 6.98 (1H, dd), 4.70 (1H, brs), 4.47-4.39 (1H, m), 3.82-3.74 (1H, m), 3.41-3.31 (1H, m), 3.29 (3H, s), 3.23-3.15 (1H, m), 2.80-2.69 (2H, m), 2.44-2.25 (4H, m), 1.96-1.86 (2H, m), 1.65-1.54 (2H, m).

EXAMPLE 4

4-Amino-N-{(2R)-3-[4-(3,4-dichlorophenoxy)piperidin-1-yl]-2-hydroxypropyl}-3-methoxybenzamide

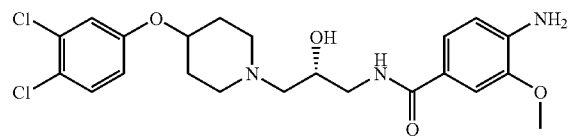

Prepared as described in Example 1 from (2R)-1-amino-3-[4-(3,4-dichlorophenoxy)piperidin-1-yl]propan-2-ol (0.1 g) and 4-amino-3-methoxybenzoic acid (0.052 g). Title compound obtained as white solid (0.053 g).

MS (APCI) 468/470 (M+H)$^+$ $^1$H NMR δ (DMSO) 8.05 (1H, t), 7.49 (1H, d), 7.31-7.27 (2H, m), 7.25 (1H, d) 6.98 (1H, dd), 6.60 (1H, d), 5.23 (2H, s), 4.74 (1H, brs), 4.47-4.38 (1H, m), 3.80 (3H, s) 3.81-3.73 (1H, m), 3.38-3.30 (1H, m), 3.18-3.09 (1H, m), 2.80-2.65 (2H, m), 2.36 (2H, dd), 2.32-2.22 (2H, m), 1.95-1.86 (2H, m), 1.66-1.54 (2H, m).

EXAMPLE 5

N-{(2R)-3-[4-(3,4-Dichlorophenoxy)piperidin-1-yl]-2-hydroxypropyl}-3-(methylsulfonyl)benzamide

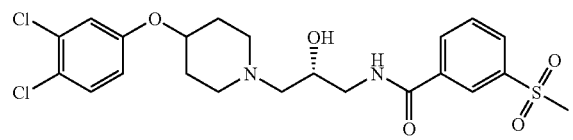

Prepared as described in Example 1 from (2R)-1-amino-3-[4-(3,4-dichlorophenoxy)piperidin-1-yl]propan-2-ol (0.1 g) and 3-(methylsulfonyl)benzoic acid (0.063 g). Title compound obtained as white solid (0.017 g).

MS (APCI) 501/503 (M+H)$^+$ $^1$H NMR δ (DMSO) 8.74 (1H, t), 8.39 (1H, t), 8.18 (1H, dt), 8.07 (1H, ddt), 7.76 (1H, t), 7.49 (1H, d), 7.25 (1H, d), 6.98 (1H, dd), 4.77 (1H, brs), 4.47-4.39 (1H, m), 3.86-3.78 (1H, m), 3.45 (1H, dt), 3.26 (3H, s), 3.24-3.14 (1H, m), 2.80-2.66 (2H, m), 2.41-2.24 (4H, m), 1.95-1.86 (2H, m), 1.65-1.54 (2H, m).

EXAMPLE 6

N-{(2R)-3-[4-(3,4-Dichlorophenoxy)piperidin-1-yl]-2-hydroxypropyl}-5-(methylsulfonyl)thiophene-2-carboxamide

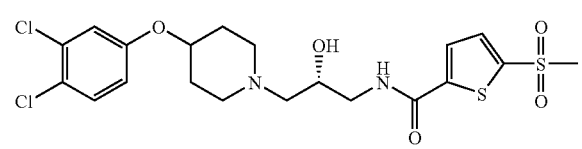

Prepared as described in Example 1 from (2R)-1-amino-3-[4-(3,4-dichlorophenoxy)piperidin-1-yl]propan-2-ol (0.1 g) and 5-(methylsulfonyl)thiophene-2-carboxylic acid (0.065 g). Title compound obtained as white solid (0.039 g).

MS (APCI) 507/509 (M+H)$^+$ $^1$H NMR δ (DMSO) 8.85 (1H, t), 7.84 (2H, dd), 7.49 (1H, d), 7.26 (1H, d), 6.98 (1H, dd), 4.80 (1H, brs), 4.47-4.39 (1H, m), 3.83-3.75 (1H, m), 3.45-3.38 (1H, m), 3.38 (3H, s), 3.18-3.09 (1H, m), 2.79-2.66 (2H, m), 2.37-2.22 (4H, m), 1.95-1.85 (2H, m), 1.65-1.53 (2H, m).

EXAMPLE 7

N-{(2R)-3-[4-(3,4-dichlorophenoxy)piperidin-1-yl]-2-hydroxypropyl}quinoline-6-carboxamide

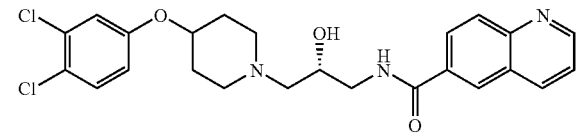

Prepared as described in Example from (2R)-1-amino-3-[4-(3,4-dichlorophenoxy)piperidin-1-yl]propan-2-ol (0.1 g) and quinoline-6-carboxylic acid (0.054 g). Title compound obtained as white solid (0.032 g).

MS (APCI) 474/476 (M+H)$^+$ $^1$H NMR δ (DMSO) 8.98 (1H, dd), 8.68 (1H, t), 8.52 (1H, d), 8.47 (1H, dd), 8.19 (1H, dd), 8.08 (1H, d), 7.61 (1H, dd), 7.49 (1H, d), 7.24 (1H, d), 6.97 (1H, dd), 4.78 (1H, brs), 4.48-4.39 (1H, m), 3.90-3.82 (1H, m), 3.46 (1H, dt), 3.31-3.23 (1H, m), 2.82-2.70 (2H, m), 2.45-2.25 (4H, m), 1.96-1.87 (2H, m), 1.67-1.55 (2H, m).

EXAMPLE 8

N-{(2R)-3-[4-(3,4-Dichlorophenoxy)piperidin-1-yl]-2-hydroxypropyl}-2-oxo-2,3-dihydro-1,3-benzothiazole-6-carboxamide acetate salt

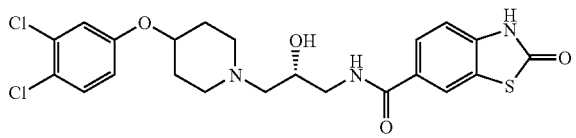

Prepared as described in Example 1 from (2R)-1-amino-3-[4-(3,4-dichlorophenoxy)piperidin-1-yl]propan-2-ol (0.1 g) and 2-oxo-2,3-dihydro-1,3-benzothiazole-6-carboxylic acid (0.061 g). Title compound obtained as acetate salt, a white solid (0.10 g).

MS (APCI) 496/498 (M+H)+

$^1$H NMR δ (DMSO) 8.36 (1H, t), 8.05 (1H, d), 7.78 (1H, dd), 7.49 (1H, d), 7.25 (1H, d), 7.15 (1H, d), 6.98 (1H, dd), 4.47-4.40 (1H, m), 3.80 (1H, quintet), 3.38 (1H, dt), 3.22-3.14 (1H, m), 2.80-2.67 (2H, m), 2.41-2.25 (4H, m), 1.95-1.86 (2H, m), 1.91 (3H, s), 1.66-1.54 (2H, m).

EXAMPLE 9

N-{(2R)-3-[4-(3,4-Dichlorophenoxy)piperidin-1-yl]-2-hydroxypropyl}-6-fluoroimidazo[1,2-a]pyridine-2-carboxamide

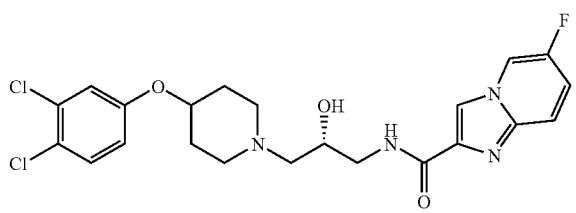

Prepared as described in Example 1 from (2R)-1-amino-3-[4-(3,4-dichlorophenoxy)piperidin-1-yl]propan-2-ol (0.1 g) and 6-fluoroimidazo[1,2-a]pyridine-2-carboxylic acid (0.056 g). Title compound obtained as white solid (0.076 g).

MS (APCI) 481/482 (M+H)+

$^1$H NMR δ (DMSO) 8.80-8.78 (1H, m), 8.63 (1H, t), 8.33 (1H, s), 7.68 (1H, dd), 7.50 (1H, d), 7.52-7.44 (1H, m), 7.28 (1H, d), 7.00 (1H, dd), 4.89 (1H, s), 4.52-4.44 (1H, m), 3.83-3.74 (1H, m), 3.44-3.28 (2H, m), 2.83-2.66 (2H, m), 2.44-2.23 (4H, m), 2.02-1.90 (2H, m), 1.82-1.72 (2H, m).

EXAMPLE 10

N-{(2R)-3-[4-(3,4-Dichlorophenoxy)piperidin-1-yl]-2-hydroxypropyl}-1-oxo-1,2-dihydroisoquinoline-4-carboxamide

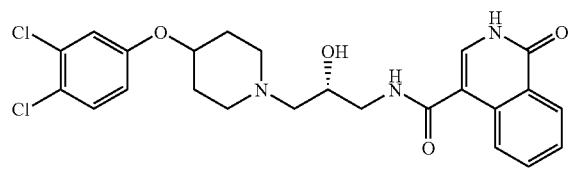

Prepared as described in Example 1 from (2R)-1-amino-3-[4-(3,4-dichlorophenoxy)piperidin-1-yl]propan-2-ol (0.1 g) and 1-oxo-1,2-dihydroisoquinoline-4-carboxylic acid (0.059 g). Title compound obtained as white solid (0.047 g).

MS (APCI) 490/492 (M+H)+

$^1$H NMR δ (DMSO) 11.59 (1H, d), 8.33 (1H, t), 8.22 (2H, dd), 7.73 (1H, t), 7.54-7.48 (3H, m), 7.26 (1H, d), 6.98 (1H, dd), 4.79 (1H, s), 4.48-4.40 (1H, m), 3.85-3.76 (1H, m), 3.43-3.31 (1H, m), 3.14 (1H, quintet), 2.83-2.69 (2H, m), 2.45-2.25 (4H, m), 1.96-1.87 (2H, m), 1.67-1.55 (2H, m).

EXAMPLE 11

N-{(2R)-3-[4-(3,4-Dichlorophenoxy)piperidin-1-yl]-2-hydroxypropyl}-1,3-benzothiazole-6-carboxamide

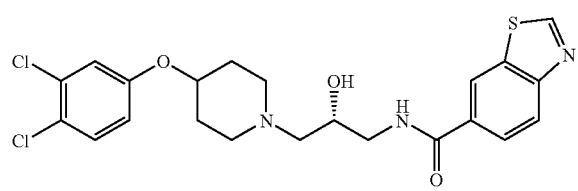

Prepared as described in Example 1 from (2R)-1-amino-3-[4-(3,4-dichlorophenoxy)piperidin-1-yl]propan-2-ol (0.1 g) and 1,3-benzothiazole-6-carboxylic acid (0.056 g). Title compound obtained as white solid (0.066 g).

MS (APCI) 480/482 (M+H)+

$^1$H NMR δ (DMSO) 9.54 (1H, s), 8.67 (1H, d), 8.60 (1H, t), 8.15 (1H, d), 8.02 (1H, dd), 7.49 (1H, d), 7.25 (1H, d), 6.98 (1H, dd), 4.78 (1H, brs), 4.47-4.39 (1H, m), 3.87-3.79 (1H, m), 3.44 (1H, dt), 3.23 (1H, quintet), 2.82-2.68 (2H, m), 2.40 (1H, dd), 2.37-2.23 (3H, m), 1.96-1.86 (2H, m), 1.66-1.54 (2H, m).

EXAMPLE 12

3-Cyano-N-{(2R)-3-[4-(3,4-dichlorophenoxy)piperidin-1-yl]-2-hydroxypropyl}benzamide

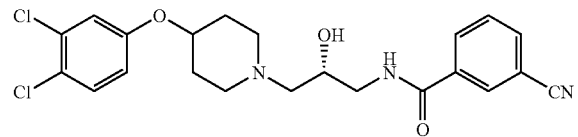

Prepared as described in Example 1 from (2R)-1-amino-3-[4-(3,4-dichlorophenoxy)piperidin-1-yl]propan-2-ol (0.2 g) and 3-cyanobenzoic acid (0.092 g). Title compound obtained as white solid (0.050 g).

MS (APCI) 448/450 (M+H)+

$^1$H NMR δ (CDCl$_3$) 8.10 (1H, s), 7.79 (1H, d), 7.58 (1H, t), 7.31 (1H, d), 7.00 (1H, d), 6.80 (1H, t), 6.75 (1H, dd), 4.38-4.25 (1H, m), 4.00-3.87 (1H, m), 3.81-3.68 (1H, m), 3.36 (1H, dt), 2.98-2.85 (1H, m), 2.75-2.63 (1H, m), 2.63-2.53 (1H, m), 2.48 (1H, dd), 2.37 (1H, d), 2.32 (2H, t), 2.07-1.90 (2H, m), 1.90-1.73 (2H, m).

EXAMPLE 13

N-{4-[4-(3,4-Dichlorophenoxy)piperidin-1-yl]-3-hydroxybutyl}-2-(methylsulfonyl)benzamide

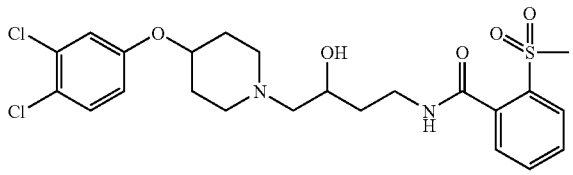

Prepared as described in Example 1 from 4-amino-1-[4-(3,4-dichlorophenoxy)piperidin-1-yl]butan-2-ol (0.26 g) and 2-(methylsulphonyl)benzoic acid (0.156 g). The title compound was obtained as a white solid (0.170 g).

MS (APCI) 515/517 (M+H)+

$^1$H NMR δ (CDCl$_3$) 8.09 (1H, dd), 7.65 (1H, dd), 7.59 (1H, td), 7.53 (1H, dd), 7.31 (1H, d), 6.99 (1H, d), 6.74 (1H, dd), 6.74 (1H, dd), 4.32-4.23 (1H, m), 3.92-3.83 (1H, m), 3.83-3.74 (1 Hz, m), 3.57-3.46 (1H, m), 3.37 (3H, s), 2.94-2.85 (1H, m), 2.60-2.50 (1H, m), 2.40 (1H, dd), 2.35 (1H, dd), 2.32-2.23 (1H, m), 2.01-1.89 (2H, m), 1.88-1.69 (2H, m), 1.67-1.55 (2H, m).

EXAMPLE 14

N-{4-[4-(3,4-Dichlorophenoxy)piperidin-1-yl]-3-hydroxybutyl}-2-oxo-2,3-dihydro-1,3-benzothiazole-6-carboxamide

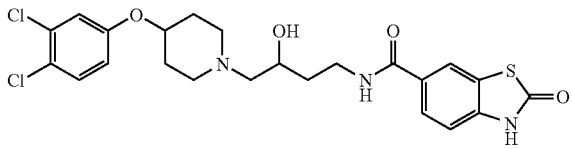

Prepared as described in Example 1 from 4-amino-1-[4-(3,4-dichlorophenoxy)piperidin-1-yl]butan-2-ol (0.26 g) and 2-oxo-2,3-dihydro-1,3-benzothiazole-6-carboxylic acid (0.152 g). Title compound obtained as a white solid (0.105 g).

MS (APCI) 510/512 (M+H)+

$^1$H NMR δ (CDCl$_3$) 7.88 (1H, d), 7.71 (1H, dd), 7.48-7.39 (1H, m), 7.31 (1H, d), 7.13 (1H, d), 7.00 (1H, d), 6.76 (1H, dd), 4.36-4.27 (1H, m), 3.93-3.83 (2H, m), 3.49-3.38 (1H, m), 2.97-2.87 (1H, m), 2.73-2.53 (2H, m), 2.46-2.32 (2H, m), 2.36-2.27 (1H, m), 2.06-1.91 (2H, m), 1.90-1.75 (3H, m), 1.66-1.53 (1H, m).

EXAMPLE 15

4-Amino-N-{4-[4-(3,4-dichlorophenoxy)piperidin-1-yl]-3-hydroxybutyl}-3-methoxybenzamide

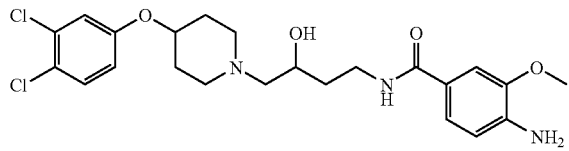

Prepared as described in Example 1 from 4-amino-1-[4-(3,4-dichlorophenoxy)piperidin-1-yl]butan-2-ol (0.26 g) and 4-amino-3-methoxybenzoic acid (0.130 g). Title compound obtained as white solid (0.080 g).

MS (APCI) 482/484 (M+H)+

$^1$H NMR δ (CDCl$_3$) 7.39 (1H, d), 7.31 (1H, d), 7.15 (1H, dd), 7.04 (1H, bs), 7.00 (1H, d), 6.75 (1H, dd), 6.65 (1H, d), 4.29 (1H, septet), 4.08 (2H, bs), 3.90 (3H, s), 3.89-3.75 (2H, m), 3.49-3.36 (1H, m), 2.96-2.85 (1H, m), 2.73-2.61 (1H, m), 2.61-2.50 (1H, m), 2.44-2.34 (2H, m), 2.35-2.23 (1H, m), 2.07-1.90 (2H, m), 1.90-1.71 (2H, m), 1.70-1.48 (2H, m).

EXAMPLE 16

N-{4-[4-(3,4-Dichlorophenoxy)piperidin-1-yl]-2-hydroxybutyl}-2-(methylsulfonyl)benzamide

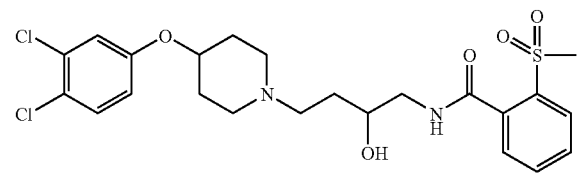

Prepared as described in Example 1 from 1-amino-4-[4-(3,4-dichlorophenoxy)piperidin-1-yl]butan-2-ol (0.2 g) and 2-(methylsulphonyl)benzoic acid (0.12 g). Title compound obtained as white solid (0.090 g).

MS (APCI) 515/517 (M+H)+

$^1$H NMR δ (CDCl$_3$) 8.10 (1H, d), 7.67 (1H, td), 7.61 (1H, td), 7.55 (1H, dd), 7.30 (1H, d), 6.98 (1H, d), 6.73 (1H, dd), 6.61 (1H, t), 4.33-4.23 (1H, m), 4.06 (1H, octet), 3.70 (1H, ddd), 3.36-3.29 (1H, m), 3.37 (3H, s), 2.97-2.82 (1H, m), 2.78-2.68 (1H, m), 2.64 (1H, dt), 2.60-2.47 (2H, m), 2.38-2.22 (1H, m), 2.02-1.41 (6H, m).

The compounds of Examples 17 and 18 were prepared in a similar way to Example 1 following Preparation 13 starting from 4-(2,4-dichloro-3-methylphenoxy)piperidine (WO 00/58305, WO 01/77101).

EXAMPLE 17

N-{(2R)-3-[4-(2,4-Dichloro-3-methylphenoxy)piperidin-1-yl]-2-hydroxypropyl}-1-oxo-1,2-dihydroisoquinoline-4-carboxamide

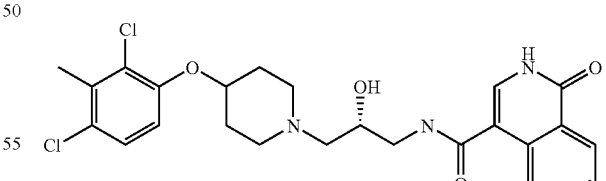

Prepared as described in Example 1 following Preparation 13.

MS (APCI) 504/506 (M+H)+

$^1$H NMR δ (DMSO) 11.58 (1H, s), 8.31 (1H, t), 8.22 (2H, d), 7.72 (1H, t), 7.56-7.48 (2H, m), 7.35 (1H, d), 7.10 (1H, d), 4.80-4.70 (1H, m), 4.53-4.44 (1H, m), 3.85-3.75 (1H, m), 3.39 (1H, dt), 3.15 (1H, quintet), 2.78-2.64 (2H, m), 2.40 (3H, s), 2.39-2.27 (4H, m), 1.96-1.83 (2H, m), 1.74-1.61 (2H, m).

EXAMPLE 18

N-{(2R)-3-[4-(2,4-Dichloro-3-methylphenoxy)piperidin-1-yl]-2-hydroxypropyl}-2-(methylsulfonyl)benzamide

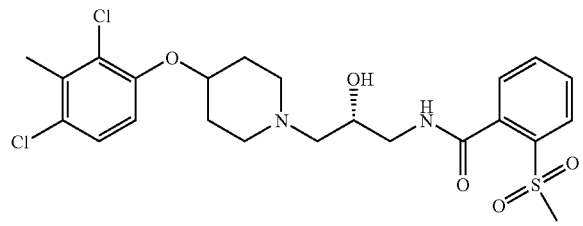

Prepared as described in Example 1 following Preparation 13.

MS (APCI) 515/517 (M+H)+

$^1$H NMR δ (CDCl$_3$) 8.10 (1H, dd), 7.67 (1H, t), 7.62 (1H, t), 7.54 (1H, dd), 7.19 (1H, d), 6.74 (1H, d), 6.55 (1H, t), 4.41-4.27 (1H, m), 4.03-3.89 (1H, m), 3.68 (1, ddd), 3.44 (1H, dt), 3.36 (3H, s), 3.00-2.87 (1H, m), 2.80-2.66 (1H, m), 2.63-2.51 (2H, m), 2.51-2.42 (1H, m), 2.47 (3H, s), 2.42-2.29 (1H, m), 2.03-1.76 (4H, m).

EXAMPLE 19

N-{(2S)-3-[4-(3,4-Dichlorophenoxy)piperidin-1-yl]-2-hydroxypropyl}-2-(methylsulfonyl)benzamide

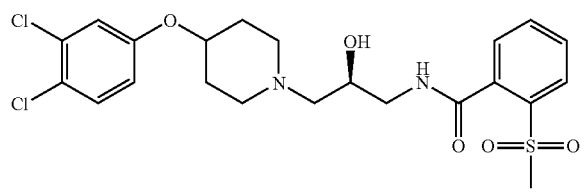

Prepared as described in Example 1 following Preparation 14.

MS (APCI) 501/503 (M+H)+

$^1$H NMR δ (CDCl$_3$) 8.10 (1H, dd), 7.68 (1H, td), 7.62 (1H, td), 7.54 (1H, dd), 7.31 (1H, d), 6.99 (1H, d), 6.75 (1H, dd), 6.53 (1H, t), 4.35-4.22 (1H, m), 3.68 (1H, ddd), 3.45 (1H, dt), 3.36 (3H, s), 2.98-2.85 (1H, m), 2.80-2.66 (1H, m), 2.65-2.52 (2H, m), 2.46 (1H, dd), 2.41-2.28 (1H, m), 2.04-1.88 (2H, m), 1.87-1.67 (2H, m).

EXAMPLE 20

N-{(2R)-3-[4-(3,4-Dichlorophenoxy)piperidin-1-yl]-2-hydroxypropyl}-3-[(methylamino)sulfonyl]benzamide

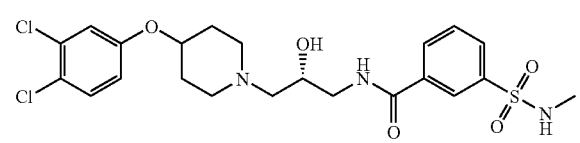

Prepared as described in Example 1 following Preparation 7.

MS (APCI) 516/518 (M+H)+

$^1$H NMR δ (CDCl$_3$) 8.25 (1H, s), 7.99 (1H, d), 7.95 (1H, d), 7.55 (1H, t), 7.41 (1H, t), 7.31 (1H, d), 7.00 (1H, d), 6.75 (1H, dd), 4.95 (1H, s), 4.36-4.25 (1H, m), 4.16-4.05 (1H, m), 3.75 (1H, ddd), 3.31 (1H, ddd), 3.02-2.90 (1H, m), 2.74-2.56 (2H, m), 2.68 (3H, s), 2.51 (1H, dd), 2.37-2.26 (1H, m), 2.37 (1H, dd), 2.07-1.91 (2H, m), 1.91-1.72 (2H, m).

EXAMPLE 21

3,5-Bis(acetylamino)-N-{(2R)-3-[4-(3,4-dichlorophenoxy)piperidin-1-yl]-2-hydroxypropyl}benzamide

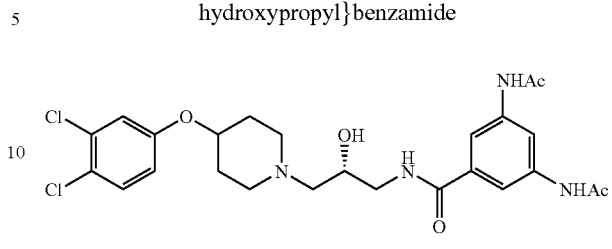

Prepared as described in Example 1 following Preparation 7.

MS (APCI) 537/539 M+H)+

$^1$H NMR δ (CDCl$_3$) 9.00 (2H, s), 7.86 (1H, s), 7.66 (2H, s), 7.50 (1H, s), 7.31 (1H, d), 6.99 (1H, d), 6.74 (1H, dd), 4.42-4.27 (1H, m), 4.19-4.03 (1H, m), 3.63-3.46 (1H, m), 3.42-3.26 (1H, m), 3.05-2.91 (1H, m), 2.91-2.74 (1H, m), 2.75-2.54 (4H, m), 2.17-1.96 (2H, m), 2.11 (6H, s), 1.97-1.79 (2H, m).

EXAMPLE 22

3-(Acetylamino)-N-{(2R)-3-[4-(3,4-dichlorophenoxy)piperidin-1-yl]-2-hydroxypropyl}benzamide

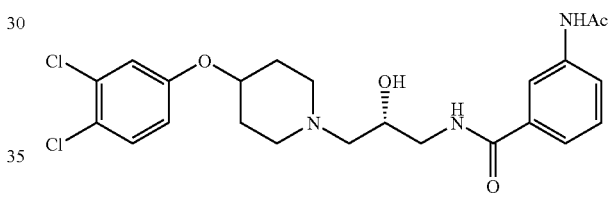

Prepared as described in Example 1 following Preparation 7.

MS (APCI) 480/482 (M+H)+

$^1$H NMR δ (CDCl$_3$) 7.88 (1H, s), 7.78 (1H, d), 7.55-7.45 (2H, m), 7.39 (1H, t), 7.31 (1H, d), 6.99 (1H, d), 6.82 (1H, t), 6.75 (1H, dd), 4.37-4.22 (1H, m), 3.99-3.85 (1H, m), 3.77-3.63 (1H, m), 3.38 (1H, quintet), 2.96-2.83 (1H, m), 2.75-2.63 (1H, m), 2.63-2.51 (1H, m), 2.52-2.24 (3H, m), 2.20 (3H, s), 2.08-1.90 (2H, m), 1.90-1.69 (2H, m).

EXAMPLE 23

N-{(2R)-3-[4-(3,4-Dichlorophenoxy)piperidin-1-yl]-2-hydroxypropyl}-1H-pyrazole-4-carboxamide

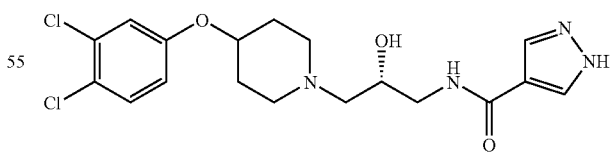

Prepared as described in Example 1 following Preparation 7.

MS (APCI) 413/415 (M+H)+

$^1$H NMR δ (CDCl$_3$) 8.02 (2H, s), 7.33 (1H, d), 7.00 (1H, s), 6.95 (1H, t), 6.76 (1H, d), 4.44-4.33 (1H, m), 4.07-3.98 (1H, m), 3.74-3.61 (1H, m), 3.40 (1H, td), 2.89-2.77 (2H, m), 2.62 (2H, d), 2.68-2.56 (1H, m), 2.18-1.99 (2H, m), 1.98-1.82 (2H, m).

EXAMPLE 24

2-(Acetylamino)-5-bromo-N-{(2R)-3-[4-(3,4-dichlorophenoxy)piperidin-1-yl]-2-hydroxypropyl}benzamide

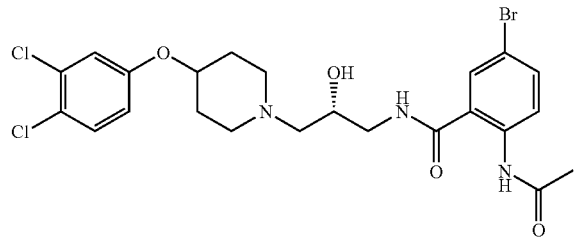

Prepared as described in Example 1 following Preparation 7.

MS (APCI) 558/460/562 (M+H)$^+$ $^1$H NMR δ (CDCl$_3$) 10.98 (1H, s), 8.52 (1H, d), 7.66 (1H, s), 7.55 (1H, d), 7.32 (1H, d), 7.26 (1H, s), 7.16-7.05 (2H, m), 7.00 (1H, s), 6.76 (1H, d), 4.42-4.30 (1H, m), 4.06-3.94 (1H, m), 3.72-3.59 (2H, m), 3.43-3.29 (1H, m), 2.95 (1H, t), 2.75 (2H, t), 2.59-2.43 (3H, m), 2.19 (3H, s), 2.13-1.96 (5H, m), 1.96-1.78 (3H, m).

EXAMPLE 25

N-{(2R)-3-[4-(3,4-Dichlorophenoxy)piperidin-1-yl]-2-hydroxypropyl}-2-oxo-1,2-dihydropyridine-3-carboxamide

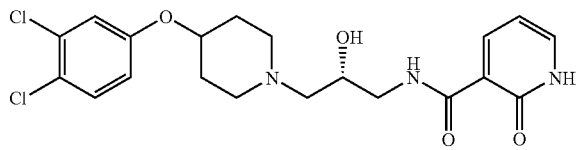

Prepared as described in Example 1 following Preparation 7.

MS (APCI) 440/442 (M+H)$^+$.

$^1$H NMR δ (CDCl$_3$) 9.86 (1H, t), 8.61 (1H, dd), 7.53 (1H, dd), 7.31 (1H, d), 6.99 (1H, d), 6.75 (1H, dd), 6.52 (1H, t), 4.33-4.24 (1H, m), 3.97-3.89 (1H, m), 3.70 (1H, ddd), 3.44 (1H, td), 2.94-2.85 (1H, m), 2.73-2.63 (1H, m), 2.59-2.50 (1H, m), 2.49-2.37 (2H, m), 2.30 (1H, t), 2.04-1.90 (2H, m), 1.87-1.72 (2H, m).

EXAMPLE 26

N-{(2R)-3-[4-(3,4-Dichlorophenoxy)piperidin-1-yl]-2-hydroxypropyl}-1-oxo-1,2-dihydroisoquinoline-5-carboxamide

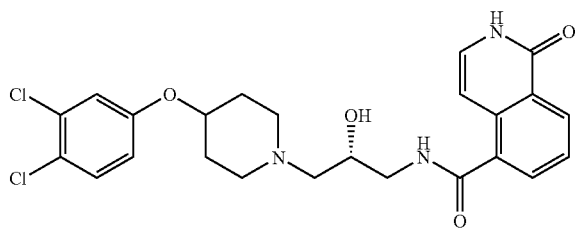

Prepared as described in Example 1 following Preparation 7.

MS (APCI) 490/492 (M+H)$^+$ $^1$H NMR δ (DMSO) 11.34 (1H, d), 8.46 (1H, t), 8.28 (1H, d), 7.78 (1H, dd), 7.50 (1H, t), 7.49 (1H, d), 7.25 (1H, d), 7.23-7.16 (1H, m), 6.98 (1H, dd), 6.81 (1H, d), 4.72 (1H, d), 4.49-4.37 (1H, m), 3.87-3.76 (1H, m), 3.46-3.35 (1H, m), 3.30-3.16 (1H, m), 2.83-2.67 (2H, m), 2.47-2.23 (4H, m), 1.97-1.84 (2H, m), 1.68-1.50 (2H, m).

EXAMPLE 27

N-{(2R)-3-[4-(3,4-Dichlorophenoxy)piperidin-1-yl]-2-hydroxypropyl}quinoline-4-carboxamide

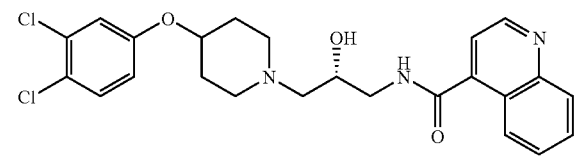

Prepared as described in Example 1 following Preparation 7.

MS (APCI) 474/476 (M+H)$^+$ $^1$H NMR δ (CD$_3$OD) 1.69-1.79 (m, 2H), 1.90-2.00 (m, 2H), 2.53-2.65 (m, 4H) 2.84-2.94 (m, 2H), 3.39 (dd, 1H), 3.54 (dd, 1H), 3.99-4.05 (m, 1H), 4.33-4.40 (m, 1H), 6.81 (dd, 1H), 7.03 (d, 1H), 7.29 (d, 1H), 7.52 (d, 1H), 7.59 (t, 1H), 7.73 (t, 1H), 8.00 (d, 1H), 8.15 (d, 1H), 8.83 (d, 1H).

EXAMPLE 28

N-{(2R)-3-[4-(3,4-Dichlorophenoxy)piperidin-1-yl]-2-hydroxypropyl}-1H-indole-4-carboxamide

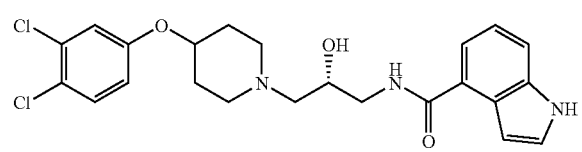

Prepared as described in Example 1 following Preparation 7.

MS (APCI) 462/464 (M+H)$^+$ $^1$H NMR δ (CD$_3$OD) 1.82-1.91 (m, 2H), 2.00-2.13 (m, 2H), 2.63-2.76 (m, 4H), 2.96-3.05 (m, 2H), 3.44 (dd, 1H), 3.54 (dd, 1H), 4.04-4.11 (m, 1H), 4.43-4.50 (m, 1H), 5.50 (s, 1H), 6.56 (d, 1H), 6.90 (dd, 1H), 7.12 (d, 1H), 7.32 (d, 1H), 7.38 (d, 1H), 7.43 (d, 1H), 7.63 (dd, 1H), 8.14 (s, 1H).

EXAMPLE 29

2-(Acetylamino)-N-{(2R)-3-[4-(3,4-dichlorophenoxy)piperidin-1-yl]-2-hydroxypropyl}benzamide

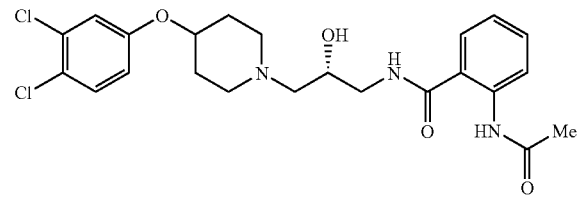

Prepared as described in Example 1 following Preparation 7.

MS (APCI) 480/482 (M+H)$^+$ $^1$H NMR δ (CDCl$_3$) 11.05 (1H, bd s), 8.60 (1H, d), 7.52-7.46 (2H, m), 7.31 (1H, d), 7.08 (1H, t), 6.99 (1H, d), 6.81 (1H, bd s), 6.76 (1H, dd), 4.36-4.28 (1H, m), 3.96-3.90 (1H, m), 3.72-3.64 (1H, m), 3.40-3.32 (1H, m), 2.94-2.86 (2H, m), 2.72-2.58 (2H, m), 2.49-2.31 (3H, m), 2.20 (3H, s), 2.03-1.93 (2H, m), 1.89-1.79 (2H, m).

EXAMPLE 30

2-(Acetylamino)-5-chloro-N-{(2R)-3-[4-(3,4-dichlorophenoxy)piperidin-1-yl]-2-hydroxypropyl}benzamide

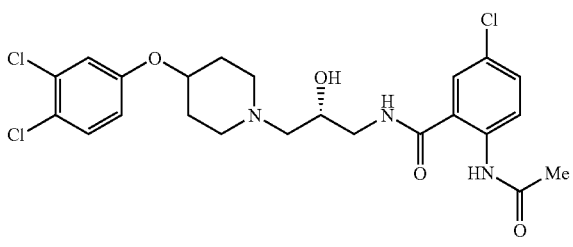

Prepared as described in Example 1 following Preparation 7.

MS (APCI) 514/516/518 (M+H)$^+$ $^1$H NMR δ (CDCl$_3$) 10.94 (1H, bd s), 8.59 (1H, d), 7.47 (1H, d), 7.43 (1H, dd), 7.32 (1H, d), 7.00 (1H, d), 6.87 (1H, bd s), 6.76 (1H, dd), 4.36-4.28 (1H, m), 3.97-3.90 (1H, m), 3.68-3.61 (1H, m), 3.38-3.32 (1H, m), 2.94-2.88 (1H, m), 2.72-2.58 (2H, m), 2.50-2.33 (3H, m), 2.19 (3H, s), 2.05-1.95 (2H, m), 1.90-1.80 (2H, m).

EXAMPLE 31

2-(Acetylamino)-4-chloro-N-{(2R)-3-[4-(3,4-dichlorophenoxy)piperidin-1-yl]-2-hydroxypropyl}benzamide

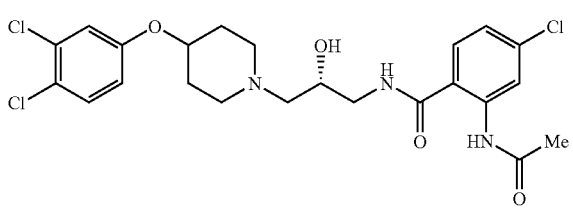

Prepared as described in Example 1 following Preparation 7.

MS (APCI) 514/516/518 (M+H)$^+$ $^1$H NMR δ (CDCl$_3$) 11.19 (1H, bd s), 8.73 (1H, d), 7.42 (1H, d), 7.32 (1H, d), 7.05 (1H, d), 7.00 (1H, d), 6.78-6.74 (2H, m), 4.36-4.28 (1H, m), 3.96-3.88 (1H, m), 3.70-3.62 (1H, m), 3.38-3.30 (1H, m), 2.94-2.88 (1H, m), 2.70-2.58 (2H, m), 2.49-2.30 (3H, m), 2.20 (3H, s), 2.04-1.96 (2H, m), 1.90-1.78 (2H, m).

EXAMPLE 32

5-Chloro-N-{(2R)-3-[4-(3,4-dichlorophenoxy)piperidin-1-yl]-2-hydroxypropyl}-2-[(methylsulphonyl)amino]benzamide

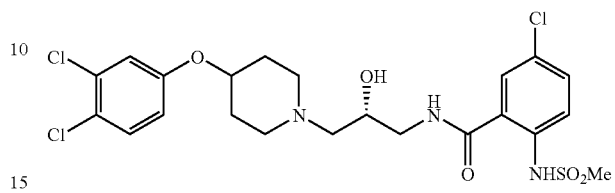

Prepared as described in Example 1 following Preparation 7.

MS (APCI) 550/552/554 (M+H)$^+$ $^1$H NMR δ (CDCl$_3$) 7.69 (1H, d), 7.52 (1H, s), 7.45 (1H, d), 7.31 (1H, d), 7.00 (1H, d), 6.75 (1H, dd), 4.36-4.28 (1H, m), 3.96-3.90 (1H, m), 3.72-3.64 (1H, m), 3.36-3.30 (1H, m), 3.04 (3H, s), 2.95-2.89 (1H, m), 2.74-2.56 (2H, m), 2.50-2.30 (3H, m), 2.05-1.95 (2H, m), 1.90-1.88 (2H, m).

EXAMPLE 33

4-Chloro-N-{(2R)-3-(4-(3,4-chlorophenoxy)piperidin-1-yl]-2-hydroxypropyl}-2-[(methylsulphonyl)amino]benzamide

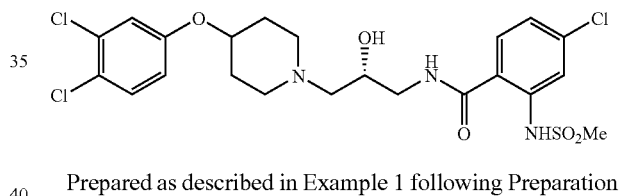

Prepared as described in Example 1 following Preparation 7.

MS (APCI) 550/552/554 (M+H)$^+$ $^1$H NMR δ (CDCl$_3$) 7.75 (1H, d), 7.48 (1H, d), 7.31 (1H, d), 7.09 (1H, dd), 7.00 (1H, d), 6.75 (1H, dd), 4.38-4.28 (1H, m), 3.97-3.87 (1H, m), 3.72-3.66 (1H, m), 3.34-3.28 (1H, m), 3.08 (3H, s), 2.98-2.90 (1H, m), 2.76-2.58 (2H, m), 2.50-2.30 (3H, m), 2.10-1.94 (2H, m), 1.90-1.74 (2H, m).

EXAMPLE 34

2-Amino-4-chloro-N-{(2R)-3-[4-(3,4-dichlorophenoxy)piperidin-1-yl]-2-hydroxypropyl}benzamide

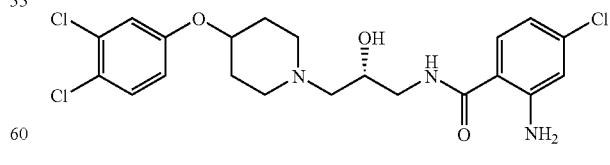

Prepared as described in Example 1 following Preparation 7.

MS (APCI) 472/474/476 (M+H)$^+$ $^1$H NMR δ (CDCl$_3$) 7.31 (1H, d), 7.27 (1H, d), 6.99 (1H, d), 6.75 (1H, dd), 6.67 (1H, d), 6.61 (1H, d), 6.55 (1H, t), 5.64 (2H, bd s), 4.34-4.24 (1H, m), 3.92-3.82 (1H, m), 3.68-3.62

(1H, m), 3.36-3.29 (1H, m), 2.94-2.86 (1H, m), 2.70-2.54 (2H, m), 2.47-2.29 (2H, m), 2.26-2.16 (1H, m), 2.04-1.94 (2H, m), 1.88-1.78 (2H, m).

EXAMPLE 35

5-Chloro-N-{(2R)-3-[4-(3,4-dichlorophenoxy)piperidin-1-yl]-6-oxo-1,6-dihydropyridine-3-carboxamide

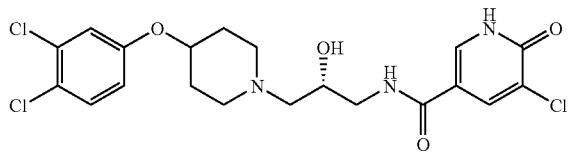

To a solution of (2R)-1-amino-3-[4-(3,4-dichlorophenoxy)piperidin-1-yl]propan-2-ol (150 mg, 0.47 mmol) and triethylamine (48 mg, 66 µl, 0.47 mmol) in dichloromethane (20 ml) was added a solution of 5-chloro-6-hydroxynicotinyl chloride (90 mg, 0.47 mmol) in dichloromethane (10 ml). The mixture was stirred at room temperature for 3 h and then the solution was concentrated in vacuo to leave a crude oil. Purification by reverse phase HPLC (Symmetry, 0.1% ammonium acetate/acetonitrile) afforded the title compound as a colourless glass (150 mg, 67%).

MS (APCI) 474/476/478 (M+H)$^+$ $^1$H NMR δ (CDCl$_3$) 8.07 (1H, d), 8.04 (1H, d), 7.31 (1H, d), 7.09 (1H, bd s), 6.99 (1H, d), 6.75 (1H, dd), 4.36-4.26 (1H, m), 4.00-3.90 (1H, m), 3.68-3.58 (1H, m), 3.32-3.22 (1H, m), 2.96-2.86 (1H, m), 2.76-2.58 (2H, m), 2.51-2.35 (3H, m), 2.04-1.94 (2H, m), 1.88-1.76 (2H, m).

EXAMPLE 36

2-(Aminosulphonyl)-4-chloro-N-{(2R)-3-[4-(3,4-dichlorophenoxy)piperidin-1-yl]-2-hydroxypropyl}benzamide

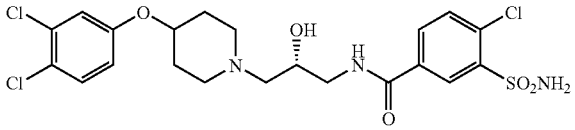

Prepared as described in Example 1 following Preparation 7.

MS (APCI) 536/538/540 (M+H)$^+$ $^1$H NMR δ (CDCl$_3$) 8.39 (1H, d), 7.90 (1H, bd s), 7.78 (1H, dd), 7.45 (1H, d), 7.32 (1H, d), 7.00 (1H, d), 6.76 (1H, dd), 4.38-4.22 (2H, m), 3.76-3.62 (1H, m), 3.30-3.20 (1H, m), 3.10-3.00 (1H, m), 2.80-2.68 (2H, m), 2.60-2.40 (3H, m), 2.10-2.00 (2H, m), 1.96-1.86 (2H, m).

EXAMPLE 37

N-{(2R)-3-[4-(3,4-Dichlorophenoxy)piperidin-1-yl]-2-hydroxypropyl}-1H-indazole-3-carboxamide

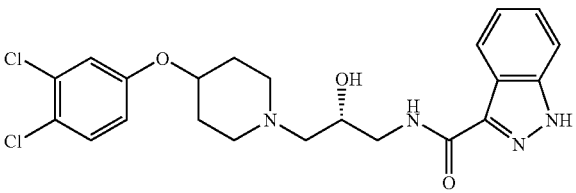

Prepared as described in Example 1 following Preparation 7.

MS (APCI) 463/465 (M+H)$^+$ $^1$H NMR δ (CDCl$_3$) 8.43-8.33 (2H, m), 7.54 (1H, d), 7.43 (1H, t), 7.32 (1H, d), 6.99 (1H, d), 6.75 (1H, dd), 4.38-4.28 (1H, m), 4.15-4.05 (1H, m), 3.75-3.65 (1H, m), 3.60-3.48 (1H, m), 3.02-2.92 (1H, m), 2.80-2.50 (4H, m), 2.45-2.37 (1H, m), 2.10-1.95 (2H, m), 1.90-1.75 (2H, m).

EXAMPLE 38

1-tert-Butyl-N-{(2R)-3-[4-(3,4-dichlorophenoxy)piperidin-1-yl]-2-hydroxypropyl}-3-methyl-1H-pyrazole-5-carboxamide

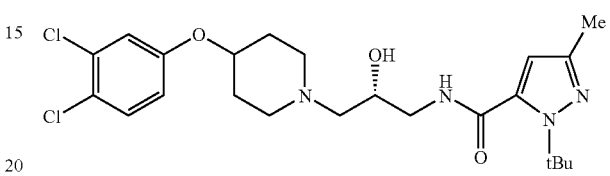

Prepared as described in Example 1 following Preparation 7.

MS (APCI) 483/485 (M+H)$^+$ $^1$H NMR δ (CDCl$_3$) 7.31 (1H, d), 6.99 (1H, d), 6.75 (1H, dd), 6.43 (1H, bd s), 6.21 (1H, s), 4.35-4.25 (1H, m), 3.92-3.82 (1H, m), 3.70-3.58 (1H, m), 3.38-3.28 (1H, m), 2.95-2.85 (2H, m), 2.70-2.50 (2H, m), 2.45-2.30 (3H, m), 2.24 (3H, s), 2.05-1.90 (2H, m), 1.90-1.78 (2H, m), 1.67 (9H, s).

EXAMPLE 39

N-{(2R)-3-[4-(3,4-Dichlorophenoxy)piperidin-1-yl]-2-hydroxypropyl}-4,5,6,7-tetrahydro-2H-indazole-3-carboxamide

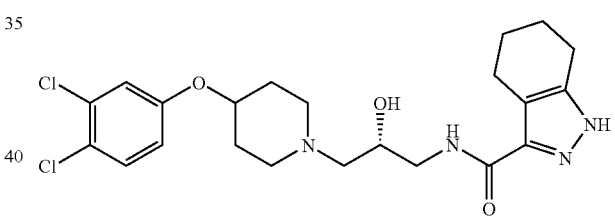

Prepared as described in Example 1 following Preparation 7.

MS (APCI) 467/469 (M+H)$^+$ $^1$H NMR δ (DMSO) 12.69 (1H, s), 7.83 (1H, bd s), 7.49 (1H, d), 7.25 (1H, d), 6.98 (1H, dd), 4.80 (1H, d), 4.43 (1H, quintet), 3.73 (1H, q), 3.39-3.16 (2H, m), 2.80-2.52 (6H, m), 2.38-2.23 (4H, m), 1.96-1.86 (2H, m), 1.78-1.58 (6H, m).

EXAMPLE 40

N-{(2R)-3-[4-(3,4-Dichlorophenoxy)piperidin-1-yl]-2-hydroxypropyl}-3-(trifluoromethyl)-1H-pyrazole-4-carboxamide

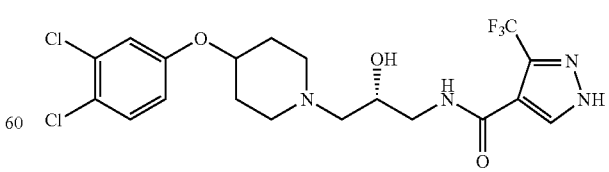

Prepared as described in Example 1 following Preparation 7.

MS (APCI) 481/483 (M+H)$^+$ $^1$H NMR δ (CDCl$_3$) 8.11 (1H, s), 7.32 (1H, d), 7.00 (1H, d), 6.75 (1H, dd), 6.70 (1H, bd s), 4.38-4.28 (1H, m), 4.00-3.90

(1H, m), 3.70-3.60 (1H, m), 3.42-3.32 (1H, m), 2.98-2.88 (1H, m), 2.75-2.58 (2H, m), 2.50-2.36 (3H, m), 2.10-1.96 (2H, m), 1.92-1.76 (2H, m).

EXAMPLE 41

N-{(2R)-3-[4-(3,4-Dichlorophenoxy)piperidin-1-yl]-2-hydroxypropyl}-2-methylimidazo[1,2-a]pyridine-3-carboxamide

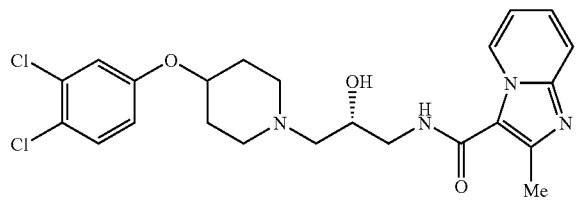

Prepared as described in Example 1 following Preparation 7.

MS (APCI) 477/479 (M+H)$^+$ $^1$H NMR δ (CDCl$_3$) 9.40 (1H, d), 7.58 (1H, d), 7.36-7.30 (2H, m), 7.00 (1H, d), 6.92 (1H, t), 6.76 (1H, dd), 6.35 (1H, bd s), 4.38-4.28 (1H, m), 4.01-3.93 (1H, m), 3.82-3.72 (1H, m), 3.48-3.40 (1H, m), 2.98-2.90 (1H, m), 2.75 (3H, s), 2.70-2.58 (1H, m), 2.54-2.30 (4H, s), 2.06-1.96 (2H, m), 1.94-1.76 (2H, m).

EXAMPLE 42

N-{(2R)-3-[4-(3,4-Dichlorophenoxy)piperidin-1-yl]-2-hydroxypropyl}-4-(1H-pyrazol-3-yl)benzamide

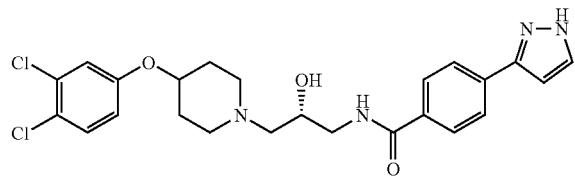

Prepared as described in Example 1 following Preparation 7.

MS (APCI) 489/491 (M+H)$^+$ $^1$H NMR δ (CDCl$_3$) 7.84 (2H, d), 7.76 (2H, d), 7.64 (1H, d), 7.34-7.29 (2H, m), 7.00 (1H, d), 6.75 (1H, dd), 6.66 (1H, d), 4.45-4.35 (1H, m), 4.18-4.08 (1H, m), 3.78-3.66 (1H, m), 3.52-3.42 (1H, m), 3.06-2.96 (1H, m), 2.90-2.80 (2H, m), 2.75-2.63 (3H, m), 2.18-2.03 (2H, m), 2.00-1.80 (2H, m).

EXAMPLE 43

N-{(2R)-3-[4-(3,4-Dichlorophenoxy)piperidin-1-yl]-2-hydroxypropyl}cinnoline-4-carboxamide

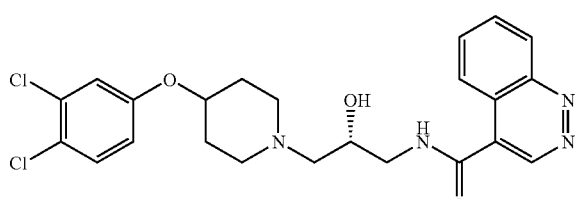

Prepared as described in Example 1 following Preparation 7.

MS (APCI) 475/477 (M+H)$^+$ $^1$H NMR δ (CDCl$_3$) 9.41 (1H, s), 8.61 (1H, d), 8.38 (1H, d), 7.94-7.82 (2H, m), 7.33 (1H, d), 7.20 (1H, bd s), 7.01 (1H, d), 6.76 (1H, dd), 4.46-4.36 (1H, m), 4.18-4.08 (1H, m), 3.88-3.78 (1H, m), 3.56-3.46 (1H, m), 3.06-2.96 (1H, m), 2.94-2.78 (2H, m), 2.70-2.60 (3H, m), 2.03-1.89 (4H, m).

EXAMPLE 44

N-{(2R)-3-[4-(3,4-Dichlorophenoxy)piperidin-1-yl]-2-hydroxypropyl}-2-oxo-1,2-dihydroquinoline-4-carboxamide

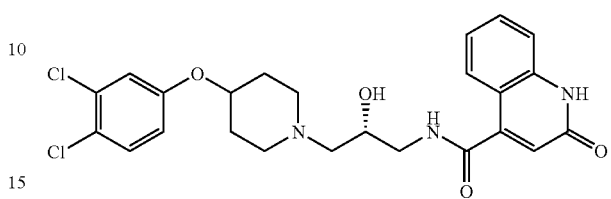

Prepared as described in Example 1 following Preparation 7.

MS (APCI) 490/492 (M+H)$^+$ $^1$H NMR δ (DMSO) 8.69 (1H, t), 7.74 (1H, d), 7.53 (1H, t), 7.49 (1H, d), 7.34 (1H, d), 7.25 (1H, d), 7.18 (1H, t), 6.98 (1H, dd), 6.54 (1H, s), 4.50-4.40 (1H, m), 3.87-3.77 (1H, m), 3.48-3.40 (1H, m), 3.28-3.18 (1H, m), 2.82-2.70 (2H, m), 2.44-2.24 (4H, m), 1.97-1.87 (2H, m), 1.68-1.56 (2H, m).

EXAMPLE 45

N-{3-[4-(3,4-Dichlorophenoxy)piperidin-1-yl]-2-hydroxypropyl}-2-oxo-2,3-dihydro-1H-benzimidazole-1-carboxamide

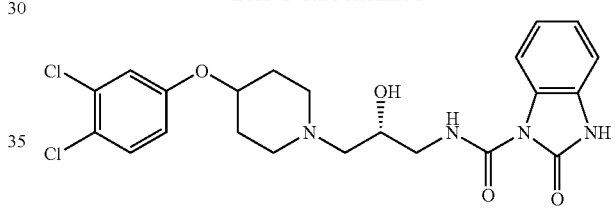

Prepared as described in Example 35, using 2-oxo-2,3-dihydro-1H-benzimidazole-1-carbonyl chloride.

MS (APCI) 479/481 (M+1)$^+$ $^1$H NMR δ (CDCl$_3$) 9.02 (1H, t), 8.17-8.14 (1H, d), 7.32 (1H, d), 7.18-7.12 (2H, m), 7.08-7.05 (1H, m), 7.00 (1H, d), 6.75 (1H, dd), 4.42-4.32 (1H, m), 4.16-4.06 (1H, m), 3.71-3.61 (1H, m), 3.49-3.39 (1H, m), 3.04-2.94 (1H, m), 2.85-2.75 (2H, m), 2.71-2.57 (3H, m), 2.16-1.98 (2H, m), 1.96-1.80 (2H, m).

EXAMPLE 46

N-{(2R)-3-[4-(3,4-Dichlorophenoxy)piperidin-1-yl]-2-hydroxypropyl}-oxo-3,4-dihydrophthalazine-1-carboxamide

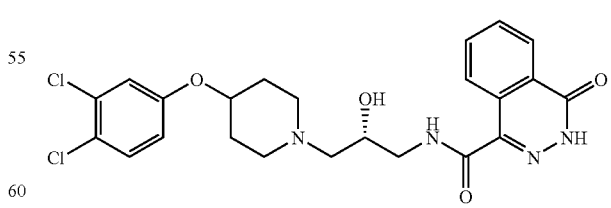

Prepared as described in Example 1 following Preparation 7.

MS (APCI) 491/493/495 (M+H)$^+$ $^1$H NMR δ (CDCl$_3$) 9.13 (1H, d), 8.43 (1H, d), 7.91-75 (3H, m), 7.32 (1H, d), 7.00 (1H, d), 6.76 (1H, dd), 4.40-4.32 (1H, m), 4.08-3.98 (1H, m), 3.76-3.66 (1H, m), 3.46-3.38

(1H, m), 3.00-2.92 (1H, m), 2.80-2.66 (2H, m), 2.58-2.44 (3H, m), 2.14-1.98 (2H, m), 1.96-1.80 (2H, m).

EXAMPLE 47

N-{(2R)-3-[4-(3,4-Dichlorophenoxy)piperidin-1-yl]-2-hydroxypropyl}-1H-indole-3-carboxamide

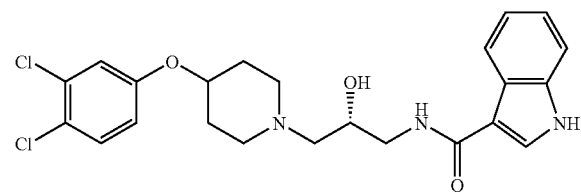

Prepared as described in Example 1 following Preparation 7.

MS (APCI) 462/464/466 (M+M)$^+$ $^1$H NMR δ (CDCl$_3$) 9.03 (1H, bd s), 8.07-8.04 (1H, d), 7.84 (1H, s), 7.45-7.41 (1H, m), 7.32 (1H, d), 7.28-7.22 (2H, m), 6.99 (1H, d), 6.82 (1H, t), 6.74 (1H, dd), 4.44-4.34 (1H, m), 4.16-4.06 (1H, m), 3.78-3.68 (1H, m), 3.56-3.44 (1H, m), 3.04-2.94 (1H, m), 2.92-2.82 (2H, m), 2.77-2.65 (3H, m), 2.18-1.98 (2H, m), 1.98-1.78 (2H, m).

EXAMPLE 48

N-{(2R)-3-[4-(4-Chlorophenoxy)piperidin-1-yl]-2-hydroxypropyl}-2-(methylsulfonyl)benzamide

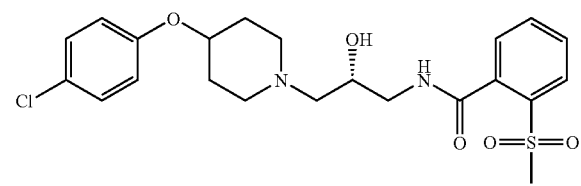

Prepared as described in Example 1 following Preparation 4.

MS (APCI) 467/469 (M+H)$^+$ $^1$H NMR δ (CD$_3$OD) 8.08 (1H, d), 7.79 (1H, t), 7.71 (1H, t), 7.61 (1H, d), 7.26 (2H, d), 6.95 (2H, d), 4.56-4.45 (1H, m), 4.21-4.08 (1H, m), 3.47 (2H, d), 3.35 (3H, s), 3.22-3.08 (2H, m), 3.01-2.77 (4H, m), 2.18-2.00 (2H, m), 1.99-1.83 (2H, m).

EXAMPLE 49

N-{(2-R)-3-[4-(4-Chlorophenoxy)piperidin-1-yl]-2-hydroxypropyl}-1-oxo-1,2-dihydroisoquinoline-4-carboxamide

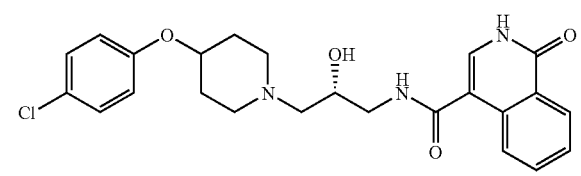

Prepared as described in Example 1 following Preparation 4.

MS (APCI) 466/468 (M+H)$^+$ $^1$H NMR δ (DMSO) 11.57 (1H, d), 8.30 (1H, t), 8.22 (2H, d), 7.73 (1H, t), 7.58-7.45 (2H, m), 7.30 (2H, d), 6.97 (2H, d), 4.75 (1H, s), 4.41-4.29 (1H, m), 3.87-3.74 (1H, m), 3.46-3.26 (1H, m), 3.22-3.07 (1H, m), 2.85-2.67 (2H, m), 2.41-2.21 (4H, m), 2.00-1.84 (2H, m), 1.70-1.51 (2H, m).

EXAMPLE 50

N-{(2R)-3-[4-(4-Chloro-3-fluorophenoxy)piperidin-1-yl]-2-hydroxypropyl}-1-oxo 1,2-dihydroisoquinoline-4-carboxamide

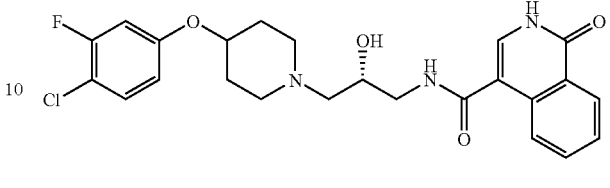

Prepared as described in Example 1 following Preparation 5.

MS (APCI) 474/476 (M+H)$^+$ $^1$H NMR δ (CD$_3$OD) 8.25 (1H, d), 8.08 (1H, d), 7.67 (1H, ddd), 7.48 (2H, t), 7.21 (1H, t), 6.75 (1H, d), 6.66 (1H, ddd), 4.30 (1H, dq), 3.95-3.87 (1H, m), 3.45 (1H, dd), 3.29-3.24 (1H, m), 2.80-2.69 (2H, m), 2.45-2.31 (4H, m), 1.95-1.86 (2H, m), 1.73-1.62 (2H, m).

EXAMPLE 51

N-{(2R)-3-[4-(3,4-Difluorophenoxy)piperidin-1-yl]-2-hydroxypropyl}-1-oxo-1,2-dihydroisoquinoline-4-carboxamide

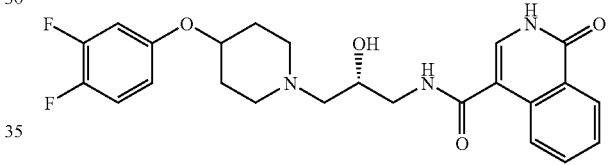

Prepared as described in Example 1 following Preparation 6.

MS (APCI) 458 (M+H)$^+$ $^1$H NMR δ (CD$_3$OD) 8.25 (1H, dd), 8.08 (1H, d), 7.67 (1H, ddd), 7.50-7.46 (2H, m), 7.03 (1H, dt), 6.76 (1H, ddd), 6.63-6.59 (1H, m), 4.24 (1H, dquintet), 3.94-3.87 (1H, m), 3.45 (1H, dd), 3.26 (1H, dd), 2.74 (2H, d), 2.45-2.30 (4H, m), 1.90 (2H, dt), 1.72-1.61 (2H, m).

EXAMPLE 52

N-{(2S)-3-[4-(3,4-Dichlorophenoxy)piperidin-1-yl]-2-hydroxypropyl}-N-methyl-1-oxo-1,2-dihydroisoquinoline-4-carboxamide

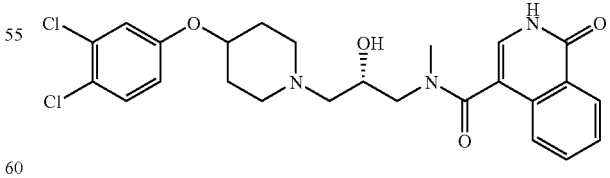

Prepared as described in Example 1 following Preparation 12.

MS (APCI) 504/506 (M+H)$^+$ $^1$H NMR δ (DMSO) 1.25-1.42 (m, 1H), 1.57-1.73 (m, 2H), 1.89-2.15 (m, 3H), 2.26-2.42 (m, 2H), 2.69-2.85 (m, 1H), 2.90-3.15 (m, 4H), 3.63-3.77 (m, 1H), 3.97-4.09 (m, 1H), 4.26-4.49 (m, 1H), 4.79-4.95 (m, 1H), 6.91-7.01 (m, 1H), 7.18-7.31 (m, 2H), 7.45-7.57 (m, 3H), 7.73 (t, 1H), 8.23 (d, 1H), 11.51 (s, 1H).

EXAMPLE 53

N-{(2S)-3-[4-(3,4-Dichlorophenoxy)piperidin-1-yl]-2-hydroxypropyl}-N-methyl-1H-indazole-3-carboxamide

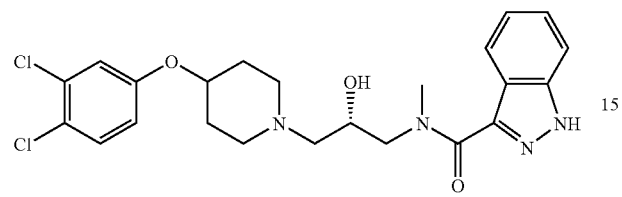

Prepared as described in Example 1 following Preparation 12.

MS (APCI) 477/479 (M+H)$^+$ $^1$H NMR δ (DMSO) 1.36-1.51 (m, 1H), 1.58-1.67 (m, 1H), 1.72-1.81 (m, 1H), 1.86-1.96 (m, 1H), 2.04-2.21 (m, 2H), 2.26-2.39 (m, 2H), 2.71-2.81 (m, 1H), 3.13 (s, 3H), 3.49-3.57 (m, 1H), 3.78-3.93 (m, 1H), 3.98-4.06 (m, 1H), 4.31-4.48 (m, 1H), 4.71-4.83 (m, 1H), 6.93-7.00 (m, 1H), 7.16-7.25 (m, 2H), 7.34-7.43 (m, 1H), 7.49 (d, 1H), 7.58 (t, 1H), 7.95 (dd, 1H), 13.34-13.49 (m, 1H).

EXAMPLE 54

N-{(2S)-3-[4-(3,4-dichlorophenoxy)piperidin-1-yl]-2-hydroxypropyl}-N-methyl-4-oxo-3,4-dihydrophthalazine-1-carboxamide

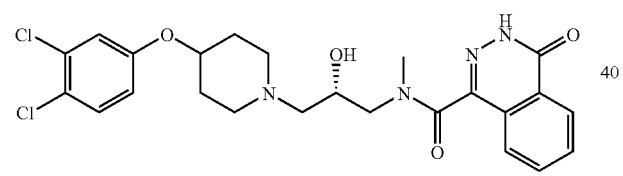

Prepared as described in Example 1 following Preparation 12.

MS (APCI) 505/507 (M+H)$^+$ $^1$H NMR δ (CD$_3$OD) 1.44-1.55 (m, 1H), 1.69-1.80 (m, 2H), 1.93-2.02 (m, 1H), 2.15-2.24 (m, 1H), 2.19 (d, 1H), 2.46-2.60 (m, 2H), 2.84-2.93 (m, 1H), 3.20 (s, 3H), 3.42-3.51 (m, 1H), 3.75 (dd, 1H), 3.84 (qt, 1H), 4.16-4.25 (m, 1H), 4.35-4.41 (m, (ddd, 1H), 7.00 (dd, 1H), 7.28 (dd, 1H), 7.72-7.89 (m, 3H), 8.31 (t, 1H).

EXAMPLE 55

Benzoic acid, 3-[[2-[[(2R)-3-[4-(3,4-dichlorophenoxy)-1-piperidinyl]-2-hydroxypropyl]amino]-2-oxoethyl]amino]-, methyl ester

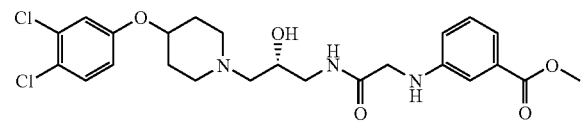

Prepared as described in Example 1 following Preparation 7.

MS (APCI) 510/512 (M+H)$^+$ $^1$H NMR δ (CDCl$_3$) 8.17 (1H, t), 7.95 (1H, dd), 7.38 (1H, t), 7.31 (1H, d), 6.98 (1H, d), 6.91 (1H, t), 6.78-6.68 (2H, m), 6.57 (1H, d), 4.32-4.20 (1H, m), 3.92 (2H, d), 3.89 (3H, s), 3.80-3.69 (1H, m), 3.52-3.40 (1H, m), 3.26 (1H, dt), 2.87-2.74 (1H, m), 2.62-2.39 (2H, m), 2.32 (1H, dd), 2.28-2.14 (2H, m), 2.00-1.84 (−2H, m), 1.83-1.66 (2H, m).

EXAMPLE 56

Propanamide, N-[2-[[2-[[(2R)-3-[3,4-dichlorophenoxy)-1-piperidinyl]-2-hydroxypropyl]amino]-2-oxoethyl]amino]phenyl]-

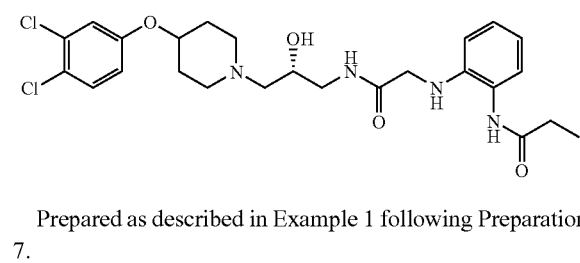

Prepared as described in Example 1 following Preparation 7.

MS (APCI) 523/525 (M+H)$^+$ $^1$H NMR δ (CDCl$_3$) 7.48 (1H, t), 7.31 (1H, d), 7.23-7.11 (2H, m), 7.05 (1H, d), 6.98 (2H, d), 6.83-6.71 (2H, m), 6.67 (1H, d), 4.54 (1H, t), 4.31-4.17 (1H, m), 3.92 (1H, d), 3.79-3.66 (1H, m), 3.45 (1H, td), 3.22 (1H, td), 2.78-2.66 (1H, m), 2.61-2.43 (1H, m), 2.49 (2H, q), 2.37 (1H, t), 2.26-2.06 (3H, m), 1.98-1.82 (2H, m), 1.82-1.64 (2H, m), 1.29 (3H, t).

EXAMPLE 57

Propanamide, N-[2-[[2-[[(2R)-3-[4-(3,4-dichlorophenoxy)-1-piperidinyl]-2-hydroxypropyl]amino]-2-oxoethyl]amino]phenyl]-

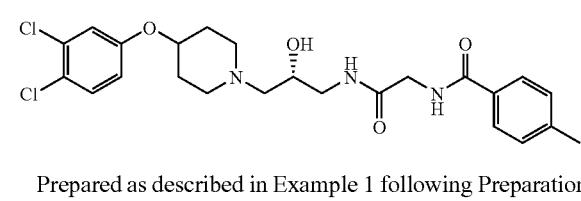

Prepared as described in Example 1 following Preparation 7.

MS (APCI) 494/496 (M+H)$^+$ $^1$H NMR δ (CDCl$_3$) 7.73 (2H, dd), 7.32 (UH, dd), 7.29-7.21 (2H, m), 7.02-6.97 (1H, m), 6.97-6.88 (1H, m), 6.80-6.71 (1H, m), 6.60-6.49 (1H, m), 4.36-4.23 (1H, m), 4.14 (2H, t), 3.89-3.75 (1H, m), 3.62-3.48 (1H, m), 3.31-3.17 (1H, m), 2.94-2.81 (1H, m), 2.72-2.59 (1H, m), 2.60-2.47 (1H, m), 2.43-2.22 (3H, m), 2.40 (3H, s), 2.05-1.89 (2H, m), 1.88-1.72 (2H, m).

EXAMPLE 58

(2S)-N-{(2R)-3-[4-(3,4-Dichlorophenoxy)piperidin-1-yl]-2-hydroxypropyl}-2-hyroxy-2-phenylethanamide

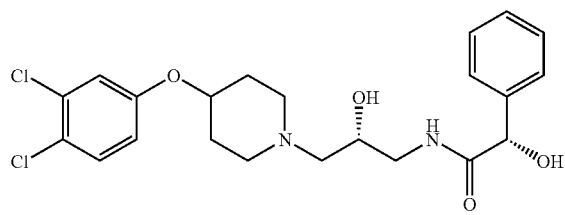

Prepared as described in Example 1 following Preparation 7.

MS (APCI) 453/455/457 (M+H)+

¹H NMR δ (CDCl₃) 7.44-7.26 (6H, m), 6.98 (1H, d), 6.74 (1H, dd), 6.54 (1H, bd s), 5.06 (1H, s), 4.34-4.24 (1H, m), 3.83-3.73 (1H, m), 3.56-3.43 (1H, m), 3.32-3.20 (1H, m), 2.88-2.80 (1H, m), 2.62-2.52 (2H, m), 2.33-2.10 (3H, m), 2.02-1.90 (2H, m), 1.86-1.70 (2H, m).

EXAMPLE 59

2-[2-({(2R)-3-[4-(3,4-Dichlorophenoxy)piperidin-1-yl]-2-hydroxypropyl}amino)-2-oxoethoxy]benzamide

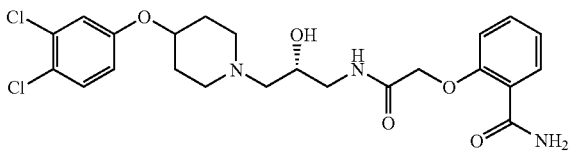

Prepared as described in Example 1 following Preparation 7.

MS (APCI) 496/498 (M+H)+

¹H NMR δ (CDCl₃) 7.97 (1H, d), 7.48 (1H, t), 7.36-7.28 (2H, m), 7.17-7.07 (1H, m), 7.13 (2H, t), 6.99 (1H, s), 6.93 (1H, d), 6.75 (1H, d), 5.99 (1H, s), 4.68 (2H, s), 4.35-4.22 (1H, m), 3.89-3.77 (1H, m), 3.67-3.54 (1H, m), 3.22 (1H, quintet), 2.91-2.79 (1H, m), 2.68-2.46 (2H, m), 2.43-2.20 (3H, in), 2.04-1.88 (2H, m), 1.88-1.71 (2H, m).

EXAMPLE 60

N-{(2R)-3-[4-(3,4-Dichlorophenoxy)piperidin-1-yl]-2-hydroxypropyl}-2-(3-oxo-2,3-dihydro-4H-1,4-benzoxazin-4-yl)acetamide

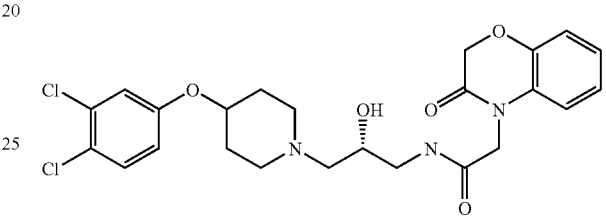

Prepared as described in Example 1 following Preparation 7.

MS (APCI) 508/510 (M+H)+

¹H NMR δ (CDCl₃) 7.31 (1H, d), 7.08-7.01 (4H, m), 6.99 (1H, d), 6.74 (1H, dd), 6.53 (1H, bd s), 4.69 (2H, s), 4.56-2H, q), 4.34-4.24 (1H, m), 3.80-3.72 (1H, m), 3.52-3.42 (1H, m), 3.28-3.18 (1H, m), 2.88-2.80 (1H, m), 2.63-2.45 (4H, m), 2.36-2.21 (3H, m), 2.00-1.90 (2H, m), 1.86-1.70 (2H, m).

Further Examples of compounds of the invention which have been prepared as described in Example 1 following Preparation 7 are presented in the Table below.

| Example | Name | (M + H)+ |
|---|---|---|
| 61 | N-{(2R)-3-[4-(3,4-dichlorophenoxy)piperidin-1-yl]-2-hydroxypropyl}-2-methoxybenzamide | 452 |
| 62 | N-{(2R)-3-[4-(3,4-dichlorophenoxy)piperidin-1-yl]-2-hydroxypropyl}-2-(methylamino)benzamide | 451 |
| 63 | N-{(2R)-3-[4-(3,4-dichlorophenoxy)piperidin-1-yl]-2-hydroxypropyl)}nicotinamide | 423 |
| 64 | N-{(2R)-3-[4-(3,4-dichlorophenoxy)piperidin-1-yl]-2-hydroxypropyl}isonicotinamide | 423 |
| 65 | N-{(2R)-3-[4-(3,4-dichlorophenoxy)piperidin-1-yl]-2-hydroxypropyl}-3-(dimethylamino)benzamide | 465 |
| 66 | N-{(2R)-3-[4-(3,4-dichlorophenoxy)piperidin-1-yl]-2-hydroxypropyl}-2-(1,3-dioxo-1,3-dihydro-2H-isoindol-2-yl)acetamide | 505 |
| 67 | N-{(2R)-3-[4-(3,4-dichlorophenoxy)piperidin-1-yl]-2-hydroxypropyl}-6-hydroxynicotinamide | 439 |
| 68 | N-{(2R)-3-[4-(3,4-dichlorophenoxy)piperidin-1-yl]-2-hydroxypropyl}-2-(1H-indol-3-yl)acetamide | 475 |
| 69 | N-{(2R)-3-[4-(3,4-dichlorophenoxy)piperidin-1-yl]-2-hydroxypropyl}bicyclo[4.2.0]octa-1,3,5-triene-7-carboxamide | 448 |
| 70 | N-{(2R)-3-[4-(3,4-dichlorophenoxy)piperidin-1-yl]-2-hydroxypropyl}-4,7-dimethylpyrazolo[5,1-c][1,2,4]triazine-3-carboxamide | 492 |
| 71 | N-{(2R)-3-[4-(3,4-dichlorophenoxy)piperidin-1-yl]-2-hydroxypropyl}pyrazine-2-carboxamide | 424 |
| 72 | N-{(2R)-3-[4-(3,4-dichlorophenoxy)piperidin-1-yl]-2-hydroxypropyl}-9H-purine-6-carboxamide | 464 |

-continued

| Example | Name | (M + H)+ |
|---|---|---|
| 73 | N-{(2R)-3-[4-(3,4-dichlorophenoxy)piperidin-1-yl]-2-hydroxypropyl}quinoline-6-carboxamide | 473 |
| 74 | N-{(2R)-3-[4-(3,4-dichlorophenoxy)piperidin-1-yl]-2-hydroxypropyl}-2,7-dimethylpyrazolo[1,5-a]pyrimidine-6-carboxamide | 491 |
| 75 | N-{(2R)-3-[4-(3,4-dichlorophenoxy)piperidin-1-yl]-2-hydroxypropyl}-2-(pyrimidin-2-ylthio)acetamide | 470 |
| 76 | N-{(2R)-3-[4-(3,4-dichlorophenoxy)piperidin-1-yl]-2-hydroxypropyl}-5-fluoro-1H-indole-2-carboxamide | 479 |
| 77 | N-{(2R)-3-[4-(3,4-dichlorophenoxy)piperidin-1-yl]-2-hydroxypropyl}-1,3-benzothiazole-6-carboxamide | 479 |
| 78 | N-{(2R)-3-[4-(3,4-dichlorophenoxy)piperidin-1-yl]-2-hydroxypropyl}-5-phenyl-1,3-oxazole-4-carboxamide | 489 |
| 79 | N-{(2R)-3-[4-(3,4-dichlorophenoxy)piperidin-1-yl]-2-hydroxypropyl}-6-hydroxypyridine-2-carboxamide | 439 |
| 80 | N-{(2R)-3-[4-(3,4-dichlorophenoxy)piperidin-1-yl]-2-hydroxypropyl}-3-oxo-3,4-dihydro-2H-1,4-benzoxazine-7-carboxamide | 493 |
| 81 | N-{(2R)-3-[4-(3,4-dichlorophenoxy)piperidin-1-yl]-2-hydroxypropyl}-3-hydroxypyridine-2-carboxamide | 439 |
| 82 | N-{(2R)-3-[4-(3,4-dichlorophenoxy)piperidin-1-yl]-2-hydroxypropyl}-1H-benzimidazole-5-carboxamide | 462 |
| 83 | N-{(2R)-3-[4-(3,4-dichlorophenoxy)piperidin-1-yl]-2-hydroxypropyl}-1H-indole-5-carboxamide | 461 |
| 84 | N-{(2R)-3-[4-(3,4-dichlorophenoxy)piperidin-1-yl]-2-hydroxypropyl}-1-methyl-1H-indole-2-carboxamide | 475 |
| 85 | N-{(2R)-3-[4-(3,4-dichlorophenoxy)piperidin-1-yl]-2-hydroxypropyl}-1H-imidazole-4-carboxamide | 412 |
| 86 | N-{(2R)-3-[4-(3,4-dichlorophenoxy)piperidin-1-yl]-2-hydroxypropyl}-1H-indole-6-carboxamide | 461 |
| 87 | N-{(2R)-3-[4-(3,4-dichlorophenoxy)piperidin-1-yl]-2-hydroxypropyl}-1-methyl-1H-indole-3-carboxamide | 475 |
| 88 | N-{(2R)-3-[4-(3,4-dichlorophenoxy)piperidin-1-yl]-2-hydroxypropyl}-1H-indole-7-carboxamide | 461 |
| 89 | N-{(2R)-3-[4-(3,4-dichlorophenoxy)piperidin-1-yl]-2-hydroxypropyl}-3-[(methylamino)sulfonyl]benzamide | 515 |
| 90 | N-{(2R)-3-[4-(3,4-dichlorophenoxy)piperidin-1-yl]-2-hydroxypropyl}-3,4-bis(methylsulfonyl)benzamide | 578 |
| 91 | N-{(2R)-3-[4-(3,4-dichlorophenoxy)piperidin-1-yl]-2-hydroxypropyl}-2-pyridin-3-ylacetamide | 437 |
| 92 | N-{(2R)-3-[4-(3,4-dichlorophenoxy)piperidin-1-yl]-2-hydroxypropyl}-5-hydroxy-1H-indole-2-carboxamide | 477 |
| 93 | N-{(2R)-3-[4-(3,4-dichlorophenoxy)piperidin-1-yl]-2-hydroxypropyl}-1,5-dimethyl-1H-pyrazole-3-carboxamide | 440 |
| 94 | N-{(2R)-3-[4-(3,4-dichlorophenoxy)piperidin-1-yl]-2-hydroxypropyl}-5-(methylsulfonyl)-1H-indole-2-carboxamide | 539 |
| 95 | N-{(2R)-3-[4-(3,4-dichlorophenoxy)piperidin-1-yl]-2-hydroxypropyl}quinoxaline-6-carboxamide | 474 |
| 96 | N-{(2R)-3-[4-(3,4-dichlorophenoxy)piperidin-1-yl]-2-hydroxypropyl}-1,8-naphthyridine-2-carboxamide | 474 |
| 97 | N-{(2R)-3-[4-(3,4-dichlorophenoxy)piperidin-1-yl]-2-hydroxypropyl}imidazo[2,1-b][1,3]benzothiazole-2-carboxamide | 518 |
| 98 | N-{(2R)-3-[4-(3,4-dichlorophenoxy)piperidin-1-yl]-2-hydroxypropyl}-2,6-dimethylimidazo[1,2-a]pyridine-3-carboxamide | 490 |
| 99 | N-{(2R)-3-[4-{3,4-dichlorophenoxy)piperidin-1-yl]-2-hydroxypropyl}-3-oxo-2,3-dihydro-1H-indazole-4-carboxamide | 478 |
| 100 | N-{(2R)-3-[4-(3,4-dichlorophenoxy)piperidin-1-yl]-2-hydroxypropyl}-3-oxo-2,3-dihydro-1H-indazole-6-carboxamide | 478 |
| 101 | N-{(2R)-3-[4-(3,4-dichlorophenoxy)piperidin-1-yl]-2-hydroxypropyl}-3-(trifluoromethyl)-1H-pyrazole-4-carboxamide | 480 |
| 102 | 2-(1H-benzimidazol-1-yl)-N-{(2R)-3-[4-(3,4-dichlorophenoxy)piperidin-1-yl]-2-hydroxypropyl}acetamide | 476 |
| 103 | N-{(2R)-3-[4-(3,4-dichlorophenoxy)piperidin-1-yl]-2-hydroxypropyl}-1-ethyl-3-methyl-1H-pyrazole-5-carboxamide | 454 |
| 104 | N-{(2R)-3-[4-(3,4-dichlorophenoxy)piperidin-1-yl]-2-hydroxypropyl}-5-methyl-1H-pyrazole-3-carboxamide | 426 |
| 105 | N-{(2R)-3-[4-(3,4-dichlorophenoxy)piperidin-1-yl]-2-hydroxypropyl}-4-methyl-1,2,5-oxadiazole-3-carboxamide | 428 |
| 106 | 6-chloro-N-{(2R)-3-[4-(3,4-dichlorophenoxy)piperidin-1-yl]-2-hydroxypropyl}imidazo[1,2-a]pyridine-2-carboxamide | 496 |
| 107 | N-{(2R)-3-[4-(3,4-dichlorophenoxy)piperidin-1-yl]-2-hydroxypropyl}-2-methylimidazo[1,2-a]pyridine-3-carboxamide | 476 |
| 108 | N-{(2R)-3-[4-(3,4-dichlorophenoxy)piperidin-1-yl]-2-hydroxypropyl}imidazo[1,2-a]pyrimidine-2-carboxamide | 463 |
| 109 | N-{(2R)-3-[4-(3,4-dichlorophenoxy)piperidin-1-yl]-2-hydroxypropyl}-2-[(4-methylpyrimidin-2-yl)thio]acetamide | 484 |

| Example | Name | (M + H)+ |
|---|---|---|
| 110 | N-{(2R)-3-[4-(3,4-dichlorophenoxy)piperidin-1-yl]-2-hydroxypropyl}-4-oxo-1,4-dihydroquinoline-2-carboxamide | 489 |
| 111 | N-{(2R)-3-[4-(3,4-dichlorophenoxy)piperidin-1-yl]-2-hydroxypropyl}quinoline-8-carboxamide | 473 |
| 112 | N-{(2R)-3-[4-(3,4-dichlorophenoxy)piperidin-1-yl]-2-hydroxypropyl}-5-methylimidazo[1,2-a]pyridine-2-carboxamide | 476 |
| 113 | N-{(2R)-3-[4-(3,4-dichlorophenoxy)piperidin-1-yl]-2-hydroxypropyl}imidazo[1,2-a]pyridine-2-caxboxamide | 462 |
| 114 | N-{(2R)-3-[4-(3,4-dichlorophenoxy)piperidin-1-yl]-2-hydroxypropyl}-1,6-naphthyridine-2-carboxamide | 474 |
| 115 | N-{(2R)-3-[4-(3,4-dichlorophenoxy)piperidin-1-yl]-2-hydroxypropyl}-2,1,3-benzoxadiazole-5-carboxamide 1-oxide | 480 |

EXAMPLE 116

N-{(2R)-3-[4-(3,4-Dichlorophenoxy)piperidin-1-yl]-2-hydroxypropyl}-6-oxo-1,6-dihydropyridine-3-carboxamide

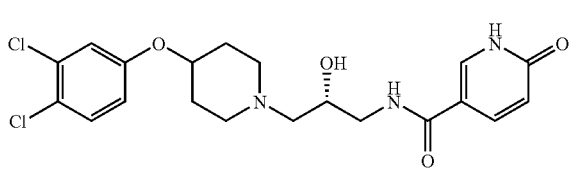

Prepared as described in Example 1 following Preparation 7.

MS (APCI) 440/442 (M+H)+

$^1$H NMR δ (CD$_3$OD) 8.07 (1H, d), 7.99 (1H, dd), 7.39 (1H, d), 7.15 (1H, d), 6.92 (1H, dd), 6.53 (1H, d), 4.52 (1H, septet), 4.09-4.01 (1H, m), 3.49 (1H, dd), 3.34 (1H, d), 3.11-3.02 (2H, m), 2.86-2.67 (4H, m), 2.14-2.03 (2H, m), 1.95 (3H, s), 1.97-1.84 (2H, m).

EXAMPLE 117

4-Chloro-N-{(2R)-3-[4-(3,4-dichlorophenoxy)piperidin-1-yl]-2-hydroxypropyl}-1H-pyrazole-3-carboxamide

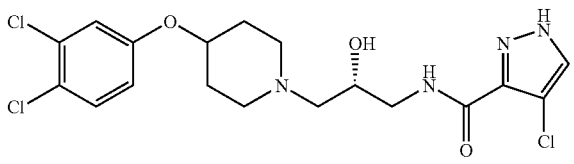

Prepared as described in Example 1 following Preparation 7.

MS (APCI) 447/449 (M+H)+

$^1$H NMR δ (CD$_3$OD) 7.77 (1H, s), 7.37 (1H, d), 7.09 (1H, d), 6.88 (1H, dd), 4.39 (1H, t), 3.95 (1H, quintet), 3.49 (1H, dd), 3.40 (1H, dd), 2.86-2.77 (2H, m), 2.52-2.39 (2H, m), 2.49 (2H, d), 2.06-1.96 (2H, m), 1.85-1.74 (2H, m).

EXAMPLE 118

N-{(2R)-3-[4-(3,4-Dichlorophenoxy)piperidin-1-yl]-2-hydroxypropyl}-5-phenyl-1,3-oxazole-4-carboxamide

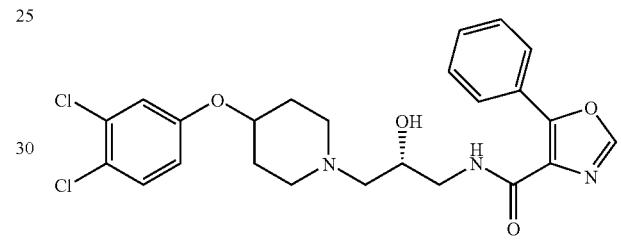

Prepared as described in Example 35 following Preparation 7 from 5-phenyl-1,3-oxazole-4-carbonyl chloride.

MS (APCI) 490/492 (M+H)+

$^1$H NMR δ (CD$_3$OD) 8.12 (1H, s), 8.10-8.08 (2H, m), 7.40-7.35 (3H, m), 7.29 (1H, d), 7.04 (1H, d), 6.81 (1H, dd), 4.39 (1H, septet), 3.95 (1H, quintet), 3.44-3.33 (2H, m), 2.96-2.87 (2H, m), 2.67-2.55 (4H, m), 2.03-1.93 (2H, m), 1.85 (3H, s), 1.85-1.75 (2H, m).

EXAMPLE 119

N-{(2R)-3-[4-(3,4-Dichlorophenoxy)piperidin-1-yl]-2-hydroxypropyl}-3,5-dimethyl-1H-pyrazole-4-carboxamide

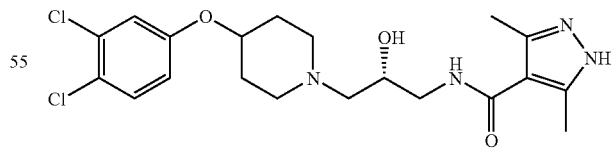

Prepared as described in Example 1 following Preparation 7.

MS (APCI) 441/443 (M+H)+

$^1$H NMR δ (CD$_3$OD) 7.28 (1H, d), 7.00 (1H, d), 6.79 (1H, dd), 4.34-4.26 (1H, m), 3.86 (1H, quintet), 3.41 (1H, dd), 3.21 (1H, dd), 2.78-2.67 (2H, m), 2.41-2.30 (4H, m), 2.29 (6H, s), 1.95-1.86 (2H, m), 1.73-1.63 (2H, m).

EXAMPLE 120

(2R)-2-(Acetylamino)-N-{(2R)-3-[4-(3,4-dichlorophenoxy)piperidin-1-yl]-2-hydroxypropyl}-2-phenylethanamide

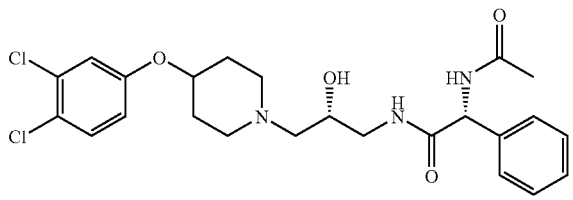

Prepared as described in Example 1 following Preparation 7.

MS (APCI) 494/496 (M+H)+

¹H NMR δ (CD₃OD) 7.34 (2H, d), 7.29-7.18 (4H, m), 6.99 (1H, t), 6.78 (1H, dd), 5.29 (1H, s), 4.27 (1H, septet), 3.76-3.65 (1H, m), 3.26-3.08 (2H, m), 2.65-2.49 (2H, m), 2.30-2.15 (4H, m), 1.91 (3H, s), 1.90-1.81 (2H, m), 1.69-1.58 (2H, m).

EXAMPLE 121

N-{(2R)-3-[4-(3,4-Dichlorophenoxy)piperidin-1-yl]-2-hydroxypropyl}-2-(2-hydroxyphenyl)acetamide

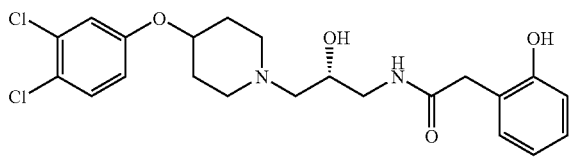

Prepared as described in Example 1 following Preparation 7.

MS (APCI) 453/455 (M+)+

¹H NMR δ (CD₃OD) 7.28 (1H, d), 7.05-6.97 (3H, m), 6.78 (1H, dd), 6.72-6.67 (2H, m), 4.27 (1H, dq), 3.72 (1H, quintet), 3.43 (2H, dd), 3.21-3.08 (2H, m), 2.68-2.57 (2H, m), 2.32-2.20 (4H, m), 1.90-1.81 (2H, m), 1.69-1.58 (–2H, m).

EXAMPLE 122

(2R)-N-{(2R)-3-[4-(3,4-Dichlorophenoxy)piperidin-1-yl]-2-hydroxypropyl}-2-[(methylsulfonyl)amino]-2-phenylethanamide

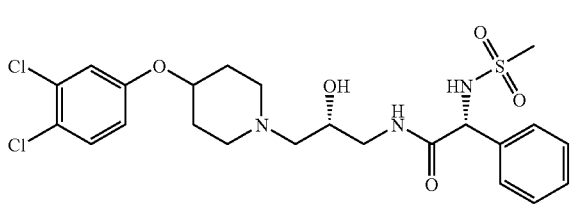

Prepared as described in Example 1 following Preparation 7.

MS (APCI) 530/532 (M+H)+

¹H NMR δ (CD₃OD) 7.37 (2H, d), 7.31-7.21 (4H, m), 6.99 (1H, d), 6.78 (1H, dd), 4.96 (1H, s), 4.27 (1H, septet), 3.70 (1H, quintet), 3.24 (1H, dd), 3.13 (1H, dd), 2.72 (3H, s), 2.66-2.56 (2H, m), 2.32-2.18 (4H, m), 1.91-1.82 (2H, m), 1.70-1.59 (2H, m).

EXAMPLE 123

(2S)-2-(Acetylamino)-N-{(2R)-3-[4-(3,4-dichlorophenoxy)piperidin-1-yl]-2-hydroxypropyl}-2-phenylethanamide

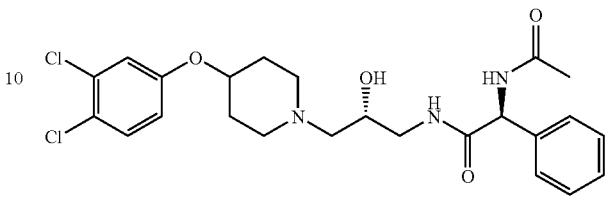

Prepared as described in Example 1 following Preparation 7.

MS (APCI) 494/496 (M+H)+

¹H NMR δ (CD₃OD) 7.34 (2H, d), 7.30-7.18 (4H, m), 6.99 (1H, dd), 6.78 (1H, ddd), 5.29 (1H, s), 4.30-4.23 (1H, m), 3.76-3.65 (1H, m), 3.17-3.07 (2H, m), 2.65-2.48 (2H, m), 2.30-2.14 (4H, m), 1.92-1.80 (2H, m), 1.91 (3H, s), 1.68-1.57 (2H, m).

EXAMPLE 124

(2S)-N-{(2R)-3-[4-(3,4-Dichlorophenoxy)piperidin-1-yl]-2-hydroxypropyl}-2-[(methylsulfonyl)amino]-2-phenylethanamide

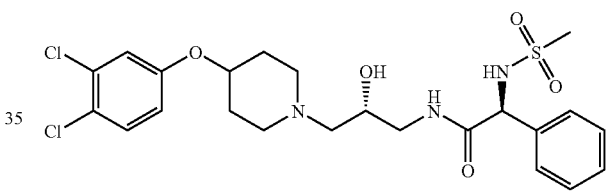

Prepared as described in Example 1 following Preparation 7.

MS (APCI) 530/5322 (M+H)+

¹H NMR δ (CD₃OD) 7.47 (2H, d), 7.40-7.30 (4H, m), 7.08 (1H, d), 6.87 (1H, dd), 5.06 (1H, s), 4.39-4.32 (1H, m), 3.83 (1H, quintet), 3.27 (2H, d), 2.80 (3H, s), 2.73-2.59 (2H, m), 2.38-2.24 (2H, m), 2.28 (2H, d), 1.99-1.89 (2H, m), 1.78-1.67 (2H, m).

EXAMPLE 125

1-{(R)-3-[4-(3,4-Dichlorophenoxy)piperidin-1-yl]-2-hydroxypropyl}-3-o-tolyl-urea

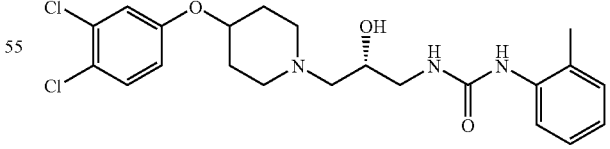

A solution of o-tolylisocyanate (64 ml, 0.51 mmol) in dichloromethane (1 ml) was added to a suspension of (2R)-1-amino-3-[4-(3,4-dichlorophenoxy)piperidin-1-yl]propan-2-ol (0.15 g, 0.47 mmol) in dichloromethane (3 ml) over a five minute period. After 1 h methanol (1 ml) was added and the solvents removed under vacuum. The residue was purified by reverse phase chromatography (C8 Symmetry column) to give the title compound (87 mg).

MS (APCI) 452/454 (M+H)+
¹H NMR δ (DMSO) 7.81 (1H, d), 7.78 (1H, s), 7.50 (1H, dd), 7.26 (1H, dd), 7.10 (1H, t), 7.05 (1H, s), 6.99 (1H, ddd), 6.86 (1H, t), 6.63 (1H, t), 4.74 (1H, d), 4.49-4.40 (1H, m), 3.72-3.63 (1H, m), 3.32-3.30 (1H, m), 2.99-2.90 (1H, m), 2.79-2.67 (2H, m), 2.35-2.24 (4H, m), 2.18 (3H, s), 1.97-1.88 (2H, m), 1.69-1.56 (2H, m).

EXAMPLE 126

1-{(R)-3-[4-(3,4-Dichlorophenoxy)piperidin-1-yl]-2-hydroxypropyl}-3-p-tolyl-urea

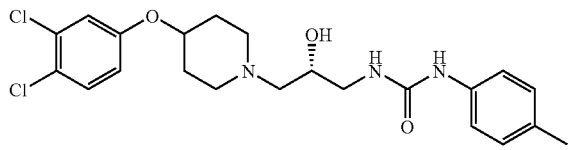

Prepared as described in Example 125 following Preparation 1.
MS (APCI) 452/454 (M+H)+
¹H NMR δ (DMSO) 8.52 (1H, s), 7.55 (1H, d), 7.31 (2H, d), 7.31 (1H, s), 7.07 (2H, d), 7.03 (1H, d), 6.15 (1H, t), 4.82-4.76 (1H, m), 4.55-4.45 (1H, m), 3.76-3.67 (1H, m), 3.36-3.32 (1H, m), 3.03-2.95 (1H, m), 2.83-2.72 (2H, m), 2.40-2.31 (4H, m), 2.27 (3H, s), 2.03-1.92 (2H, m), 1.75-1.61 (2H, m).

EXAMPLE 127

N-{(2S)-3-[4-(3,4-Dichlorophenoxy)piperidin-1-yl]-2-hydroxy-2-methylpropyl}-1-oxo-1,2-dihydroisoquinoline-4-carboxamide

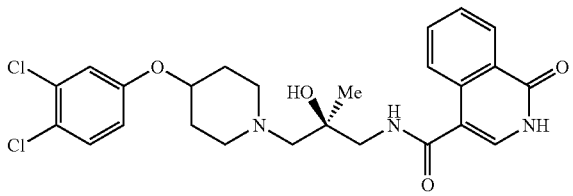

Prepared as described in Example 1 following Preparation 9.
MS (APCI) 504/506/508 (M+H)+
¹H NMR δ (CD₃OD) 8.37 (1H, d), 8.18 (1H, d), 7.78 (1H, t), 7.59 (1H, s), 7.58 (1H, t), 7.37 (1H, d), 7.07 (1H, d), 6.86 (1H dd), 4.33-4.28 (1H, m), 3.60-3.45 (2H, m), 3.04-2.92 (2H, m), 2.60-2.45 (4H, m), 1.98-1.86 (2H, m), 1.72-1.60 (2H, m), 1.25 (3H, s).

EXAMPLE 128

N-{(2S)-3-[4-(3,4-Dichlorophenoxy)piperidin-1-yl]-2-hydroxy-2-methylpropyl}-2-oxo-1,2-dihydroquinoline-4-carboxamide

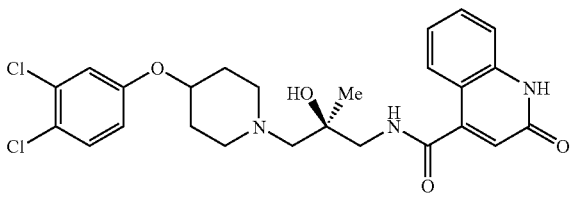

Prepared as described in Example 1 following Preparation 9.
MS (APCI) 504/506/508 (M+H)+
¹H NMR δ (CDCl₃) 7.93 (1H, d), 7.53 (1H, t), 7.34-7.20 (4H, m), 6.98 (1H, d), 6.75-6.69 (2H, m), 4.32-4.22 (1H, m), 3.68-3.40 (2H, m), 3.00-2.80 (2H, m), 2.70-2.48 (4H, m), 2.00-1.86 (2H, m), 1.84-1.72 (2H, m), 1.26 (3H, s).

EXAMPLE 129

N-{(2S)-3-[4-(3,4-Dichlorophenoxy)piperidin-1-yl]-2-hydroxy-2-methylpropyl}-4-oxo-3,4-dihydrophthalazine-1-carboxamide

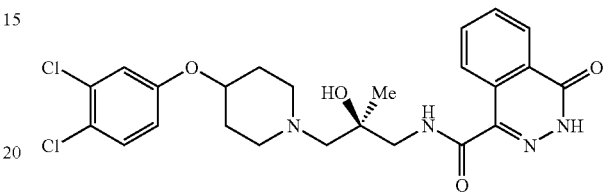

Prepared as described in Example 1 following Preparation 9.
MS (APCI) 505/507/509 (M+H)+
¹H NMR δ (CDCl₃) 10.18 (1H, bs), 9.15 (1H, d), 8.44 (1H, d), 8.06 (1H, bd s), 7.89 (1H, t), 7.81 (1H, t), 7.31 (1H, d), 7.01 (1H, d), 6.78 (1H, dd), 4.35-4.25 (1H, m), 3.58-3.37 (2H, m), 3.04-2.82 (2H, m), 2.66-2.46 (4H, m), 2.06-1.96 (2H, m), 1.94-1.80 (2H, m), 1.23 (3H, s).

EXAMPLE 130

(2S)-N-{(2S)-3-[4-(3,4-Dichlorophenoxy)piperidin-1-yl]-2-hydroxy-2-methylpropyl}-2-hydroxy-2-phenethanamide

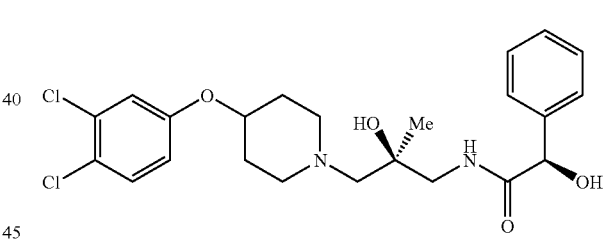

Prepared as described in Example 1 following Preparation 9.
MS (APCI) 467/469/471 (M+H)+
¹H NMR δ (CDCl₃) 7.46-7.29 (6H, m), 6.98 (1H, d), 6.78 (1H, bd s), 6.75 (1H, dd), 5.08 (1H, s), 4.28-4.20 (1H, m), 3.71 (1H, bd s), 3.35-3.20 (2H, m), 2.86-2.69 (2H, m), 2.53-2.39 (2H, m), 2.31 (2H, s), 1.97-1.85 (2H, m), 1.82-1.70 (2H, m), 1.04 (3H, s).

EXAMPLE 131

N-{(2R)-3-[4-(4-Chloro-2-methylphenoxy)piperidin-1-yl]-2-hydroxypropyl}-1-oxo-1,2-dihydroisoquinoline-4-carboxamide

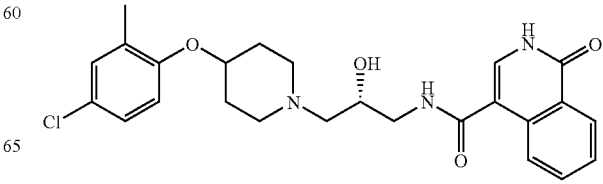

Prepared as described in Example 1 following Preparation 10.

MS (APCI) 470/472 (M+H)+

$^1$H NMR δ (CD$_3$OD) 8.25 (1H, d), 8.08 (1H, d), 7.67 (1H, t), 7.48 (2H, t), 7.05-6.96 (2H, m), 6.77 (1H, d), 4.36-4.25 (1H, m), 3.98-3.87 (1H, m), 3.45 (1H, dd), 3.28 (1H, dd), 2.80-2.67 (2H, m), 2.49-2.34 (4H, m), 2.08 (3H, s), 1.98-1.84 (2H, m), 1.78-1.64 (2H, m).

EXAMPLE 132

N-((2R)-3-{4-[2-Aminocarbonyl)-3,4-dichlorophenoxy]piperidin-1-yl}-2-hydroxypropyl)-1-oxo-1,2-dihydroisoquinoline-4-carboxamide

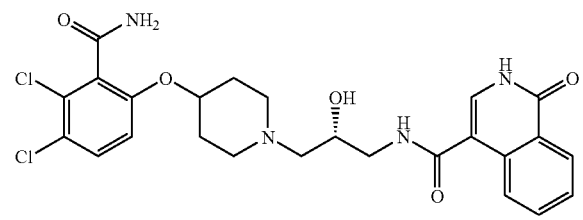

The crude amine product obtained from Preparation 11 was redissolved in dichloromethane and treated with diisopropylethylamine 0.85 ml) and 1-oxo-1,2-dihydroisoquinoline-4-carbonyl chloride (0.40 g) at room temperature. The reaction was quenched with saturated aqueous sodium hydrogen carbonate solution and the mixture concentrated in vacuo, azeotoping with toluene. Extraction of the solid residue into dichloromethane/methanol, filtering solids and chromatography on silica (dichloromethane:7N ammonia in methanol/15:2) gave the target compound as a white solid (0.31 g).

MS (APCI) 533/535 (M+H)+

$^1$H NMR δ (CD$_3$OD) 8.25 (1H, d), 8.12 (1H, d), 7.69 (1H, m), 7.55 (1H, s), 7.49 (1H, m), 7.44 (1H, d), 7.05 (1H, d), 4.20 (1H, m), 3.55-2.96 (10H, m), 2.25-1.98 (4H, m).

EXAMPLE 133

3-Cyano-N-{(2S)-3-[4-(3,4-dichlorophenoxy)piperidin-1-yl]-2-hydroxypropyl}benzenesulfonamide

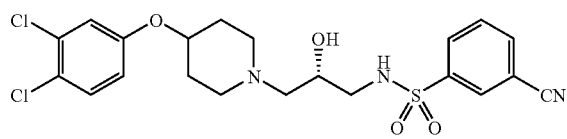

To a solution of (2-R)-1-amino-3-[4-(3,4-dichlorophenoxy)piperidin-1-yl]propan-2-ol (0.200 g, 0.63 mmol) in 4 ml of pyridine at 0° C. was added 3-cyanobenzenesulfonyl chloride (0.127 g, 0.63 mmol). After 30 min, the reaction was allowed to warm to room temperature and was stirred for 2 h. The reaction was concentrated under vacuum, and the residue partitioned between 10% aqueous sodium hydrogen carbonate and ethyl acetate. The organic layer was washed with water, then brine and dried over magnesium sulfate. The crude material was purified on silica gel (0 to 5% 7N ammonia in methanol/dichloromethane) to afford the title compound as a white foam (0.120 g).

MS (ESI) 484/486 (M+H)+

$^1$H NMR δ (DMSO) 8.22 (1H, d), 8.16-8.07 (2H, d), 7.82 (2H, t), 7.50 (1H, d), 7.25 (1H, d), 6.97 (1H, dd), 4.71 (d, 1H), 4.47-4.34 (1H, m), 3.63-3.51 (1H, m), 2.93 (1H, dd), 2.71 (1H, dd), 2.69-2.55 (2H, m), 2.32-2.12 (4H, m), 1.95-1.79 (2H, m), 1.65-1.45 (2H, m), 1.65-1.45 (2H, m).

EXAMPLE 134

5-[({(2S)-3-[4-(3,4-Dichlorophenoxy)piperidin-1-yl]-2-hydroxypropyl}amino)-sulfonyl]-2-methoxybenzamide

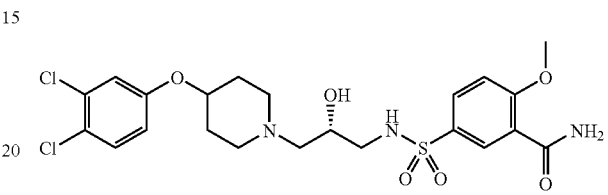

Prepared as described in Example 133 following Preparation 7 using 3-(aminocarbonyl) 4-methoxybenzenesulfonyl chloride.

MS (APCI) 531/533 (M+H)+

$^1$H NMR δ (DMSO) 8.20 (1H, d), 7.87 (1H, dd), 7.73 (2H, s), 7.55 (1H, s), 7.49 (1H, d), 7.32 (1H, d), 7.25 (1H, d), 6.97 (1H, dd), 4.67 (1H, d), 4.41 (1H, septet), 3.96 (3H, s), 3.58 (1H, q), 2.82 (1H, d), 2.68-2.57 (3H, m), 2.30-2.16 (4H, m), 1.91-1.82 (2H, m), 1.60-1.49 (2H, m).

EXAMPLE 135

N-{(2S)-3-[4-(3,4-Dichlorophenoxy)piperidin-1-yl]-2-hydroxypropyl}-1-oxo-1,2-dihydroisoquinoline-4-sulfonamide acetate salt

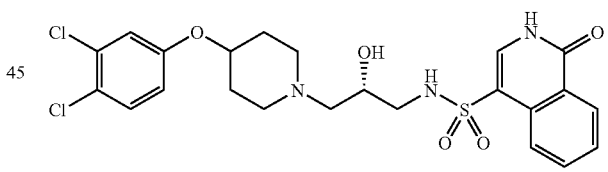

(2R)-1-Amino-3-[4-(3,4-dichlorophenoxy)piperidin-1-yl]propan-2-ol (0.1 g) in pyridine (2 ml) was treated with 1-oxo-1,2-dihydroisoquinoline-4-sulfonyl chloride (0.11 g) and the mixture was stirred at ambient temperature for 18 h. After further additions of the sulfonyl chloride (0.05 g) and stirring for 24 h the solvent was evaporated. Purification by column chromatography and reverse phase HPLC (symmetry C8 column and acetonitrile/0.1% aqueous ammonium acetate) yielded the title compound as a white solid (0.06 g).

MS (APCI) 526/528 (M+H)+

$^1$H NMR δ (DMSO) 8.39 (1H, d), 8.32 (1H, d), 7.95 (1H, s), 7.86 (1H, ddd), 7.64 (1H, t), 7.39 (1H, d), 7.11 (1H, d), 6.89 (1H, dd), 4.45-4.39 (1H, m), 3.82-3.75 (1H, m), 3.34 (1H, s), 2.97 (1H, dd), 2.92 (1H, dd), 2.81-2.72 (2H, m), 2.55-2.42 (2H, m), 2.02-1.92 (2H, m), 1.95 (3H, s, OAc), 1.82-1.72 (2H, m).

EXAMPLE 136

N-{(2S)-3-[4-(3,4-Dichlorophenoxy)piperidin-1-yl]-2-hydroxypropyl}-2,4-difluorobenzenesulfonamide

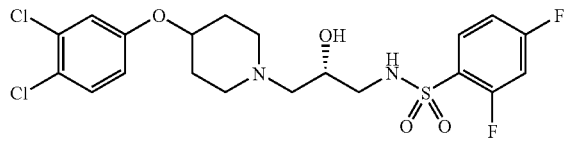

Prepared as described in Example 133 following Preparation 7 using 2,4-difluorobenzenesulfonyl chloride.

MS (APCI) 493/495 (M+H)+

$^1$H NMR δ (DMSO) 7.94 (1H, s), 7.86 (1H, td), 7.55 (1H, ddd), 7.49 (1H, d), 7.28 (1H, ddd), 7.25 (1H, d), 6.97 (1H, dd), 4.69 (1H, d), 4.42 (1H, septet), 3.60 (1H, sextet), 2.96 (1H, dd), 2.81 (1H, dd), 2.68-2.58 (2H, m), 2.34-2.16 (4H, m), 1.91-1.82 (2H, m), 1.60-1.49 (2H, m).

Further Examples of compounds of the invention which have been prepared according to Example 133 following Preparation 7 are now listed in the following table.

| Example | Name | (M + H)+ |
|---|---|---|
| 137 | N-{(2S)-3-[4-(3,4-dichlorophenoxy)piperidin-1-yl]-2-hydroxypropyl}methanesulfonamide | 396 |
| 138 | N-{(2S)-3-[4-(3,4-dichlorophenoxy)piperidin-1-yl]-2-hydroxypropyl}benzenesulfonamide | 458 |
| 139 | N-{(2S)-3-[4-(3,4-dichlorophenoxy)piperidin-1-yl]-2-hydroxypropyl}-1-phenylmethanesulfonamide | 472 |
| 140 | N-{(2S)-3-[4-(3,4-dichlorophenoxy)piperidin-1-yl]-2-hydroxypropyl}-4-methoxybenzenesulfonamide | 488 |
| 141 | N-({5-[({(2S)-3-[4-(3,4-dichlorophenoxy)piperidin-1-yl]-2-hydroxypropyl}amino)sulfonyl]-2-thienyl}methyl)benzamide | 597 |
| 142 | 4-cyano-N-{(2S)-3-[4-(3,4-dichlorophenoxy)piperidin-1-yl]-2-hydroxypropyl}benzenesulfonamide | 483 |
| 143 | N-{5-[({(2S)-3-[4-(3,4-dichlorophenoxy)piperidin-1-yl]-2-hydroxypropyl}amino)sulfonyl]-4-methyl-1,3-thiazol-2-yl}acetamide | 536 |
| 144 | N-{(2S)-3-[4-(3,4-dichlorophenoxy)piperidin-1-yl]-2-hydroxypropyl}thiophene-2-sulfonamide | 464 |
| 145 | 4-[({(2S)-3-[4-(3,4-dichlorophenoxy)piperidin-1-yl]-2-hydroxypropyl}amino)sulfonyl]benzoic acid | 502 |
| 146 | N-{(2S)-3-[4-(3,4-dichlorophenoxy)piperidin-1-yl]-2-hydroxypropyl}-2,5-dimethoxybenzenesulfonamide | 518 |
| 147 | N-{(2S)-3-[4-(3,4-dichlorophenoxy)piperidin-1-yl]-2-hydroxypropyl}-4-(phenylsulfonyl)thiophene-2-sulfonamide | 604 |
| 148 | N-{(2S)-3-[4-(3,4-dichlorophenoxy)piperidin-1-yl]-2-hydroxypropyl}-5-(1,3-oxazol-5-yl)thiophene-2-sulfonamide | 531 |
| 149 | N-{(2S)-3-[4-(3,4-dichlorophenoxy)piperidin-1-yl]-2-hydroxypropyl}-5-[1-methyl-5-(trifluoromethyl)-1H-pyrazol-3-yl]thiophene-2-sulfonamide | 612 |
| 150 | N-{(2S)-3-[4-(3,4-dichlorophenoxy)piperidin-1-yl]-2-hydroxypropyl}-5-(pyridin-2-yl)thiophene-2-sulfonamide | 541 |
| 151 | 5-chloro-N-{(2S)-3-[4-(3,4-dichlorophenoxy)piperidin-1-yl]-2-hydroxypropyl}-1,3-dimethyl-1H-pyrazole-4-sulfonamide | 510 |
| 152 | N-{(2S)-3-[4-(3,4-dichlorophenoxy)piperidin-1-yl]-2-hydroxypropyl}-3,5-dimethylisoxazole-4-sulfonamide | 477 |
| 153 | N-{(2S)-3-[4-(3,4-dichlorophenoxy)piperidin-1-yl]-2-hydroxypropyl}-2,1,3-benzothiadiazole-4-sulfonamide | 516 |
| 154 | N-{(2S)-3-[4-(3,4-dichlorophenoxy)piperidin-1-yl]-2-hydroxypropyl}-1-methyl-1H-imidazole-4-sulfonamide | 462 |
| 155 | N-{(2S)-3-[4-(3,4-dichlorophenoxy)piperidin-1-yl]-2-hydroxypropyl}-2,1,3-benzoxadiazole-4-sulfonamide | 500 |
| 156 | N-{(2S)-3-[4-(3,4-dichlorophenoxy)piperidin-1-yl]-2-hydroxypropyl}-5-(isoxazol-3-yl)thiophene-2-sulfonamide | 531 |
| 157 | methyl 3-[({(2S)-3-[4-(3,4-dichlorophenoxy)piperidin-1-yl]-2-hydroxypropyl}amino)sulfonyl]thiophene-2-carboxylate | 522 |
| 158 | 2,6-dichloro-N-{(2S)-3-[4-(3,4-dichlorophenoxy)piperidin-1-yl]-2-hydroxypropyl}benzenesulfonamide | 526 |
| 159 | N-{(2S)-3-[4-(3,4-dichlorophenoxy)piperidin-1-yl]-2-hydroxypropyl}-3-methylbenzenesulfonamide | 472 |
| 160 | 3-chloro-N-{(2S)-3-[4-(3,4-dichlorophenoxy)piperidin-1-yl]-2-hydroxypropyl}benzenesulfonamide | 492 |
| 161 | N-{(2S)-3-[4-(3,4-dichlorophenoxy)piperidin-1-yl]-2-hydroxypropyl}propane-2-sulfonamide | 424 |
| 162 | N-{(2S)-3-[4-(3,4-dichlorophenoxy)piperidin-1-yl]-2-hydroxypropyl}propane-1-sulfonamide | 424 |
| 163 | N-{(2S)-3-[4-(3,4-dichlorophenoxy)piperidin-1-yl]-2-hydroxypropyl}-5-methyl-1-phenyl-1H-pyrazole-4-sulfonamide | 538 |
| 164 | 3-chloro-N-{(2S)-3-[4-(3,4-dichlorophenoxy)piperidin-1-yl]-2-hydroxypropyl}-2-methylbenzenesulfonamide | 506 |

-continued

| Example | Name | (M + H)+ |
|---|---|---|
| 165 | methyl 5-[({(2S)-3-[4-(3,4-dichlorophenoxy)piperidin-1-yl]-2-hydroxypropyl}amino)sulfonyl]-2-methyl-3-furoate | 520 |
| 166 | methyl 5-[({(2S)-3-[4-(3,4-dichlorophenoxy)piperidin-1-yl]-2-hydroxypropyl}amino)sulfonyl]-1-methyl-1H-pyrrole-2-carboxylate | 519 |
| 167 | N-{(2S)-3-[4-(3,4-dichlorophenoxy)piperidin-1-yl]-2-hydroxypropyl}-3,4-dimethoxybenzenesulfonamide | 518 |
| 168 | 5-chloro-N-{(2S)-3-[4-(3,4-dichlorophenoxy)piperidin-1-yl]-2-hydroxypropyl}thiophene-2-sulfonamide | 498 |
| 169 | N-{(2S)-3-[4-(3,4-dichlorophenoxy)piperidin-1-yl]-2-hydroxypropyl}-6-(morpholin-4-yl)pyridine-3-sulfonamide | 544 |
| 170 | N-{2-chloro-4-[({(2S)-3-[4-(3,4-dichlorophenoxy)piperidin-1-yl]-2-hydroxypropyl}amino)sulfonyl]phenyl}acetamide | 549 |
| 171 | N-{(2S)-3-[4-(3,4-dichlorophenoxy)piperidin-1-yl]-2-hydroxypropyl}-2,3-dihydroxyquinoxaline-6-sulfonamide | 542 |
| 172 | N-{(2S)-3-[4-(3,4-dichlorophenoxy)piperidin-1-yl]-2-hydroxypropyl}-2,4-dimethoxybenzenesulfonamide | 518 |
| 173 | 5-[({(2S)-3-[4-(3,4-dichlorophenoxy)piperidin-1-yl]-2-hydroxypropyl}amino)sulfonyl]-2-methoxybenzamide | 531 |
| 174 | N-{(2S)-3-[4-(3,4-dichlorophenoxy)piperidin-1-yl]-2-hydroxypropyl}-2-methylbenzenesulfonamide | 472 |
| 175 | N-{(2S)-3-[4-(3,4-dichlorophenoxy)piperidin-1-yl]-2-hydroxypropyl}-2,4-dimethyl-1,3-thiazole-5-sulfonamide | 493 |
| 176 | N-{(2S)-3-[4-(3,4-dichlorophenoxy)piperidin-1-yl]-2-hydroxypropyl}-2-hydroxyquinoxaline-6-sulfonamide | 526 |
| 177 | N-{(2S)-3-[4-(3,4-dichlorophenoxy)piperidin-1-yl]-2-hydroxypropyl}-4-methyl-3,4-dihydro-2H-1,4-benzoxazine-7-sulfonamide | 529 |
| 178 | N-{(2S)-3-[4-(3,4-dichlorophenoxy)piperidin-1-yl]-2-hydroxypropyl}pyridine-3-sulfonamide | 459 |
| 179 | 4'-cyano-N-{(2S)-3-[4-(3,4-dichlorophenoxy)piperidin-1-yl]-2-hydroxypropyl}biphenyl-2-sulfonamide | 559 |
| 180 | N-{(2S)-3-[4-(3,4-dichlorophenoxy)piperidin-1-yl]-2-hydroxypropyl}-1,2-dimethyl-1H-imidazole-4-sulfonamide | 476 |
| 181 | 4-acetyl-N-{(2S)-3-[4-(3,4-dichlorophenoxy)piperidin-1-yl]-2-hydroxypropyl}benzenesulfonamide | 500 |
| 182 | N-{(2S)-3-[4-(3,4-dichlorophenoxy)piperidin-1-yl]-2-hydroxypropyl}-4-(methylsulfonyl)benzenesulfonamide | 536 |
| 183 | 2-chloro-4-cyano-N-{(2S)-3-[4-(3,4-dichlorophenoxy)-piperidin-1-yl]-2-hydroxypropyl}benzenesulfonamide | 517 |
| 184 | N-{(2S)-3-[4-(3,4-dichlorophenoxy)piperidin-1-yl]-2-hydroxypropyl}-1,3,5-trimethyl-1H-pyrazole-4-sulfonamide | 490 |

EXAMPLE 185

N-[(2R)-3-[4-(3,4-Dichlorophenoxy)-1-piperidinyl]-2-hydroxypropyl]-1,4-dihydro-4-oxo-3-quinolinecarboxamide

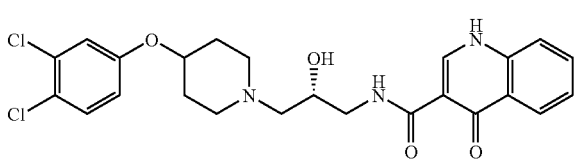

Prepared as described in Example 1 following Preparation 7 using 4-oxo-1,4-dihydroquinoline-3-carboxylic acid.

MS (APCI) 490/492 (M+H)+

$^1$H NMR δ (DMSO) 10.21 (5H, t), 8.74 (6H, s), 8.26 (6H, dd), 7.74 (10H, ddd), 7.68 (8H, d), 7.49 (11H, d), 7.48-7.44 (1H, m), 7.25 (6H, d), 6.98 (6H, dd), 4.80 (4H, s), 4.44 (6H, septet), 3.75 (6H, s), 3.55 (7H, ddd), 3.26-3.19 (20H, m), 2.78-2.68 (12H, m), 2.34 (20H, d), 2.33-2.25 (24H, m), 1.96-1.88 (12H, m), 1.69-1.58 (12H, m).

EXAMPLE 186

N-{(2S)-3-[4-(4-Chloro-2-methylphenoxy)piperidin-1-yl]-2-hydroxypropyl}-1-oxo-1,2-dihydroisoquinoline-4-carboxamide acetate salt

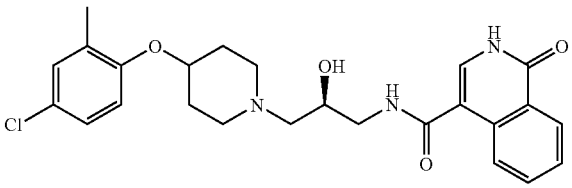

Prepared as described in Example 35 following Preparation 10 using (2S)-oxiran-2-ylmethyl-3-nitrobenzenesulfonate and 1-oxo-1,2-dihydroisoquinoline-4-carbonyl chloride.

MS (APCI) 470/472 (M+H)+

$^1$H NMR δ (DMSO) 8.32 (1H, t), 8.22 (2H, d), 7.73 (1H, td), 7.52 (1H, td), 7.52 (1H, s), 7.20 (1H, d), 7.14 (1H, dd), 6.98 (1H, d), 4.38 (1H, septet), 3.81 (1H, quintet), 3.43-3.36 (1H, m), 3.18-3.11 (1H, m), 2.75-2.63 (2H, m), 2.42-2.28 (4H, m), 2.14 (3H, s), 1.94-1.84 (2H, m), 1.88 (3H, s, OAc), 1.70-1.58 (2H, m).

EXAMPLE 187

N-{(2S)-3-{4-(3,4-Dichlorophenoxy)piperidin-1-yl]-2-hydroxypropyl}-1-oxo-1,2-dihydroisoquinoline-4-carboxamide

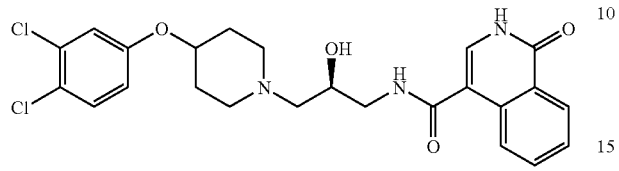

Prepared as described in Example 35 following Preparation 14 using 1-oxo-1,2-dihydroisoquinoline-4-carbonyl chloride.

MS (APCI) 490/492/494 (M+H)+

$^1$H NMR δ (CD$_3$OD) 8.40 (1H, d), 8.21 (1H, d), 7.74 (1H, t), 7.54 (1H, t), 7.50 s), 7.32 (1H, d), 7.00 (1H, d), 6.76 (1H, dd), 4.36-4.24 (1H, m), 3.99-3.93 (1H, d), 3.73-3.68 (1H, d), 3.33-3.28 (1H, m), 2.96-2.84 (1H, m), 2.75-2.30 (5H, m), 2.04-1.94 (2H, m), 1.88-1.76 (2H, s).

EXAMPLE 188

N-{(2S)-3-{4-(3,4-Dichlorophenoxy)piperidin-1-yl]-2-hydroxypropyl}-1-oxo-1,2-dihydroisoquinoline-4-carboxamide

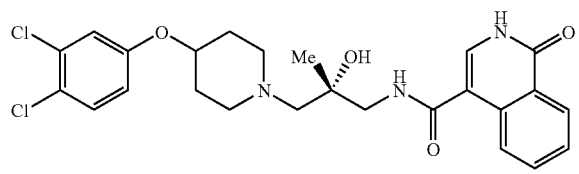

Prepared as described in Example 35-following Preparation 15 using 1-oxo-1,2-dihydroisoquinoline-4-carbonyl chloride.

MS (APCI) 504/506/508 (M+H)+

$^1$H NMR δ (CD$_3$OD) 8.38 (1H, d), 8.19 (1H, d) 7.80 (1H, t), 7.61 (1H, t), 7.60 (1H, t), 7.38 (1H, d), 7.09 (1H, d), 6.87 (1H, dd), 4.37-4.30 (1H, m), 3.64 (1H, d), 3.42 (1H, d), 3.03-2.83 (2H, m), 2.60-2.46 (4H, m), 1.96-1.86 (2H, m), 1.72-1.60 (2H, m), 1.26 (3H, s).

EXAMPLE 189

N-{(2R)-3-[4-(3,4-Dichlorophenoxy)piperidin-1-yl]-2-hydroxypropyl}-7-[(methylamino)sulfonyl]-1-oxo-1,2-dihydroisoquinoline-4-carboxamide

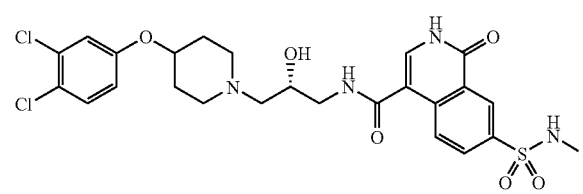

7-[(Methylamino)sulfonyl]-1-oxo-1,2-dihydroisoquinoline-4-carboxylic acid (0.1 g) in dimethyl formamide (7 ml) was treated with N,N-carbonyldiimidazole (0.06 g) and the mixture was heated at 55° C. for 45 min. (2R)-1-Amino-3-[4-(3,4-dichlorophenoxy)piperidin-1-yl]propan-2-ol (0.11 g) in dimethyl formamide (1 ml) was added and the mixture was stirred at ambient temperature for 18 h. 1 Drop of water was added and the solvent was evaporated. Purification using revere phase HPLC (Symmetry C8 column) and acetonitrile/aqueous ammonium acetate as eluent yielded the title compound as a white solid (0.03 g).

MS (APCI) 583/585 (M+H)+

$^1$H NMR δ (DMSO) 8.59 (1H, s), 8.44 (1H, d), 8.42 (1H, t), 8.04 (1H, dd), 7.73 (1H, s), 7.62 (1H, s), 7.49 (1H, d), 7.25 (1H, d), 6.98 (1H, dd), 4.79 (1H, s), 4.44 (1H, septet), 3.80 (1H, quintet), 3.45-3.37 (1H, m), 3.18-3.11 (1H, m), 2.81-2.69 (2H, m), 2.42 (3H, s), 2.39-2.25 (4H, m), 1.96-1.87 (2H, m), 1.66-1.55 (2H, m).

EXAMPLE 190

N-{(2R)-3-[4-(3,4-Dichlorophenoxy)piperidin-1-yl]-2-hydroxypropyl}-7-{[(2-hydroxyethyl)amino]sulfonyl}-1-oxo-1,2-dihydroisoquinoline-4-carboxamide acetate salt

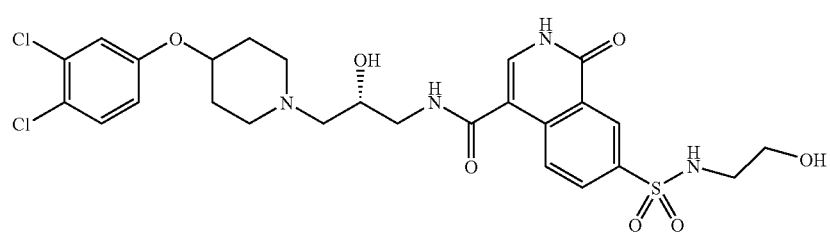

Prepared as described in Example 189 following Preparation 7 using 1,2-dihydro-7-[[(2-hydroxyethyl)amino]sulfonyl]-1-oxo-4 isoquinolinecarboxylic acid.

MS (APCI) 613/615 (M+H)+

$^1$H NMR δ (DMSO) 8.61 (1H, s), 8.42 (1H, d), 8.07 (1H, dd), 7.71 (1H, s), 7.49 (1H, d), 7.25 (1H, d), 6.98 (1H, d), 4.44 (1H, septet), 3.81 (1H, quintet), 3.46-3.37 (1H, m), 3.35 (2H, t), 3.18-3.10 (1H, m), 2.80-2.68 (2H, m), 2.80 (2H t), 2.42-2.25 (4H, m), 1.96-1.87 (2H, m), 1.88 (3H, s, OAc), 1.66-1.55 (2H, m).

EXAMPLE 191

7-[(Cyclopropylamino)sulfonyl]-N-{(2R)-3-[4-(3,4-dichlorophenoxy)piperidin-1-yl]-2-hydroxypropyl}-1-oxo-1,2-dihydroisoquinoline-4-carboxamide

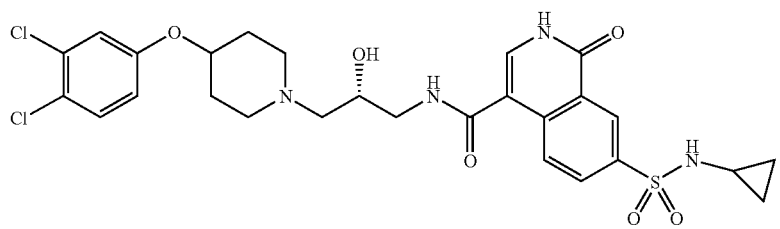

Prepared as described in Example 189 following Preparation 7 using 7-[(cyclopropylamino)sulfonyl]-1,2-dihydro-1-oxo-4-isoquinolinecarboxylic acid.

MS (APCI) 609/611 (M+H)+

$^1$H NMR δ (DMSO) 8.64 (1H, s), 8.44 (1H, d), 8.41 (1H, t), 8.07 (1H, dd), 7.72 (1H, s), 7.49 (1H, d), 7.25 (1H, d), 6.98 (1H, dd), 4.78 (1H, s), 4.44 (1H, septet), 3.81 (1H, quintet), 3.45-3.38 (1H, m), 3.18-3.10 (1H, m), 2.81-2.69 (2H, m), 2.42-2.25 (4H, m), 2.15-2.09 (1H, m), 1.96-1.86 (2H, m), 1.66-1.54 (2H, m), 0.50-0.44 (2H, m), 0.38-0.32 (2H, m).

EXAMPLE 192

7-(Azetidin-1-ylsulfonyl)-N-{(2R)-3-[4-(3,4-dichlorophenoxy)piperidin-1-yl]-2-hydroxypropyl}-1-oxo-1,2-dihydroisoquinoline-4-carboxamide Acetate Salt

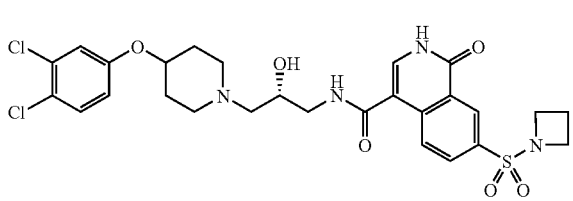

Prepared as described in Example 189 following Preparation 7 using 7-(azetidin-1-ylsulfonyl)-1-oxo-1,2-dihydroisoquinoline-4-carboxylic acid.

MS (APCI) 609/611 (M+H)+

$^1$H NMR δ (DMSO) 8.53 (1H, t), 8.52 (1H, d), 8.44 (1H, t), 8.09 (1H, dd), 7.77 (1H, s), 7.50 (1H, d), 7.25 (1H, d), 6.98 (1H, dd), 4.43 (1H, septet), 3.81 (1H, quintet), 3.69 (4H, t), 3.47-3.37 (1H, m), 3.21-3.10 (1H, m), 2.83-2.68 (2H, m), 2.40-2.24 (4H, m), 2.05-1.86 (2H, m), 1.97 (2H, quintet), 1.88 (3H, s, OAc), 1.68-1.53 (2H, m).

EXAMPLE 193

7-(Aminosulfonyl)-N-{(2R)-3-[4-(3,4-dichlorophenoxy)piperidin-1-yl]-2-hydroxypropyl}-1-oxo-1,2-dihydroisoquinoline-4-carboxamide

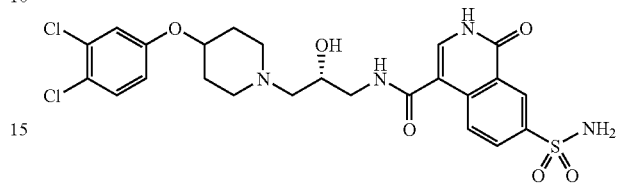

Prepared as described in Example 189 following Preparation 7 using 7-(aminosulfonyl)-1-oxo-1,2-dihydroisoquinoline-4-carboxylic acid.

MS (APCI) 569/571 (M+H)+

$^1$H NMR δ (DMSO) 8.65 (1H, s), 8.40 (1H, d), 8.39 (1H, t), 8.09 (1H, dd), 7.69 (1H, s), 7.49 (1H, d), 7.50 (2H, s), 7.25 (1H, d), 6.98 (1H, dd), 4.77 (1H, s), 4.44 (1H, septet), 3.85-3.77 (1H, m), 3.41 (1H, dt), 3.14 (1H, dt), 2.81-2.69 (2H, m), 2.41-2.25 (4H, m), 1.96-1.86 (2H, m), 1.67-1.54 (2H, m).

EXAMPLE 194

N-{(2R)-3-[4-(3,4-Dichlorophenoxy)piperidin-1-yl]-2-hydroxypropyl}-7-[(dimethylamino)sulfonyl]-1-oxo-1,2-dihydroisoquinoline-4-carboxamide Prepared as described in Example 189 following Preparation 7 using 7-[(dimethylamino)sulfonyl]-1-oxo-1,2-dihydroisoquinoline-4-carboxylic acid

MS (APCI) 597/599 (M+H)+

$^1$H NMR δ (DMSO) 8.49 (1H, s), 8.48 (1H, d), 8.43 (1H, t), 8.04 (1H, dd), 7.75 (1H, s), 7.49 (1H, d), 7.25 (1H, d), 6.98 (1H, dd), 4.44 (1H, septet), 3.81 (1H, quintet), 3.46-3.37 (1H, m), 3.18-3.11 (1H, m), 2.82-2.69 (2H, m), 2.64 (6H, s), 2.42-2.26 (4H, m), 1.95-1.86 (2H, m), 1.89 (3H, s, OAc), 1.60 (2H, dt).

EXAMPLE 195

N-{(2R)-3-[4-(3,4-Dichlorophenoxy)piperidin-1-yl]-2-hydroxypropyl}-7-[(3-hydroxy-3-methylazetidin-1-yl)sulfonyl]-1-oxo-1,2-dihydroisoquinoline-4-carboxamide acetate salt

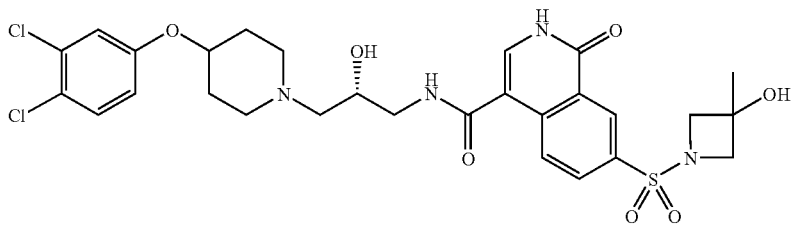

Prepared as described in Example 189 following Preparation 7 using 7-[(3-hydroxy-3-methylazetidin-1-yl)sulfonyl]-1-oxo-1,2-dihydroisoquinoline-4-carboxylic acid.

MS (APCI) 639/641 (M+H)$^+$ $^1$H NMR δ (DMSO) 8.53 (1H, d), 8.51 (1H, d), 8.45 (1H, t), 8.08 (1H, dd), 7.77 (1H, s), 7.49 (1H, d), 7.25 (1H, d), 6.98 (1H, dd), 4.44 (1H, septet), 3.82 (1H, quintet), 3.60 (2H, d), 3.45 (2H, d), 3.45-3.40 (1H, m), 3.19-3.10 (1H, m), 2.81-2.69 (2H, m), 2.42-2.25 (4H, m), 1.96-1.84 (2H, m), 1.88 (3H, s, OAc), 1.66-1.55 (2H, m).

EXAMPLE 196

N-[(2R)-3-(4-{3,4-Dichloro-2-[(cyclopropylamino)carbonyl]phenoxy}piperidin-1-yl)-2-hydroxypropyl]-1-oxo-1,2-dihydroisoquinoline-4-carboxamide acetate salt

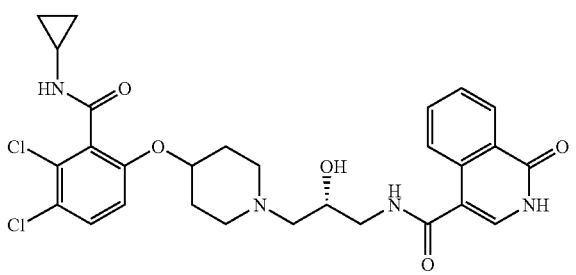

Prepared as described in Example 35 following Preparation 35 using 1-oxo-1,2-dihydroisoquinoline-4-carbonyl chloride.

MS (APCI) 573/575 (M+H)$^+$ $^1$H NMR δ (CD$_3$OD) 8.25 (1H, d), 8.09 (1H, d), 7.68 (1H, t), 7.49 (1H, s), 7.48 (1H, t), 7.38 (1H, d), 6.97 (1H, d), 4.54-4.48 (1H, m), 4.03-3.97 (1H, m), 3.44 (1H, dd), 3.30 (1H, dd), 2.90-2.79 (2H, m), 2.76-2.58 (5H, m), 1.98-1.89 (2H, m), 1.87-1.79 (2H, m), 1.85 (3H, s, OAc), 0.70-0.65 (2H, m), 0.52-0.48 (2H, m).

EXAMPLE 197

N-{(2R)-3-[4-(3-Chloro-4-cyanophenoxy)piperidin-1-yl]-2-hydroxypropyl}-1-oxo-1,2-dihydroisoquinoline-4-carboxamide

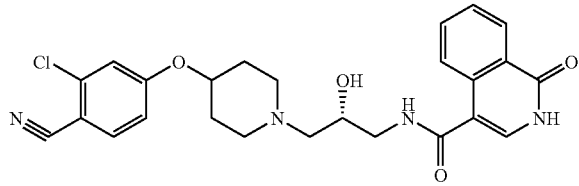

Prepared as described in Example 35 following Preparation 24 using 1-oxo-1,2-dihydroisoquinoline-4-carbonyl chloride.

MS (APCI) 481 (M+H)$^+$ $^1$H NMR δ (CD$_3$OD) 8.36 (1H, dd), 8.19 (1H, d), 7.86 (2H, d), 7.77-7.75 (2H, m), 7.57 (2H, td), 7.12 (2H, d), 4.62-4.56 (1H, m), 4.07-4.01 (1H, m), 3.57 (1H, dd), 3.38 (1H, dd), 3.08 (3H, s), 2.98-2.88 (2H, m), 2.66-2.55 (4H, m), 2.12-2.04 (2H, m), 1.92-1.83 (2H, m).

EXAMPLE 198

N-((2R)-2-Hydroxy-3-{4-[4-(methylsulfonyl)phenoxy]piperidin-1-yl}propyl)-1-oxo-1,2-dihydroisoquinoline-4-carboxamide

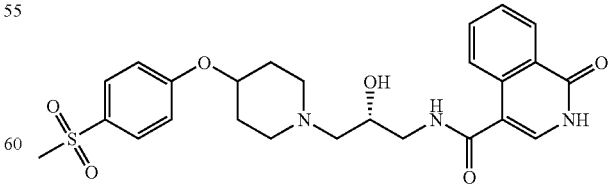

Prepared as described in Example 35 following Preparation 25 using 1-oxo-1,2-dihydroisoquinoline-4-carbonyl chloride.

MS (APCI) 500 (M+H)$^+$

¹H NMR δ (CD₃OD) 8.36 (1H, dd), 8.19 (1H, d), 7.86 (2H, d), 7.77-7.75 (2H, m), 7.57 (2H, td), 7.12 (2H, d), 4.62-4.56 (1H, m), 4.07-4.01 (1H, m), 3.57 (1H, dd), 3.38 (1H, dd), 3.08 (3H, s), 2.98-2.88 (2H, m), 2.66-2.55 (4H, m), 2.12-2.04 (2H, m), 1.92-1.83 (2H, m).

EXAMPLE 199

N-{(2R)-3-[4-(4-Cyanophenoxy)piperidin-1-yl]-2-hydroxypropyl}-1-oxo-1,2-dihydroisoquinoline-4-carboxamide

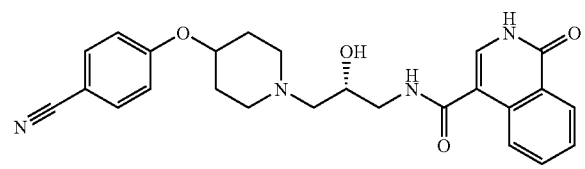

Prepared as described in Example 35 following Preparation 26 using 1-oxo-1,2-dihydroisoquinoline-4-carbonyl chloride.

MS (APCI) 447 (M+H)⁺

¹H NMR δ (DMSO) 8.31 (1H, t), 8.22 (2H, d), 7.75-7.71 (3H, m), 7.54-7.50 (2H, m), 7.12 (2H, d), 4.80-4.73 (1H, m), 4.56-4.49 (1H, m), 3.83-3.77 (1H, m), 3.42-3.35 (2H, m), 3.18-3.11 (1H, m), 2.81-2.71 (2H, m), 2.41-2.27 (4H, m), 1.98-1.91 (2H, m), 1.68-1.59 (2H, m).

EXAMPLE 200

N-((2R)-3-{4-[2-(Aminocarbonyl)-4-chlorophenoxy]piperidin-1-yl}-2-hydroxypropyl)-1-oxo-1,2-dihydroisoquinoline-4-carboxamide

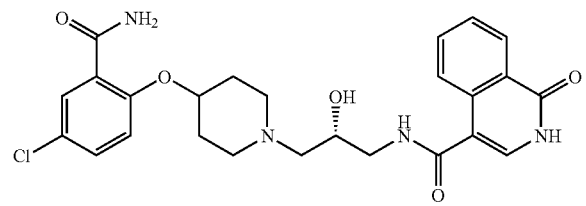

Prepared as described in Example 35 following Preparation 33 using 3-oxo-1,2-dihydroisoquinoline-4-carbonyl chloride.

MS (APCI) 499 (M+H)⁺

¹H NMR δ (CD₃OD) 8.25 (1H, d), 8.08 (1H, d), 7.78 (1H, d), 7.467 (1H, td), 7.48 (1H, t), 7.47 (1H, s), 7.35 (1H, dd), 7.08 (1H, d), 4.56-4.50 (1H, m), 3.94-3.89 (1H, m), 3.46 (1H, dd), 3.27 (1H, dd), 2.79-2.70 (2H, m), 2.46-2.36 (4H, m), 2.03-1.95 (2H, m), 1.82-1.73 (2H, m).

EXAMPLE 201

N-[(2R)-3-(4-{4-Chloro-2-[(methylamino)carbonyl]phenoxy}piperidin-1-yl)-2-hydroxypropyl]-1-oxo-1,2-dihydroisoquinoline-4-carboxamide

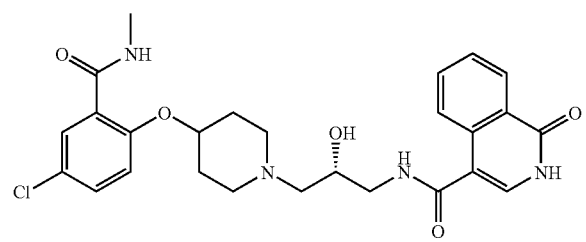

Prepared as described in Example 35 following Preparation 32 using 1-oxo-1,2-dihydroisoquinoline-4-carbonyl chloride.

MS (APCI) 513 (M+H)⁺

¹H NMR δ (CD₃OD) 8.25 (1H, d), 8.09 (1H, d), 7.67 (1H, td), 7.63 (1H, d), 7.48 (1H, s), 7.48 (1H, td), 7.33 (1H, dd), 7.07 (1H, d), 4.59-4.51 (1H, m), 4.01-3.94 (1H, m), 3.46 (1H, dd), 3.28 (1H, dd), 2.91-2.80 (2H, m), 2.83 (3H, s), 2.66-2.54 (4H, m), 2.05-1.94 (2H, m), 1.90-1.79 (2H, m).

EXAMPLE 202

Methyl 5-chloro-2-{[1-((2R)-2-hydroxy-3-{[(1-oxo-1,2-dihydroisoquinolin-4-yl)carbonyl]amino}propyl)piperidin-4-yl]oxy}benzoate acetate salt

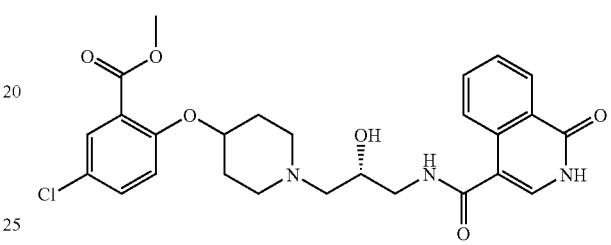

Prepared as described in Example 35 following Preparation 31 using 1-oxo-1,2-dihydroisoquinoline-4-carbonyl chloride.

MS (APCI) 513 (M+H)⁺

¹H NMR δ (CD₃OD) 8.25 (1H, dd), 8.09 (1H, d), 7.67 (1H, td), 7.60 (1H, d) (1H, s), 7.48 (1H, td), 7.38 (1H, dd), 7.06 (1H, d), 4.59-4.54 (1H, m), 4.05-3.99 (1H, m), 3.76 (3H, s), 3.45 (1H, dd), 3.30 (1H, dd), 3.03-2.92 (2H, m), 2.79-2.61 (4H, m), 2.00-1.86 (4H, m), 1.84 (3H, s, OAc).

EXAMPLE 203

N-((2R)-3-{4-[2-(Aminosulfonyl)-3,4-dichlorophenoxy]piperidin-1-yl}-2-hydroxypropyl)-1-oxo-1,2-dihydroisoquinoline-4-carboxamide trifluoroacetate salt

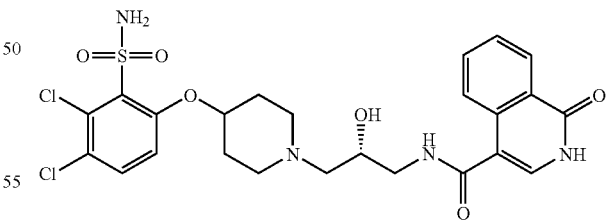

Prepared as described in Example 35 following Preparation 40 using 1-oxo-1,2-dihydroisoquinoline-4-carbonyl chloride.

MS (APCI) 569/571 (M+H)⁺

¹H NMR δ (CD₃OD) 8.26 (1H, d), 8.09 (1H, d), 7.71 (1H, t), 7.62 (1H, d), 7.52 (1H, s), 7.48 (1H, t), 7.18 (1H, d), 5.02 (1H, s), 4.23-4.15 (1H, m), 3.55 (1H, m), 3.46-3.33 (5H, m), 3.16-3.08 (2H, m), 2.26 (2H, t), 2.15-2.00 (2H, m).

EXAMPLE 204

N-[(2R)-3-(4-{3,4-Dichloro-2-[(methylamino)sulfonyl]phenoxy}piperidin-1-yl)-2-hydroxypropyl]-1-oxo-1,2-dihydroisoquinoline-4-carboxamide acetate salt

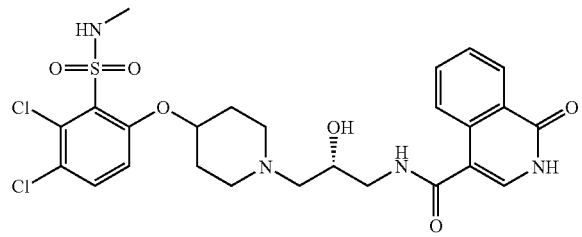

Prepared as described in Example 35 following Preparation 41 using 1-oxo-1,2-dihydroisoquinoline 4 carbonyl chloride.

MS (APCI) 583/585 (M+H)$^+$ $^1$H NMR δ (CD$_3$OD) 8.25 (1H, d), 8.08 (1H, d), 7.69 (1H, td), 7.60 (1H, d), 7.49 (1H, s), 7.48 (1H, td), 7.16 (1H, d), 4.73-4.68 (1H, m), 4.05-3.99 (1H, m), 3.44 (1H, dd), 3.30 (1H, dd), 3.15-3.04 (2H, m), 2.78-2.63 (4H, m), 2.52 (3H, s), 2.07-1.93 (4H, m), 1.85 (3H, s, OAc).

EXAMPLE 205

N-[(2R)-3-(4-{3,4-Dichloro-2-[(cyclopropylamino)sulfonyl]phenoxy}piperidin-1-yl)-2-hydroxypropyl]-1-oxo-1,2-dihydroisoquinoline-4-carboxamide acetate salt

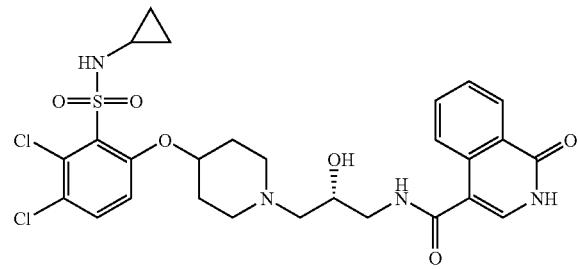

Prepared as described in Example 35 following Preparation 42 using 1-oxo-1,2-dihydroisoquinoline-4-carbonyl chloride.

MS (APCI) 609/611 (M+H)$^+$ $^1$H NMR δ (CD$_3$OD) 8.25 (1H, d), 8.08 (1H, d), 7.68 (1H, t), 7.61 (1H, d), 7.49 (1H, s), 7.47 (1H, t), 7.17 (1H, d), 4.72-4.65 (1H, m), 4.03-3.96 (1H, m), 3.44 (1H, dd), 3.30 (1H, dd), 3.11-2.99 (2H, m), 2.73-2.58 (4H, m), 2.19-2.13 (1H, m), 2.04-1.90 (4H, m), 1.83 (3H, s, OAc), 0.50-0.43 (4H, m).

EXAMPLE 206

N-{(2R)-3-[4-(3-Chloro-4-cyanophenoxy)piperidin-1-yl]-2-hydroxypropyl}-7-(methylsulfonyl)-1-oxo-1,2-dihydroisoquinoline-4-carboxamide

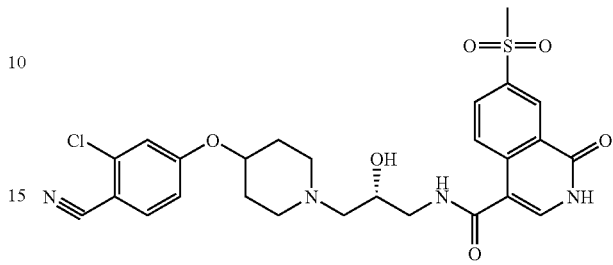

Prepared as described in Example 189 following Preparation 24 using 7-(methylsulfonyl)-1-oxo-1,2-dihydroisoquinoline-4-carboxylic acid.

MS (APCI) 559 (M+H)$^+$ $^1$H NMR δ (CD$_3$OD) 8.78 (1H, d), 8.35 (1H, d), 8.14 (1H, dd), 7.68 (1H, s), 7.60 (1H, d), 7.12 (1H, d), 6.95 (1H, dd), 4.56-4.51 (1H, m), 4.01-3.95 (1H, m), 3.47 (1H, dd), 3.28 (1H, dd), 3.10 (3H, s), 2.94-2.85 (2H, m), 2.64-2.52 (4H, m), 2.04-1.95 (2H, m), 1.86 (3H, s), 1.83-1.74 (2H, m).

EXAMPLE 207

N-{(2R)-3-{4-(4-Chloro-2-methylphenoxy)piperidin-1-yl]-2-hydroxy-2-methylpropyl}-6-(methylsulphonyl)-1H-indole-3-carboxamide

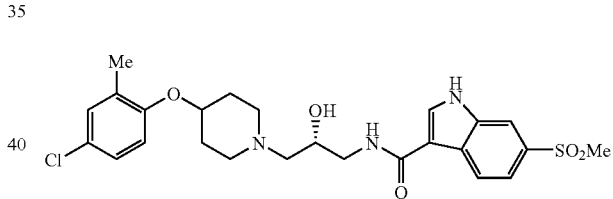

Prepared as described in Example 189 following Preparation 10 using 6-(methylsulphonyl)-1H-indole-3-carboxylic acid.

MS (APCI) 520/522/524 (M+H)$^+$ $^1$H NMR δ (CD$_3$OD) 8.35 (1H, d), 8.19 (1H, s), 8.07 (1H, d), 7.69 (1H, dd), 7.11 (1H, d), 7.08 (1H, dd), 6.88 (1H, d), 4.56-4.48 (1H, m), 4.20-4.12 (1H, m), 3.57 (1H, dd), 3.43 (1H, dd), 3.19-3.12 (5H, s), 3.03-2.98 (2H, m), 2.94 (1H, dd), 2.85 (1H, m), 2.18 (3 h, s), 2.16-2.08 (2H, m), 2.03-1.94 (2H, m).

EXAMPLE 208

N-{(2R)-3-{4-(3,4-Dichlorophenoxy)piperidin-1-yl]-2-hydroxypropyl}-6-(methylsulphonyl)-1H-indole-3-carboxamide

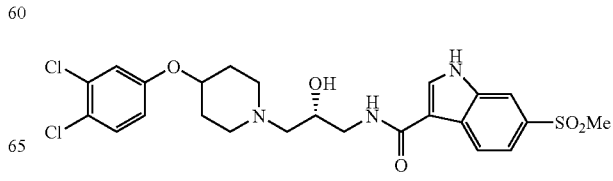

Prepared as described in Example 189 following Preparation 8 using 6-(methylsulphonyl)-1H-indole-3-carboxylic acid.

MS (APCI) 540/542/544 (M+H)+

¹H NMR δ (CD₃OD) 8.35 (1H, d), 8.34 (1H, s), 8.06 (1H, d), 7.69 (1H, dd), 7.38 (1H, d), 7.09 (1H, d), 6.87 (1H, dd), 4.50-4.43 (1H, m), 4.12-4.06 (1H, m), 3.57 (1H, dd), 3.41 (1H, dd), 3.13 (3H, s), 3.07-2.99 (2H, m), 2.81-2.68 (4H, m), 2.12-2.04 (2H, m), 1.94-1.82 (2H, m).

EXAMPLE 209

N-{(2R)-3-[(3,4-Dichlorophenoxy)piperidin-1-yl]-2-hydroxypropyl}-7-fluoro-1-oxo-1,2-dihydroisoquinoline-4-carboxamide

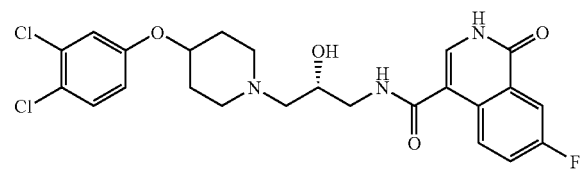

Prepared as described in Example 189 following Preparation 7 using 7-fluoro-1-oxo-1,2-dihydroisoquinoline-4-carboxylic acid.

MS (APCI) 508/510 (M+H)+

¹H NMR δ (DMSO) 11.73 (1H, s), 8.39-8.26 (2H, m), 7.88 (1H, dd), 7.64 (1H, td), 7.54 (1H, s), 7.49 (1H, d), 7.25 (1H, d), 6.98 (1H, dd), 4.79-4.71 (1H, m), 4.48-4.38 (1H, m), 3.85-3.75 (1H, m), 3.46-3.34 (1H, m), 3.19-3.09 (1H, m), 2.82-2.65 (2H, m), 2.43-2.23 (4H, m), 1.97-1.84 (2H, m), 1.67-1.53 (2H, m).

EXAMPLE 210

N-{(2R)-3-[4-(4-Chloro-2-methylphenoxy)piperidin-1-yl]-2-hydroxypropyl}-7-fluoro-1-oxo-1,2-dihydroisoquinoline-4-carboxamide

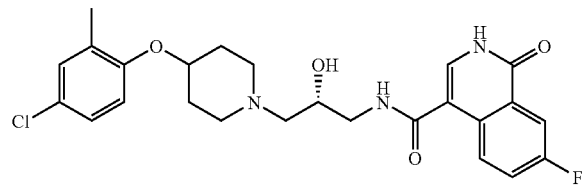

Prepared as described in Example 189 following Preparation 10 using 7-fluoro-1-oxo-1,2-dihydroisoquinoline-4-carboxylic acid.

MS (APCI) 488 (M+H)+

¹H NMR δ (DMSO) 8.42-8.28 (2H, m), 7.88 (1H, dd), 7.64 (1H, td), 7.55 (1H, s), 7.20 (1H, d), 7.14 (1H, dd), 6.98 (1H, d), 4.43-4.33 (1H, m), 3.85-3.75 (1H, m), 3.45-3.34 (1H, m), 3.20-3.08 (1H, m), 2.75-2.60 (2H, m), 2.42-2.25 (4H, m), 2.14 (3H, s), 1.94-1.81 (2H, m), 1.70-1.56 (2H, m).

EXAMPLE 211

N-{(2R)-3-[4-(4-Chloro-2-methylphenoxy)piperidin-1-yl]-2-hydroxypropyl}-6-(methylsulfonyl)-1-oxo-1,2-dihydroisoquinoline-4-carboxamide

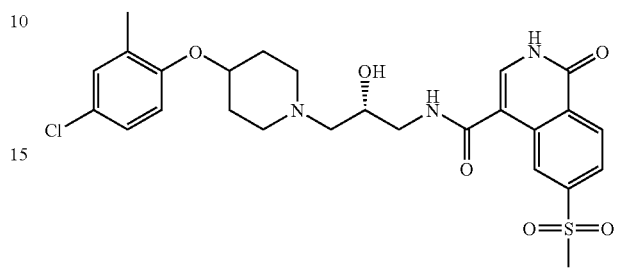

Prepared as described in Example 189 following Preparation 10 using 6-(methylsulfonyl)-1-oxo-1,2-dihydroisoquinoline-4-carboxylic acid.

MS (APCI) 548 (M+H)+

¹H NMR δ (DMSO) 11.98 (1H, s), 8.89 (1H, d), 8.44 (1H, d), 8.42 (1H, t), 8.01 (1H, dd), 7.76-7.72 (1H, m), 7.20 (1H, d), 7.14 (1H, dd), 6.98 (1H, d), 4.77 (1H, d), 4.43-4.34 (1H, m), 3.86-3.77 (1H, m), 3.42 (1H, td), 3.28 (3H, s), 3.17 (1H, quintet), 2.77-2.63 (2H, m), 2.42-2.29 (4H, m), 2.14 (3H, s), 1.95-1.84 (2H, m), 1.71-1.58 (2H, m).

EXAMPLE 212

N-{(2R)-3-[4-(2,4-Dichloro-3-methylphenoxy)piperidin-1-yl]-2-hydroxypropyl}-6-(methylsulfonyl)-1-oxo-1,2-dihydroisoquinoline-4-carboxamide

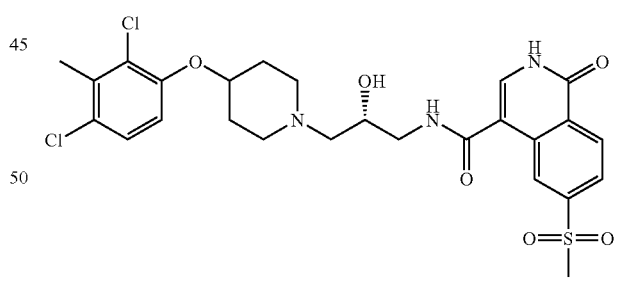

Prepared as described in Example 189 following Preparation 13 using 6-(methylsulfonyl)-1-oxo-1,2-dihydroisoquinoline-4-carboxylic acid.

MS (APCI) 581/583 (M+H)+

¹H NMR δ (DMSO) 11.97 (1H, d), 8.89 (1H, d), 8.44 (1H, d), 8.42 (1H, t), 8.01 (1H, dd), 7.76-7.72 (1H, m), 7.35 (1H, d), 7.10 (1H, d), 4.80-4.73 (1H, m), 4.53-4.44 (1H, m), 3.86-3.76 (1H, m), 3.42 (1H, td), 3.28 (3H, s), 3.21-3.12 (1H, m), 2.79-2.65 (2H, m), 2.40 (3H, s), 2.42-2.30 (4H, m), 1.95-1.85 (2H, m), 1.74-1.61 (2H, m).

EXAMPLE 213

N-{(2R)-3-[4-(3,4-Dichlorophenoxy)piperidin-1-yl]-2-hydroxypropyl}-7-(methylsulfonyl)-1-oxo-1,2-dihydroisoquinoline-4-carboxamide acetate salt

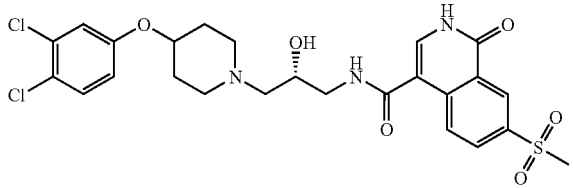

Prepared as described in Example 189 following Preparation 7 using 7-(methylsulfonyl)-1-oxo-1,2-dihydroisoquinoline-4-carboxylic acid.

MS (APCI) 568/566 (M+H)+

$^1$H NMR δ (DMSO) 8.70 (1H, s), 8.46 (1H, d), 8.16 (1H, dd), 8.10 (1H, t), 7.70 (1H, s), 7.45 (1H, d), 7.18 (1H, d), 6.94 (1H, dd), 4.39 (1H, septet), 3.82 (1H, quintet), 3.42 (1H, dt), 3.30-3.09 (1H, m), 3.22 (3H, s), 2.82-2.67 (2H, m), 2.45-2.27 (4H, m), 1.99-1.80 (2H, m), 1.89 (3H, s, OAc), 1.72-1.53 (2H, m).

EXAMPLE 214

N-{(2R)-3-[4-(3,4-Dichlorophenoxy)piperidin-1-yl]-2-hydroxypropyl}-7-(methylsulfonyl)-1-oxo-1,2-dihydroisoquinoline-4-carboxamide acetate salt

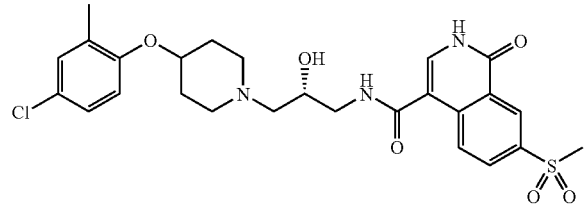

Prepared as described in Example 189 following Preparation 10 using 7-(methylsulfonyl)-1-oxo-1,2-dihydroisoquinoline-4-carboxylic acid.

MS (APCI) 548/550 (M+H)+

$^1$H NMR δ (DMSO) 8.68 (1H, d), 8.48 (1H, d), 8.43 (1H, t), 8.20 (1H, dd), 7.76 (1H, s), 7.21 (1H, d), 7.15 (1H, dd), 6.98 (1H, d), 4.84-4.72 (1H, m), 4.46-4.31 (1H, m), 3.88-3.74 (1H, m), 3.49-3.34 (1H, m), 3.28 (3H, s), 3.22-3.08 (1H, m), 2.78-2.60 (2H, m), 2.44-2.24 (4H, m), 2.14 (3H, s), 1.98-1.79 (2H, m), 1.74-1.54 (2H, m).

EXAMPLE 215

N-{(2R)-3-[4-(2,4-Dichloro-3-methylphenoxy)piperidin-1-yl]-2-hydroxypropyl}-7-(methylsulfonyl)-1-oxo-1,2-dihydroisoquinoline-4-carboxamide acetate salt

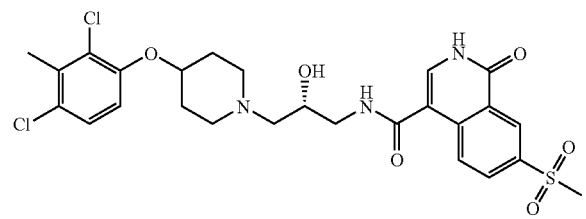

Prepared as described in Example 189 following Preparation 13 using 7-(methylsulfonyl)-1-oxo-1,2-dihydroisoquinoline-4-carboxylic acid.

MS (APCI) 582/584 (M+H)+

$^1$H NMR δ (DMSO) 8.68 (1H, d), 8.47 (1H, d), 8.44 (1H, t), 8.20 (1H, dd), 7.76 (1H, s), 7.35 (1H, d), 7.10 (1H, d), 4.53-4.44 (1H, m), 3.81 (1H, quintet), 3.42 (1H, dt), 3.20-3.09 (1H, m), 2.77-2.65 (2H, m), 2.40 (3H, s), 2.39-2.28 (4H, m), 1.95-1.85 (2H, m), 1.87 (3H, s, OAc), 1.73-1.61 (2H, m).

EXAMPLE 216

N-{(2R)-3-[4-(3,4-Dichlorophenoxy)piperidin-1-yl]-2-hydroxypropyl}-6-(methylsulfonyl)-1-oxo-1,2-dihydroisoquinoline-4-carboxamide

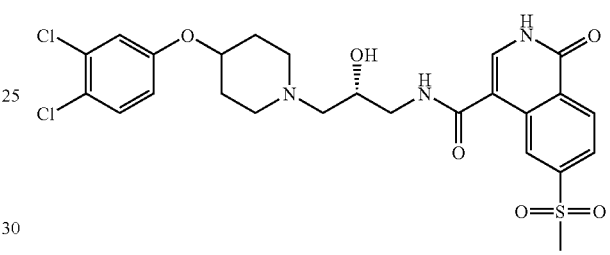

Prepared as described in Example 189 following Preparation 7 using 6-(methylsulfonyl)-1-oxo-1,2-dihydroisoquinoline-4-carboxylic acid.

MS (ESI) 568/570 (M+H)+

EXAMPLE 217

N-{(2R)-3-[4-(3,4-Dichlorophenoxy)piperidin-1-yl]-2-hydroxypropyl}-6-fluoro-1-oxo-1,2-dihydroisoquinoline-4-carboxamide

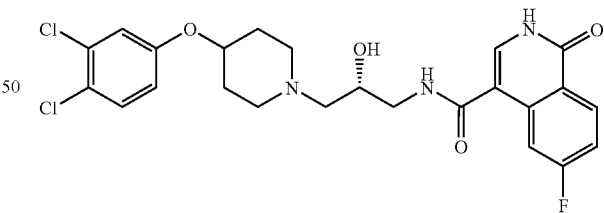

Prepared as described in Example 189-following Preparation 7 using 6-fluoro-1-oxo-1,2-dihydroisoquinoline-4-carboxylic acid.

MS (APCI) 508/510 (M+H)+

$^1$H NMR δ (DMSO) 11.70 (1H, d), 8.34 (1H, t), 8.28 (1H, dd), 8.03 (1H, dd), 7.64 (1H, d), 7.49 (1H, d), 7.38 (1H, td), 7.25 (1H, d), 6.98 (1H, dd), 4.80-4.70 (1H, m), 4.44 (1H, septet), 3.87-3.73 (1H, m), 3.45-3.36 (1H, m), 3.14 (1H, quintet), 2.84-2.66 (2H, m), 2.43-2.21 (4H, m), 1.99-1.84 (2H, m), 1.69-1.51 (2H, m).

EXAMPLE 218

N-{(2R)-3-[4-(4-Chloro-2-methylphenoxy)piperidin-1-yl]-2-hydroxypropyl}-6-fluoro-1-oxo-1,2-dihydroisoquinoline-4-carboxamide

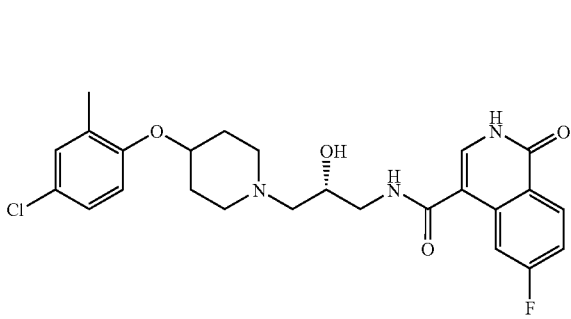

Prepared as described in Example 189 following Preparation 10 using 6-fluoro-1-oxo-1,2-dihydroisoquinoline-4-carboxylic acid.

MS (ESI) 488/490 (M+H)+

EXAMPLE 219

N-{(2R)-3-[4-(4-Chloro-2-methylphenoxy)piperidin-1-yl]-2-hydroxypropyl}-2-oxo-4-(trifluoromethyl)-1,2-dihydropyrimidine-5-carboxamide

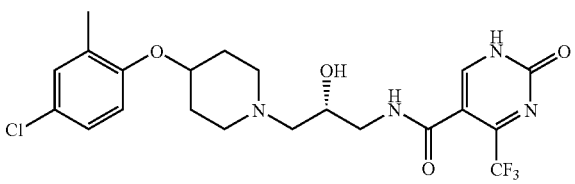

Prepared as described in Example 35 following Preparation 10 using 2-oxo-4-(trifluoromethyl)-1,2-dihydropyrimidine-5-carbonyl chloride.

MS (ESI) 489/491 (M+H)+

EXAMPLE 220

N-{(2R)-3-[4-(2,4-Dichloro-3-methylphenoxy)piperidin-1-yl]-2-hydroxypropyl}-2-oxo-4-(trifluoromethyl)-1,2-dihydropyrimidine-5-carboxamide

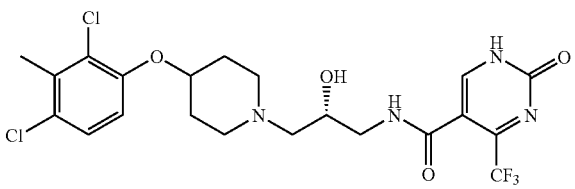

Prepared as described in Example 35 following Preparation 13 using 2-oxo-4-(trifluoromethyl)-1,2-dihydropyrimidine-5-carbonyl chloride.

MS (ESI) 523/525 (M+H)+

EXAMPLE 221

N-((2R)-3-{4-[3,4-Dichloro-2-(methylsulfonyl)phenoxy]piperidin-1-yl}-2-hydroxypropyl)-1-oxo-1,2-dihydroisoquinoline-4-carboxamide acetate

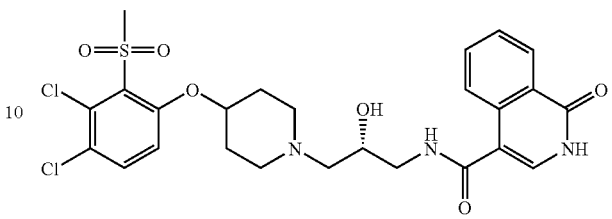

Prepared as described in Example 35 following Preparation 48 using 1-oxo-1,2-dihydroisoquinoline-4-carbonyl chloride.

MS (APCI) 568/570 (M+H)+

$^1$H NMR δ (CD$_3$OD) 8.35 (1H, d), 8.18 (1H, d), 7.78 (1H, t), 7.76 (1H, d), 7.58 (1H, s), 7.57 (1H, t), 7.28 (1H, d), 4.87-4.80 (1H, m), 4.13-4.07 (1H, m), 3.54 (1H, dd), 3.40 (1H, dd), 3.35 (3H, s), 3.16-3.06 (2H, m), 2.85-2.69 (4H, m), 2.16-2.00 (4H, m), 1.94 (3H, s).

EXAMPLE 222

N-{(2R)-3-[4-(3,4-Dichlorophenoxy)piperidin-1-yl]-2-hydroxypropyl}-6-oxo-4-(trifluoromethyl)-1,6-dihydropyridine-3-carboxamide acetate salt

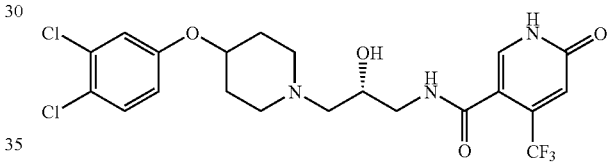

Prepared as described in Example 35 following Preparation 7 using 6-oxo-4-(trifluoromethyl)-1,6-dihydropyridine-3-carbonyl chloride, which was prepared by hydrolysis with sodium hydroxide followed by treatment with thionyl chloride of the commercially available 6-chloro 1-trifluoromethyl methyl nicotinoate).

MS (APCI) 508/510 (M+H)+

$^1$H NMR δ (DMSO) 8.35 (1H, t), 7.77 (1H, s), 7.49 (1H, d), 7.25 (1H, d), 6.98 (1H, dd), 6.72 (1H, s), 4.43 (1H, septet), 3.71 (1H, quintet), 3.29 (1H, dt), 3.06 (1H, dt), 2.78-2.66 (2H, m), 2.36-2.24 (4H, m), 1.95-1.86 (2H, m), 1.90 (3H, s), 1.65-1.54 (2H, m).

EXAMPLE 223

N-{(2R)-3-[4-(4-Chloro-2-methylphenoxy)piperidin-1-yl]-2-hydroxypropyl}-6-oxo-4-(trifluoromethyl)-1,6-dihydropyridine-3-carboxamide acetate salt

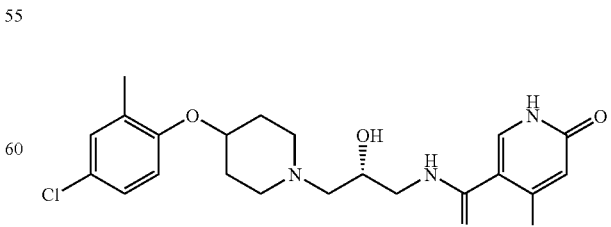

Prepared as described in Example 35 following Preparation 10 using 6-oxo-4-(trifluoromethyl)-1,6-dihydropyridine-3-carbonyl chloride.

MS (APCI) 488/490 (M+H)⁺

¹H NMR δ (DMSO) 8.35 (1H, t), 7.77 (1H, s), 7.20 (1H, s), 7.15 (1H, dd), 6.98 (1H, d), 6.73 (1H, s), 4.42-4.34 (1H, m), 3.72 (1H, quintet), 3.33-3.27 (1H, m), 3.06 (1H, dt), 2.71-2.61 (2H, m), 2.37-2.25 (4H, m), 2.14 (3H, s), 1.93-1.84 (2H, m), 1.91 (3H, s), 1.69-1.58 (2H, m).

EXAMPLE 224

N-{(2R)-3-[4-(2,4-Dichloro-3-methylphenoxy)piperidin-1-yl]-2-hydroxypropyl}-6-oxo-4-(trifluoromethyl)-1,6-dihydropyridine-3-carboxamide

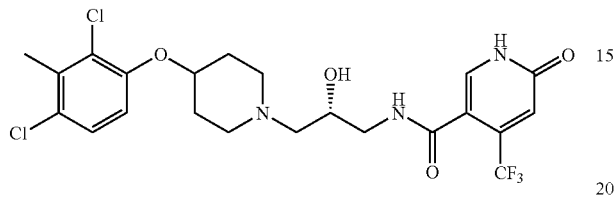

Prepared as described in Example 35 following Preparation 13 using 6-oxo-4-(trifluoromethyl)-1,6-dihydropyridine-3-carbonyl chloride.

MS (APCI) 522/524 (M+H)⁺

¹H NMR δ (DMSO) 8.32 (1H, t), 7.79 (1H, s), 7.35 (1H, d), 7.10 (1H d), 6.69 (1H, s), 4.49 (1H, septet), 3.72 (1H, quintet), 3.30 (1H, dt), 3.07 (1H, dt), 2.74-2.64 (2H, m), 2.40 (3H, s), 2.37-2.25 (4H, m), 1.94-1.84 (2H, m), 1.89 (3H, s), 1.71-1.61 (2H, m).

EXAMPLE 225

N-{(2R)-3-[4-(3,4-dichlorophenoxy)piperidin-1-yl]-2-hydroxypropyl}-2-(2-oxoquinoxalin-1(2H)-yl)acetamide

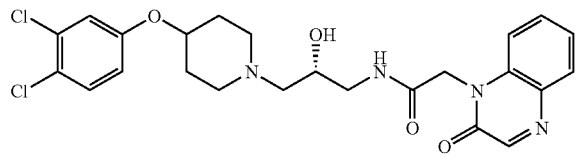

Prepared as described in Example 1 following Preparation 7 using (2-oxo-quinoxalin-1-(2H)-yl)acetic acid.

MS (APCI) 505/507 (M+H)⁺

¹H NMR δ (CDCl₃) 8.37 (1H, s), 7.92 (1H, d), 7.61 (1H, t), 7.49 (1H, d), 7.40 (1H, t), 7.32 (1H, d), 6.99 (1H, d), 6.74 (1H, dd), 6.72 (1H, bd s), 4.91 (2H, m), 4.36-4.26 (1H, m), 3.86-3.76 (1H, m), 3.52-3.42 (1H, m), 3.26-3.18 (1H, m), 2.88-2.80 (1H, m), 2.63-2.53 (2H, m), 2.40-2.26 (3H, m), 2.06-1.92 (2H, m), 1.87-1.73 (2H, m).

EXAMPLE 226

N-{(2R)-3-[4-(3,4-dichlorophenoxy)piperidin-1-yl]-2-hydroxypropyl}-3-oxo-3,4-dihydroquinoxaline-1(2H)-carboxamide

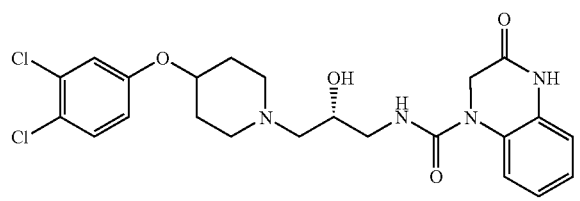

Prepared as described in Example 35 following Preparation 7 using 3-oxo-3,4-dihydroquinoxaline-1(2H)-carbonyl chloride.

MS (APCI) 505/507 (M+H)⁺

¹H NMR δ (CDCl₃) 8.26 (1H, s), 7.43 (1H, d), 7.31 (1H, d), 7.19-7.09 (1H, m), 6.99 (1H, d), 6.94 (1H, d), 6.75 (1H, dd), 5.72 (1H, t), 4.44 (2H, s), 4.30-4.22 (1H, m), 3.88-3.81 (1H, m), 3.58-3.52 (1H, m), 3.17-3.11 (1H, m), 2.93-2.85 (1H, m), 2.67-2.61 (1H, m), 2.57-2.53 (1H, m), 2.44-2.40 (1H, m), 2.36-2.29 (2H, m), 2.00-1.90 (2H, m), 1.80-1.70 (2H, m).

EXAMPLE 227

N-{(2R)-3-[4-(4-Chloro-2-methylphenoxy)piperidin-1-yl]-2-hydroxypropyl}-3-(trifluoromethyl)-1H-pyrazole-4-carboxamide

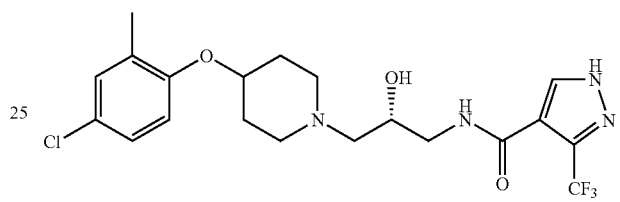

Prepared as described in Example 1 following Preparation 10 using 3-(trifluoromethyl)-1H-pyrazole-4-carboxylic acid.

MS (APCI) 460/462 (M+H)⁺

¹H NMR δ (DMSO) 8.41 (1H, s), 8.15 (1H, t), 7.20 (1H, d), 7.14 (1H, dd), 6.98 (1H, d), 4.42-4.36 (1H, m), 3.77-3.71 (1H, m), 3.39-3.33 (1H, m), 3.10-3.04 (1H, m), 2.73-2.63 (2H, m), 2.36-2.26 (4H, m), 2.14 (3H, s), 1.92-1.82 (2H, m), 1.70-1.60 (2H, m).

EXAMPLE 228

N-{(2R)-3-[4-(2,4-dichloro-3-methylphenoxy)piperidin-1-yl]-2-hydroxypropyl}-3-(trifluoromethyl)-1H-pyrazole-4-carboxamide

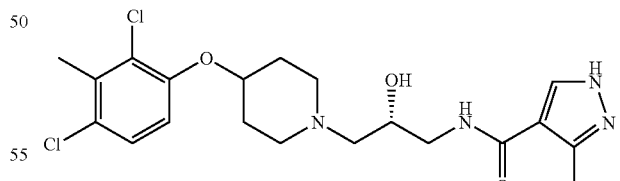

Prepared as described in Example 1 following Preparation 13 using 3-(trifluoromethyl)-1H-pyrazole-4-carboxylic acid.

MS (APCI) 495/497 (M+H)⁺

¹H NMR δ (DMSO) 8.41 (1H, s), 8.15 (1H, t), 7.34 (1H, d), 7.09 (1H, dd), 4.50-4.42 (1H, m), 3.77-3.71 (1H, m), 3.37-3.33 (1H, m), 3.10-3.04 (1H, m), 2.74-2.64 (2H, m), 2.39 (3H, s), 2.36-2.26 (4H, m), 1.96-1.86 (2H, m), 1.69-1.62 (2H, m).

EXAMPLE 229

N-{(2R)-3-{4-(3,4-Dichlorophenoxy)piperidin-1-yl}-2-hydroxypropyl}-1-oxo-1,2-dihydro-2-methyl-isoquinoline-4-carboxamide

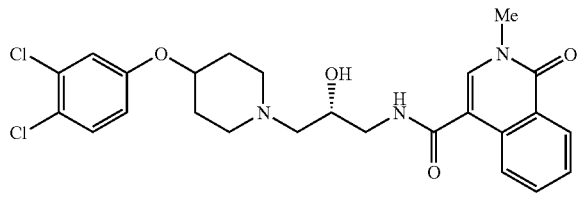

Prepared as described in Example 1 following Preparation 7 using 2-methyl-1-oxo-1,2-dihydroisoquinoline-carboxylic acid.

MS (APCI) 504/506/508 (M+H)+

$^1$H NMR δ (CDCl$_3$) 8.47 (1H, d), 8.14 (1H, d), 7.70 (1H, t), 7.61 (1H, s), 7.53 (1H, t), 7.33 (1H, d), 7.00 (1H, d), 6.76 (1H, dd), 6.58 (1H, bd t), 4.42-4.32 (1H, m), 4.06-3.96 (1H, m), 3.80-3.70 (1H, m), 3.63 (3H, s), 3.44-3.34 (1H, m), 3.02-2.92 (1H, m), 2.78-2.68 (2H, m), 2.59-2.45 (3H, m), 2.16-2.00 (2H, m), 1.96-1.80 (2H, m).

EXAMPLE 230

N-{(2R)-3-{4-(3,4-Dichlorophenoxy)piperidin-1-yl]-2-hydroxypropyl}-2-oxo-1,2-dihydro-1-methylquinoline-4-carboxamide

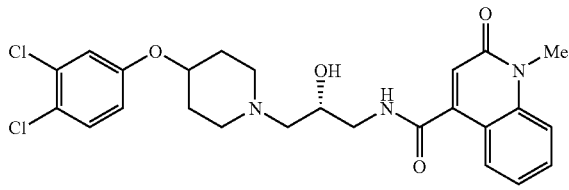

Prepared as described in Example 1 following Preparation 7 using 1-methyl-2-oxo-1,2-dihydroquinoline-4-carboxylic acid.

MS (APCI) m/z 504/506/508 (M+H)+

$^1$H NMR δ (CDCl$_3$) 7.97 (1H, d), 7.62 (1H, t), 7.40 (1H, d), 7.32 (1H, d), 7.28 (1H, t), 7.00 (1H, d), 6.83 (1H, s), 6.76 (1H, dd), 6.72 (1H, t), 4.39-4.31 (1H, m), 4.04-3.94 (1H, m), 3.78-3.70 (1H, m), 3.72 (3H, s), 3.47-3.37 (1H, m), 3.00-2.90 (1H, m), 2.75-2.67 (2H, m), 2.56-2.42 (3H, m), 2.10-1.94 (2H, m), 1.94-1.78 (2H, m).

EXAMPLE 231

N-{(2R)-3-[4-(3,4-dichlorophenoxy)piperidin-1-yl]-2-hydroxypropyl}-8-fluoro-1-oxo-1,2-dihydroisoquinoline-4-carboxamide

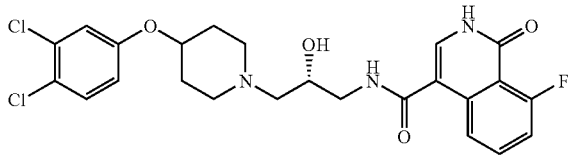

Prepared as described in Example 35 following Preparation 7 using 8-fluoro-1-oxo-1,2-dihydroisoquinoline-4-carbonyl chloride.

MS (APCI) 508/510 (M+H)+

EXAMPLE 232

N-{(2R)-3-[4-(4-chloro-2-methylphenoxy)piperidin-1-yl]-2-hydroxypropyl}-8-fluoro-1-oxo-1,2-dihydroisoquinoline-4-carboxamide

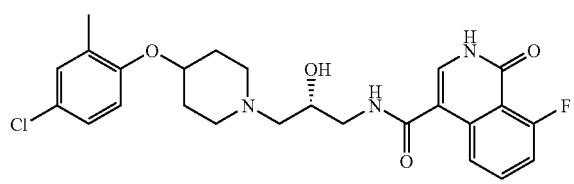

Prepared as described in Example 35 following Preparation 10 using 8-fluoro-1-oxo-1,2-dihydroisoquinoline-4-carbonyl chloride.

MS (APCI) 488/490 (M+H)+

EXAMPLE 233

N-{(2R)-3-[4-(3,4-Dichlorophenoxy)piperidin-1-yl]-2-hydroxypropyl}-2-oxo-4-(trifluoromethyl)-1,2-dihydropyrimidine-5-carboxamide

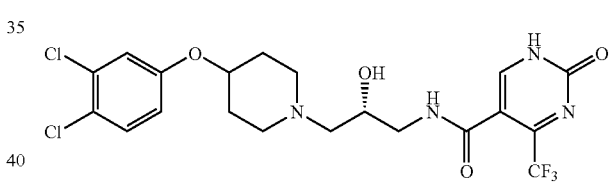

Prepared as described in Example 35 following Preparation 7 using 2-oxo-4-(trifluoromethyl)-1,2-dihydropyrimidine-5-carbonyl chloride.

MS (EPCI) 509/511 (M+H)+

EXAMPLE 234

N-{(2R)-3-[4-(3,4-Dichlorophenoxy)piperidin-1-yl]-2-hydroxypropyl}-4-methyl-2-oxo-1,2-dihydropyrimidine-5-carboxamide

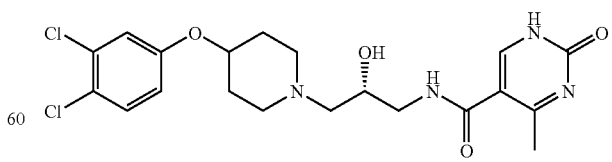

Prepared as described in Example 35 following Preparation 7 using 4-methyl-2-oxo-1,2-dihydropyrimidine-5-carbonyl chloride.

MS (EPCI) 455/457 (M+H)+

EXAMPLE 235

Pharmacological Analysis: Calcium Flux $[Ca^{2+}]_i$ assay.

Human Eosinophils

Human eosinophils were isolated from EDTA anticoagulated peripheral blood as previously described (Hansel et al., *J. Immunol. Methods*, 1991, 145, 105-110). The cells were resuspended ($5 \times 10^6$ ml$^{-1}$) and loaded with 5 µM FLUO-3/AM+Pluronic F127 2.2 µl/ml (Molecular Probes) in low potassium-solution (LKS; NaCl 118 mM, MgSO$_4$ 0.8 mM; glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at $2.5 \times 10^6$ ml$^{-1}$. The cells were then transferred to 96 well FLIPr plates (Poly-D-Lysine plates from Becton Dickinson pre-incubated with 5 µM fibronectin for twoh) at 25 µl/well. The plate was centrifuged at 200 g for 5 min and the cells were washed twice with LKS (200 µl; room temperature).

A compound of the Examples was pre-dissolved in DMSO and added to a final concentration of 0.1%(v/v) DMSO. Assays were initiated by the addition of an A$_{50}$ concentration of eotaxin and the transient increase in fluo-3 fluorescence ($1_{Ex}$=490 nm and $1_{Em}$=520 nm) monitored using a FLIPR (Fluorometric Imaging Plate Reader, Molecular Devices, Sunnyvale, U.S.A.).

Compounds of the Examples were found to be antagonists if the increase in fluorescence induced by eotaxin (a selective CCR3 agonist) was inhibited in a concentration dependent manner. The concentration of antagonist Expired to inhibit the fluorescence by 50% can be used to determine the IC$_{50}$ for the antagonist at the CCR3 receptor.

EXAMPLE 236

Human Eosinophil Chemotaxis

Human eosinophils were isolated from EDTA anticoagulated peripheral blood as previously described (Hansel et al., *J. Immunol. Methods*, 1991, 145, 105-110). The cells were resuspended at $10 \times 10^6$ ml$^{-1}$ in RPMI containing 200 IU/ml penicillin, 200 µg/ml streptomycin sulfate and supplemented with 10% SACS, at room temperature.

Eosinophils (700 µl) were pre-incubated for 15 mins at 37° C. with 7 µl of either vehicle or compound 100× required final concentration in 10% DMSO). The chemotaxis plate (ChemoTX, 3 µm pore, Neuroprobe) was loaded by adding 28 µl of a concentration of eotaxin 0.1 to 100 nM (a selective CCR3 agonist over this concentration range) containing a concentration of a compound according to the Examples or solvent to the lower wells of the chemotaxis plate. The filter was then placed over the wells and 25+ to of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 µl of PBS-containing 0.5% Tritonx100 followed by two cycles of freeze/thawing. The cell lysate was then added to the supernatant. The number of eosinophils migrating was quantified according to the method of Strath et. al., *J. Immunol. Methods*, 1985, 83, 209 by measuring eosinophil peroxidase activity in the supernatant.

Compounds of the Examples were found to be antagonists of eotaxin mediated human eosinophil chemotaxis if the concentration response to eotaxin was shifted to the right of the control curve. Measuring the concentration of eotaxin required to give 50% chemotaxis in the presence or absence of compounds enables the apparent affinity of the compounds at CCR3 to be calculated, or the assay can be used to determine activity of compounds at a set concentration of compound against a predefined concentration of eotaxin.

| Example | % inhibition at 3 nM eotaxin (1 uM compound) |
|---------|----------------------------------------------|
| 10 | 106 |
| 17 | 103 |
| 45 | 102 |
| 46 | 105 |
| 47 | 104 |
| 52 | 95 |
| 53 | 105 |
| 58 | 104 |
| 132 | 101 |
| 186 | 104 |
| 192 | 103 |
| 197 | 103 |
| 206 | 99 |
| 212 | 103 |
| 215 | 103 |
| 227 | 103 |

EXAMPLE 237

Guinea-Pig Isolated Trachea (See for example, Harrison, R. W. S., Carswell, H. & Young, J. M. (1984) European J. Pharmacol., 106, 405-409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (mM): NaCl 117.6, NaH$_2$PO$_4$ 0.9, NaHCO$_3$ 25.0, MgSO$_4$ 1.2, KCl 5.4, CaCl$_2$ 2.6 and glucose 11.1. The buffer was maintained at 37° C. and gassed with 5% CO$_2$ in oxygen. Indometacin (2.8 µM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 log$_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies (p[$A_{50}$] values) of histamine in the absence and presence of the test compound. Affinity (p$A_2$) values of test compounds were subsequently-calculated using the following equation:

$$\log(r-1) = \log[B] + pA_2$$

where r=[$A$]$_{50}$ in presence of test compound/$A$]$_{50}$ in absence of antagonist and [B] is the concentration of test compound. Compounds of the Examples were found to be H1 antagonists.

EXAMPLE 238

Histamine H1 receptor binding activity of compounds of the invention was assessed by competition displacement of 1 nM [3H]-pyrilamine (Amersham, Bucks, Product code TRK 608, specific activity 30 Ci/mmol) to 2 μg membranes prepared from recombinant CHO-K1 cells expressing the human H1 receptor (Euroscreen SA, Brussels, Belgium, product code ES-390-M) in assay buffer (50 mM Tris pH 7.4 containing 2 nM $MgCl_2$, 250 mM sucrose and 100 mM NaCl) for 1 hour at room temperature.

| Example | H1 pKi/[1328_S] |
|---------|-----------------|
| 10      | 8.4             |
| 17      | 8.1             |
| 45      | 7.7             |
| 46      | 8.2             |
| 47      | 8.1             |
| 52      | 8.4             |
| 53      | 8.1             |
| 58      | 7.2             |
| 132     | 6.6             |
| 186     | 7.9             |
| 192     | 8.7             |
| 197     | 6.8             |
| 206     | 6.6             |
| 212     | 7.8             |
| 215     | 7.3             |
| 227     | 7.6             |

The invention claimed is:

1. A compound of formula (I):

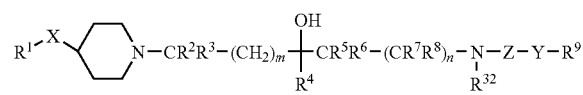

(I)

wherein:
X is O;
Y is a bond;
Z is C(O);
$R^1$ is phenyl optionally substituted by halogen, cyano, $C_{1-4}$ alkyl, $C_{1-4}$ alkoxy, $S(O)_2(C_{1-4}$alkyl), $S(O)_2NH_2$, $S(O)_2NH(C_{1-4}$ alkyl), $S(O)_2NH(C_{3-6}$ cycloalkyl), $C(O)_2(C_{1-4}$ alkyl), $C(O)NH(C_{1-4}$ alkyl) or $C(O)NH_2$;
$R^4$ is hydrogen, $C_{1-6}$ alkyl (optionally substituted by $C_{3-6}$ cycloalkyl) or $C_{3-6}$ cycloalkyl;
$R^2$, $R^3$, $R^5$, and $R^6$ are, independently, hydrogen, $C_{1-6}$ alkyl or $C_{3-6}$ cycloalkyl;
m and n are both 0;
$R^9$ is aryl or heterocyclyl, each of which is unsubstituted or substituted by one or more of: oxo (where possible), halogen, $C_{1-4}$ alkyl, $CF_3$, $C_{1-4}$ alkoxy, $S(O)_2(C_{1-4}$ alkyl), $S(O)_2NH_2$, $S(O)_2NH(C_{1-4}$ alkyl), $S(O)_2N(C_{1-4}$ alkyl)$_2$ or $OCF_3$;
$R^{32}$ is hydrogen, $C_{1-6}$ alkyl or $C_{3-6}$ cycloalkyl;
or an N-oxide thereof; or a pharmaceutically acceptable salt thereof.

2. A compound as claimed in claim 1, wherein $R^{32}$ is hydrogen.

3. A compound as claimed in claim 1 wherein $R^2$, $R^3$, $R^4$, $R^5$, and $R^6$ are all hydrogen.

4. A compound as claimed in claim 1 wherein $R^9$ is optionally substituted heterocyclyl; wherein the heterocyclyl group is: thienyl, pyrrolyl, thiazolyl, pyrazolyl, oxazolyl, isoxazolyl, imidazolyl, 1,2,5-oxadiazolyl, pyridinyl, 1,6-dihydropyridinyl, pyrimidinyl, indolyl, indazolyl, 2,3-dihydro-1H-indazolyl, an imidazopyridinyl, 2,1,3-benzothiadiazolyl, quinoxalinyl, quinolinyl, 1,2-dihydroquinolinyl, 1,4-dihydroquinoline, isoquinolinyl, 1,2-dihydroisoquinolinyl, cinnolinyl, 3,4-dihydrophthalazinyl, 2,3-dihydro-4H-1,4-benzoxazinyl, 3,4-dihydro-2H-1,4-benzoxazinyl, 1,3-dihydro-2H-isoindolyl, pyrazolotriazinyl, pyrazolopyrimidinyl, imidazobenzothiazolyl, imidazopyrimidinyl, or 2,1,3-benzoxadiazolyl, 1,3-benzothiazole, 2,3-dihydro-1,3-benzothiazole, 4,5,6,7-tetrahydroindazole or 2,3-dihydro-1H-benzimidazole; wherein the heterocyclyl is unsubstituted or substituted by one or more of: oxo (where possible), halogen, $C_{1-4}$ alkyl, $CF_3$, $C_{1-4}$ alkoxy, $S(O)_2(C_{1-4}$ alkyl), $S(O)_2NH_2$, $S(O)_2NH(C_{1-4}$ alkyl), $S(O)_2N(C_{1-4}$ alkyl)$_2$ or $OCF_3$.

5. A process for preparing a compound as claimed in claim 1, the process comprising reacting a compound of formula (II):

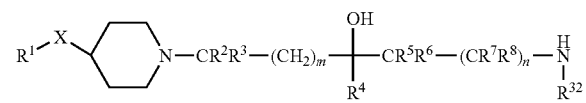

(II)

wherein X, $R^1$, $R^2$, $R^3$, $R^4$, $R^5$, $R^6$, $R^7$, $R^8$, $R^{32}$, m and n are as defined in claim 1, with a compound of formula (IIIa):

(IIIa)

wherein $R^9$ is as defined in claim 1 and $L^1$ is a leaving group in the presence of a base, optionally in the presence of a coupling agent.

6. A composition comprising a compound of formula (I), or a pharmaceutically acceptable salt thereof, as claimed in claim 1, and a pharmaceutically acceptable adjuvant, diluent or carrier thereof.

7. A method of treating obstructive disease of airways a in a mammal suffering from, or at risk of, said disease, which comprises administering to a mammal in need of such treatment a therapeutically effective amount of a compound of formula (I), or a pharmaceutically acceptable salt, salt thereof, as claimed in claim 1.

8. A method according to claim 7, wherein the obstructive disease of airways is selected from the group consisting of chronic obstructive pulmonary disease (COPD); asthma; bronchitis; acute, allergic, atrophic, or chronic rhinitis; membranous rhinitis; seasonal rhinitis; sarcoidosis; farmer's lung and related diseases; nasal polyposis; fibroid lung; idiopathic interstitial pneumonia; antitussive activity; chronic cough associated with inflammatory conditions of the airways; and iatrogrenic induced cough.

9. A method according to claim 8, wherein the acute, allergic, atrophic, or chronic rhinitis is rhinitis caseoa, hypertrophic rhinitis, rhinitis purulenta, rhinitis sicca or rhinitis medicamentosa.

10. A method according to claim 8, wherein the membranous rhinitis is croupous, fibrinous or pseudomembranous rhinitis or scrofulous rhinitis.

11. A method according to claim 8, wherein the seasonal rhinitis including rhinitis nervosa (hay fever) or vasomotor rhinitis.

12. A method according to claim 7, wherein the obstructive disease of airways is asthma.

13. A method according to claim 7, wherein the obstructive disease of airways is rhinitis.

14. A method of treating a disease or condition selected from psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata, and vernal conjunctivitis a in a mammal suffering from, or at risk of, said disease, which comprises administering to a mammal in need of such treatment a therapeutically effective amount of a compound of formula (I), or a pharmaceutically acceptable salt thereof, as claimed in claim 1.

\* \* \* \* \*

UNITED STATES PATENT AND TRADEMARK OFFICE
CERTIFICATE OF CORRECTION

PATENT NO. : 7,709,500 B2  Page 1 of 1
APPLICATION NO. : 10/504936
DATED : May 4, 2010
INVENTOR(S) : Lilian Alcaraz et al.

It is certified that error appears in the above-identified patent and that said Letters Patent is hereby corrected as shown below:

Column 122, line 57, "airways a n", should read --airways in--.

Column 123, line 4, "iatrogrenic" should read -- iatrogenic --.

Column 124, line 6 "eczmatous dermitides, seborrhoetic" should read -- eczematous dermatitis, seborrheic --.

Column 124, line 9, "greata" should read -- areata, --.

Column 124, line 10, delete the first occurrence of "a".

Signed and Sealed this

Sixteenth Day of November, 2010

David J. Kappos
*Director of the United States Patent and Trademark Office*